United States Patent
Labrijn et al.

(10) Patent No.: US 9,150,663 B2
(45) Date of Patent: Oct. 6, 2015

(54) HETERODIMERIC ANTIBODY FC-CONTAINING PROTEINS AND METHODS FOR PRODUCTION THEREOF

(75) Inventors: Aran Frank Labrijn, Nigtevecht (NL); Joyce I. Meesters, Utrecht (NL); Ewald T. J. Van Den Bremer, Best (NL); Joost J. Neijssen, Werkhoven (NL); Patrick Van Berkel, Utrecht (NL); Bart De Goeij, Maarssen (NL); Tom Vink, Alphen aan den Rijn (NL); Jan Van De Winkel, Zeist (NL); Janine Schuurman, Diemen (NL); Paul Parren, Odijk (NL)

(73) Assignee: GENMAB A/S, Copenhagen (DK)

(*) Notice: Subject to any disclaimer, the term of this patent is extended or adjusted under 35 U.S.C. 154(b) by 0 days.

(21) Appl. No.: 13/642,253

(22) PCT Filed: Apr. 20, 2011

(86) PCT No.: PCT/EP2011/056388
§ 371 (c)(1),
(2), (4) Date: Oct. 24, 2012

(87) PCT Pub. No.: WO2011/131746
PCT Pub. Date: Oct. 27, 2011

(65) Prior Publication Data
US 2013/0039913 A1 Feb. 14, 2013

Related U.S. Application Data

(60) Provisional application No. 61/326,082, filed on Apr. 20, 2010.

(30) Foreign Application Priority Data

Apr. 20, 2010 (DK) .................... 2010 00330
Nov. 24, 2010 (DK) .................... 2010 01066

(51) Int. Cl.
*C07K 16/46* (2006.01)
*C07K 16/10* (2006.01)
*C07K 16/28* (2006.01)
*C07K 16/32* (2006.01)

(52) U.S. Cl.
CPC ........... *C07K 16/468* (2013.01); *C07K 16/1063* (2013.01); *C07K 16/2809* (2013.01); *C07K 16/2863* (2013.01); *C07K 16/2887* (2013.01); *C07K 16/32* (2013.01); *C07K 2317/21* (2013.01); *C07K 2317/24* (2013.01); *C07K 2317/41* (2013.01); *C07K 2317/526* (2013.01); *C07K 2317/53* (2013.01); *C07K 2317/55* (2013.01); *C07K 2317/73* (2013.01); *C07K 2317/734* (2013.01); *C07K 2317/77* (2013.01); *C07K 2317/94* (2013.01)

(58) Field of Classification Search
CPC .............. C07K 16/46–16/468; C07K 2317/10; C07K 2317/14; C07K 2317/31; C07K 2317/526; C07K 2317/53; C07K 2317/66; C07K 1/113–1/1136
See application file for complete search history.

(56) References Cited

U.S. PATENT DOCUMENTS

| | | | |
|---|---|---|---|
| 5,292,668 A | 3/1994 | Paulus | |
| 5,807,706 A | 9/1998 | Carter et al. | |
| 6,737,056 B1 * | 5/2004 | Presta | 424/133.1 |
| 2004/0038894 A1 | 2/2004 | Daeron et al. | |
| 2008/0051469 A1 * | 2/2008 | Brahmbhatt et al. | 514/773 |
| 2010/0015133 A1 * | 1/2010 | Igawa et al. | 424/133.1 |
| 2014/0141000 A1 * | 5/2014 | Chiu et al. | 424/136.1 |
| 2014/0170148 A1 * | 6/2014 | De Goeij et al. | 424/136.1 |
| 2014/0170149 A1 * | 6/2014 | Neijssen et al. | 424/136.1 |
| 2014/0303356 A1 * | 10/2014 | Gramer et al. | 530/387.3 |

FOREIGN PATENT DOCUMENTS

| | | |
|---|---|---|
| DE | 19859115 A1 | 3/2000 |
| EP | 1693386 A1 | 8/2006 |
| EP | 1870459 A1 | 12/2007 |
| WO | 96/27011 A1 | 9/1996 |
| WO | 98/04592 A1 | 2/1998 |
| WO | 98/50431 A2 | 11/1998 |
| WO | 02/100348 A2 | 12/2002 |
| WO | 2004/035607 A2 | 4/2004 |
| WO | 2005/000899 A2 | 1/2005 |
| WO | 2005/062916 A2 | 7/2005 |
| WO | 2006/047340 A2 | 5/2006 |
| WO | WO2006/106905 A1 * | 10/2006 |
| WO | 2007/059782 A1 | 5/2007 |
| WO | 2007/103112 A2 | 9/2007 |
| WO | 2007/110205 A2 | 10/2007 |
| WO | 2008/119353 A1 | 10/2008 |
| WO | 2008/145140 A2 | 12/2008 |

(Continued)

OTHER PUBLICATIONS

Mori et al., Cytotechnol. 2007; 55:109-114.*

(Continued)

*Primary Examiner* — Sheela J Huff
*Assistant Examiner* — Jessica H Roark
(74) *Attorney, Agent, or Firm* — Nelson Mullins Riley & Scarborough LLP; Jane E. Remillard, Esq.; Christopher L. Frank

(57) ABSTRACT

Heterodimeric antibody-Fc-containing proteins, such as bispecific antibodies, and novel methods for producing such proteins.

37 Claims, 64 Drawing Sheets

(56) References Cited

FOREIGN PATENT DOCUMENTS

| WO | 2008/145142 A1 | 12/2008 |
|---|---|---|
| WO | WO 2009089004 A1 * | 7/2009 |
| WO | 2010/063785 A2 | 6/2010 |
| WO | 2010/129304 A2 | 11/2010 |
| WO | 2011/143545 A1 | 11/2011 |
| WO | 2012/058768 A1 | 5/2012 |
| WO | 2012/116453 A1 | 9/2012 |

OTHER PUBLICATIONS

Scinicariello et al., Immunol 2004; 111:66-74.*
Labrijn et al., J. Immunol. 2011; 187:3238-46.*
Labrijn et al., Proc. Nat'l Acad. Sci., 2013; 110(13):5145-50.*
Aalberse, Rob C. et al., "IgG4 breaking the rules," Immunology, vol. 105:9-19 (2002).
Aalberse, Rob C., "Physiological Fab arm exchange of IgG4 generates an anti-inflammatory antibody," Genmab, European Antibody Congress, 36 pages (2008).
Aalberse, Rob C. et al., "Serologic Aspects of IgG4 Antibodies. I. Prolonged Immunization Results in an IgG4-Restricted Response," The Journal of Immunology, vol. 130(2):722-726 (1983).
Aalberse, Rob C. et al., "The Apparent Monovalency of Human IgG4 Is Due to Bispecificity," International Archives of Allergy and Immunology, vol. 118:187-189 (1999).
Angal, S. et al., "A Single Amino Acid Substitution Abolishes the Heterogeneity of Chimeric Mouse/Human (IgG4) Antibody," Molecular Immunology, vol. 30(1):105-108 (1993).
Bloom, James W. et al., "Interchain disulfide bond in the core hinge region of human IgG4," Protein Science, vol. 6:407-415 (1997).
Dall'Acqua, William et al., "Contribution of Domain Interface Residues to the Stability of Antibody CH3 Domain Homodimers," Biochemistry, vol. 37:9266-9273 (1998).
Deng, Liang et al., "Detection and quantification of the human IgG4 half-molecule, HL, from unpurified cell-culture supernatants," Biotechnol. Appl. Biochem., vol. 40:261-269 (2004).
Genmab, "Better Antibodies by Design," www.genmab.com, 2 pages (2011).
Genmab, "DuoBody: Innovative Bispecific Antibody Platform," Poster for R&D Day, 1 page (2011).
Genmab, "DuoBody, The next generation of therapeutic antibodies," www.genmab.com, 2 pages (2011).
Genmab, "Genmab, Beter Antibodies by Design," slideshow, 18 pages (2011).
Genmab, "Building for a Commercial Future: Research, Development and Business Update," slideshow, 65 pages (2006).
Genmab, "DuoBody, Genmab's proprietary bispecifiic antibody platform," slideshow, 13 pages (2011).
Genmab, "DuoBody platform, Genmab's proprietary bispecific antibody platform," slideshow, 15 pages, (2011).
Genmab, "The physiological generation of bispecific IgG4 antibodies," Sanquin Spring Symposium, slideshow, 54 pages (2007).
Genmab, "Therapeutic IgG4 antibodies engage in Fab-arm exchange with patients' IgG4 in vivo," Antibodies as Drugs, Poster #214, 14 pages (2009).
Labrijn, Aran F. et al., "Species-specific determinants in the immunoglobulin CH3 domain enable Fab-arm exchange by affecting the non-covalent CH3-CH3 interaction strength," Keystone Symposium, Antibodies as Drugs Poster Presentation, 1 page (2011).
Labrijn, Aran F. et al., "Species-Specific Determinants in the IgG CH3 Comain Enable Fab-Arm Exchange by Affecting the Noncovalent CH3-CH3 Interaction Strength," The Journal of Immunology, vol. 187, 9 pages (2011).

Labrijn, Aran F. et al., "Therapeutic IgG4 antibodies engage in Fab-arm exchange with endogenous human IgG4 in vivo," Nature Biotechnology, vol. 27(8):767-771 (2009).
Lewis, Kenneth B. et al., "Comparison of the ability of wild type and stabilized human IgG4 to undergo Fab arm exchange with endogenous IgG4 in vitro and in vivo," Molecular Immunology, vol. 46:3488-3494 (2009).
Marvin, Jonathan S. et al., "Recombinant approaches to IgG-like bispecific antibodies," Acta Pharmacologica Sinica, vol. 26(6):649-658 (2005).
Merchant, A. Margaret et al., "An efficient route to human bispecific IgG," Nature Biotechnology, vol. 16:677-681 (1998).
Ooijevaar-De Heer, Pleuni G. et al., "Fc binding activity of IgG4 is a confounding factor in the measurement of IgG4 bispecificity," Sanquin Spring Symposium, 1 page (2007).
Parren, Paul, "UniBody, a novel nonactivating antibody format," Beyond Antibodies, slideshow, 35 pages (2009).
Rispens, Theo et al., "Human IgG4 Binds to IgG4 and Conformationally Altered IgG1 via Fc-Fc Interactions," The Journal of Immunology, vol. 182:4275-4281 (2009).
Rispens, Theo, "IgG4: an odd antibody, Fc interactions and the relation to half-molecule exchange," Sanquin, slideshow, 41 pages (2009).
Schuurman, Janine et al., "Anti-Inflammatory Activity of Human IgG4 Antibodies by Dynamic Fab Arm Exchange," World BioPharm Forum, Poster, 1 page (2009).
Schuurman, Janine, "IgG4 therapeutic antibodies," World BioPharm Forum, slideshow, 26 pages (2009).
Schuurman, J. et al., "Normal human immunoglobulin G4 is bispecific: it has two different antigen-combining sites," Immunology, vol. 97:693-698 (1999).
Schuurman, Janine, "Post-Transcriptional Modifications," Genmab, slideshow, 43 pages (2008).
Schuurman, Janine, "The impact of Fab-arm exchange on the development of antibody therapeutics," Antibody Discovery & Development Forum, slideshow, 30 pages (2011).
Schuurman, Janine, "The impact of Fab-arm exchange on the development of antibody therapeutics," Genmab, slideshow, 26 pages (2010).
Schuurman, Janine, "The impact of Fab-arm exchange on the development of antibody therapeutics," Antibody Engineering and Design, slideshow, 29 pages (2011).
Schuurman, Janine et al., "The inter-heavy chain disulfide bonds of IgG4 are in equilibrium with intra-chain disulfide bonds," Molecular Immunology, vol. 38:1-8 (2001).
Stubenrauch, Kay et al., "Impact of Molecular Processing in the Hinge Region of Therapeutic IgG4 Antibodies on Disposition Profiles in Cynomolgus Monkeys," Drug Metabolism and Disposition, vol. 38(1):84-91 (2010).
Van Berkel, Patrick H.C., "Development of a production process for DuoBody: a novel human bispecific platform," Informa/IBC Life Sciences' Bioproduction Conference, Poster, 1 page (2011).
Van Der Neut Kolfschoten, Marijn et al., "Anti-Inflammatory Activity of Human IgG4 Antibodies by Dynamic Fab Arm Exchange," Science, vol. 317:1554-1557 (2007).
Van De Winkel, Jan et al., "Better Antibodies by Design, 2011 R&D Day," slideshow, 109 pages (2011).
Van Der Zee, J.S. et al., "Inhibition of complement activation by IgG4 antibodies," Clin. exp. Immunol., vol. 64:415-422 (1986).
Final Office Action for U.S. Appl. No. 12/593,759, dated Oct. 14, 2014 (pp. 1-15).

* cited by examiner

Figure 2

| Species (common name) | Isotype | Amino-acid position* |||||||||||||||||||||
|---|---|---|---|---|---|---|---|---|---|---|---|---|---|---|---|---|---|---|---|---|---|
| | | Core-hinge ||||| CH3-CH3 interface ||||||||||||||||
| | | 226 | 227 | 228 | 229 | 230 | 347 | 349 | 350 | 351 | 366 | 368 | 370 | 392 | 394 | 395 | 397 | 398 | 399 | 405 | 407 | 409 |
| Homo sapiens | IgG1 | C | P | P | C | P | Q | Y | T | L | T | L | K | K | T | P | V | L | D | F | Y | K |
| | IgG2 | - | - | - | - | - | - | - | - | - | - | - | - | - | - | - | M | - | - | - | - | - |
| | IgG3 | - | - | R | - | - | - | - | - | - | - | - | N | - | - | M | - | - | - | - | - | - |
| | IgG4 | - | - | S | - | - | - | - | - | - | - | - | - | - | - | - | - | - | - | - | - | R |
| Macaca mulatta (Rhesus Monkey) | IgG1 | - | - | - | - | - | - | - | - | - | - | - | - | - | - | - | - | - | - | - | - | - |
| | IgG2 | - | - | - | - | - | - | - | - | - | - | - | - | - | - | - | - | - | - | - | - | - |
| | IgG3 | - | - | - | - | - | - | - | I | - | - | - | T | - | - | - | - | - | - | - | - | - |
| | IgG4 (In)** | - | - | - | - | - | - | - | I | - | - | - | T | - | - | - | - | - | - | - | L | - |
| | IgG4 (Ch)*** | - | - | A | - | - | - | - | I | - | - | - | T | - | - | - | - | - | - | - | L | - |

*EU numbering; In, Indian; *Ch, Chinese

A
IgG1-2F8-ITL X IgG4-7D8-CPPC

B

Figure 7
A
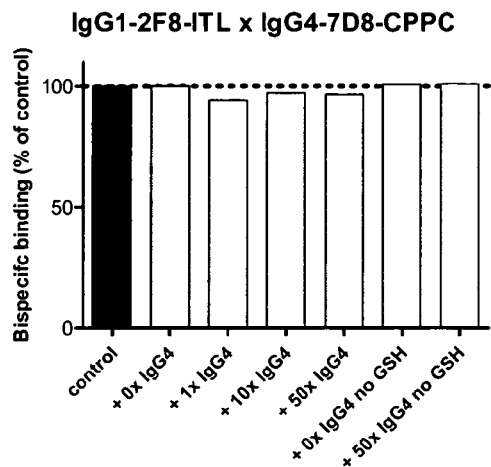
B
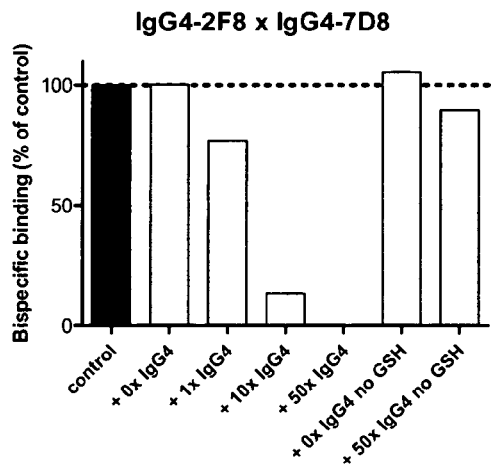

Figure 8
A
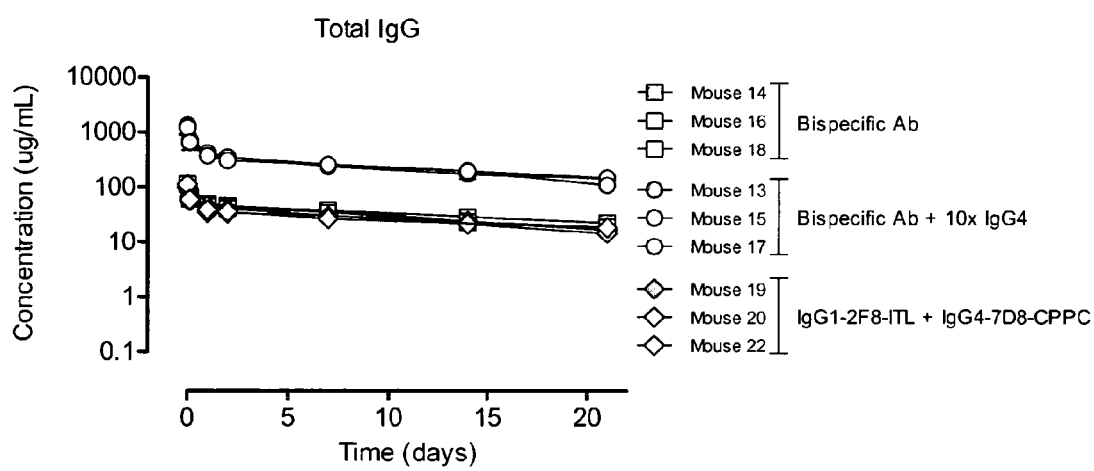
B
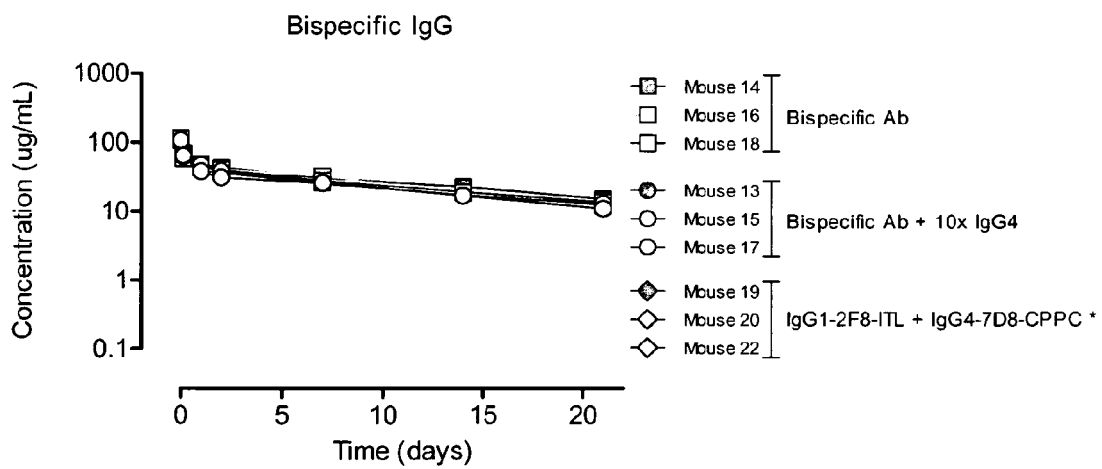

M: Marker
C: IgG1 Control
S: Bispecific Sample

Peak results:

|   | RT (min) | Area | Height | % Height |
|---|----------|------|--------|----------|
| 1 | 5.362 | 18309 | 448 | 0.21 |
| 2 | 7.584 | 82197 | 2876 | 1.36 |
| 3 | 8.869 | 4431069 | 207416 | 98.42 |

Figure 9C
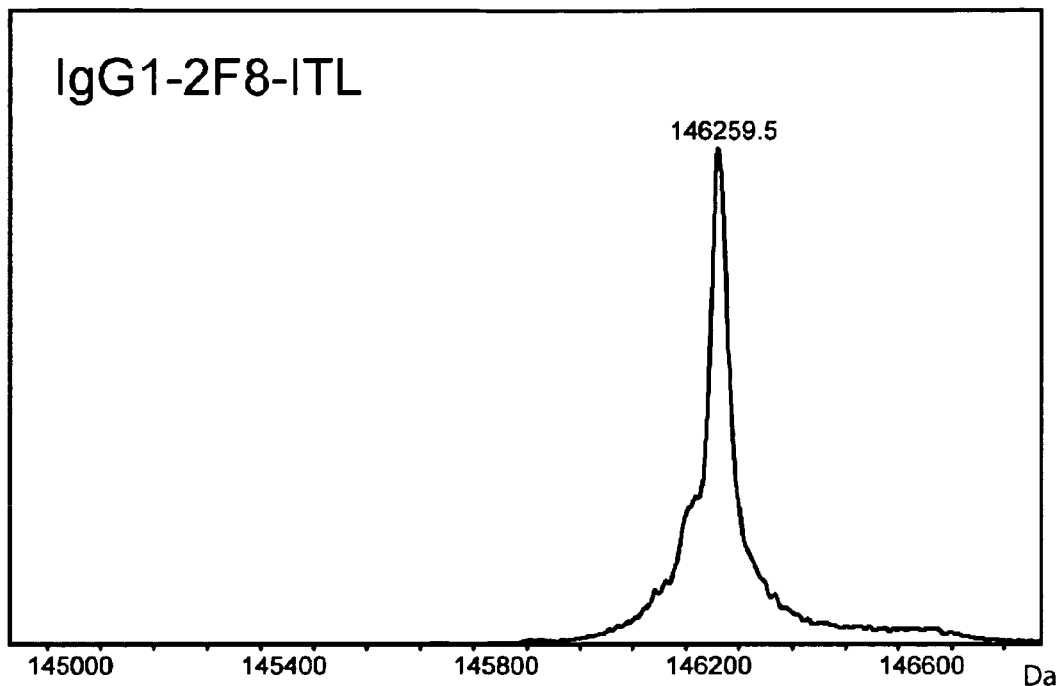
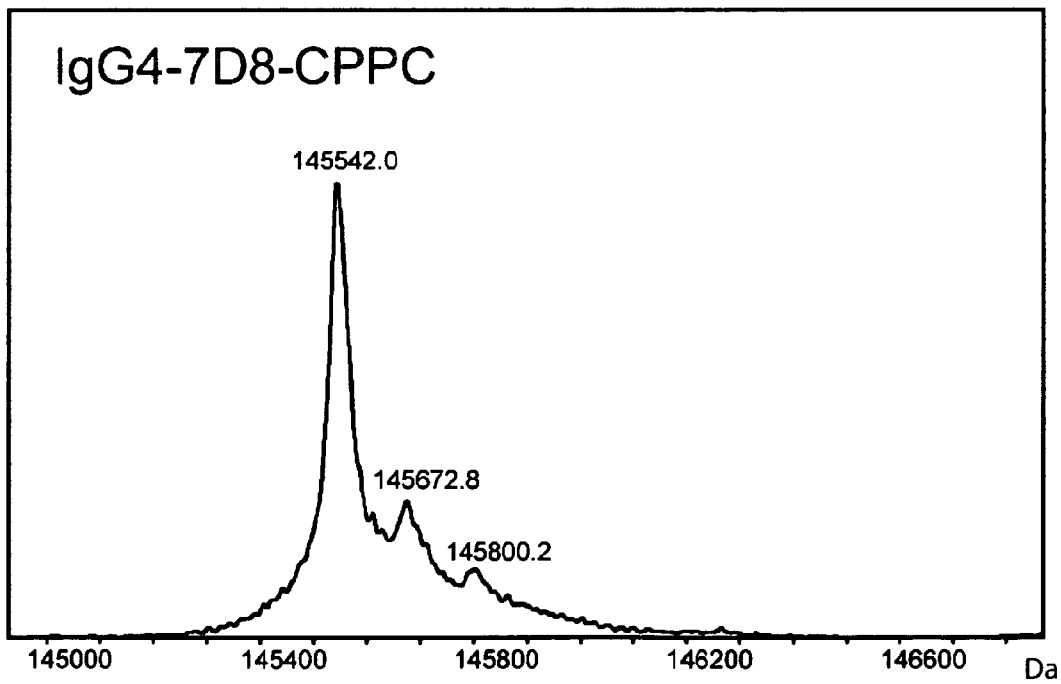

|  | Measured | Measured | Measured |
|---|---|---|---|
| IgG1-2F8-ITL | 146259.5 | | |
| IgG4-7D8-CPPC | 145542.0 | 145672.8 | 145800.2 |
| IgG1-2F8-ITL x IgG4-7D8- | 145901.2 | 146027.7 | |

Figure 10
(A)
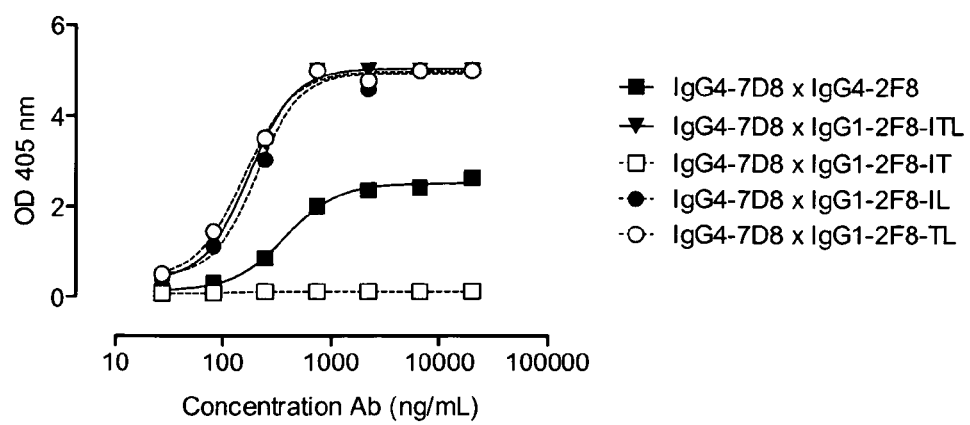
(B)
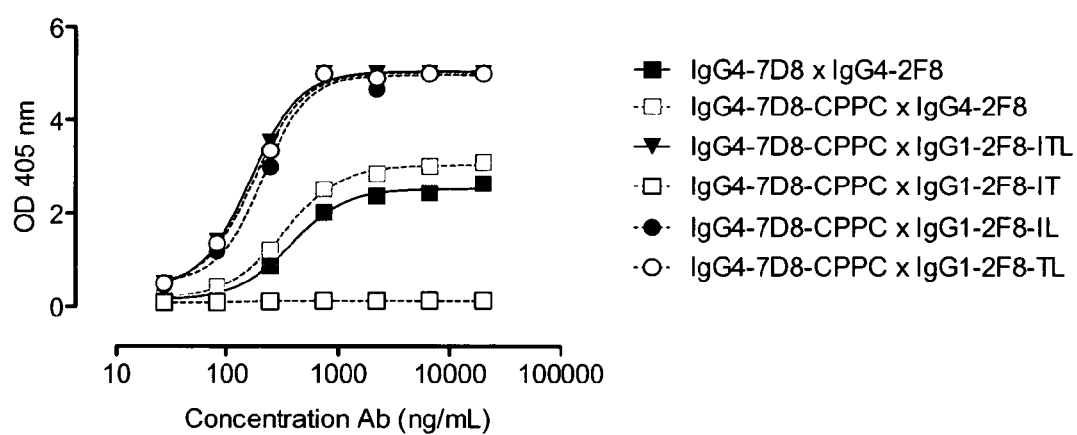
(C)
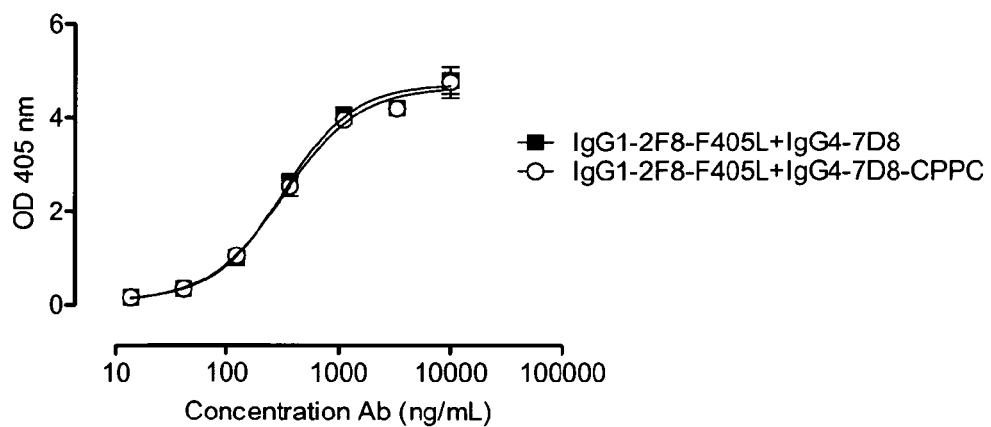

Figure 13
A
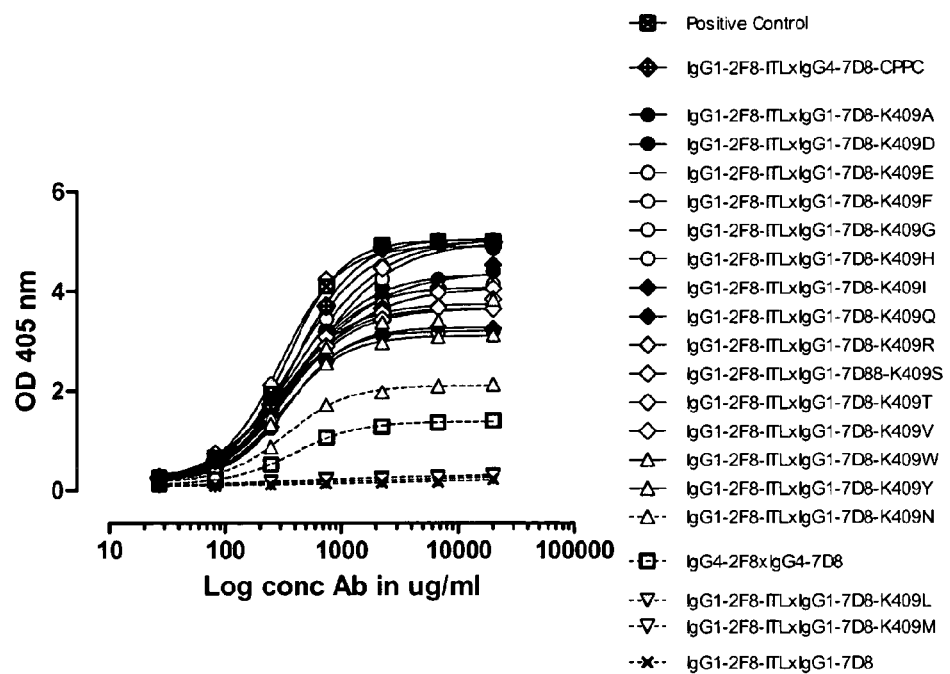
B
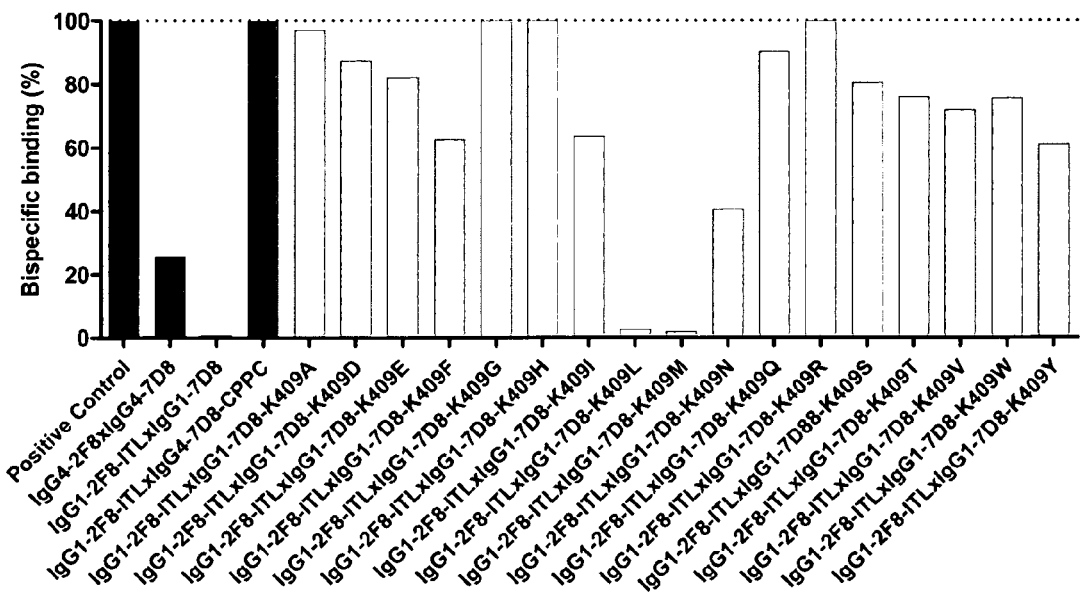

Figure 15
A
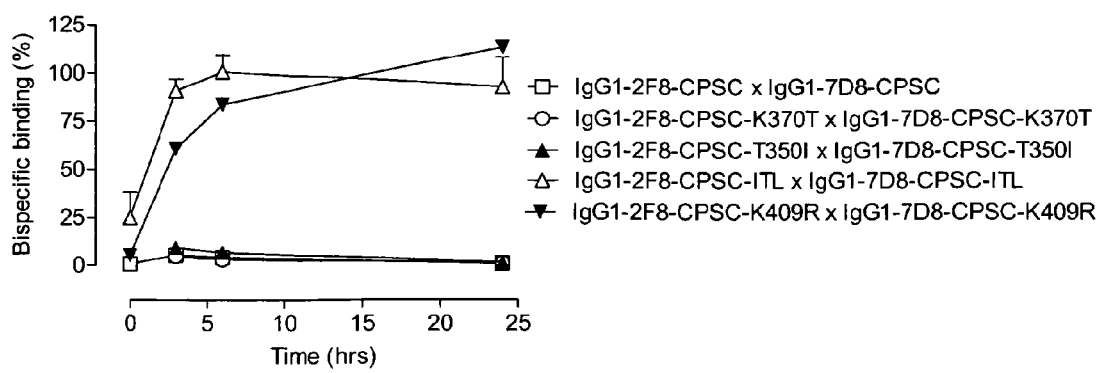
B
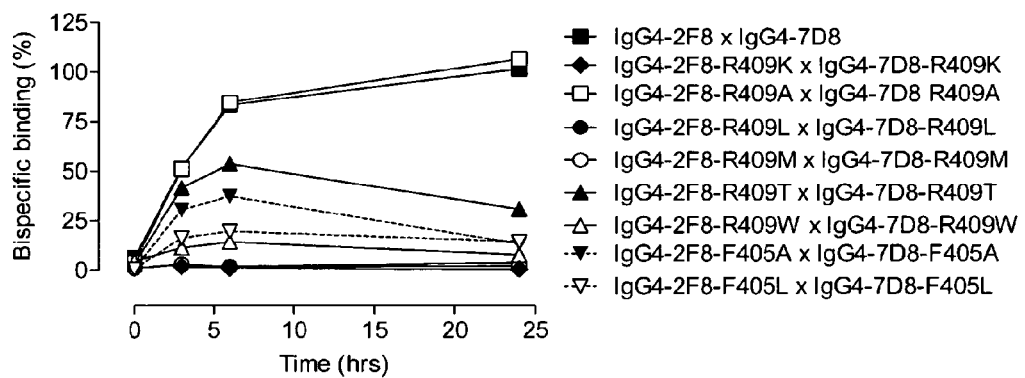
C
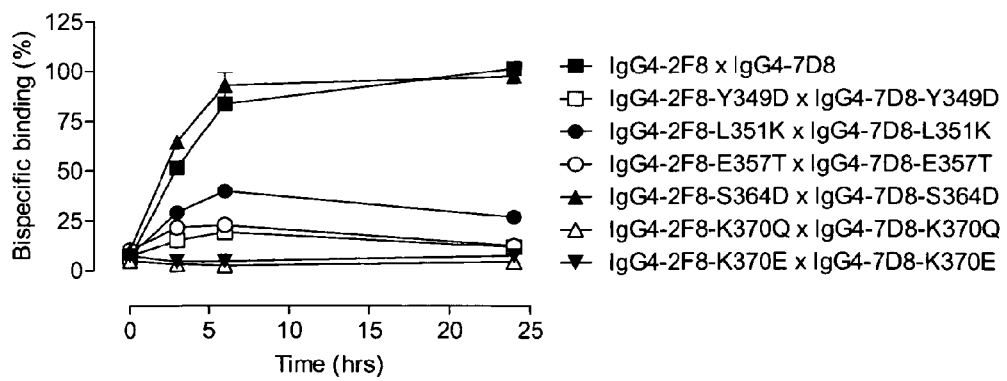

Figure 15 (continued)
D
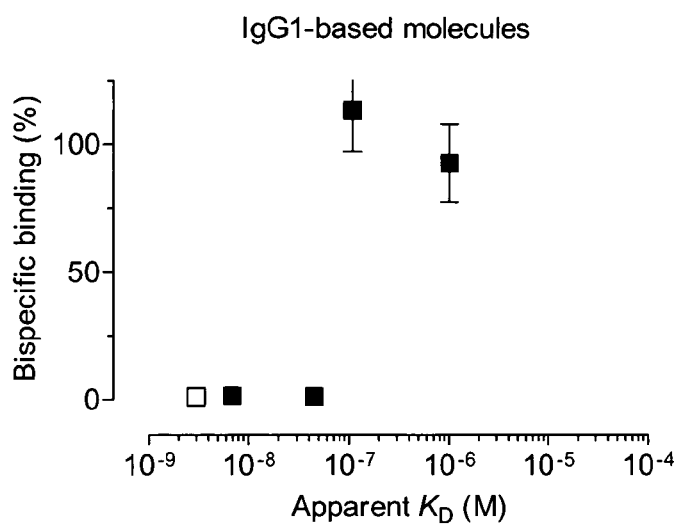
E
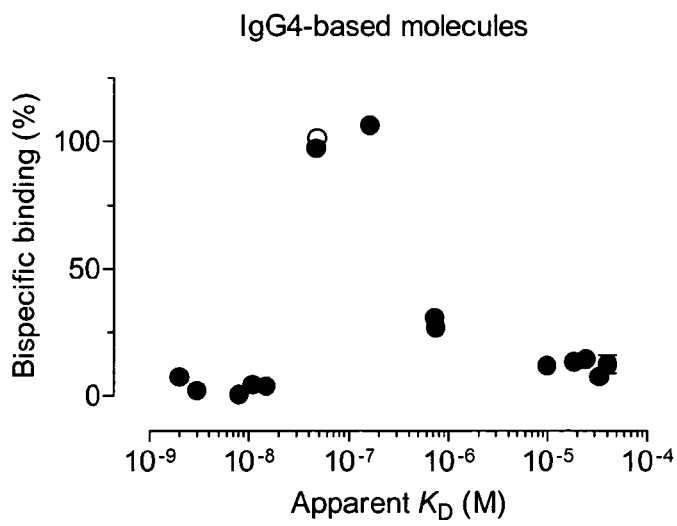

Figure 16

```
EU               1         2         3         4         5         6         7         8         9         1
                 1234567890123456789012345678901234567890123456789012345678901234567890123456789012345678901234567890         0
2F8-G1   QVQLVESGGGVVQPGRSLRLSCAASGFTFSTYGMH--WVRQAPGKGLENVAVIWD--DGSYKYYGDSVKGRFTISRDNSKNTLYLQMNSLRAEDTAVYYCARDGITMVRGVMKDYFDY
2F8-G4   QVQLVESGGGVVQPGRSLRLSCAASGFTFSTYGMH--WVRQAPGKGLENVAVIWD--DGSYKYYGDSVKGRFTISRDNSKNTLYLQMNSLRAEDTAVYYCARDGITMVRGVMKDYFDY 12
KABAT            1234567890123456789012345  6789012345 4567890123456789012222222345678901234567890000000012
                                                                                           ABC                    ABCDEFGH

EU                      1         1         1         1         1         1         1         1       2
                345678901234567 8901234567890123456 78 90123456 7890123456789012345  6 7890
2F8-G1   WGQGTLVTVSS----ASTKGPSVFPLAPSSKS--TSGGTAALGCLVKDYFPEPVTV-SW----NSGALTSG-VHTFPAVLQS-SGLYSLSSVVTVPSSSLGT--Q-TYIC
2F8-G4   WGQGTLVTVSS----ASTKGPSVFPLAPCSRS--TSESTAALGCLVKDYFPEPVTV-SW----NSGALTSG-VHTFPAVLQS-SGLYSLSSVVTVPSSSLGT--K-TYTC
KABAT         1         1         1         1         1         1         1       2        2
              0       3                                       4                    5     6           7     8       9  0
              345678901233333345678901234567890123456789012345678901234567890123456789012345678
                         ABCDE

EU              2         2                                         2       2       2
                1         2                                         7       8       9  0       2         2         2
               12345678901 234 567890 1 2345678                                                  12  345678  901234567890
2F8-G1   NVNHKFSNTKV-DKR------VEPKSC-D--KTHTCPP------------------------CP-------AP-----ELLGGP--SVFLFPPKPKDT
2F8-G3   NVNHKFSNTKV-DKR------VELKTP-LGDTTHTCPRCPEPKSCDTPPPCPRCPEPKSCDTPPPCPRCP-----AP-----ELLGGP--SVFLFPPKPKDT
2F8-G4   NVDHKFSNTKV-DKR------VESKYG-------PPCPS------------------------CP-------AP-----EFLGGP--SVFLFPPKPKDT
KABAT    22                  2                  2                   2      2        2       2    2
         01                  3                  4                   5      6        6       5    6
         9012345678990123334567890111111111111111111111111111111111112233333333333345555556789011123456789011123
                       A    ABC    ABCDEFGHIJKLMNOPQRSTUVWXYZABCDEFGHIJKLMNOPQRS  ABCDEFGHI  ABC     AB
                                                                                   ABCDEFGHIJKLMNOPQRS

EU              2       2       2                                 3
                5       6       7                                 0
                12345678901234567890123456789  01 234567890123456 789
2F8-G1   LMISRTPEVTCVVVDVSHEDPEVKFNWYV--DG--VEVHNAKTKPREEQYN--STY
2F8-G4   LMISRTPEVTCVVVDVSQEDPEVQFNWYV--DG--VEVHNAKTKPREEQFN--STY
KABAT        2       2       2       3              3
             6       7       8       0              3
             456789012345678901234567890123456789

EU              3         3         3         3         3         3         4
                1         2         3         4         5         6         0
                12345678901234567 89012345 6 789012 3456 78901 2345 67890123456789 012 34 56 7890123456789 0
2F8-G1   RVVSVLTVLHQDWLNGKEYKCKVSNKALPAP1-EKTI-SKAKG-QPREPQVYTLPPSRDE--LTKNQVSLTCLVKGFYPSDIAV--EWESN-GQ--PENNYKTTPPVLDS
2F8-G4   RVVSVLTVLHQDWLNGKEYKCKVSNKGLPSSI-EKTI-SKAKG-QPREPQVYTLPPSQEE--MTKNQVSLTCLVKGFYPSDIAV--EWESN-GQ--PENNYKTTPPVLDS
KABAT     3         3       3      3            3       3             3              4          4
          1         3       4      5            6       7             8              0          2
          012345678901234567890123 3456      78901 2345 67890112345678      9012345678 90123456 7890123456 78

EU              4         4
                1         4
                2345678901234567890123456789012345 67
2F8-G1   -D--GSFFLYSKLTVDKSRWQQGNVFSCSVMHEALHNHYTQKSLSLSPGK
2F8-G4   -D--GSFFLYSKLTVDKSRWQEGNVFSCSVMHEALHNHYTQKSLSLSLGK
KABAT   4         4         4
        3         4         4
        90123456789012345678901234567890123456 78
```

Figure 18
A
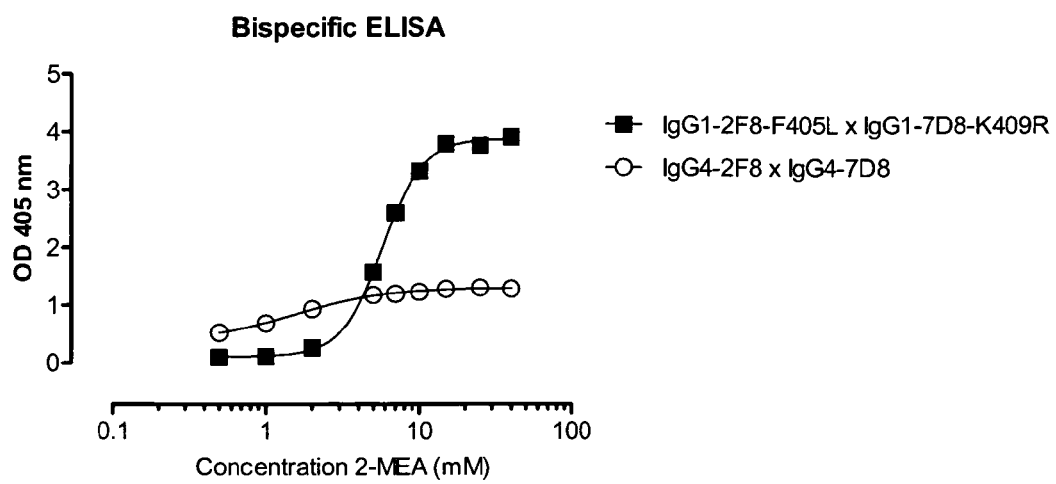
B
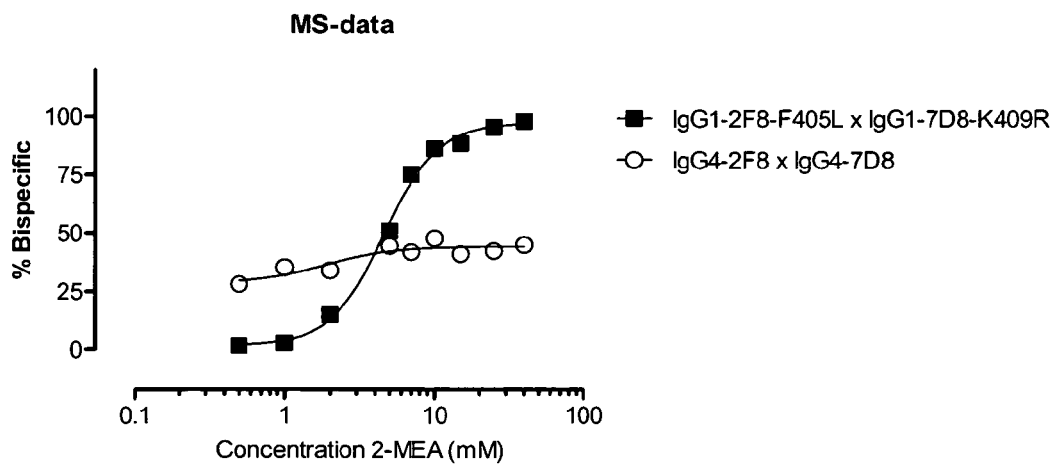

Figure 19
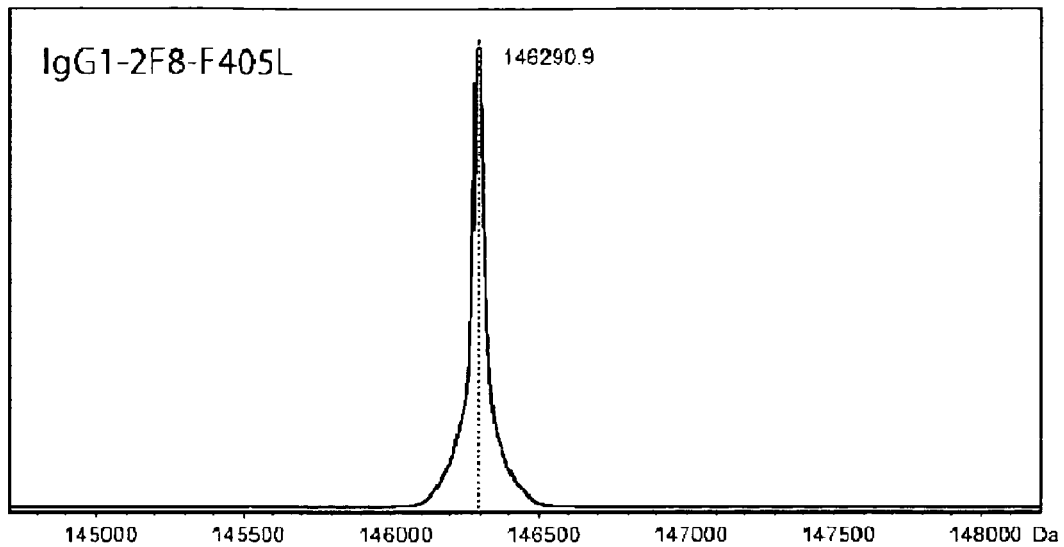
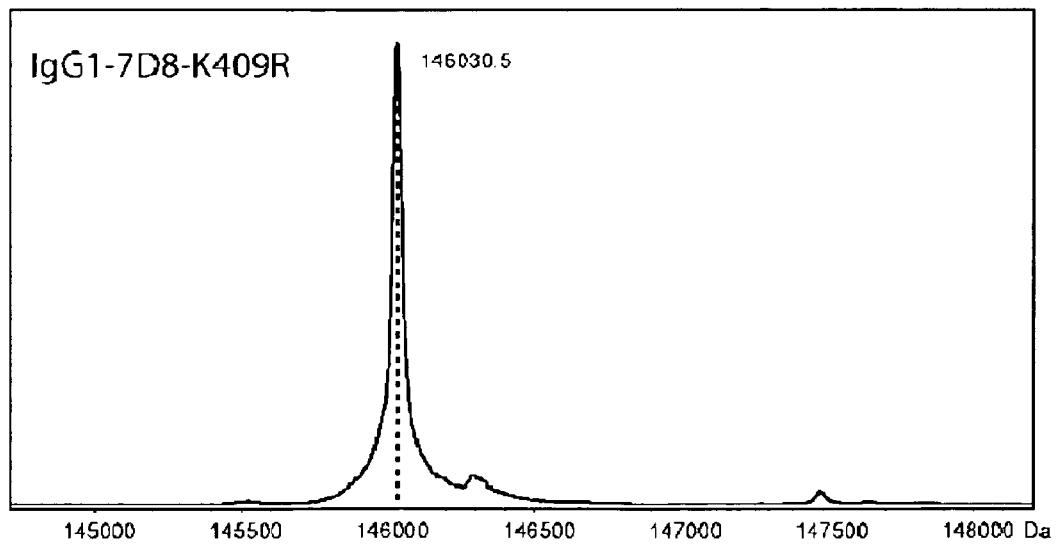

| | Measured MW |
|---|---|
| IgG1-2F8-F405L | 146,290.9 |
| IgG1-7D8-K409R | 146,030.5 |
| IgG1-2F8-F405L x IgG1-7D8-K409R | 146,160.7 |

Figure 20
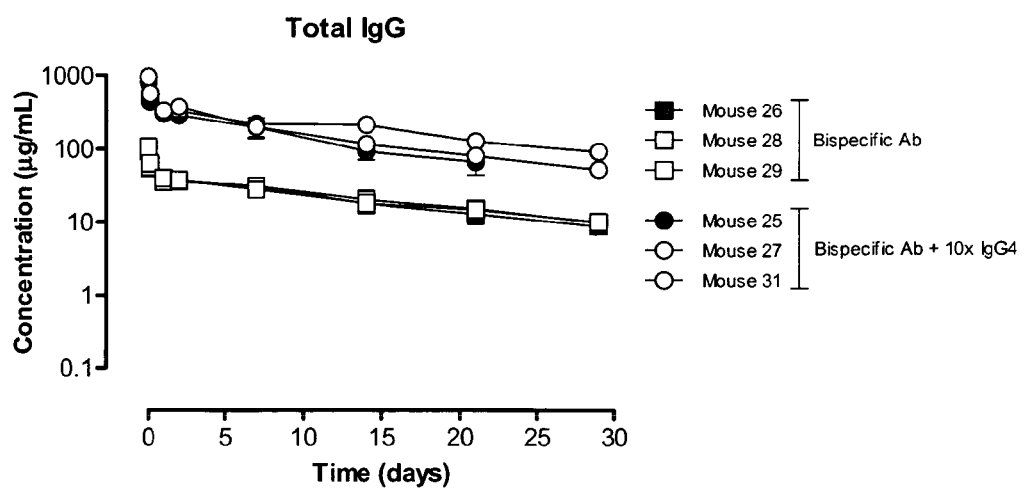
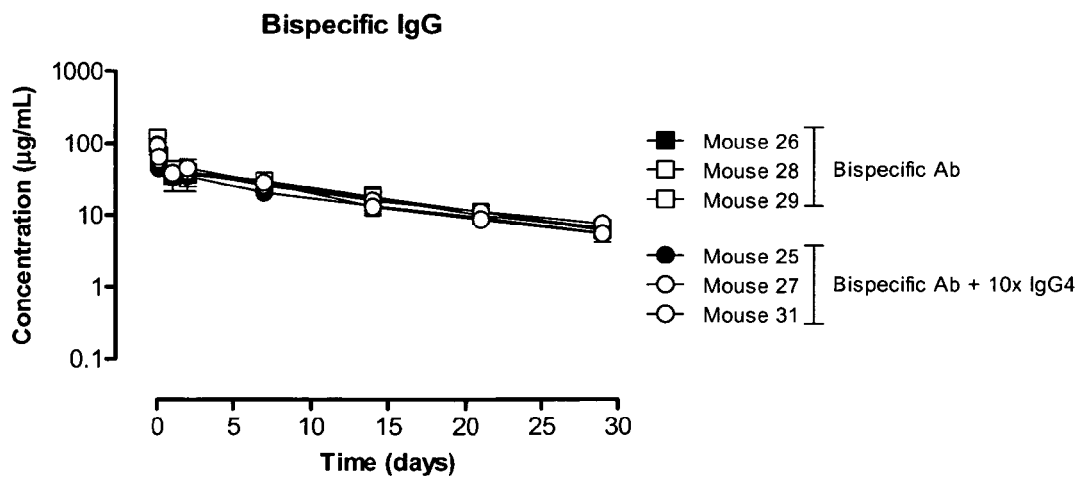

Figure 21
A
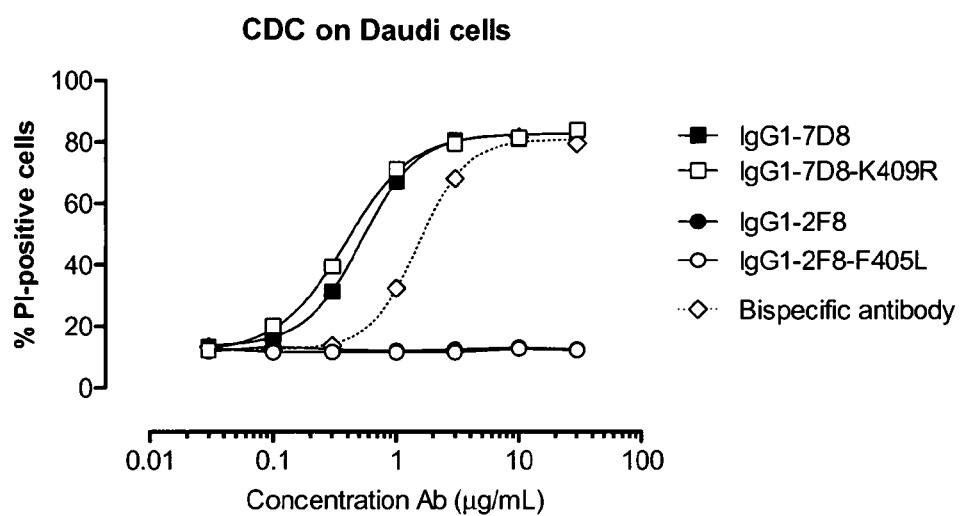
B
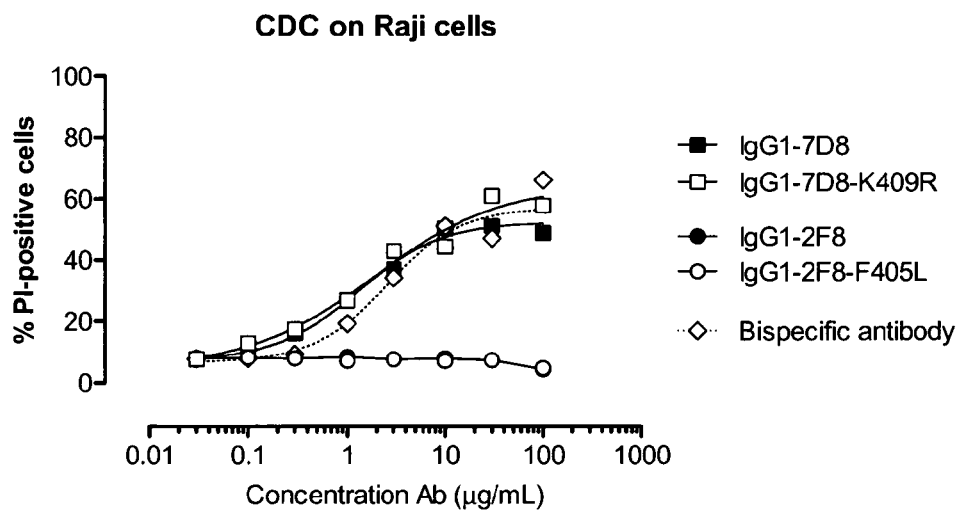

Figure 23
A
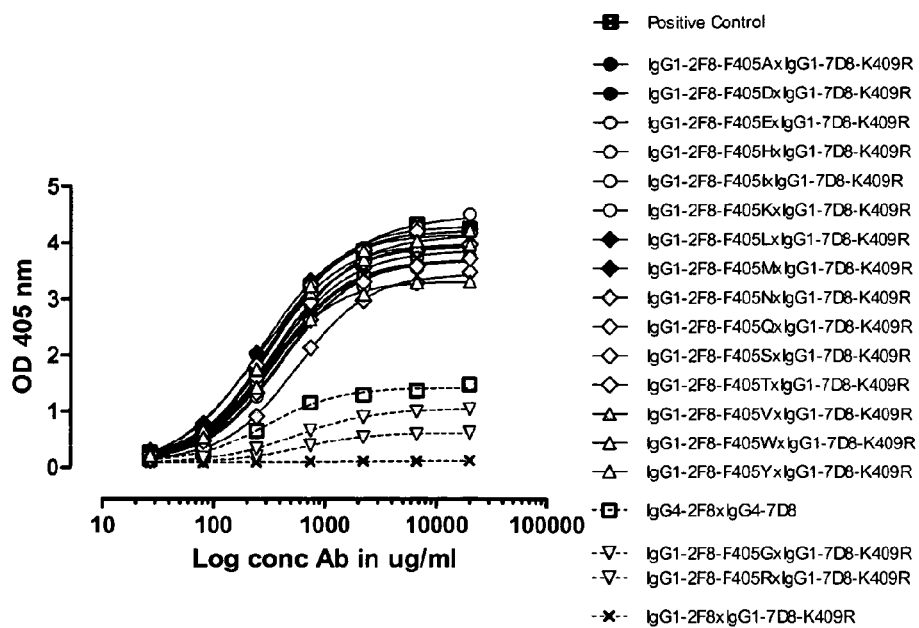
B
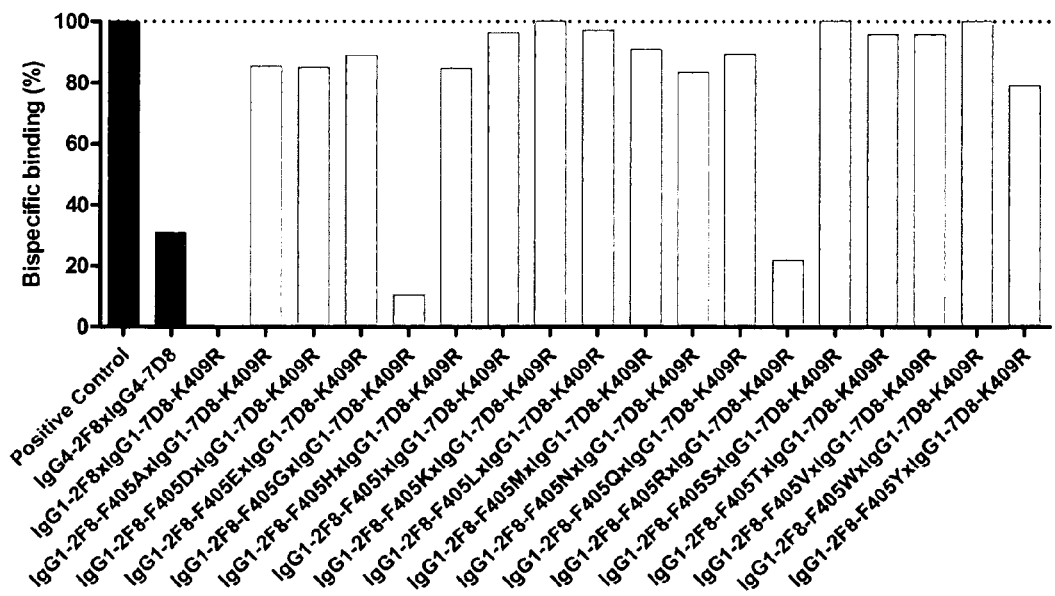

Figure 24
A
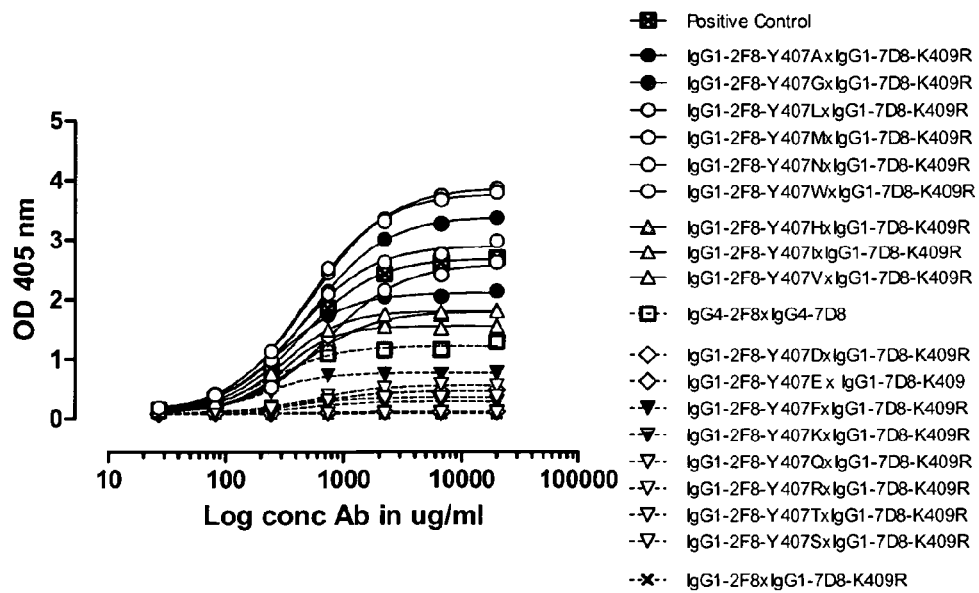
B
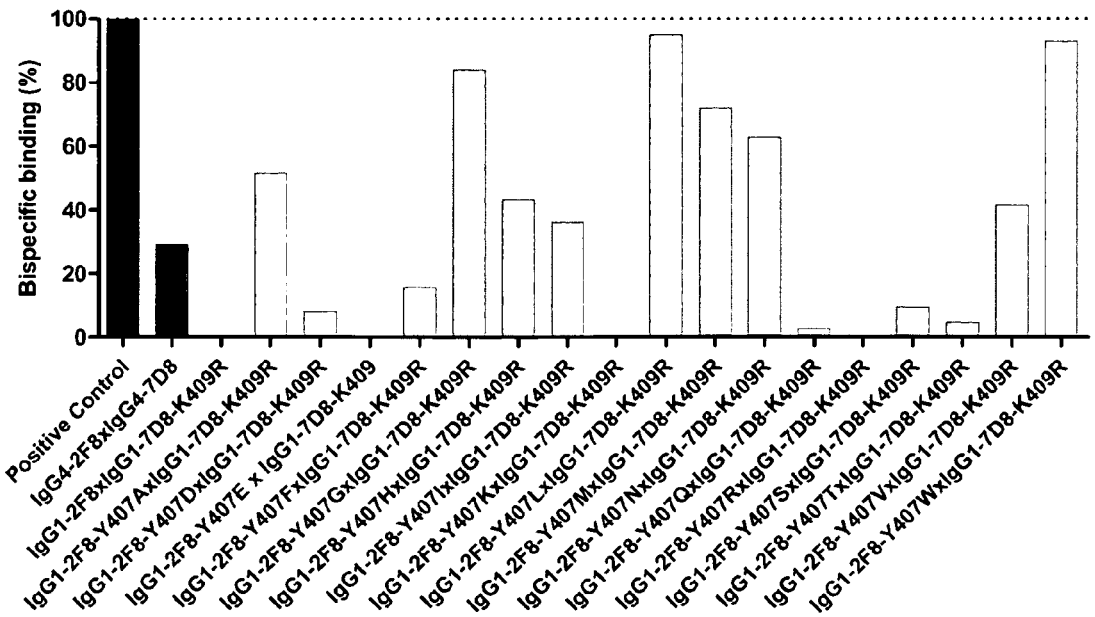

Figure 28
A
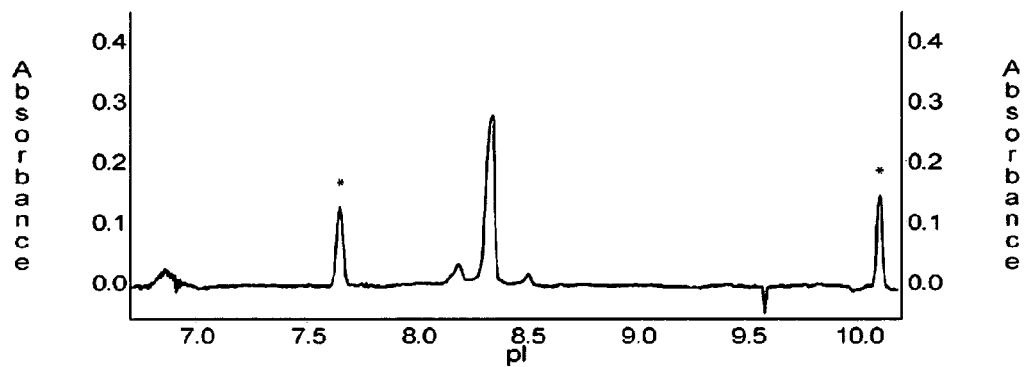
B
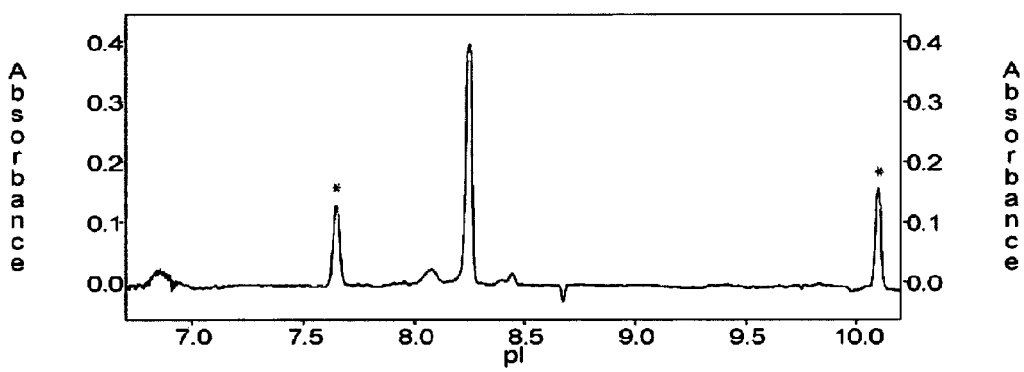
C
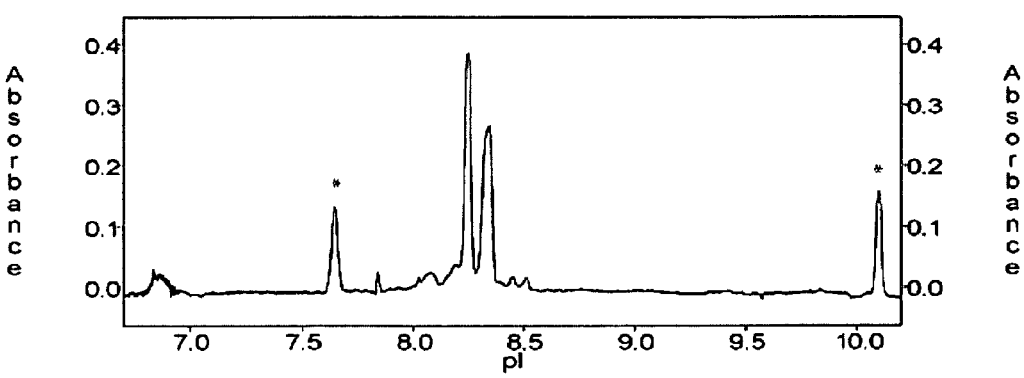

D

Figure 33
A
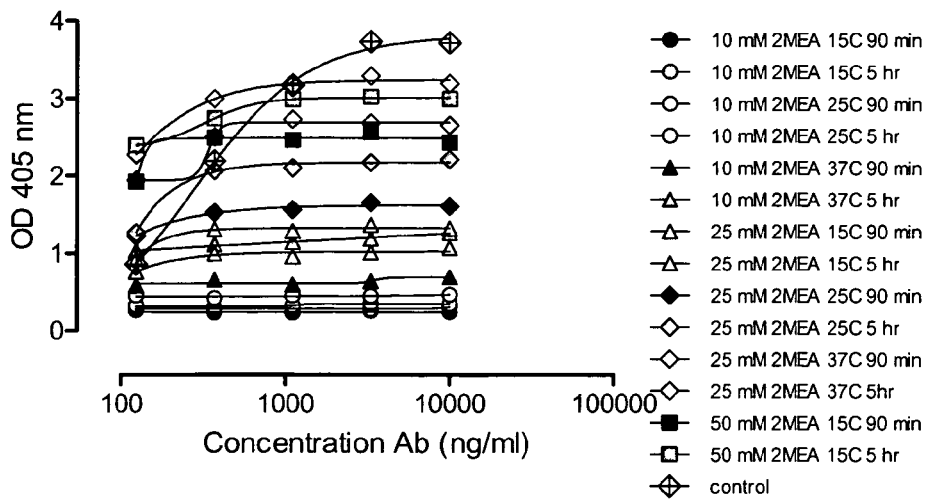
B
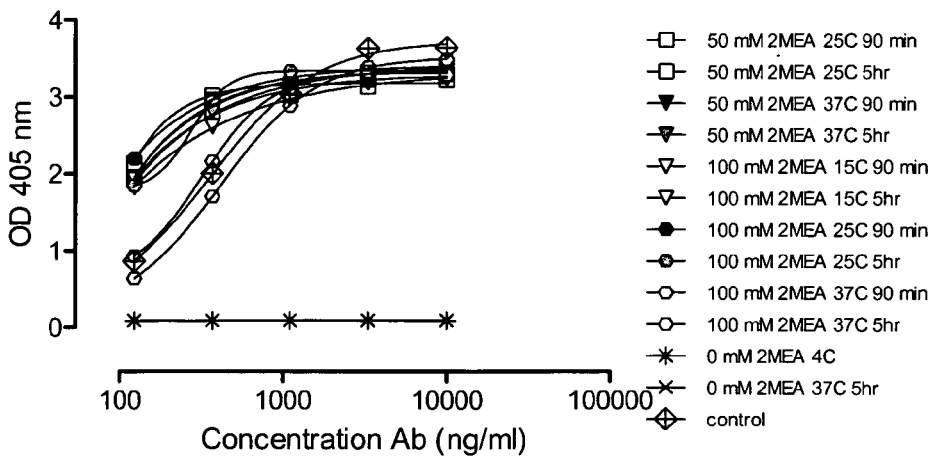

Figure 33 (continued)
C
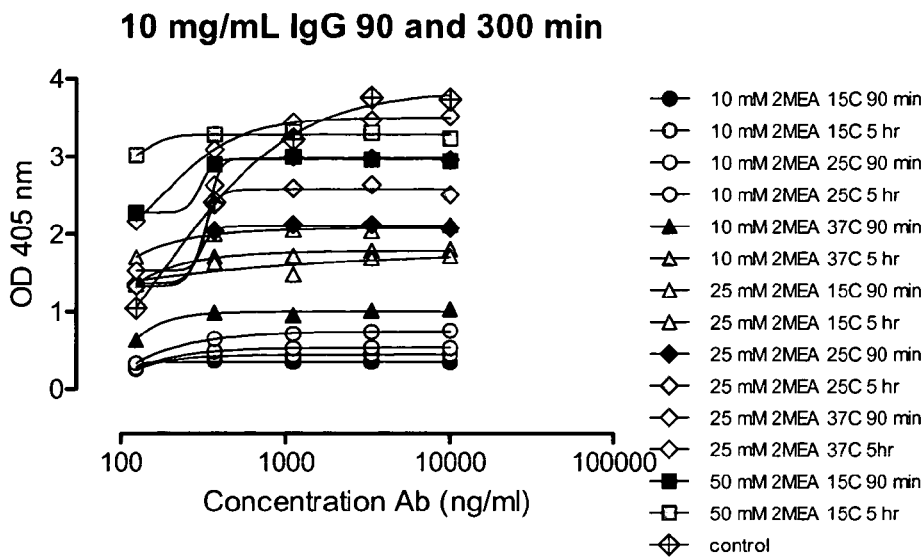
D
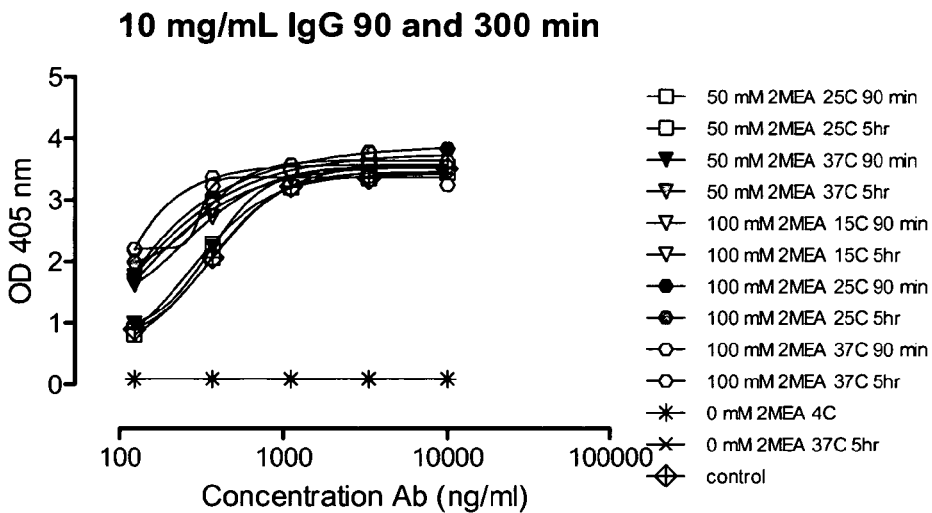

Figure 33 (continued)
E
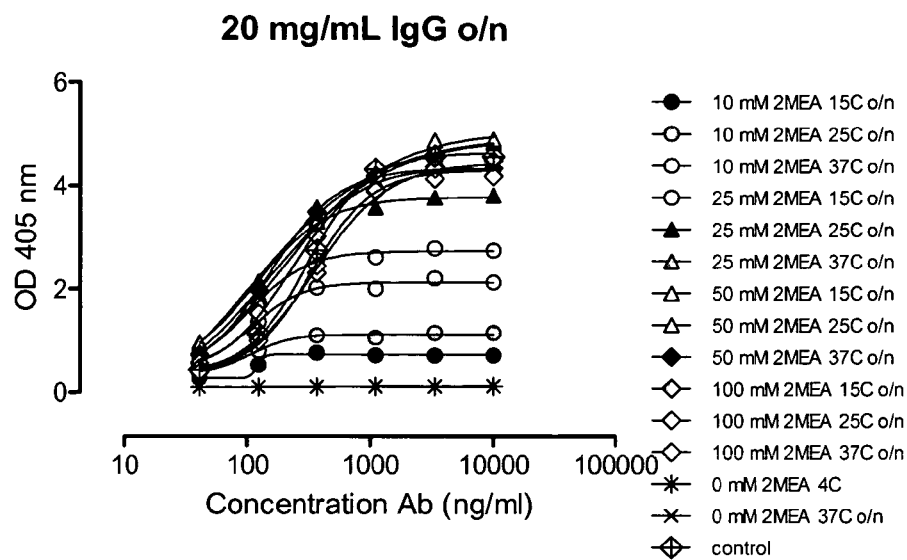
F
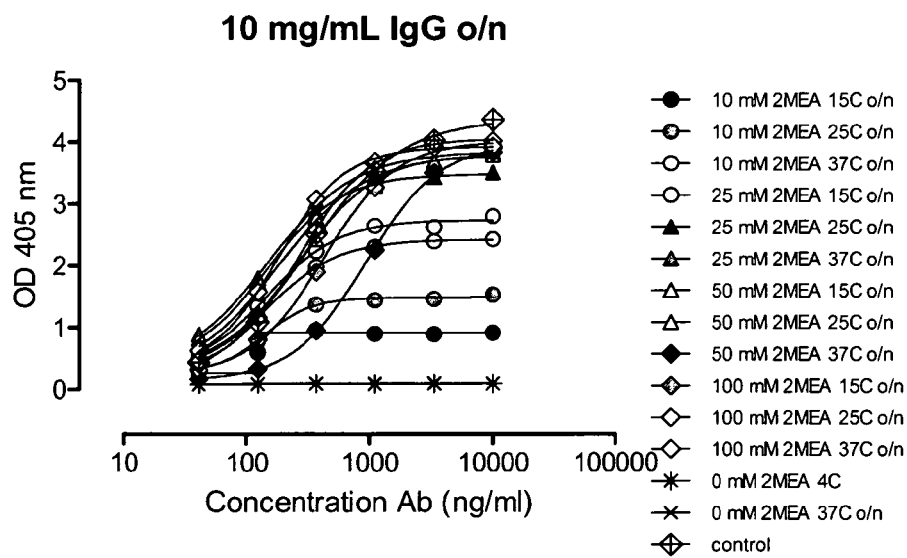

Figure 34
A
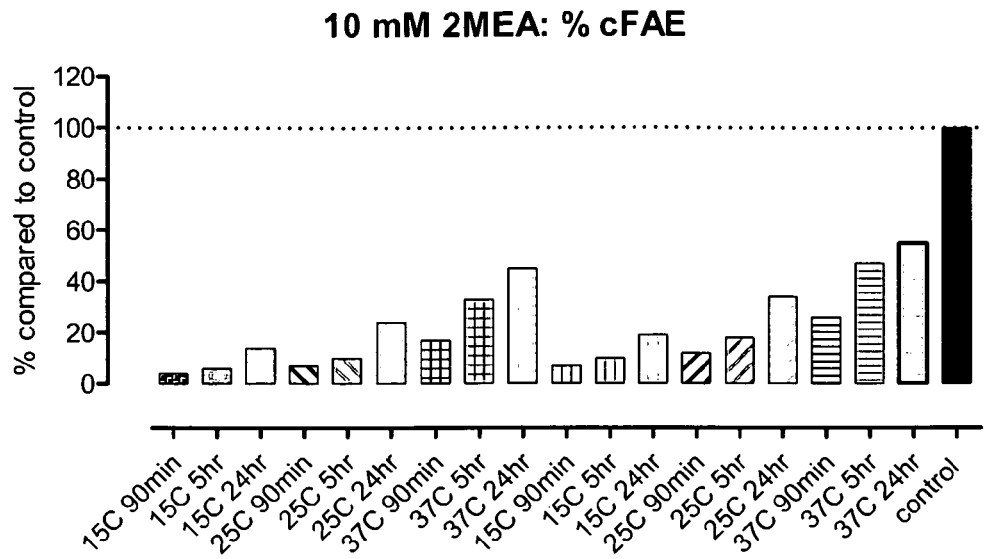
B
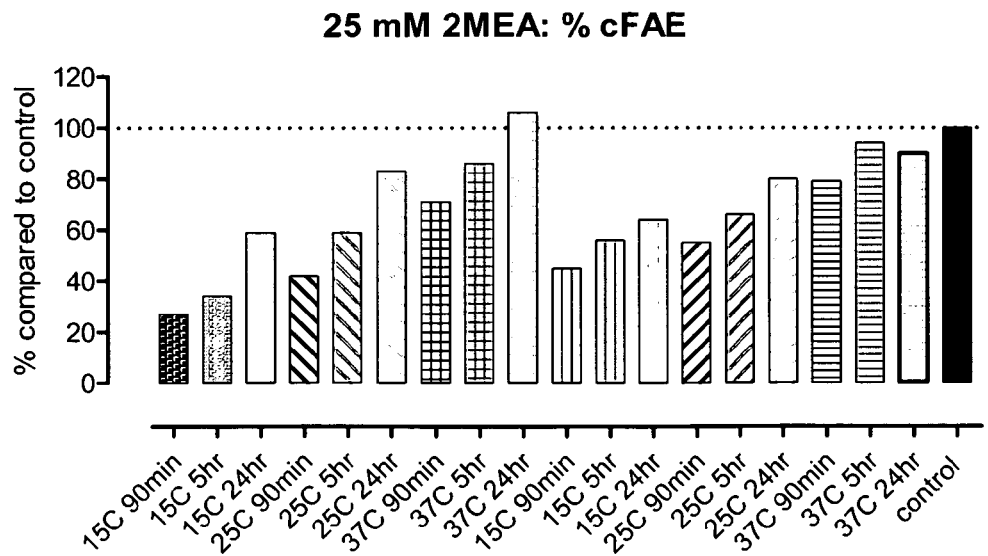

Figure 34 (continued)
C
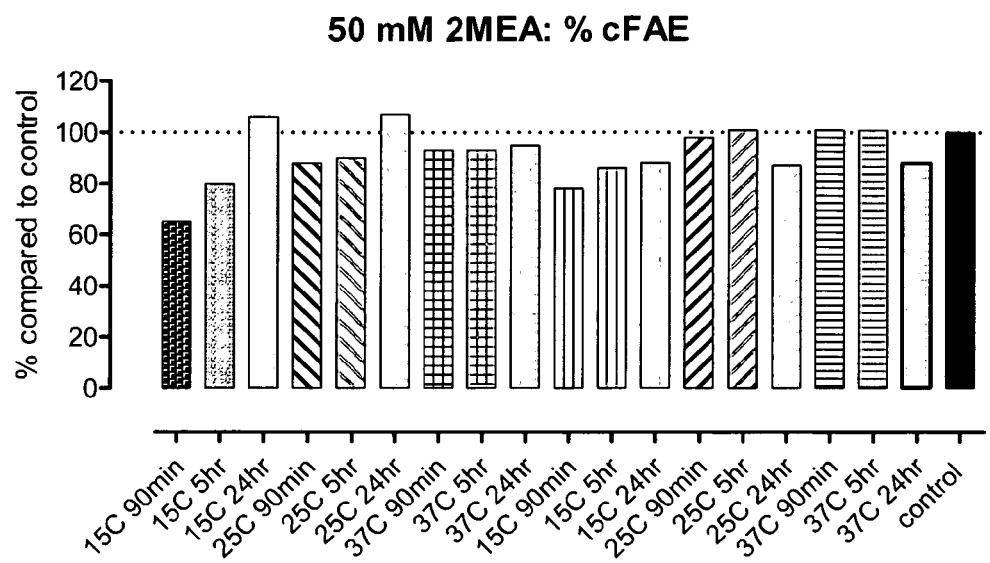
D
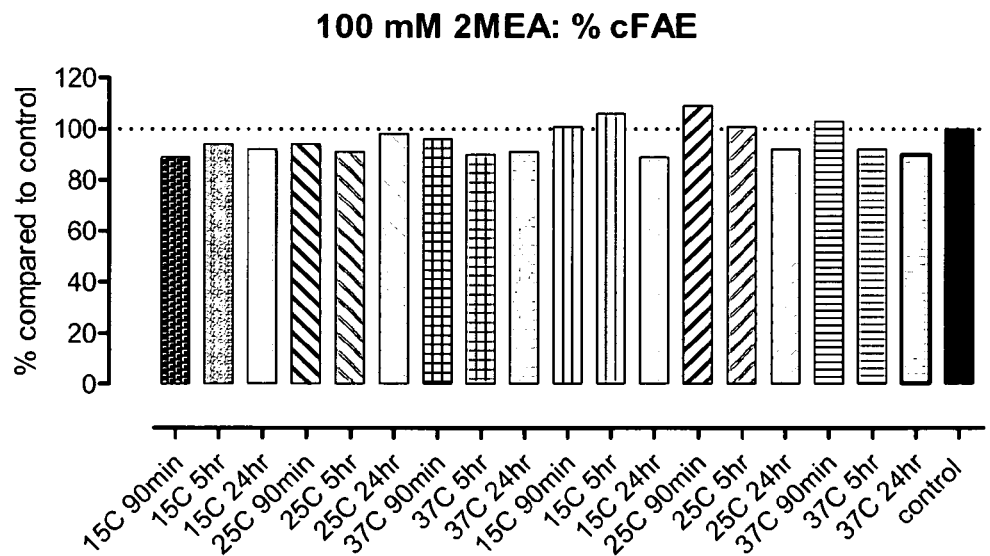

A

Figure 36
A
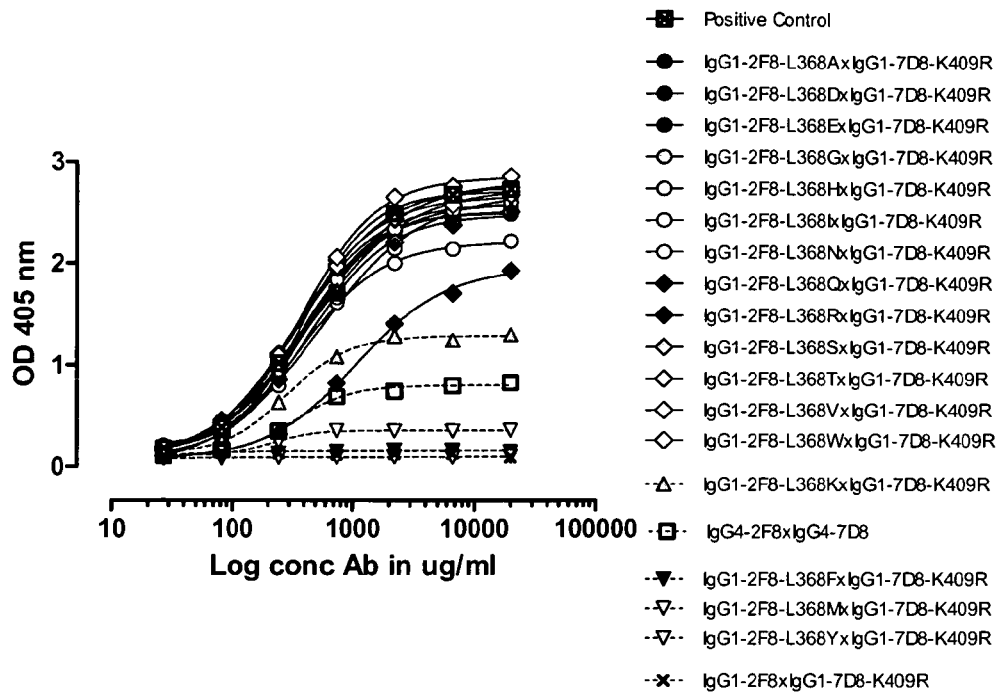
B
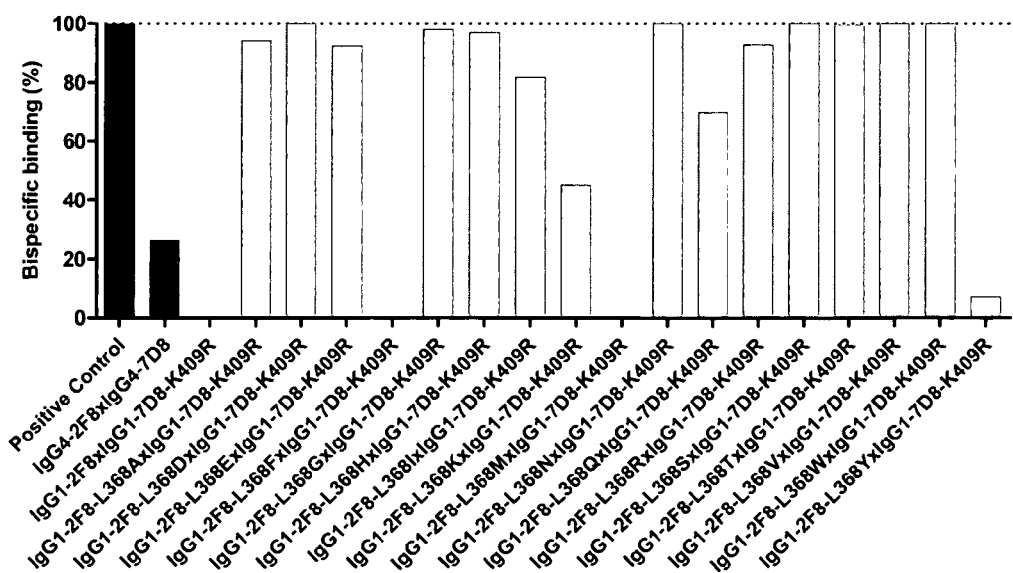

Figure 37
A
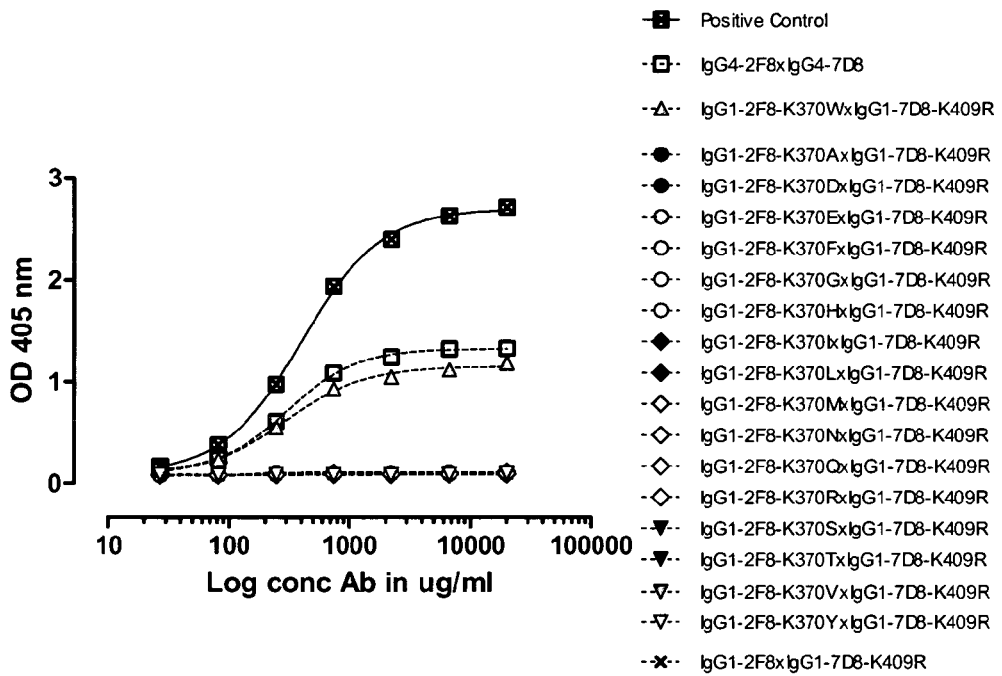
B
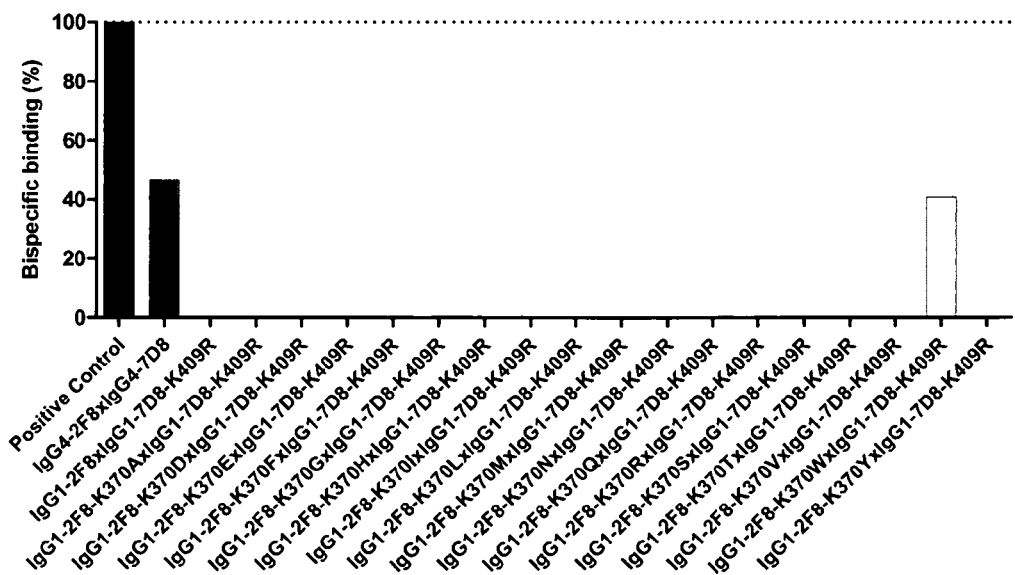

Figure 38
A
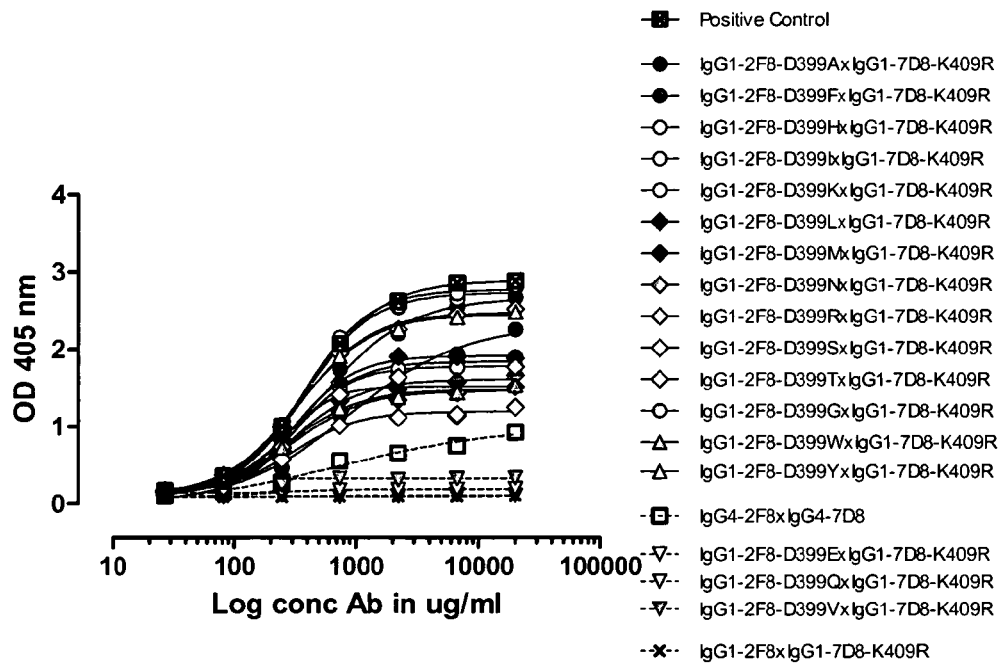
B
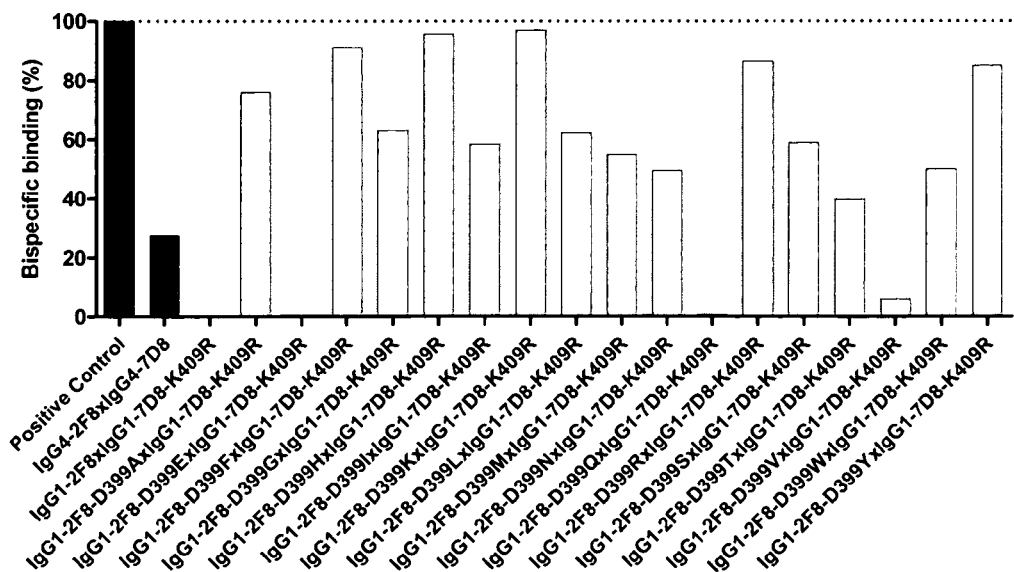

Figure 43
A
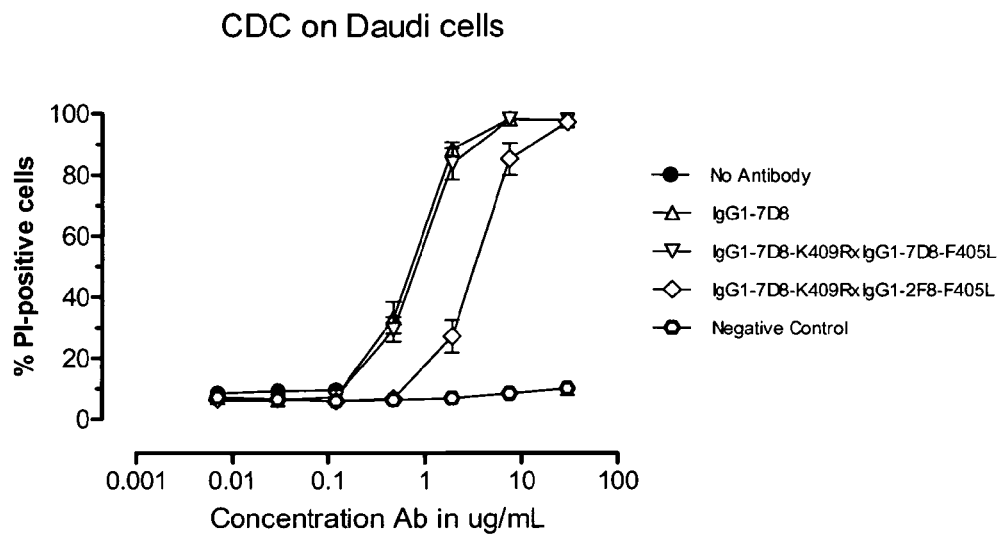
B
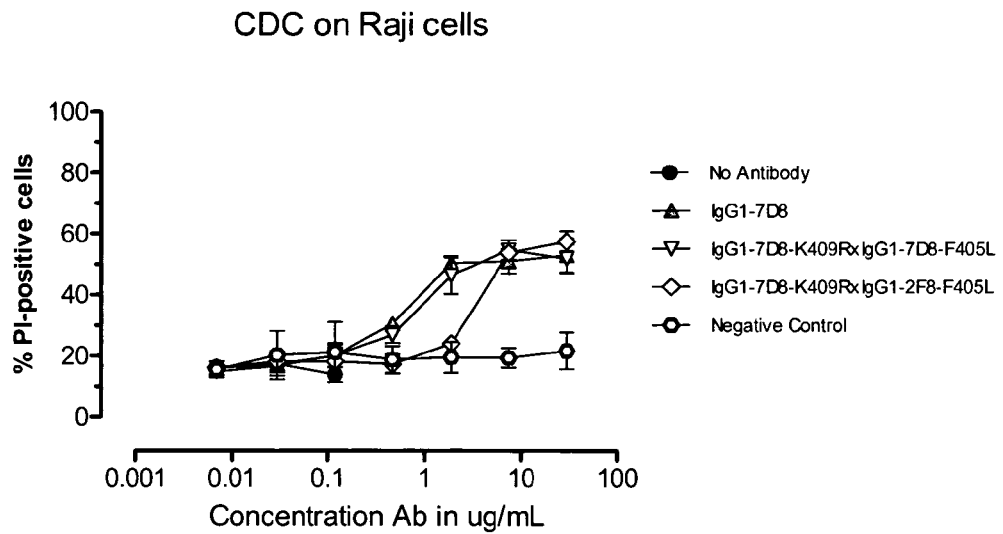

Figure 46
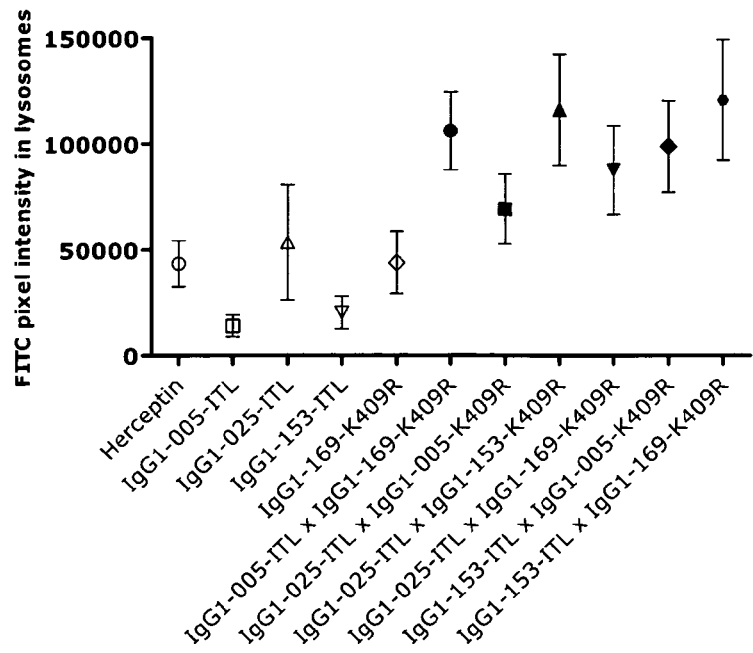
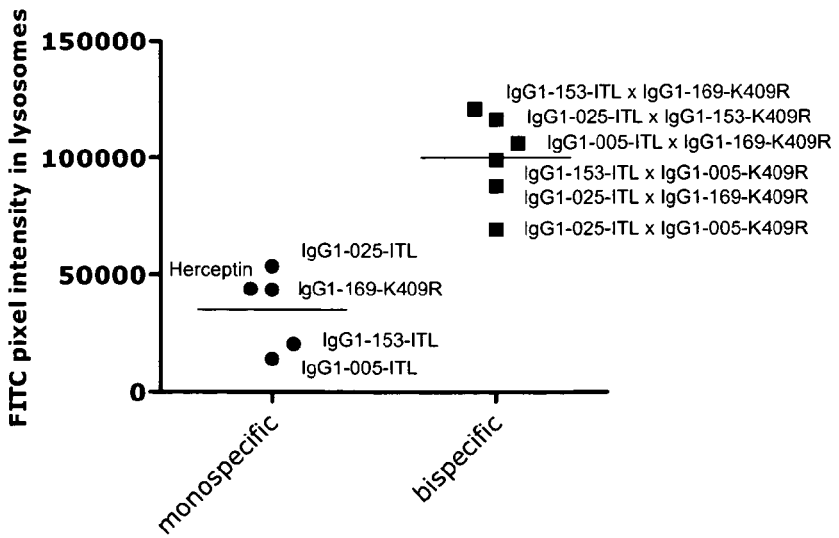

A

HETERODIMERIC ANTIBODY FC-CONTAINING PROTEINS AND METHODS FOR PRODUCTION THEREOF

RELATED APPLICATIONS

This application is a 35 U.S.C. 371 national stage filing of International Application No. PCT/EP2011/056388 filed 20 Apr. 2011, which claims priority to Denmark Patent Application No. PA 2010-00330 filed 20 Apr. 2010, U.S. Provisional Patent Application No. 61/326,082 filed 20 Apr. 2010, and Denmark Patent Application No. PA 2010-01066 filed 24 Nov. 2010. The contents of the aforementioned applications are hereby incorporated by reference.

FIELD OF THE INVENTION

The present invention relates to novel heterodimeric antibody-Fc-containing proteins, such as bispecific antibodies, and novel methods for producing such proteins.

BACKGROUND OF THE INVENTION

Monoclonal antibodies have in recent years become successful therapeutic molecules, in particular for the treatment of cancer. Unfortunately, however, monoclonal antibodies are often unable to cure diseases when used as monotherapy. Bispecific antibodies can potentially overcome some of the limitations of monoclonal antibody therapy, e.g. they could be used as mediators to target a drug or toxic compound to target cells, as mediators to retarget effector mechanisms to disease-associated sites or as mediators to increase specificity for tumor cells, for example by binding to a combination of targets molecules that is exclusively found on tumor cells.

Different formats and uses of bispecific antibodies have recently been reviewed by Chames and Baty (2009) Curr Opin Drug Disc Dev 12: 276. One of the major obstacles in the development of bispecific antibodies has been the difficulty of producing the material in sufficient quality and quantity by traditional technologies, such as the hybrid hybridoma and chemical conjugation methods (Marvin and Zhu (2005) Acta Pharmacol Sin 26:649). Co-expression in a host cell of two antibodies, consisting of different heavy and light chains, leads to a mixture of possible antibody products in addition to the desired bispecific antibody.

Several strategies have been described to favor the formation of a heterodimeric, i.e. bispecific, product upon co-expression of different antibody constructs.

Lindhofer et al. (1995 J Immunol 155:219) have described that fusion of rat and mouse hydridomas producing different antibodies leads to enrichment of functional bispecific antibodies, because of preferential species-restricted heavy/light chain pairing. Another strategy to promote formation of heterodimers over homodimers is a "knob-into-hole" strategy in which a protuberance is introduced at the interface of a first heavy-chain polypeptide and a corresponding cavity in the interface of a second heavy-chain polypeptide, such that the protuberance can be positioned in the cavity so as to promote heterodimer formation and hinder homodimer formation. "Protuberances" are constructed by replacing small amino-acid side-chains from the interface of the first polypeptide with larger side chains. Compensatory "cavities" of identical or similar size to the protuberances are created in the interface of the second polypeptide by replacing large amino-acid side-chains with smaller ones (U.S. Pat. No. 5,731,168). EP1870459 (Chugai) and WO 2009089004 (Amgen) describe other strategies for favoring heterodimer formation upon co-expression of different antibody domains in a host cell. In these methods, one or more residues that make up the CH3-CH3 interface in both CH3 domains are replaced with a charged amino acid such that homodimer formation is electrostatically unfavorable and heterodimerization is electrostatically favorable. WO2007110205 (Merck) describe yet another strategy, wherein differences between IgA and IgG CH3 domains are exploited to promote heterodimerization.

Dall'acqua et al. (1998 Biochemistry 37:9266) have identified five energetically key amino-acid residues (366, 368, 405, 407 and 409) that are involved in the CH3-CH3 contact in the interface of a CH3 homodimer.

WO 2008119353 (Genmab) describes an in vitro method for producing bispecific antibodies wherein a bispecific antibody is formed by "Fab-arm" or "half-molecule" exchange (swapping of a heavy chain and attached light chain) between two monospecific IgG4- or IgG4-like antibodies upon incubation under reducing conditions. This Fab-arm exchange reaction is the result of a disulfide-bond isomerization reaction and dissociation-association of CH3 domains wherein heavy-chain disulfide bonds in the hinge regions of the parent (originally monospecific) antibodies are reduced and the resulting free cysteines form an inter heavy-chain disulfide bond with cysteine residues of another parent antibody molecule (originally with a different specificity), and simultaneously CH3 domains of the parent antibodies release and reform by dissociation-association. The resulting product is a bispecific antibody having two Fab arms which potentially are compassed different sequences. It should be noted that the process is random however and Fab-arm exchange can also occur between two molecules with identical sequence or two bispecific molecules can engage in Fab-arm exchange to regenerate antibodies comprising the original monospecific parent antibody specificity.

It has now surprisingly been found that by introducing asymmetrical mutations in the CH3 regions of the two monospecific starting proteins, the Fab-arm exchange reaction can be forced to become directional and thereby yield highly stable heterodimeric proteins.

SUMMARY OF THE INVENTION

Accordingly, in one aspect, the present invention provides an efficient in vitro method for the production of highly stable heterodimeric Fc-containing proteins on the basis of stable homodimeric Fc-containing starting materials. For example, a highly stable bispecific antibody can be formed with high yield and purity on the basis of two stable monospecific antibodies as starting material.

Thus, in one aspect, the invention relates to an in vitro method for generating a heterodimeric protein, said method comprising the following steps:

a) providing a first homodimeric protein comprising an Fc region of an immunoglobulin, said Fc region comprising a first CH3 region, b) providing a second homodimeric protein comprising an Fc region of an immunoglobulin, said Fc region comprising a second CH3 region, wherein the sequences of said first and second CH3 regions are different and are such that the heterodimeric interaction between said first and second CH3 regions is stronger than each of the homodimeric interactions of said first and second CH3 regions, c) incubating said first protein together with said second protein under reducing conditions sufficient to allow the cysteines in the hinge region to undergo disulfide-bond isomerization, and d) obtaining said heterodimeric protein.

The method can for example be used for in vitro production of heterodimeric proteins, such as bispecific antibodies, for various uses, such as therapeutic or diagnostic uses. An advantage of this in vitro method is that heavy-chain/light-chain pairing stays intact during the reaction, so no undesired combinations of heavy chain and light chains are obtained in the product. This in contrast to some of the co-expression methods described in the prior art (see above) where a common light chain which can form a functional antibody with both heavy chain needs to be found in order to avoid the formation of non-functional heavy-chain/light-chain products, because of random heavy-chain/light-chain pairing in the cell. In addition, the in vitro process can be performed in the laboratory which allows greater control, flexibility and yield of the heterodimeric protein than is allowed by co-expression.

The in vitro method of the invention can also be used to create compound libraries of larger size, e.g. in a screening method to identify advantageous combinations of specificities. For example, for some combinations of antibody targets, not any bispecific antibody will be functional, i.e. be able to bind to both targets at the same time and mediate the desired functional effects. In such cases, a bispecific antibody having a desired property, e.g. optimal target binding or cell killing, may be identified by:
 a) providing a first set of homodimeric antibodies having different variable regions, wherein said antibodies of said first set comprise a first CH3 region,
 b) providing a second set of homodimeric antibodies having different variable regions, wherein said antibodies of said second set comprise a second CH3 region,
 wherein the sequences of said first and second CH3 regions are different and are such that the heterodimeric interaction between said first and second CH3 regions is stronger than each of the homodimeric interactions of said first and second CH3 regions,
 c) incubating combinations of antibodies of said first set and of said second set under reducing conditions sufficient to allow the cysteines in the hinge region to undergo disulfide-bond isomerization, thus generating a set of bispecific antibodies,
 d) optionally restoring the conditions to non-reducing,
 e) assaying the resulting set of bispecific antibodies for a given desired property, and
 f) selecting a bispecific antibody having the desired property.

In further aspects, the present invention relates to heterodimeric proteins obtained or obtainable by the method of the invention and to methods for producing heterodimeric proteins of the invention by co-expression in a suitable host cell.

BRIEF DESCRIPTION OF THE DRAWINGS

FIG. 2: Alignment of the amino acid sequences of the core hinge (SEQ ID NO: 28) (i.e. the CPPC (SEQ ID NO: 4) sequence in human IgG1 which includes the two cysteine residues that potentially form the interheavy chain disulphide bonds and corresponding residues in other human isotypes or other species) and CH3-CH3 interface (SEQ ID NO: 29) of the human and rhesus antibody isotypes.

FIG. 7: Stability analysis of heterodimeric bispecific antibodies obtained by 2-MEA-induced Fab-arm exchange. The stability of bispecific samples generated by 2-MEA induced Fab-arm exchange by combining either IgG1-2F8-ITL× IgG4-7D8-CPPC (A), or IgG4-2F8×IgG4-7D8 (B) was tested by measuring EGFR/CD20 bispecific binding in an ELISA after a GSH-induced Fab-arm exchange reaction in the presence of the indicated concentrations irrelevant IgG4. Bispecific binding is presented relative to the bispecific binding of the starting material (control), which was set to 100%. (A) Bispecific binding of the 2-MEA-induced bispecific product derived from IgG1-2F8-ITL×IgG4-7D8-CPPC was preserved, indicating a stable product that did not participate in Fab-arm exchange under GSH conditions. (B) Bispecific EGFR/CD20 binding of the 2-MEA-induced bispecific product derived from IgG4-2F8×IgG4-7D8 was diminished, indicating that the product participated in Fab-arm exchange with the irrelevant IgG4 under GSH conditions.

FIG. 8: Plasma clearance rate of a heterodimeric bispecific antibody generated by 2-MEA-induced Fab-arm exchange. Three groups of mice (3 mice per group) were injected with the indicated antibodies: (1) 100 μg bispecific antibody, generated by in vitro 2-MEA-induced Fab-arm exchange between IgG1-2F8-ITL×IgG4-7D8-CPPC; (2) 100 μg bispecific antibody+1,000 μg irrelevant IgG4; (3) 50 μg IgG1-2F8-ITL+50 μg IgG4-7D8-CPPC. (A) Total antibody concentrations over time, determined by ELISA. The curves of the total antibody plasma concentrations were the same for all antibodies. (B) Bispecific antibody concentration as determined by an ELISA. The bispecificity of the injected antibody was the same with and without the addition of an excess irrelevant IgG4. (*) Bispecific binding for the IgG1-2F8-ITL+IgG4-7D8-CPPC mixture was below the detection limit and therefore the corresponding symbols could not be plotted in this graph. Mean values of two ELISA experiments are shown.

FIG. 10: Comparison between triple mutant (ITL), double mutants (IT, IL, TL) and single mutant (L) human IgG1-2F8 in the generation of bispecific antibodies by Fab-arm exchange with human IgG4-7D8. The generation of bispecific antibodies after 2-MEA-induced in vitro Fab-arm exchange between the human IgG1-2F8 triple and double mutants and wild type IgG4-7D8 with a CPSC hinge (A) or mutant IgG4-7D8-CPPC with a stabilized hinge (B), or the single mutant IgG1-2F8-F405L and IgG4-7D8 with a wild type CPSC or stabilized CPPC hinge (C), was determined by an ELISA. A concentration series (total antibody) of 0-20 μg/mL or 0-10 μg/mL was analyzed in the ELISA for the experiments including the double and single mutants, respectively. Combinations with the double mutants IgG1-2F8-IL and -TL result in bispecific EGFR/CD20 binding similar as the triple mutant IgG1-ITL. Combinations with the IgG1-2F8-IT do not result in a bispecific product. Combinations with the single mutant IgG1-2F8-F405L result in bispecific EGFR/CD20 binding.

FIG. 13: 2-MEA-induced Fab-arm exchange between IgG1-2F8-ITL and IgG1-7D8-K409X mutants. The generation of bispecific antibodies after 2-MEA-induced in vitro Fab-arm exchange between IgG1-2F8-ITL and the indicated IgG1-7D8-K409X mutants was determined by an ELISA. (A) A concentration series (total antibody) of 0-20 μg/mL was analyzed. The positive control is a purified batch of bispecific antibody, derived from IgG1-2F8-ITL×IgG4-7D8-CPPC. (B) The exchange is presented as bispecific binding at 20 μg/mL relative to the positive control (black bar). Dark grey bars represents the bispecific binding between the IgG4 control (IgG4-7D8×IgG4-2F8), the negative control (IgG1-2F8× IgG1-7D8-K409R) and between IgG1-2F8-ITL and IgG4-7D8-CPPC. Light grey bars represent results from simultaneously performed Fab-arm-exchange reactions between the indicated IgG1-7D8-K409X mutants and IgG1-2F8-ITL.

FIG. 15: The ability to engage in Fab-arm exchange is correlated to the CH3-CH3 interaction strength. (A), (B) and (C) Generation of bispecific antibodies by GSH-induced Fab-arm exchange between IgG1-2F8 and IgG1-7D8 (A) or IgG4-2F8 and IgG4-7D8 (B and C) constructs with the indicated mutations, presented as bispecific binding in an ELISA over time. Bispecificity is presented relative to the IgG4-2F8× IgG4-7D8 control after 24 h. (D) and (E) Relation between apparent $K_D$ (Table 2) and bispecific antibody generation after 24 hrs (FIGS. 15A/B/C) for IgG1-based (D) or IgG4-based (E) molecules.

FIG. 16: Sequence alignment of anti-EGFr antibody 2F8 in an IgG1 (SEQ ID NO: 30), IgG4 (SEQ ID NO: 31) and (partial) IgG3 backbone (SEQ ID NO: 32). Amino acid numbering according to Kabat and according to the EU-index are depicted (both described in Kabat et al., Sequences of Proteins of Immunological Interest, 5th Ed. Public Health Service, National Institutes of Health, Bethesda, Md. (1991)).

FIG. 18: Generation of bispecific antibodies using 2-MEA-induced Fab-arm-exchange between human IgG1-2F8-F405L and IgG1-7D8-K409R.
(A) The generation of bispecific antibodies after 2-MEA-induced in vitro Fab-arm-exchange was determined by an ELISA. The presented graph shows the result of the ELISA in which a total antibody concentration of 20 μg/mL was used. 2-MEA efficiently induced Fab-arm-exchange. (B) The generation of bispecific antibodies after 2-MEA-induced in vitro Fab-arm-exchange was determined by mass spectrometry for all samples of the concentration series of 0-40 mM 2-MEA. After quantification of the mass spectrometry data, the percentage bispecific antibody was calculated and plotted against the concentration of 2-MEA in the Fab-arm-exchange reaction. IgG1-2F8-F405L×IgG1-7D8-K409R resulted in ~100% bispecific antibody, confirming the ELISA data.

FIG. 20: Plasma clearance of a bispecific antibody generated by 2-MEA-induced Fab-arm-exchange. Two groups of mice (3 mice per group) were injected with the indicated antibodies: (1) 100 μg bispecific antibody, generated by in vitro 2-MEA-induced Fab-arm-exchange between IgG1-2F8-F405L×IgG1-7D8-K409R; (2) 100 μg bispecific antibody+1,000 μg irrelevant IgG4. (A) Total antibody concentrations over time, determined by ELISA. The curves of the total antibody plasma concentrations were the same for all antibodies. (B) Bispecific antibody concentration as determined by an ELISA. The bispecificity of the injected antibody was the same with and without the addition of an excess irrelevant IgG4.

FIG. 21: CDC-mediated cell kill of CD20-expressing cells by a bispecific antibody generated by 2-MEA-induced Fab-arm-exchange between IgG1-2F8-F405L×IgG1-7D8-K409R. Concentration series of the indicated antibodies were used to test their capacity to mediate CDC on Daudi (A) and Raji (B) cells. Both cell lines express CD20 but not EGFR. Introduction of the K409R in IgG1-7D8 did not influence its capacity to induce CDC. The bispecific antibody derived from 2-MEA-induced Fab-arm-exchange between IgG1-2F8-F405L×IgG1-7D8-K409R was still capable to induce CDC.

FIG. 23: 2-MEA-induced Fab-arm-exchange between IgG1-2F8-F405X mutants and IgG1-7D8-K409R. The generation of bispecific antibodies after 2-MEA-induced in vitro Fab-arm-exchange between the indicated IgG1-2F8-F405X mutants and IgG1-7D8-K409R was determined by an ELISA. (A) A concentration series (total antibody) of 0-20 μg/mL was analyzed in the ELISA. The positive control is a purified batch of bispecific antibody, derived from IgG1-2F8-F405L×IgG1-7D8-K409R. (B) The exchange is presented as bispecific binding at 20 μg/mL antibody concentration relative to the positive control (black bar). Dark grey bars represents the bispecific binding between the IgG4 control (IgG4-7D8×IgG4-2F8) and the negative control (IgG1-2F8×IgG1-7D8-K409R). Light grey bars represent results from simultaneously performed Fab-arm-exchange reactions between the indicated IgG1-2F8-F405X mutants and IgG1-7D8-K409R or controls.

FIG. 24: 2-MEA-induced Fab-arm-exchange between IgG1-2F8-Y407X mutants and IgG1-7D8-K409R. The generation of bispecific antibodies after 2-MEA-induced in vitro Fab-arm-exchange between the indicated IgG1-2F8-Y407X mutants and IgG1-7D8-K409R was determined by an ELISA. (A) A concentration series (total antibody) of 0-20 μg/mL was analyzed in the ELISA. The positive control is a purified batch of bispecific antibody, derived from IgG1-2F8-F405L×IgG1-7D8-K409R. (B) The exchange is presented as bispecific binding at 20 μg/mL antibody concentration relative to the positive control (black bar). Dark grey bars represents the bispecific binding between the IgG4 control (IgG4-7D8×IgG4-2F8) and the negative control (IgG1-2F8×IgG1-7D8-K409R). Light grey bars represent results from simultaneously performed Fab-arm-exchange reactions between the indicated IgG1-2F8-Y407X mutants and IgG1-7D8-K409R or controls.

FIG. 31B, t=45; FIG. 31C, t=90; FIG. 31D, t=135; FIG. 31E, t=180; FIG. 31F, t=225; FIG. 31G, t=270; FIG. 31H, t=450).

FIGS. 33A-33F show the generation of bispecific antibodies at various IgG concentrations, 2-MEA concentrations, incubation temperatures and times as determined by an ELISA.

FIG. 34A-34D=show the generation of bispecific antibodies at various IgG concentrations, 2-MEA concentrations, incubation temperatures and times as determined by an ELISA and compared to control which was arbitrarily set to 100%.

FIG. 36: Generation of bispecific antibodies after 2-MEA-induced in vitro Fab-arm exchange between the indicated IgG1-2F8-L368X mutants and IgG1-7D8-K409R was determined by an ELISA using a concentration series (total antibody) of 0-20 μg/mL (FIG. 37(A)). The positive control is a purified batch of bispecific antibody, derived from IgG1-2F8-F405L×IgG1-7D8-K409R. FIG. 37(B) shows the bispecific binding at 20 μg/mL relative to the positive control (black bar). Dark grey bars represents the bispecific binding between the IgG4 control (IgG4-7D8×IgG4-2F8) and the negative control (IgG1-2F8×IgG1-7D8-K409R). Light grey bars represent results from simultaneously performed Fab-arm-exchange reactions between the indicated IgG1-2F8-L368X mutants and IgG1-7D8-K409R.

FIG. 37: Generation of bispecific antibodies after 2-MEA-induced in vitro Fab-arm exchange between the indicated IgG1-2F8-K370X mutants and IgG1-7D8-K409R was determined by an ELISA using a concentration series (total antibody) of 0-20 μg/mL (FIG. 37(A)). The positive control is a purified batch of bispecific antibody, derived from IgG1-2F8-F405L×IgG1-7D8-K409R. FIG. 37(B) shows the bispecific binding at 20 μg/mL relative to the positive control (black bar). Dark grey bars represents the bispecific binding between the IgG4 control (IgG4-7D8×IgG4-2F8) and the negative control (IgG1-2F8×IgG1-7D8-K409R). Light grey bars represent results from simultaneously performed Fab-arm-exchange reactions between the indicated IgG1-2F8-D370X mutants and IgG1-7D8-K409R.

FIG. 38: Generation of bispecific antibodies after 2-MEA-induced in vitro Fab-arm exchange between the indicated IgG1-2F8-D399X mutants and IgG1-7D8-K409R was determined by an ELISA using a concentration series (total antibody) of 0-20 μg/mL (FIG. 38(A)). FIG. 38(B) shows the bispecific binding at 20 μg/mL antibody concentration relative to the positive control (black bar). Dark grey bars represents the bispecific binding between the IgG4 control (IgG4-7D8×IgG4-2F8) and the negative control (IgG1-2F8×IgG1-7D8-K409R). Light grey bars represent results from simultaneously performed Fab-arm-exchange reactions between the indicated IgG1-2F8-D399X mutants and IgG1-7D8-K409R.

FIG. 43: CDC-mediated cell kill of CD20 expressing cells by bispecific antibodies generated by 2-MEA-induced Fab-arm-exchange between IgG1-7D8-F405L or IgG1-2F8-F405L and IgG1-7D8-K409R. Concentration series of the indicated antibodies were used to test their capacity to mediate CDC on Daudi (A) and Raji (B) cells. Both cell lines express CD20 but not EGFR. The bispecific antibody generated by 2-MEA-induced Fab-arm-exchange between IgG1-7D8-F405L×IgG1-7D8-K409R was as effective as IgG1-7D8 in induction of CDC mediated cell kill. The bispecific antibody derived from 2-MEA-induced Fab-arm-exchange between IgG2-2F8-F405L×IgG1-7D8-K409R results in a monovalent CD20 binding bispecific antibody, which slightly affected the induction of CDC mediated cell kill with slightly.

FIGS. 46A and 46B: Colocalization analysis of HER2× HER2 bispecific antibodies (FITC) with lysosomal marker LAMP1 (Cy5). FITC pixel intensity overlapping with Cy5 for various monospecific HER2 antibodies and HER2×HER2 bispecific antibodies (FIG. 46(B)). FITC pixel intensity in LAMP1/Cy5 positive pixels of three different images is plotted for each antibody tested (FIG. 46(A)). Monospecifics show lower FITC pixel intensities in the LAMP1/Cy5 positive pixels compared to bispecifics. FIG. 46(B) represents the mean value of FITC pixel intensity per LAMP1/Cy5 positive pixel calculated from the three different images. Together these results indicate that after internalization higher levels of bispecific antibodies, compared to monospecifics antibodies, localize to Lamp1/Cy5 positive vesicles.

DETAILED DESCRIPTION OF THE INVENTION

Definitions

Figure 1:
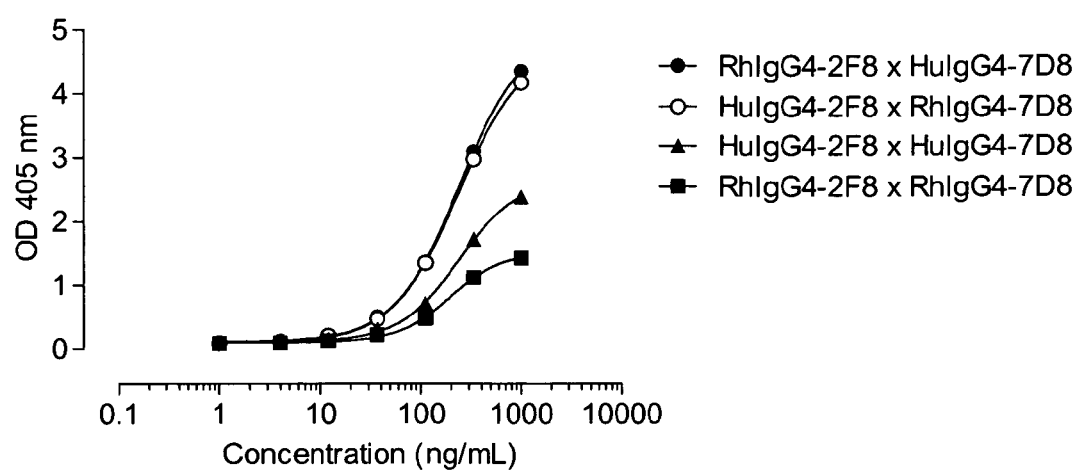
FIG. 1: Generation of bispecific antibodies by interspecies Fab-arm exchange. The generation of bispecific antibodies after GSH-induced in vitro Fab-arm exchange between the indicated EGFR (2F8) and CD20 (7D8) IgG4 antibodies was determined by an ELISA. A concentration series (total antibody) of 0-1 μg/mL was analyzed in the ELISA. Bispecific binding was higher after Fab-arm exchange between rhesus (Rh) and human (Hu) IgG4 antibodies than between two antibodies of the same species.

The term "immunoglobulin" refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH) and a heavy chain constant region. The heavy chain constant region typically is comprised of three domains, CH1, CH2, and CH3. The heavy chains are inter-connected via disulfide bonds in the so-called "hinge region". Each light chain typically is comprised of a light chain variable region (abbreviated herein as VL) and a light chain constant region. The light chain constant region typically is comprised of one domain, CL. Typically, the numbering of amino acid residues in the constant region is performed according to the EU-index as described in Kabat et al., Sequences of Proteins of Immunological Interest, 5th Ed. Public Health Service, National Institutes of Health, Bethesda, Md. (1991). FIG. 16 gives an overview of the EU and Kabat numbering for different isotype forms of antibody 2F8 (WO 02/100348). The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901 917 (1987)).

When used herein, the term "Fab-arm" refers to one heavy chain-light chain pair.

When used herein, the term "Fc region" refers to an antibody region comprising at least the hinge region, a CH2 domain and a CH3 domain.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 min, at least about 45 min, at least about one hour, at least about two hours, at least about four hours, at least about 8 hours, at least about 12 hours (h), about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. An antibody may also be a bispecific antibody, diabody, or similar molecule. The term "bispecific antibody" refers to antibody having specificities for at least two different epitopes, typically non-overlapping epitopes. As indicated above, the term antibody herein, unless otherwise stated or clearly contradicted by the context, includes fragments of an antibody that retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody, e.g. a F(ab')2 fragment. It also should be understood that the term antibody, unless specified otherwise, also includes polyclonal antibodies, monoclonal antibodies (mAbs), antibody-like polypeptides, such as chimeric antibodies and humanized antibodies. An antibody as generated can possess any isotype.

The term "full-length antibody" when used herein, refers to an antibody which contains all heavy and light chain constant and variable domains that are normally found in an antibody of that isotype.

As used herein, "isotype" refers to the immunoglobulin class (for instance IgG1, IgG2, IgG3, IgG4, IgD, IgA, IgE, or IgM) that is encoded by heavy chain constant region genes.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

When used herein, the term "heavy chain antibody" or "heavy-chain antibody" refers to an antibody which consists only of two heavy chains and lacks the two light chains usually found in antibodies. Heavy chain antibodies, which naturally occur in e.g. camelids, can bind antigens despite having only VH domains.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the footprint of the specifically antigen binding peptide).

As used herein, the term "binding" in the context of the binding of an antibody to a predetermined antigen typically is a binding with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold. The term "$K_D$" (M), as used herein, refers to the dissociation equilibrium constant of a particular antibody-antigen interaction.

When used herein the term "heterodimeric interaction between the first and second CH3 regions" refers to the interaction between the first CH3 region and the second CH3 region in a first-CH3/second-CH3 heterodimeric protein.

When used herein the term "homodimeric interactions of the first and second CH3 regions" refers to the interaction between a first CH3 region and another first CH3 region in a first-CH3/first-CH3 homodimeric protein and the interaction between a second CH3 region and another second CH3 region in a second-CH3/second-CH3 homodimeric protein.

An "isolated antibody," as used herein, denotes that the material has been removed from its original environment (e.g., the natural environment if it is naturally occurring or the host cell if it is recombinantly expressed). It is also advantageous that the antibodies be in purified form. The term "purified" does not require absolute purity; rather, it is intended as a relative definition, indicating an increase of the antibody concentration relative to the concentration of contaminants in a composition as compared to the starting material.

The term "host cell", as used herein, is intended to refer to a cell into which an expression vector has been introduced, e.g. an expression vector encoding an antibody of the invention. Recombinant host cells include, for example, transfectomas, such as CHO cells, HEK293 cells, NS/0 cells, and lymphocytic cells.

When used herein, the term "co-expression" of two or more nucleic acid constructs, refers to expression of the two constructs in a single host cell.

The term "tumor cell protein" refers to a protein located on the cell surface of a tumor cell.

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, polymorphonuclear cells, such as neutrophils, granulocytes, mast cells, and basophils. Some effector cells express specific Fc receptors and carry out specific immune functions. In some embodiments, an effector cell is capable of inducing antibody-dependent cellular cytotoxicity (ADCC), such as a natural killer cell, capable of inducing ADCC. In some embodiments, an effector cell may phagocytose a target antigen or target cell.

The term "reducing conditions" or "reducing environment" refers to a condition or an environment in which a substrate, here a cysteine residue in the hinge region of an antibody, is more likely to become reduced than oxidized.

The term "disulfide bond isomerization" refers to an exchange of disulfide bonds between different cysteines, i.e., the shuffling of disulfide bonds.

FURTHER ASPECTS AND EMBODIMENTS OF THE INVENTION

As described above, in a first aspect, the invention relates to an in vitro method for generating a heterodimeric protein, said method comprising the following steps:

a) providing a first homodimeric protein comprising an Fc region of an immunoglobulin, said Fc region comprising a first CH3 region, b) providing a second homodimeric protein comprising an Fc region of an immunoglobulin, said Fc region comprising a second CH3 region, wherein the sequences of said first and second CH3 regions are different and are such that the heterodimeric interaction between said first and second CH3 regions is stronger than each of the homodimeric interactions of said first and second CH3 regions, c) incubating said first protein together with said second protein under reducing conditions sufficient to allow the cysteines in the hinge region to undergo disulfide-bond isomerization, and d) obtaining said heterodimeric protein.

The bispecific format may be used in many ways to generate desired combinations of bispecific antibodies. In addition to being able of combining antibodies targeting different antigens in a very selective way it can be used to change a desired property, e.g. to increase CDC, by combining two different antibodies targeting the same antigen. Furthermore, it can be used to remove partial agonistic activity of an antagonistic antibody or convert an agonistic antibody into an antagonistic antibody by making a bispecific antibody thereof with an irrelevant (inactive) antibody.

In one embodiment, the homodimeric proteins are selected from the group consisting of (i) an Fc region, (ii) an antibody, (iii) a fusion protein comprising an Fc region, such as an Fc region fused to a receptor, cytokine or hormone, and (iv) a Fc region conjugated to a prodrug, peptide, drug or a toxin.

In some embodiments, said first and/or second homodimeric protein comprise, in addition to the Fc region, one or more or all of the other regions of an antibody, i.e. a CH1 region, a VH region, a CL region and/or a VL region. Thus, in one embodiment, said first homodimeric protein is a full-length antibody. In another embodiment, said second homodimeric protein is a full-length antibody.

In an important embodiment, said first and second homodimeric proteins are both antibodies, preferably full-length antibodies, and bind different epitopes. In such an embodiment, the heterodimeric protein that is generated is a bispecific antibody. Said epitopes may be located on different antigens or on the same antigen.

In other embodiments, however, only one of the homodimeric proteins is a full-length antibody and the other homodimeric protein is not a full-length antibody, e.g. an Fc region without a variable region, expressed in conjunction to another protein or peptide sequence like a receptor, cytokine or hormone, or conjugated to a prodrug, peptide, a drug or a toxin. In a further embodiment, neither of the homodimeric proteins is a full-length antibody. For example, both homodimeric proteins may be Fc regions that are fused to another protein or peptide sequence like a receptor, cytokine or hormone, or conjugated to a prodrug, peptide, a drug or a toxin.

In one embodiment, the Fc region of the first homodimeric protein is of an isotype selected from the group consisting of IgG1, IgG2, IgG3 and IgG4 and the Fc region of the second homodimeric protein is of an isotype selected from the group consisting of IgG1, IgG2, IgG3 and IgG4. In a preferred embodiment, the Fc regions of both said first and said second homodimeric protein are of the IgG1 isotype. In another preferred embodiment, one of the Fc regions of said homodimeric proteins is of the IgG1 isotype and the other of the IgG4 isotype. In the latter embodiment, the resulting heterodimeric comprises an Fc region of an IgG1 and an Fc region of IgG4 and may thus have interesting intermediate properties with respect to activation of effector functions. A similar product can be obtained if said first and/or said second homodimeric protein comprises a mutation removing the acceptor site for Asn-linked glycosylation or is otherwise manipulated to change the glycosylation properties.

In a further embodiment, one or both of the homodimeric proteins is glyco-engineered to reduce fucose and thus enhance ADCC, e.g. by addition of compounds to the culture media during antibody production as described in US2009317869 or as described in van Berkel et al. (2010) Biotechnol. Bioeng. 105:350 or by using FUT8 knockout cells, e.g. as described in Yamane-Ohnuki et al (2004) Biotechnol. Bioeng 87:614. ADCC may alternatively be optimized using the method described by Umaha et al. (1999) Nature Biotech 17:176.

In a further embodiment, one or both of the homodimeric proteins has been engineered to enhance complement activation, e.g. as described in Natsume et al. (2009) Cancer Sci. 100:2411.

In a further embodiment, one or both of the homodimeric proteins has been engineered to reduce or increase the binding to the neonatal Fc receptor (FcRn) in order to manipulate the serum half-life of the heterodimeric protein.

In a further embodiment, one of the homodimeric starting proteins has been engineered to not bind Protein A, thus allowing to separate the heterodimeric protein from said homodimeric starting protein by passing the product over a protein A column. This may in particular be useful for embodiments wherein an excess of one homodimeric protein is used relative to the other homodimeric protein as starting material. In such embodiments, it may be useful to engineer the homodimeric protein that is in excess so that is looses its ability to bind protein A. Following the heterodimerization reaction, the heterodimeric protein may then be separated from a surplus of unexchanged homodimeric protein by passage over a protein A column.

In a further embodiment, one of the homodimeric proteins is an Fc region or a full-length antibody recognizing a non-relevant epitope or a full-length antibody containing germ-line-derived sequences that have not undergone somatic hypermutation and do not bind self-antigens. In such an embodiment the heterodimeric protein functions as a monovalent antibody. In another embodiment, both homodimeric proteins comprises the same heavy chain, but only one of the homodimeric proteins contains a light chain which forms a functional antigen-binding site with said heavy chain, whereas the other homodimeric protein contains a non-functional light chain, which does not bind any antigen in combination with said heavy chain. In such an embodiment, the heterodimeric protein functions as a monovalent antibody. Such a non-functional light chain can e.g. be a germ-line-derived sequence that has not undergone somatic hyper-mutation and does not bind self-antigens.

Antibodies to be used as homodimeric starting material of the present invention may e.g. be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624 628 (1991) and Marks et al., J. Mol. Biol. 222, 581 597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

Antibodies to be used as homodimeric starting material of the present invention may e.g. chimeric or humanized antibodies. In another embodiment, one or both of the homodimeric starting proteins, except for any specified mutations, is a human antibody. Human monoclonal antibodies may be generated using transgenic or transchromosomal mice, e.g. HuMAb mice, carrying parts of the human immune system rather than the mouse system. The HuMAb mouse contains a human immunoglobulin gene miniloci that encodes unrearranged human heavy ($\mu$ and $\gamma$) and K light chain immunoglobulin sequences, together with targeted mutations that inactivate the endogenous $\mu$ and $\kappa$ chain loci (Lonberg, N. et al., Nature 368, 856 859 (1994)). Accordingly, the mice exhibit reduced expression of mouse IgM or $\kappa$ and in response to immunization, the introduced human heavy and light chain transgenes, undergo class switching and somatic mutation to generate high affinity human IgG, $\kappa$ monoclonal antibodies (Lonberg, N. et al. (1994), supra; reviewed in Lonberg, N. Handbook of Experimental Pharmacology 113, 49 101 (1994), Lonberg, N. and Huszar, D., Intern. Rev. Immunol. Vol. 13 65 93 (1995) and Harding, F. and Lonberg, N. Ann. N.Y. Acad. Sci. 764 536 546 (1995)). The preparation of HuMAb mice is described in detail in Taylor, L. et al., Nucleic Acids Research 20, 6287 6295 (1992), Chen, J. et al., International Immunology 5, 647 656

(1993), Tuaillon et al., J. Immunol. 152, 2912 2920 (1994), Taylor, L. et al., International Immunology 6, 579 591 (1994), Fishwild, D. et al., Nature Biotechnology 14, 845 851 (1996). See also U.S. Pat. No. 5,545,806, U.S. Pat. No. 5,569,825, U.S. Pat. No. 5,625,126, U.S. Pat. No. 5,633,425, U.S. Pat. No. 5,789,650, U.S. Pat. No. 5,877,397, U.S. Pat. No. 5,661, 016, U.S. Pat. No. 5,814,318, U.S. Pat. No. 5,874,299, U.S. Pat. No. 5,770,429, U.S. Pat. No. 5,545,807, WO 98/24884, WO 94/25585, WO 93/1227, WO 92/22645, WO 92/03918 and WO 01/09187. Splenocytes from these transgenic mice may be used to generate hybridomas that secrete human monoclonal antibodies according to well known techniques.

Further, human antibodies of the present invention or antibodies of the present invention from other species may be identified through display-type technologies, including, without limitation, phage display, retroviral display, ribosomal display, mammalian display, and other techniques, using techniques well known in the art and the resulting molecules may be subjected to additional maturation, such as affinity maturation, as such techniques are well known in the art.

In a further embodiment of the invention, the antibody or a part thereof, e.g. one or more CDRs, is of a species in the family Camelidae, see WO2010001251, or a species of cartilaginous fish, such as the nurse shark or heavy-chain or domain antibodies.

In one embodiment of the method of the invention, said first and second homodimeric proteins provided in step a) and b) are purified.

In one embodiment, the first and/or second homodimeric protein is conjugated to a drug, a prodrug or a toxin or contains an acceptor group for the same. Such acceptor group may e.g. be an unnatural amino acid.

As described above, the sequences of the first and second CH3 regions of the homodimeric starting proteins are different and are such that the heterodimeric interaction between said first and second CH3 regions is stronger than each of the homodimeric interactions of said first and second CH3 regions.

In one embodiment, the increased strength of the heterodimeric interaction as compared to each of the homodimeric interactions is due to CH3 modifications other than the introduction of covalent bonds, cysteine residues or charged residues.

In some embodiments, the product of the invention is highly stable and does not undergo Fab-arm exchange under mildly reducing conditions in vitro or, importantly, in vivo upon administration to a human being. Thus, in one embodiment, the heterodimeric interaction between said first and second proteins in the resulting heterodimeric protein is such that no Fab-arm exchange can occur at 0.5 mM GSH under the conditions described in Example 13.

In another embodiment, the heterodimeric interaction between said first and second proteins in the resulting heterodimeric protein is such that no Fab-arm exchange occurs in vivo in mice under the conditions described in Example 14.

In another embodiment, the heterodimeric interaction between said first and second proteins in the resulting heterodimeric protein is more than two times stronger, such as more than three times stronger, e.g. more than five times stronger than the strongest of the two homodimeric interactions, e.g. when determined as described in Example 30.

In a further embodiment, the sequences of said first and second CH3 regions are such that the dissociation constants of the heterodimeric interaction between said first and second proteins in the resulting heterodimeric protein is below 0.05 micromolar when assayed as described in Example 30.

In a further embodiment, the sequences of said first and second CH3 regions are such that the dissociation constants of both homodimeric interactions are above 0.01 micromolar, such as above 0.05 micromolar preferably between 0.01 and 10 micromolar, such as between 0.05 and 10 micromolar, more preferably between 0.01 and 5, such as between 0.05 and 5 micromolar, even more preferably between 0.01 and 1 micromolar, such as between 0.05 and 1 micromolar, between 0.01 and 0.5 or between 0.01 and 0.1 when assayed as described in Example 21. Embodiments wherein the homodimeric starting proteins are relatively stable can have the advantage that it is easier to produce a large quantity of starting protein and e.g. avoid aggregation or misfolding.

In some embodiments, a stable heterodimeric protein can be obtained at high yield using the method of the invention on the basis of two homodimeric starting proteins containing only a few, fairly conservative, asymmetrical mutations in the CH3 regions.

Thus, in one embodiment, the sequences of said first and second CH3 regions contain amino acid substitutions at non-identical positions.

The amino acid substituents may be natural amino acids or unnatural amino acids. Examples of unnatural amino acids are e.g. disclosed in Xie J and Schultz P. G., Current Opinion in Chemical Biology (2005), 9:548-554, and Wang Q. et al., Chemistry & Biology (2009), 16:323-336.

In one embodiment, the amino acids are natural amino acids.

In one embodiment, said first homodimeric protein has no more than one amino acid substitution in the CH3 region, and the second homodimeric protein has no more than one amino acid substitution in the CH3 region relative to the wild-type CH3 regions.

In one embodiment, the first homodimeric protein has an amino acid substitution at a position selected from the group consisting of: 366, 368, 370, 399, 405, 407 and 409, and said second homodimeric protein has an amino acid substitution at a position selected from the group consisting of: 366, 368, 370, 399, 405, 407 and 409, and wherein said first homodimeric protein and said second homodimeric protein is not substituted in the same positions.

In one embodiment, the first homodimeric protein has an amino acid substitution at position 366, and said second homodimeric protein has an amino acid substitution at a position selected from the group consisting of: 368, 370, 399, 405, 407 and 409. In one embodiment the amino acid at position 366 is selected from Arg, Lys, Asn, Gln, Tyr, Glu and Gly.

In one embodiment, the first homodimeric protein has an amino acid substitution at position 368, and said second homodimeric protein has an amino acid substitution at a position selected from the group consisting of: 366, 370, 399, 405, 407 and 409.

In one embodiment, the first homodimeric protein has an amino acid substitution at position 370, and said second homodimeric protein has an amino acid substitution at a position selected from the group consisting of: 366, 368, 399, 405, 407 and 409.

In one embodiment, the first homodimeric protein has an amino acid substitution at position 399, and said second homodimeric protein has an amino acid substitution at a position selected from the group consisting of: 366, 368, 370, 405, 407 and 409.

In one embodiment, the first homodimeric protein has an amino acid substitution at position 405, and said second homodimeric protein has an amino acid substitution at a position selected from the group consisting of: 366, 368, 370, 399, 407 and 409.

In one embodiment, the first homodimeric protein has an amino acid substitution at position 407, and said second homodimeric protein has an amino acid substitution at a position selected from the group consisting of: 366, 368, 370, 399, 405, and 409.

In one embodiment, the first homodimeric protein has an amino acid substitution at position 409, and said second homodimeric protein has an amino acid substitution at a position selected from the group consisting of: 366, 368, 370, 399, 405, and 407.

Accordingly, in one embodiment, the sequences of said first and second CH3 regions contain asymmetrical mutations, i.e. mutations at different positions in the two CH3 regions, e.g. a mutation at position 405 in one of the CH3 regions and a mutation at position 409 in the other CH3 region.

In one embodiment, the first homodimeric protein has an amino acid other than Lys, Leu or Met at position 409 and said second homodimeric protein has an amino-acid substitution at a position selected from the group consisting of: 366, 368, 370, 399, 405 and 407.

In one such embodiment, said first homodimeric protein has an amino acid other than Lys, Leu or Met at position 409 and said second homodimeric protein has an amino acid other than Phe at position 405. In a further embodiment hereof, said first homodimeric protein has an amino acid other than Lys, Leu or Met at position 409 and said second homodimeric protein has an amino acid other than Phe, Arg or Gly at position 405.

In another embodiment, said first homodimeric protein comprises a Phe at position 405 and an amino acid other than Lys, Leu or Met at position 409 and said second homodimeric protein comprises an amino acid other than Phe at position 405 and a Lys at position 409. In a further embodiment hereof, said first homodimeric protein comprises a Phe at position 405 and an amino acid other than Lys, Leu or Met at position 409 and said second homodimeric protein comprises an amino acid other than Phe, Arg or Gly at position 405 and a Lys at position 409.

In another embodiment, said first homodimeric protein comprises a Phe at position 405 and an amino acid other than Lys, Leu or Met at position 409 and said second homodimeric protein comprises a Leu at position 405 and a Lys at position 409. In a further embodiment hereof, said first homodimeric protein comprises a Phe at position 405 and an Arg at position 409 and said second homodimeric protein comprises an amino acid other than Phe, Arg or Gly at position 405 and a Lys at position 409.

In another embodiment, said first homodimeric protein comprises Phe at position 405 and an Arg at position 409 and said second homodimeric protein comprises a Leu at position 405 and a Lys at position 409.

In a further embodiment, said first homodimeric protein comprises an amino acid other than Lys, Leu or Met at position 409 and said second homodimeric protein comprises a Lys at position 409, a Thr at position 370 and a Leu at position 405.

In a further embodiment, said first homodimeric protein comprises an Arg at position 409 and said second homodimeric protein comprises a Lys at position 409, a Thr at position 370 and a Leu at position 405.

In an even further embodiment, said first homodimeric protein comprises a Lys at position 370, a Phe at position 405 and an Arg at position 409 and said second homodimeric protein comprises a Lys at position 409, a Thr at position 370 and a Leu at position 405.

In another embodiment, said first homodimeric protein comprises an amino acid other than Lys, Leu or Met at position 409 and said second homodimeric protein comprises a Lys at position 409 and: a) an Ile at position 350 and a Leu at position 405, or b) a Thr at position 370 and a Leu at position 405.

In another embodiment, said first homodimeric protein comprises an Arg at position 409 and said second homodimeric protein comprises a Lys at position 409 and: a) an Ile at position 350 and a Leu at position 405, or b) a Thr at position 370 and a Leu at position 405.

In another embodiment, said first homodimeric protein comprises a Thr at position 350, a Lys at position 370, a Phe at position 405 and an Arg at position 409 and said second homodimeric protein comprises a Lys at position 409 and: a) an Ile at position 350 and a Leu at position 405, or b) a Thr at position 370 and a Leu at position 405.

In another embodiment, said first homodimeric protein comprises a Thr at position 350, a Lys at position 370, a Phe at position 405 and an Arg at position 409 and said second homodimeric protein comprises an Ile at position 350, a Thr at position 370, a Leu at position 405 and a Lys at position 409.

In another embodiment, said first homodimeric protein has an amino acid other than Lys, Leu or Met at position 409 and said second homodimeric protein has an amino acid other than Tyr, Asp, Glu, Phe, Lys, Gln, Arg, Ser or Thr at position 407.

In another embodiment, said first homodimeric protein has an amino acid other than Lys, Leu or Met at position 409 and said second homodimeric protein has an Ala, Gly, His, Ile, Leu, Met, Asn, Val or Trp at position 407.

In another embodiment, said first homodimeric protein has an amino acid other than Lys, Leu or Met at position 409 and said second homodimeric protein has a Gly, Leu, Met, Asn or Trp at position 407.

In another embodiment, said first homodimeric protein has a Tyr at position 407 and an amino acid other than Lys, Leu or Met at position 409 and said second homodimeric protein has an amino acid other than Tyr, Asp, Glu, Phe, Lys, Gln, Arg, Ser or Thr at position 407 and a Lys at position 409.

In another embodiment, said first homodimeric protein has a Tyr at position 407 and an amino acid other than Lys, Leu or Met at position 409 and said second homodimeric protein has an Ala, Gly, His, Ile, Leu, Met, Asn, Val or Trp at position 407 and a Lys at position 409.

In another embodiment, said first homodimeric protein has a Tyr at position 407 and an amino acid other than Lys, Leu or Met at position 409 and said second homodimeric protein has a Gly, Leu, Met, Asn or Trp at position 407 and a Lys at position 409.

In another embodiment, said first homodimeric protein has a Tyr at position 407 and an Arg at position 409 and said second homodimeric protein has an amino acid other than Tyr, Asp, Glu, Phe, Lys, Gln, Arg, Ser or Thr at position 407 and a Lys at position 409.

In another embodiment, said first homodimeric protein has a Tyr at position 407 and an Arg at position 409 and said second homodimeric protein has an Ala, Gly, His, Ile, Leu, Met, Asn, Val or Trp at position 407 and a Lys at position 409.

In another embodiment, said first homodimeric protein has a Tyr at position 407 and an Arg at position 409 and said second homodimeric protein has a Gly, Leu, Met, Asn or Trp at position 407 and a Lys at position 409.

In one embodiment, the first homodimeric protein has an amino acid other than Lys, Leu or Met at position 409, and the second homodimeric protein has (i) an amino acid other than Phe, Leu and Met at position 368, or (ii) a Trp at position 370, or (iii) an amino acid other than Asp, Cys, Pro, Glu or Gln at position 399.

In one embodiment, the first homodimeric protein has an Arg, Ala, His or Gly at position 409, and the second homodimeric protein has (i) a Lys, Gln, Ala, Asp, Glu, Gly, His, Ile, Asn, Arg, Ser, Thr, Val, or Trp at position 368, or (ii) a Trp at position 370, or (iii) an Ala, Gly, Ile, Leu, Met, Asn, Ser, Thr, Trp, Phe, His, Lys, Arg or Tyr at position 399.

In one embodiment, the first homodimeric protein has an Arg at position 409, and the second homodimeric protein has (i) an Asp, Glu, Gly, Asn, Arg, Ser, Thr, Val, or Trp at position 368, or (ii) a Trp at position 370, or (iii) a Phe, His, Lys, Arg or Tyr at position 399.

In addition to the above-specified amino-acid substitutions, said first and second homodimeric protein may contain further amino-acid substitutions, deletion or insertions relative to wild-type Fc sequences.

In a further embodiment, said first and second CH3 regions, except for the specified mutations, comprise the sequence set forth in SEQ ID NO:1 (IgG1m(a)):

```
SEQ ID NO: 1:
GQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHY

TQKSLSLSPGK
```

In a further embodiment, said first and second CH3 regions, except for the specified mutations, comprise the sequence set forth in SEQ ID NO:2 (IgG1m(f)):

```
SEQ ID NO: 2:
GQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHY

TQKSLSLSPGK
```

In a further embodiment, said first and second CH3 regions, except for the specified mutations, comprise the sequence set forth in SEQ ID NO:3 (IgG1m(ax)):

```
SEQ ID NO: 3:
GQPREPQVYTLPPSRDELTKNQVSLTCLVKGFYPSDIAVEWESNGQPE

NNYKTTPPVLDSDGSFFLYSKLTVDKSRWQQGNVFSCSVMHEGLHNHY

TQKSLSLSPGK
```

In a further embodiments, the homodimeric proteins provided may be a rat antibody and a mouse antibody, who show preferential pairing, as described by Lindhofer et al. (1995) J Immunol 155:219 (see above), or so-called knob-in-hole variant antibodies, as described in U.S. Pat. No. 5,731,168 (see above). In some cases, however, the latter homodimeric starting proteins may be more difficult to produce, because of too weak homodimeric CH3-CH3 interactions. Thus, the herein described variants having mutations at positions 350, 370, 405 and 409, may be preferred.

The sequence of the hinge region of the homodimeric starting proteins may vary. However, the resulting heterodimeric protein may be more stable under some circumstances if the hinge region is not IgG4-like, and, preferably is IgG1-like.

Thus, in one embodiment, neither said first nor said second homodimeric protein comprises a Cys-Pro-Ser-Cys (SEQ ID NO: 5) sequence in the (core) hinge region.

In a further embodiment, both said first and said second homodimeric protein comprise a Cys-Pro-Pro-Cys (SEQ ID NO: 4) sequence in the (core) hinge region.

In many embodiments wherein first and said second homodimeric proteins are antibodies, said antibodies further comprise a light chain. As explained above, said light chains may be different, i.e. differ in sequence and each form a functional antigen-binding domain with only one of the heavy chains. In another embodiment, however, said first and second homodimeric proteins are heavy-chain antibodies, which do not need a light chain for antigen binding, see e.g. Hamers-Casterman (1993) Nature 363:446.

As described above, step c) of the method of the invention comprises incubating said first protein together with said second protein under reducing conditions sufficient to allow the cysteines in the hinge region to undergo disulfide-bond isomerisation. Examples of suitable conditions are given herein. The minimal requirements for the cysteines in the hinge region for undergoing disulfide-bond isomerisation may differ depending on the homodimeric starting proteins, in particular depending on the exact sequence in the hinge region. It is important that the respective homodimeric interactions of said first and second CH3 regions are sufficiently weak to allow cysteines in the hinge region to undergo disulfide-bond isomerisation under the given conditions.

In one embodiment, the reducing conditions in step c) comprise the addition of a reducing agent, e.g. a reducing agent selected from the group consisting of: 2-mercaptoethylamine (2-MEA), dithiothreitol (DTT), dithioerythritol (DTE), glutathione, tris(2-carboxyethyl)phosphine (TCEP), L-cysteine and beta-mercapto-ethanol, preferably a reducing agent selected from the group consisting of: 2-mercaptoethylamine, dithiothreitol and tris(2-carboxyethyl)phosphine.

In one embodiment, the reducing conditions enabling controlled Fab-arm exchange are described in terms of the required redox potential. The tripeptide glutathione (GSH) is the major low-molecular weight thiol in cells and controls thiol-disulphide redox state which is essential for normal redox signaling in vivo. The dynamics of cellular redox balance are achieved by maintenance of the thiol-to-disulphide status of reduced GSH and its oxidized form GSSG (SEQ ID NO: 6). The values for the reduction potential can be measured as in Rost and Rapoport, Nature 201: 185 (1964) and Aslund et al., J. Biol. Chem. 272:30780-30786 (1997). The redox potential Eh, which takes into consideration the stoichiometry of two GSH oxidized per GSSG (SEQ ID NO: 6) is a quantitative measure for the redox state. Eh is calculated by the Nernst equation: $Eh=Eo+(RT/nF)\ln([GSSG\ (SEQ\ ID\ NO:\ 6)(ox)]/[GSH\ (red)]^2)$. Eo is the standard potential for the redox couple at defined pH, R is the gas constant, T is the absolute temperature, F is Faraday's constant and n is the number of electrons transferred. In vivo estimates for Eh for the GSH/GSSG (SEQ ID NO: 6) couple are in the range of −260 to −200 mV (Aw, T., News Physiol. Sci. 18:201-204 (2003)). Terminally differentiated cells thereby maintain an Eh in the order of −200 mV, whereas actively proliferating cells maintain a more reduced Eh of approximately −260 mV.

The standard redox potential for DTT is −330 mV (Cleland et al. Biochemistry 3: 480-482 (1964)). TCEP has been shown to reduce DTT in solution and therefore has a more negative redox potential than DTT. The precise value however has not been reported. Reducing conditions allowing controlled Fab-arm exchange conditions can therefore be described in terms of a required redox potential Eh, which is optimally below the value that is achieved under normal plasma conditions in vivo and that is above the redox potential which reduces antibody disulphide bonds outside those located in the hinge region and involved in inter-heavy chain disulphide bond formation.

Thus, in a further embodiment, step c) is performed under reducing conditions with a redox potential ranging below −50 mV, such as below −150 mV, preferably between −150 and −600 mV, such as between −200 and −500 mV, more preferably between −250 and −450 mV, such as between −250 and −400 mV, even more preferably between −260 and −300 mV.

In a further embodiment, step c) comprises incubation for at least 90 min at a temperature of at least 20° C. in the presence of at least 25 mM 2-mercaptoethylamine or in the presence of at least 0.5 mM dithiothreitol. The incubation may be performed at a pH of from 5 to 8, such as at pH 7.0 or at pH 7.4.

In a further embodiment, step d) comprises restoring the conditions to become non-reducing or less reducing, for example by removal of a reducing agent, e.g. by desalting.

In some embodiments, the method of the invention yields an antibody product wherein more than 80%, such as more than 90%, e.g. more than 95%, such as more than 99% of the antibody molecules are the desired bispecific antibodies.

The post-production is more flexible and easier to control compared to the prior art methods based on co-expression.

The post-production nature of making bispecific antibodies by Fab-exchange under reducing conditions (such as by addition of 2-MEA) as disclosed herein makes it a highly suitable strategy for (high-throughput) screening of multiple combinations of specificities for bispecific antibody discovery. In addition, the in vitro process can be performed in the laboratory which allows greater control, flexibility and yield of the heterodimeric protein than is allowed by co-expression. An additional advantage of this strategy is that the screening can be done in the final therapeutic format, precluding the need for engineering upon lead selection.

As explained above, in a further aspect, the method of the invention may be used for "matrix" screening, i.e. for generating a large number of different combinations of binding specificities on the basis of two sets of antibodies, one set having identical first CH3 regions and the other set having identical second CH3 regions, wherein the sequences of said first and second CH3 regions are different and are such that the heterodimeric interaction between said first and second CH3 regions is stronger than each of the homodimeric interactions of said first and second CH3 regions.

Thus, in one embodiment the invention relates to a method for the selection of a heterodimeric protein having a desired property, said method comprising the steps of:
a) providing a first set of homodimeric proteins comprising an Fc region wherein the homodimeric proteins have identical first CH3 regions,
b) providing a second set of homodimeric proteins comprising an Fc region wherein the homodimeric proteins have identical second CH3 regions,
wherein the sequences of said first and second CH3 regions are different and are such that the heterodimeric interaction between said first and second CH3 regions is stronger than each of the homodimeric interactions of said first and second CH3 regions,
c) incubating combinations of the homodimeric proteins of said first set and of said second set under reducing conditions sufficient to allow the cysteines in the hinge region to undergo disulfide-bond isomerization, thus generating a set of bispecific antibodies,
d) optionally restoring the conditions to non-reducing,
e) assaying the resulting set of heterodimeric proteins for a given desired property, and
f) selecting a heterodimeric protein having the desired property.

In one embodiment, the invention relates to a method for the selection of a bispecific antibody having a desired property, said method comprising the steps of:
a) providing a first set of homodimeric antibodies comprising antibodies with different variable regions, wherein said antibodies of said first set comprise identical first CH3 regions,
b) providing a second set of homodimeric antibodies comprising antibodies with different variable regions or identical variable regions, wherein said antibodies of said second set comprise identical second CH3 regions,
wherein the sequences of said first and second CH3 regions are different and are such that the heterodimeric interaction between said first and second CH3 regions is stronger than each of the homodimeric interactions of said first and second CH3 regions,
c) incubating combinations of antibodies of said first set and of said second set under reducing conditions sufficient to allow the cysteines in the hinge region to undergo disulfide-bond isomerization, thus generating a set of bispecific antibodies,
d) optionally restoring the conditions to non-reducing,
e) assaying the resulting set of bispecific antibodies for a given desired property, and
f) selecting a bispecific antibody having the desired property.

In one embodiment, the homodimeric antibodies of the second set have different variable regions.

In one embodiment, the homodimeric antibodies of the second set have identical variable regions, but have different amino acid or structural variations outside of the antigen binding region.

The two sets can be composed in many different ways as desired. Thus, the two sets may target the same epitope or different epitopes on the same antigen. The two sets may also target different antigens, and each set may contain antibodies binding to the same epitope or different epitopes on the antigen in question. Furthermore, one of the sets or both sets may each contain antibodies targeting different antigens.

In another embodiment, said desired property is cell killing, cell lysis, inhibition of cell proliferation, or binding to cells expressing both antigen targets.

The screening strategy includes two panels of antibody vectors containing a range of specificities, where one panel is cloned into a backbone that is able to engage in Fab-arm exchange under reducing conditions (such as by addition of 2-MEA) with the backbone of the second panel. For example, the first panel is cloned into an IgG1-F405L backbone and the second panel is cloned into a IgG1-K409R backbone (for other possible backbone combination see also Examples 19, 28, 29, 30, 35, 36, 37, 38, and 39).

Each member of the two panels of antibody vectors is then expressed individually at small scale. For example, all antibody vectors are transfected transiently in HEK293 cells and expressed in 2.3 mL cultures in 24-well plates. Alternatively, other suitable (small-scale) production systems known in the art may be used.

The expressed antibodies of the two panels of antibodies are then mixed pair-wise in a matrix-like fashion at equimolar ratios. For example, all individual antibodies are purified by small-scale protein A chromatography and antibody concentration are measured by absorbance at a wavelength of 280 nm. Other suitable (small-scale) purification methods or methods for determining protein concentration known in the art may alternatively be used. In another embodiment, the purification step may be left out if down-stream applications are not affected by the expression medium. Thereafter, the antibody concentrations are normalized so that a suitable volume contains equimolar amounts of both antibodies. For example, a panel of 8 antibodies in the F405L backbone is individually mixed with 8 antibodies in the K409R backbone so that 64 mixtures of 100 μl contain 80 μg/mL of antibody A (F405L) and 80 μg/mL of antibody B (K409R). Alternatively, if the strategy contains a bispecific antibody-specific purification step down-stream, the step to normalize antibody amounts may be left out.

To the mixtures of antibodies, a suitable amount of reducing agent is added and incubated for a suitable period of time at a permissive temperature. For example, to 100 μl containing 80 μg/mL of antibody A (F405L) and 80 μg/mL of antibody B (K409R), 25 μl of 125 mM 2-MEA is added (final concentration 25 mM 2-MEA) and incubated overnight at 25° C.

The reducing agent is thereupon removed from the mixtures (now containing bispecific antibodies) to promote oxidation of the disulfide bonds and to avoid interference of the reducing agent in the screening assays. For example, 2-MEA is removed by performing a buffer exchange of the 64 mixtures using Zeba Spin 96-well desalting plates (Pierce Biotechnology, #89807). Alternatively, other suitable methods to remove the reducing agent known in the art may be used The bispecific antibodies are then characterized biochemically or functionally to identify the lead candidates. For example, the 64 bispecific antibodies are assessed for proliferation inhibition of suitable cell-lines or binding to suitable cell-lines. Identified lead candidates will then be produced at larger scale and characterized in more detail.

Production by Co-Expression

The heterodimeric proteins of the invention may also be obtained by co-expression of constructs encoding the first and second polypeptides in a single cell.

Thus, in a further aspect, the invention relates to a method for producing a heterodimeric protein, said method comprising the following steps:

a) providing a first nucleic-acid construct encoding a first polypeptide comprising a first Fc region of an immunoglobulin, said first Fc region comprising a first CH3 region, b) providing a second nucleic-acid construct encoding a second polypeptide comprising a second Fc region of an immunoglobulin, said second Fc region comprising a first CH3 region, wherein the sequences of said first and second CH3 regions are different and are such that the heterodimeric interaction between said first and second CH3 regions is stronger than each of the homodimeric interactions of said first and second CH3 regions, and wherein said first homodimeric protein has an amino acid other than Lys, Leu or Met at position 409 and said second homodimeric protein has an amino-acid substitution at a position selected from the group consisting of: 366, 368, 370, 399, 405 and 407.

and/or wherein the sequences of said first and second CH3 regions are such that the dissociation constants of homodimeric interactions of each of the CH3 regions are between 0.01 and 10 micromolar, such as between 0.05 and 10 micromolar, more preferably between 0.01 and 5, such as between 0.05 and 5 micromolar, even more preferably between 0.01 and 1 micromolar, such as between 0.05 and 1 micromolar, between 0.01 and 0.5 or between 0.01 and 0.1 when assayed as described in Example 21.

c) co-expressing said first and second nucleic-acid constructs in a host cell, and d) obtaining said heterodimeric protein from the cell culture.

Suitable expression vectors, including promoters, enhancers, etc., and suitable host cells for the production of antibodies are well-known in the art.

Examples of host cells include yeast, bacterial and mammalian cells, such as CHO or HEK cells.

In one embodiment of this method, said first CH3 region has an amino acid other than Lys, Leu or Met at position 409 and said second CH3 region has an amino acid other than Phe at position 405.

and/or the sequences of said first and second CH3 regions are such that the dissociation constants of homodimeric interactions of each of the CH3 regions are between 0.01 and 10 micromolar, such as between 0.05 and 10 micromolar, more preferably between 0.01 and 5, such as between 0.05 and 5 micromolar, even more preferably between 0.01 and 1 micromolar, such as between 0.05 and 1 micromolar, between 0.01 and 0.5 or between 0.01 and 0.1 when assayed as described in Example 21.

In another embodiment of this method:

said first CH3 region has an amino acid other than Lys, Leu or Met at position 409 and said second CH3 region has an amino acid other than Phe at position 405, such as other than Phe, Arg or Gly at position 405 or said first CH3 region has an amino acid other than Lys, Leu or Met at position 409 and said second CH3 region has an amino acid other than Tyr, Asp, Glu, Phe, Lys, Gln, Arg, Ser or Thr at position 407.

In some embodiments, said first and second polypeptides are full-length heavy chains of two antibodies that bind different epitopes (i.e. said first and second nucleic-acid constructs encode full-length heavy chains of two antibodies that bind different epitopes), and thus the heterodimeric protein is a bispecific antibody. This bispecific antibody can be a heavy-chain antibody, or said host cell may further express one or more nucleic-acid constructs encoding a light-chain. If only one light-chain construct is co-expressed with the heavy chain constructs, then a functional bispecific antibody is only formed if the light chain sequence is such that it can form a functional antigen-binding domain with each of the heavy chains. If two or more different light-chain constructs are co-expressed with the heavy chain, multiple products will be formed.

In further embodiments, the co-expression method according to the invention comprises any of the further features described under the in vitro method above.

In a further aspect, the invention relates to an expression vector comprising the first and second nucleic-acid constructs specified herein above. In an even further aspect, the invention relates to a host cell comprising the first and second nucleic-acid constructs specified herein above.

Heterodimeric Proteins

In a further aspect, the invention relates to a heterodimeric protein obtained or obtainable by the method of the invention.

Furthermore, the method of the invention enables the formation of asymmetrical molecules, molecules with different characteristics on each of the Fab-arms or on each of the CH3 domains or molecules with distinct modifications throughout the molecules, e.g. molecules with unnatural amino acid substitution(s) for conjugation. Such asymmetrical molecules can be generated in any suitable combinations. This is illustrated further below by some non-limiting examples.

Bispecific antibodies can be used to pretarget a target cell of interest, including but not limited to, a tumor cell. Pretargeting of a target cell could be used for imaging studies or for immunotherapeutic purposes.

In an embodiment of the method of the invention, the first Fab-arm of the bispecific molecule binds to a tumor cell, such as a tumor cell surface protein or tumor cell surface carbohydrate, such as one of the tumor cell surface proteins listed herein and the second Fab-arm recognizes a radioactive effector molecule including but not limited to, a radiolabel coupled or linked (via a chelator) to a peptide or hapten. An example of such radiolabelled peptide is indium-labelled diethylenetriaminepentaacetic acid (anti-DTPA(In) van Schaijk et al. Clin. Cancer Res. 2005; 11: 7230s-7126s). Another example is using hapten-labelled colloidal particles such as liposomes, nanoparticles of polymeric micelles carrying radionuclides such as for example technetium-99 (Jestin et al. Q J Nucl Med Mol Imaging 2007; 51:51-60).

In another embodiment, a hapten-coupled alternative cytostatic molecule such as a toxin is used.

In a further embodiment of the method of the invention, the first Fab-arm of the bispecific molecule is glycosylated at position N297 (EU numbering) and the second Fab-arm of the bispecific molecules is aglycosylated (nonglycosylated for instance by mutating N297 to Q or A or E mutation (Bolt S et al., Eur J Immunol 1993, 23:403-411)). Asymmetrical glycosylation in the Fc-region impacts the interaction to Fcγ-receptors and has impact on antibody-dependent cell cytotoxicity effect of the antibody (Ha et al., Glycobiology 2011, Apr. 5) as well as interaction with other effector function molecules such as C1q.

In another embodiment of the method of the invention, the first Fab-arm of the bispecific molecule interacts with FcRn, the neonatal Fc receptor (Roopenian D C, et al. Nat. Rev. Immunol. 2007, 7:715-725) and the second Fab-arm is impaired in binding to FcRn by mutation of the FcRn interaction site on the molecules for instance by making a H435A mutation (Shields, R. L., et al, J Biol Chem, 2001, Firan, M., et al, Int Immunol, 2001).

In another embodiment of the method of the invention, the first Fab-arm of the bispecific molecule interacts with staphylococcal protein A (protein A, Deisenhofer et al, Biochemistry 20, 2361-2370 (1981) and streptococcal protein G (protein G, Derrick et al., Nature 359, 752-754 (1992), often used for purification of antibodies, and the second Fab-arm of bispecific molecules is impaired in the interaction with protein A of G. As a result, removal of residual amounts of homodimer with impaired protein A or G binding after the exchange into heterodimer is easily obtained by purification of the bispecific molecule with protein A or G.

In another embodiment, the binding to either Fcγ-receptors or FcRn is improved or decreased on one of the two Fab-arms of the bispecific molecule.

In another embodiment, the binding to C1q is improved or decreased on one of the two Fab-arms of the bispecific molecule.

In another embodiment, the protein has been engineered to enhance complement activation on one or both of the two Fab-arms of the molecule.

In another embodiment, each of the Fab-arms present in the bispecific molecule is derived from a different IgG subclass.

In another embodiment, each of the Fab-arms present in the bispecific molecule carry different allotypic mutations (Jefferis & Lefranc, 2009, MABs 1:332-8).

In another embodiment, another category of asymmetric immunotherapeutic molecules is generated by replacement of the Fab of one of the Fab-arms of the bispecific molecule by an immuno active, stimulating or inhibiting cytokine. Non-limiting examples of such cytokines are IL-2, IFN-α, IFN-β, IFN-γ, TNF-α, G-CSF, GM-CSF, IL-10, IL-4, IL-6, IL-13. Alternatively, a (growth) factor or hormone stimulating or inhibition agent is included in the molecules.

In another embodiment, a Fab of one of the Fab-arms is replaced by a lytic peptide, i.e. peptides that are able to lyse tumor cells, bacteria, fungi etc, including but not limited to antimicrobial peptides like magainin, mellitin, cecropin, KLAKKLAK and variants thereof (Schweizer et al. Eur. J. Pharmacology 2009; 625: 190-194, Javadpour, J. Med. Chem., 1996, 39: 3107-3113, Marks et al, Cancer Res 2005; 65:2373-2377, Rege et al, Cancer Res. 2007; 67:6368-6375) or cationic lytic peptides (CLYP technology, US2009/0269341).

In another embodiment, one or both of the Fabs on the Fab arms is replaced by receptors for cytokines and/or growth factors, creating socalled decoy receptors, of which Enbrel® (etanercept) targeting TNF-α and VEGF-trap, targeting VEGF, are well-known examples. Combining these two decoy receptors into one molecule showed superior activity over the single decoy receptors (Jung, J. Biol. Chem. 2011; 286:14410-14418).

In another embodiment, another category of asymmetric immunotherapeutic molecules is generated by fusion of immuno-active, -stimulating or inhibiting cytokines to the N-terminus or C-terminus of one, or both, of the Fab-arms present in the bispecific molecules. This may positively impact anti-tumor activity of the bispecific molecule. Examples of such molecules, however not limited to the list below, are IL-2 (Fournier et al., 2011, Int. J. Oncology, doi: 10.3892/ijo.2011.976), IFN-α, IFN-β or IFN-γ (Huan et al., 2007; J. Immunol. 179:6881-6888, Rossie et al., 2009; Blood 114: 3864-3871), TNF-α. Alternatively, N-terminal or C-terminal fusion of cytokines, such as for example G-CSF, GM-CSF, IL-10, IL-4, IL-6, or IL-13 may positively impact the bispecific antibody molecule effector function. Alternatively a (growth) factor or hormone stimulating or inhibition agent is included in the molecules on the N-terminus or C-terminus.

In another embodiment, N-terminal or C-terminal fusion of a lytic peptide, such as for example antimicrobial peptides like magainin, mellitin, cecropin, KLAKKLAK (SEQ ID NO: and variants thereof (Schweizer et al. Eur. J. Pharmacology 2009; 625: 190-194, Javadpour, J. Med. Chem., 1996, 39: 3107-3113, Marks et al, Cancer Res 2005; 65:2373-2377, Rege et al, Cancer Res. 2007; 67:6368-6375) or cationic lytic peptides (CLYP technology, US2009/0269341) on one or both of the Fab-ams may enhance the activity of the molecule.

In another embodiment, another category of asymmetric immunotherapeutic molecules is monovalent antibodies, molecules which interact with one Fab-arm to the target of choice. In such molecule one of the Fab-arms present in the bispecific molecule is directed against the target molecule of choice, the second Fab-arm of the molecule does not carry a Fab or has a non-binding/non-functional Fab such as described for MetMab (Genentech; WO 96/38557). Alternatively, monomeric Fc-fusion proteins such as those described for Factor VIII and IX (Peters et al., *Blood* 2010; 115: 2057-2064) may be generated.

Alternatively, combinations of any of the above mentioned asymmetrical molecules may be generated by the method of the invention.

In an even further aspect, the invention relates to a heterodimeric protein comprising a first polypeptide comprising a first Fc region of an immunoglobulin, said first Fc region comprising a first CH3 region, and a second polypeptide comprising a second Fc region of an immunoglobulin, said second Fc region comprising a second CH3 region, wherein the sequences of said first and second CH3 regions are different and are such that the heterodimeric interaction between said first and second CH3 regions is stronger than each of the homodimeric interactions of said first and second CH3 regions, and wherein said first homodimeric protein has an amino acid other than Lys, Leu or Met at position 409 and said second homodimeric protein has an amino-acid substitution at a position selected from the group consisting of: 366, 368, 370, 399, 405 and 407 and/or wherein the sequences of said first and second CH3 regions are such that the dissociation constants of homodimeric interactions of each of the CH3 regions are between 0.01 and 10 micromolar, such as between 0.05 and 10 micromolar, more preferably between 0.01 and 5, such as between 0.05 and 5 micromolar, even more preferably between 0.01 and 1 micromolar, such as between 0.05 and 1 micromolar, between 0.01 and 0.5 or between 0.01 and 0.1 when assayed as described in Example 21.

In one embodiment, said first CH3 region has an amino acid other than Lys, Leu or Met at position 409 and said second CH3 region has an amino acid other than Phe at position 405 and/or the sequences of said first and second CH3 regions are such that the dissociation constants of homodimeric interactions of each of the CH3 regions are between 0.01 and 10 micromolar, such as between 0.05 and 10 micromolar, more preferably between 0.01 and 5, such as between 0.05 and 5 micromolar, even more preferably between 0.01 and 1 micromolar, such as between 0.05 and 1 micromolar, between 0.01 and 0.5 or between 0.01 and 0.1 when assayed as described in Example 21.

In a further embodiment of the heterodimeric protein said first CH3 region has an amino acid other than Lys, Leu or Met at position 409 and said second CH3 region has an amino acid other than Phe at position 405, such as other than Phe, Arg or Gly, at position 405 or said first CH3 region has an amino acid other than Lys, Leu or Met at position 409 and said second CH3 region has an amino acid other than Tyr, Asp, Glu, Phe, Lys, Gln, Arg, Ser or Thr at position 407.

In further embodiments, the heterodimeric protein according to the invention comprises any of the further features described above for the methods of production.

Thus, in a further embodiment of the heterodimeric protein of the invention, said first polypeptide is a full-length heavy chain of an antibody, preferably a human antibody.

In another embodiment of the heterodimeric protein of the invention, said second polypeptide is a full-length heavy chain of an antibody, preferably a human antibody.

In a further embodiment of the heterodimeric protein of the invention, said first and second polypeptides are both full-length heavy chains of two antibodies, preferably both human antibodies that bind different epitopes, and thus the resulting heterodimeric protein is a bispecific antibody. This bispecific antibody can be a heavy-chain antibody, or an antibody which in addition to the heavy chains comprises two full-length light chains, which may be identical or different.

In a further embodiment of the heterodimeric protein of the invention, the Fc region of the first polypeptide is of an isotype selected from the group consisting of IgG1, IgG2, IgG3 and IgG4 (except for the specified mutations) and the Fc region of the second polypeptide is of an isotype selected from the group consisting of IgG1, IgG2, IgG3 and IgG4 (except for the specified mutations).

In a further embodiment of the heterodimeric protein of the invention, the Fc regions of both said first and said second polypeptides are of the IgG1 isotype.

In a further embodiment of the heterodimeric protein of the invention, one of the Fc regions of said polypeptides is of the IgG1 isotype and the other of the IgG4 isotype.

In a further embodiment of the heterodimeric protein of the invention, the increased strength of the heterodimeric interaction as compared to each of the homodimeric interactions is due to CH3 modifications other than the introduction of covalent bonds, cysteine residues or charged residues.

In a further embodiment of the heterodimeric protein of the invention, the heterodimeric interaction between said first and second polypeptides in the heterodimeric protein is such that no Fab-arm exchange can occur at 0.5 mM GSH under the conditions described in Example 13.

In a further embodiment of the heterodimeric protein of the invention, the heterodimeric interaction between said first and second polypeptides in the resulting heterodimeric protein is such that no Fab-arm exchange occurs in vivo in mice under the conditions described in Example 14.

In a further embodiment of the heterodimeric protein of the invention, said first CH3 region comprises a Phe at position 405 and an amino acid other than Lys, Leu or Met at position 409 and said second CH3 region comprises an amino acid other than Phe at position 405 and a Lys at position 409.

In a further embodiment of the heterodimeric protein of the invention, said first CH3 region comprises a Phe at position 405 and an amino acid other than Lys, Leu or Met at position 409 and said second CH3 region comprises a Leu at position 405 and a Lys at position 409.

In a further embodiment of the heterodimeric protein of the invention, said first CH3 region comprises Phe at position 405 and an Arg at position 409 and said second CH3 region comprises a Leu at position 405 and a Lys at position 409.

In a further embodiment of the heterodimeric protein of the invention, said first CH3 region comprises an amino acid other than Lys, Leu or Met at position 409 and said second CH3 region comprises a Lys at position 409 and: a) an Ile at position 350 and a Leu at position 405, or b) a Thr at position 370 and a Leu at position 405.

In a further embodiment of the heterodimeric protein of the invention, said first CH3 region comprises an Arg at position 409 and said second CH3 region comprises a Lys at position 409 and: a) an Ile at position 350 and a Leu at position 405, or b) a Thr at position 370 and a Leu at position 405.

In a further embodiment of the heterodimeric protein of the invention, said first CH3 region comprises a Thr at position 350, a Lys at position 370, a Phe at position 405 and an Arg at position 409 and said second CH3 region comprises a Lys at position 409 and: a) an Ile at position 350 and a Leu at position 405, or b) a Thr at position 370 and a Leu at position 405.

In a further embodiment of the heterodimeric protein of the invention, said first CH3 region comprises a Thr at position 350, a Lys at position 370, a Phe at position 405 and an Arg at position 409 and said second CH3 region comprises an Ile at position 350, a Thr at position 370, a Leu at position 405 and a Lys at position 409.

In a further embodiment of the heterodimeric protein of the invention, neither said first nor said second polypeptide comprises a Cys-Pro-Ser-Cys (SEQ ID NO: 5) sequence in the hinge region.

In a further embodiment of the heterodimeric protein of the invention, both said first and said second polypeptide comprise a Cys-Pro-Pro-Cys (SEQ ID NO: 4) sequence in the hinge region.

In a further embodiment of the heterodimeric protein of the invention, said first and/or said second polypeptide comprises a mutation removing the acceptor site for Asn-linked glycosylation.

Target Antigens

As explained above, in an important embodiment of the invention, the heterodimeric protein is a bispecific antibody comprising two variable regions that differ in binding specificity, i.e. bind different epitopes.

In principle, any combination of specificities is possible. As mentioned above, bispecific antibodies can potentially be used to overcome some of the limitations of monospecific antibodies. One possible limitation of a monospecific antibody is a lack of specificity for the desired target cells due to expression of the target antigen on other cell types towards which no antibody binding is desired. For example, a target antigen overexpressed on tumor cells may also be expressed in healthy tissues which could result in undesired side-effects upon treatment with an antibody directed against that antigen. A bispecific antibody having a further specificity against a protein which is exclusively expressed on the target cell type could potentially improve specific binding to tumor cells.

Thus, in one embodiment of the invention, said first and second epitopes are located on the same cell, e.g. a tumor cell. Suitable targets on tumor cells include, but are not limited to, the following: erbB1 (EGFR), erbB2 (HER2), erbB3, erbB4, MUC-1, CD19, CD20, CD4, CD38, CD138, CXCR5, c-Met, HERV-envelop protein, periostin, Bigh3, SPARC, BCR, CD79, CD37, EGFrvIII, L1-CAM, AXL, Tissue Factor (TF), CD74, EpCAM and MRP3. Possible combinations of tumor cell targets include, but are not limited to: erbB1+erbB2, erbB2+erbB3, erbB1+erbB3, CD19+CD20, CD38+CD34, CD4+CXCR5, CD38+RANKL, CD38+CXCR4, CD20+CXCR4, CD20+CCR7, CD20+CXCR5, CD20+RANKL, erbB2+AXL, erbB1+cMet, erbB2+c-Met, erbB2+EpCAM, c-Met+AXL, c-Met+TF, CD38+CD20, CD38+CD138.

In a further embodiment, said first and second epitopes may be located on the same target antigen, wherein the location of the two epitopes on the target antigen is such that binding of an antibody to one epitope does not interfere with antibody binding to the other epitope. In a further embodiment hereof, said first and second homodimeric proteins are antibodies that bind to two different epitopes located on the same target antigen, but have a different mode-of-action for killing the target cell, e.g. a tumor cell. For example, in one embodiment, the target antigen is erbB2 (HER2) and the bispecific antibody combines the pertuzumab and trastuzumab antigen-binding sites. In another embodiment, the target antigen is erbB1 (EGfr) and the bispecific antibody combines the zalutumumab and nimotuzumab antigen-binding sites.

Bispecific antibodies can also be used as mediators to retarget effector mechanisms to disease-associated tissues, e.g. tumors. Thus, in a further embodiment, said first or said second epitope is located on a tumor cell, such as a tumor cell protein or tumor cell carbohydrate, and the other epitope is located on an effector cell.

In one embodiment, the effector cell is a T cell.

Possible targets on effector cells include the following: FcgammaRI (CD64): expressed on monocytes and macrophages and activated neutrophils; FcgammaRIII (CD16): expressed on natural killer and macrophages; CD3: expressed on circulating T cells; CD89: expressed on PMN (polymorphonuclear neutrophils), eosinophils, monocytes and macrophages; CD32a: expressed on macrophages, neutrophils, eosinophils; FcER1 expressed on basophils and mast cells. In one embodiment the epitope is located on CD3 expressed on T cells.

In another embodiment, the first antibody has binding specificity for a pathogenic microorganism and the second antibody has binding specificity for an effector cell protein, such as CD3, CD4, CD8, CD40, CD25, CD28, CD16, CD89, CD32, CD64, FcER1 or CD1.

Furthermore, bispecific antibodies can be used to target a chemotherapeutic agent more specifically to the cells on which the agent should act. Thus, in one embodiment, one of the homodimeric proteins is an antibody which recognizes a small molecule or peptide, or is able to form a covalent bond with such a molecule, e.g. according to the principle described in Rader et al, (2003) PNAS 100:5396. In a further embodiment of the method of the invention, the first antibody has binding specificity for (i.e. binds to an epitope on) a tumor cell or tumor cell surface protein, such as erbB1, erbB2, erbB3, erbB4, EGFR3vIII, CEA, MUC-1, CD19, CD20, CD4, CD38, EPCAM, c-Met, AXL, L1-CAM, Tissue Factor, CD74 or CXCR5 and the second antibody has a binding specificity for a chemotherapeutic agent, such as a toxin (including a radiolabelled peptide), a drug or a prodrug.

Bispecific antibodies may also be used to target a vesicle, e.g. an electron dense vesicles, or minicell containing a toxin, drug or prodrug to a tumor. See e.g. MacDiamid et al. (2009) Nature Biotech 27:643. Minicells are achromosomal cells that are products of aberrant cell division which do not contain chromosomal DNA. Thus, in another embodiment, wherein said first or said second epitope is located on a tumor cell, such as a tumor cell protein or tumor cell carbohydrate, and the other epitope is located on an electron dense vesicle or minicell.

Furthermore, serum half-life of an antibody may be altered by including in a bispecific antibody a binding specificity for a serum protein. For instance, serum half-life may be prolonged by including in a bispecific antibody, a binding specificity for serum albumin. Thus, in a further embodiment of the method of the invention, the first antibody has binding specificity for a tumor cell or tumor cell protein, such as erbB1 (EGFR), erbB2 (HER2), erbB3, erbB4, MUC-1, CD19, CD20, CD4, CD38, CD138, CXCR5, c-Met, HERV-envelope protein, periostin, Bigh3, SPARC, BCR, CD79, CD37, EGFrvIII, L1-CAM, AXL, Tissue Factor (TF), CD74, EpCAM or MRP3, CEA and the second antibody has a binding specificity for a blood protein, such as serum albumin. A second binding specificity can also be used to target an antibody to a specific tissue, such as the central nervous system or brain (across the blood brain barrier). Thus, in a further embodiment of the method of the invention, the first antibody has binding specificity for a brain-specific target, such as amyloid-beta (e.g. for treatment of Alzheimer's disease), Her-2 (e.g. for treatment of breast cancer metastases in brain), EGFr (e.g. for treatment of primary brain cancer), Nogo A (e.g. for treatment of brain injury), TRAIL (e.g. for treatment of HIV), alpha-synuclein (e.g. for treatment of Parkinson), Htt (e.g. for treatment of Huntington), a prion (e.g. for treatment of mad cow disease), a West Nile virus protein, and the second antibody has a binding specificity for a blood brain barrier protein, such as transferrin receptor (TfR), insulin receptor, melanotransferrin receptor (MTfR), lactoferrin receptor (LfR), Apolipoprotein E receptor 2 (ApoER2), LDL-receptor-related protein 1 and 2 (LRP1 and LRP2), receptor for advanced glycosylation end-products (RAGE), diphtheria toxin-receptor=heparin-binding epidermal growth factor-like growth factor (DTR=HB-EGF), gp190 (Abbott et al, Neurobiology of Disease 37 (2010) 13-25).

A binding specificity for a blood brain barrier protein can also be used to target another, non-antibody, molecule, to a specific tissue, such as the central nervous system or brain (across the blood brain barrier). Thus, in a further embodiment, one of the homodimeric proteins is a full-length antibody having a binding specificity for a blood brain barrier protein (such as TfR, insulin receptor, MTfR, LfR, ApoER2, LRP1, LRP2, RAGE, DTR (=HB-EGF) or gp190) and the other homodimeric protein is an Fc region linked at the N- or C-terminus to another protein, such as a cytokine, a soluble receptor or other protein, e.g. VIP (vasoactive intestinal peptide), BDNF (brain-derived neurotrophic factor), FGF (fibroblast growth factor), multiple FGFs, EGF (epidermal growth factor), PNA (peptide nucleic acid), NGF (Nerve growth factor), Neurotrophin (NT)-3, NT-4/5, glial derived neurotrophic factor, ciliary neurotrophic factor, neurturin, neuregulins, interleukins, transforming growth factor (TGF)-alpha, TGF-beta, erythropoietin, hepatocyte growth factor, platelet derived growth factor, artemin, persephin, netrins, cardiotrophin-1, stem cell factor, midkine, pleiotrophin, bone morphogenic proteins, saposins, semaphorins, leukocyte inhibitory factor, alpha-L-iduronidase, iduronate-2-sulfatase, N-acetyl-galactosamine-6-sulfatase, arylsulphatase B, acid alpha-glucosidase, or sphingomyelinase (Pardridge, Biopармaceutical drug targeting to the brain, Journal of Drug Targeting 2010, 1-11; Pardridge, Re-engineering Biopharmaceuticals for delivery to brain with molecular Trojan horses. Bioconjugate Chemistry 2008, 19: 1327-1338.

Moreover, a second binding specificity can be used to target blood clotting factors to a particular desired site of action. For example, a bispecific antibody having a first binding specificity for a tumor cell and a second binding specificity for a blood clotting factor could direct blood clotting to a tumor, and thus stop tumor growth. Thus, in a further embodiment of the method of the invention, the first antibody has binding specificity for a tumor cell or tumor cell protein, such as erbB1, erbB2, erbB3, erbB4, MUC-1, CD19, CD20, CD4 or CXCR5 and the second antibody has a binding specificity for a protein involved in blood clotting, such as tissue factor.

Further particularly interesting binding specificity combinations include: CD3+HER2, CD3+CD20, IL-12+IL18, IL-1a+IL-1b, VEGF+EGFR, EpCAM+CD3, GD2+CD3, GD3+CD3, HER2+CD64, EGFR+CD64, CD30+CD16, NG2+CD28, HER2+HER3, CD20+CD28, HER2+CD16, Bcl2+CD3, CD19+CD3, CEA+CD3, EGFR+CD3, IgE+CD3, EphA2+CD3, CD33+CD3, MCSP+CD3, PSMA+CD3, TF+CD3, CD19+CD16, CD19+CD16a, CD30+CD16a, CEA+HSG, CD20+HSG, MUC1+HSG, CD20+CD22, HLA-DR+CD79, PDGFR+VEGF, IL17a+IL23, CD32b+CD25, CD20+CD38, HER2+AXL, CD89+HLA class II, CD38+CD138, TF+cMet, Her2+EpCAM, HER2+HER2, EGFR+EGFR, EGFR+c-Met, c-Met+non-binding arm and combinations of G-protein coupled receptors.

In a further embodiment, the bispecific antibodies according to the invention may be used to clear pathogens, pathogenic autoantibodies or harmful compounds such as venoms and toxins from the circulation by targeting to erythrocytes essentially as described in Taylor et al. J. Immunol. 158:842-850 (1997) and Taylor and Ferguson, J. Hematother. 4:357-362, 1995. Said first epitope is located on an erythrocyte (red blood cell) protein including, but not limited to, the erythrocyte complement receptor 1 and said second epitope is located on the compound or organism to be targeted for clearance.

In a further embodiment, the second Fab-arm comprises a fusion protein representing an autoantigen or a conjugation site to attach an autoantigen such as dsDNA. Targeting of pathogens, autoantibodies or harmful compounds by the bispecific antibodies of the invention followed by erythrocyte-mediated clearance may thus have therapeutic utility in the treatment of various diseases and syndromes.

Conjugation

In further embodiments of the invention, the first and/or second homodimeric protein is linked to a compound selected from the group consisting of: a toxin (including a radioisotope) a prodrug or a drug. Such compound may make killing of target cells more effective, e.g. in cancer therapy. The resulting heterodimeric protein is thus an immunoconjugate. The compound may alternatively be coupled to the resulting heterodimeric protein, i.e. after the Fab-arm exchange has taken place.

Suitable compounds for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydro-testosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *momordica charantia* inhibitor, curcin, crotin, sapaonaria officinalis inhibitor, gelonin, mitogellin, restrictocin, phenomycin, and enomycin toxins. Other suitable conjugated molecules include ribonuclease (RNase), DNase I, Staphylococcal enterotoxin-A, pokeweed antiviral protein, diphtherin toxin, *Pseudomonas* endotoxin, Maytansinoids, Auristatins (MMAE, MMAF), Calicheamicins and Duocarmycin analogs (Ducry and Stump, Bioconjugate Chem. 2010, 21: 5-13), Dolostatin-10, Dolostatin-15, Irinotecan or its active metabolite SN38, pyrrolobenzodiazepines (PBD's).

In a further embodiment of the invention, the first and/or second homodimeric protein is linked to an alpha emitter, including but not limited to Thorium-227, Radium-223, Bismuth-212, and Actinium-225.

In a further embodiment of the invention, the first and/or second homodimeric protein is linked to a beta emitting radionuclide, including but not limited to Iodium-313, Yttrium-90, Fluorine-18, Rhenium-186, Gallium-68, Technetium-99, Indium-111, and Lutetium-177.

In another embodiment, the compound to be conjugated comprises a nucleic acid or nucleic acid-associated molecule. In one such facet of the present invention, the conjugated nucleic acid is a cytotoxic ribonuclease, an antisense nucleic acid, an inhibitory RNA molecule (e.g., a siRNA molecule) or an immunostimulatory nucleic acid (e.g., an immunostimulatory CpG motif-containing DNA molecule).

Any method known in the art for conjugating may be employed, including the methods described by Hunter et al., Nature 144, 945 (1962), David et al., Biochemistry 13, 1014 (1974), Pain et al., J. Immunol. Meth. 40, 219 (1981) and Nygren, J. Histochem. and Cytochem. 30, 407 (1982). Conjugates may be produced by chemically conjugating the other moiety to the N-terminal side or C-terminal side of the protein (see, e.g., Antibody Engineering Handbook, edited by Osamu Kanemitsu, published by Chijin Shokan (1994)). Such conjugated antibody derivatives may also be generated by conjugation at internal residues or sugars, where appropriate. The agents may be coupled either directly or indirectly to a protein of the present invention. One example of indirect coupling of a second agent is coupling by a spacer moiety. Linking technologies for drug-conjugates have recently been summarized by Ducry and Stump (2010) Bioconjugate Chem. 21: 5.

Compositions and Uses

In a further main aspect, the invention relates to a pharmaceutical composition comprising a heterodimeric protein according to the invention as described herein and a pharmaceutically-acceptable carrier.

The pharmaceutical compositions may be formulated in accordance with conventional techniques such as those disclosed in Remington: The Science and Practice of Pharmacy, 19th Edition, Gennaro, Ed., Mack Publishing Co., Easton, Pa., 1995. A pharmaceutical composition of the present invention may e.g. include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol). Pharmaceutically acceptable carriers include sterile aqueous solutions or dispersions and sterile powders for the extemporaneous preparation of sterile injectable solutions or dispersion. Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole, butylated hydroxytoluene, lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art.

Sterile injectable solutions may be prepared by incorporating the active compound in the required amount in an appropriate solvent with one or a combination of ingredients e.g. as enumerated above, as required, followed by sterilization microfiltration.

The actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. In one embodiment, a pharmaceutical composition of the present invention is administered parenterally. "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment that pharmaceutical composition is administered by intravenous or subcutaneous injection or infusion.

In a main aspect, the invention relates to a heterodimeric protein according to the invention, such as a bispecific antibody according to the invention, for use as a medicament. The heterodimeric protein of the invention may be used for a number of purposes. In particular, as explained above the heterodimeric proteins of the invention may be used for the treatment of various forms of cancer, including metastatic cancer and refractory cancer.

Thus, in one aspect, the invention relates to a method for inhibiting growth and/or proliferation of and/or for killing of a tumor cell comprising administration of a heterodimeric protein according to the invention as described herein to an individual in need thereof.

In another embodiment the heterodimeric proteins of the invention are used for the treatment of immune and autoimmune diseases, inflammatory diseases, infectious diseases, cardiovascular diseases, CNS and musculo-skeletal diseases.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation.

The efficient dosages and the dosage regimens for the heterodimeric proteins depend on the disease or condition to be treated and may be determined by the persons skilled in the art. An exemplary, non-limiting range for a therapeutically effective amount of a bispecific antibody of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3, about 5, or about 8 mg/kg.

A physician or veterinarian having ordinary skill in the art may readily determine and prescribe the effective amount of the pharmaceutical composition required. For example, the physician or veterinarian could start doses of the heterodimeric protein employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Administration may e.g. be parenteral, such as intravenous, intramuscular or subcutaneous.

A heterodimeric protein of the invention may also be administered prophylactically in order to reduce the risk of developing disease, such as cancer, delay the onset of the occurrence of an event in disease progression, and/or reduce the risk of recurrence when a disease, such as cancer is in remission.

Heterodimeric proteins, such as bispecific antibodies, of the present invention may also be administered in combination therapy, i.e., combined with other therapeutic agents relevant for the disease or condition to be treated. Accordingly, in one embodiment, the Heterodimeric-protein-containing medicament is for combination with one or more further therapeutic agents, such as a cytotoxic, chemotherapeutic or anti-angiogenic agents. Such combined administration may be simultaneous, separate or sequential. In a further embodiment, the present invention provides a method for treating or preventing disease, such as cancer, which method comprises administration to a subject in need thereof of a therapeutically effective amount of a heterodimeric protein, such as a bispecific antibody of the present invention, in combination with radiotherapy and/or surgery.

Heterodimeric proteins, such as bispecific antibodies, of the present invention may also be used for diagnostic purposes.

EXAMPLES

Example 1

Expression Vectors for the Expression of Human IgG1-2F8 and IgG1-7D8

The VH and VL coding regions of HuMab 2F8 (WO 02/100348) and HuMab 7D8 (WO 04/035607) were cloned in the expression vector pConG1f (containing the genomic sequence of the human IgG1f allotype constant region (Lonza Biologics)) for the production of the human IgG1 heavy chain and pConKappa (containing the human kappa light chain constant region, Lonza Biologics) for the production of the kappa light chain. For IgG4 antibodies the VH regions were inserted in the pTomG4 vector (containing the genomic sequence of the human IgG4 constant region in the pEE12.4 vector (Lonza Biologics)). Alternatively, in follow-up constructs, vectors were used containing the fully codon-optimized coding regions of the heavy chain (IgG1 or IgG4) in the pEE12.4 vector or the human kappa light chain of HuMab 2F8 or HuMab 7D8 in the pEE6.4 vector (Lonza Biologics).

Example 2

Expression Vectors for the Expression Hinge-Deleted-IgG1-2F8, and Human IgG1 and IgG4 CH2-CH3 Fragments Containing Specific Mutations To introduce mutations in the hinge and CH3 regions of the antibody heavy chains, Quickchange site-directed mutagenesis kit (Stratagene, La Jolla, Calif.) was used according to the manufacturer's recommendations. Alternatively the constructs were fully synthesized or VH regions were cloned in a vector already containing the specific amino acid encoding substitutions.

Constructs encoding the CH2 and CH3 fragments were constructed either by PCR or synthesized fully codon optimized. These constructs had an N-terminal signal peptide and a 6 amino acid His tag and contained amino acids 341-447 of the human IgG1/4 constant region. The constructs were cloned in pEE12.4.

To construct hinge-deleted-IgG1 (Uni-G1) molecules, a synthetic DNA construct were was made encoding the Uni-G1 format for human IgG1 isotypes with EGFR specificity. In this construct the natural hinge region (as defined by the hinge exon) was deleted. An extra Ser to Cys mutation at position 158 was made in the IgG1 construct to salvage the Cys bond between the HC and LC chains in this subtype. The protein sequence is shown below (SEQ ID NO: 8). The construct was inserted in the pEE6.4 vector and named pHG1-2F8.

QVQLVESGGGVVQPGRSLRLSCAASGFTFSTYGMHWVRQAPGKGLEWV

AVIWDDGSYKYYGDSVKGRFTISRDNSKNTLYLQMNSLRAEDTAVYYC

ARDGITMVRGVMKDYFDYWGQGTLVTVSSASTKGPSVFPLAPCSKSTS

GGTAALGCLVKDYFPEPVTVSWNSGALTSGVHTFPAVLQSSGLYSLSS

VVTVPSSSLGTQTYICNVNHKPSNTKVDKRVAPELLGGPSVFLFPPKP

KDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQP

-continued

REPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQK

SLSLSPGK--

Example 3

Expression Vectors for the Expression of Rhesus IgG4-2F8 and IgG4-7D8

Vectors containing the coding regions for the IgG4 heavy and kappa light chains Chinese Rhesus monkey and the VH and VL regions of Humab 2F8 and 7D8 were synthesized, fully codon-optimized and inserted in pEE12.4 (heavy chain) and pEE6.4 (light chain). The heavy chain constant region sequence as used (based on the sequences described by Scinicariello et al., Immunology 111: 66-74, 2004) was the following (aligned to the human sequence):

```
Human IgG4                              (SEQ ID NO: 9)
ASTKGPSVFPLAPCSRSTSESTAALGCLVKDYFPEPVTVSWNSGALTS
GVH Rhesus (Ch) IgG4                        (SEQ ID NO: 10)
-STKGPSVFPLASCSRSTSESTAALGCLVKDYFPEPVTVSWNSGALTS
GVH Human IgG4
TFPAVLQSSGLYSLSSVVTVPSSSLGTKTYTCNVDHKPSNTKVDKRVE
SKYG Rhesus (Ch) IgG4
TFPAVLQSSGLYSLSSVVTVPSSSLGTQTYVCNVVHEPSNTKVDKRVE
FT--

Human IgG4
PPCPSCPAPEFLGGPSVFLFPPKPKDTLMISRTPEVTCVVVDVSQEDP
EV

Rhesus (Ch) IgG4
PPCPACPAPELLGGPSVFLFPPKPKDTLMISRTPEVTCVVVDVSQEDP
EV

Human IgG4
QFNWYVDGVEVHNAKTKPREEQFNSTYRVVSVLTVLHQDWLNGKEYKC
KV

Rhesus (Ch) IgG4
QFNWYVDGAEVHHAQTKPRERQFNSTYRVVSVLTVTHQDWLNGKEYTC
KV

Human IgG4
SNKGLPSSIEKTISKAKGQPREPQVYTLPPSQEEMTKNQVSLTCLVKG
FY

Rhesus (Ch) IgG4
SNKGLPAPIEKTISKAKGQPREPQVYILPPPQEELTKNQVSLTCLVTG
FY

Human IgG4
PSDIAVEWESNGQPENNYKTTPPVLDSDGSFFLYSRLTVDKSRWQEGN
VF

Rhesus (Ch) IgG4
PSDIAVEWESNGQPENTYKTTPPVLDSDGSYLLYSKLTVNKSRWQPGN
IF

Human IgG4
SCSVMHEALHNHYTQKSLSLSLGK

Rhesus (Ch) IgG4
TCSVMHEALHNHYTQKSLSVSPGK
```

The Rhesus light chain constant region (CL) sequence used was:

```
                                        (SEQ ID NO: 11)
AVAAPSVFIFPPSEDQVKSGTVSVVCLLNNFYPREASVKWKVDGVLKT

GNSQESVTEQDSKDNTYSLSSTLTLSSTDYQSHNVYACEVTHQGLSSP

VTKSFNRGEC--
```

Example 4

Antibody Production by Transient Expression in HEK-293F Cells

Antibodies were produced, under serum-free conditions, by cotransfecting relevant heavy and light chain expression vectors in HEK-293F cells (Invitrogen), using 293fectin (Invitrogen), according to the manufacturer's instructions.

Example 5

Purification of IgG1 and IgG4 Antibodies

IgG1 and IgG4 antibodies were purified by protein A affinity chromatography.
The cell culture supernatants were filtered over a 0.20 μM dead-end filter, followed by loading on a 5 mL Protein A column (rProtein A FF, GE Healthcare, Uppsala, Sweden) and elution of the IgG with 0.1 M citric acid-NaOH, pH 3. The eluate was immediately neutralized with 2 M Tris-HCl, pH 9 and dialyzed overnight to 12.6 mM sodium phosphate, 140 mM NaCl, pH 7.4 (B. Braun, Oss, The Netherlands). After dialysis, samples were sterile filtered over a 0.20 μM dead-end filter. Concentration of the purified IgGs was determined by nephelometry and absorbance at 280 nm. Purified proteins were analyzed by SDS-PAGE, IEF, mass spectrometry and glycoanalysis.

Example 6

Purification of CH2-CH3 Fragments

The His-tagged CH2-CH3 proteins were purified by immobilized metal ion ($Ni^{2+}$) affinity chromatography (Macherey-Nagel GmbH, Duren, Germany), desalted using PD-10 columns (GE Healthcare) equilibrated with PBS and filtered-sterilized over 0.2 μM dead-end filters. The concentration of the purified proteins was determined by absorbance at 280 nm. The quality of the purified proteins was analyzed by SDS-PAGE.

Example 7

Generation of Bispecific Antibodies by GSH-Induced Fab-Arm Exchange Between Human and Rhesus IgG4 Antibodies As mentioned above, WO 2008119353 (Genmab) describes an in vitro method for producing bispecific antibodies wherein a bispecific antibody is formed by "Fab-arm" or "half-molecule" exchange (swapping of a heavy chain and attached light chain) between two monospecific IgG4- or IgG4-like antibodies upon incubation under reducing conditions. This Fab-arm exchange reaction is the result of a disulfide-bond isomerization reaction wherein the inter heavy-chain disulfide bonds in the hinge regions of monospecific antibodies are reduced and the resulting free cysteines form a new inter heavy-chain disulfide bond with cysteine residues of another antibody molecule with a different specificity. The resulting product is a bispecific antibody having two Fab arms with different sequences.

To test for Fab-arm exchange between human and rhesus IgG4 antibodies, human IgG4-2F8 (anti-EGFR), Human IgG4-7D8 (anti-CD20), Rhesus IgG4-2F8 and Rhesus IgG4-7D8 were used to make all possible combinations of two antibodies. For the in vitro Fab-arm exchange, the antibody mixtures, containing each antibody at a final concentration of 4 µg/mL in 0.5 mL PBS with 0.5 mM reduced glutathione (GSH), were incubated at 37° C. for 24 h. To stop the reduction reaction, 0.5 mL PBS/0.05% Tween 20 (PBST) was added to the reaction mixture.

The presence of bispecific antibodies was tested by determination of bispecific binding using a sandwich enzyme-linked immunosorbent assay (ELISA). ELISA plates (Greiner bio-one, Frickenhausen, Germany) were coated overnight with 2 µg/mL (100 µL/well) of recombinant extracellular domain of EGFR in PBS at 4° C. The plates were washed once with PBST. Dilution series of the antibody samples (0-1 µg/mL in 3-fold dilutions) in PBST/0.2% BSA (PBSTB) were transferred to the coated ELISA plates (100 µL/well) and incubated on a plate shaker (300 rpm) for 60 min at room temperature (RT). Samples were discarded and the plates were washed once with PBS/0.05% Tween 20 (PBST). Next, the plates were incubated on a plate shaker (300 rpm) with 2 µg/mL mouse anti-idiotypic monoclonal antibody 2F2 SAB1.1 (directed against 7D8; Genmab) in PBTB (100 µL/well) for 60 min. The plates were washed once with PBS/0.05% Tween 20 (PBST). Next, the plates were incubated on a plate shaker (300 rpm) with an HRP-conjugated goat anti-mouse IgG (15G; Jackson ImmunoResearch Laboratories, Westgrove, Pa., USA; 1:5.000) in PBSTB (100 µL/well) for 60 min at RT. The plates were washed once with PBS/0.05% Tween 20 (PBST). ABTS (50 mg/mL; Roche Diagnostics GmbH, Mannheim, Germany) was added (100 µL/well) and incubated protected from light for 30 min at RT. The reaction was stopped with 2% oxalic acid (100 µL/well; Riedel de Haen Seelze, Germany). After 10 min at RT, absorbance at 405 nm was measured in an ELISA plate reader.

FIG. 1 shows that a combination of human and rhesus IgG4 resulted in more bispecific binding (a higher OD 405 nm) compared with each of the combinations of IgG4 molecules of the same species. These data show that Fab-arm exchange occurs between human IgG4 and rhesus IgG4. Moreover, the higher bispecific binding suggests that human IgG4 half molecules show preferential dimerisation to rhesus IgG4 half molecules (heterodimerization), resulting in an equilibrium of the Fab-arm exchange reaction that is shifted towards the bispecific heterodimer instead of a stochastic exchange with 50% heterodimer and 50% homodimers.

Example 8

Sequence Analysis of Human and Rhesus IgG4

The ability of an antibody to engage in Fab-arm exchange has been described to involve the third constant domain (CH3) in addition to a so-called permissive (for example CPSC (SEQ ID NO: 5) containing-) hinge region that only requires a reducing environment to be activated (Van der Neut Kolfschoten, 2007, Science). For human antibodies, Fab-arm exchange was found to be an inherent feature of IgG4, characterized by an arginine (R) at position 409 in the CH3 domain and a permissive hinge (226-CPSC-229)(SEQ ID NO: 5) (see WO 2008145142 (Genmab)). In contrast, human IgG1, which does not engage in Fab-arm exchange, has a Lysine (K) at position 409 and a stable (i.e. non-permissive) hinge (226-CPPC-229) (SEQ ID NO: 4) (EU numbering, see also FIG. 16).

In an attempt to elucidate the increased Fab-arm exchange between human and rhesus IgG4 compared to the Fab-arm exchange between IgG4 molecules of the same species, the core hinge and CH3-CH3 interface amino acids of human and rhesus antibodies were analyzed (see e.g. Dall'Acqua, et al (1998) Biochemistry 37:9266 for an overview of the residues of the human CH3-CH3 interface). FIG. 2 shows that the core hinge sequence in Chinese rhesus IgG4 is 226-CPAC-229 (SEQ ID NO: 33) and that the CH3 domain contains a Lysine (K) at position 409. In addition, sequence alignment showed that rhesus IgG4 is characterized by three more amino acid substitutions in the CH3-CH3 interface as compared to human IgG4: isoleucine (I) at position 350 in rhesus versus threonine (T) in human; threonine (T) at position 370 in rhesus versus lysine (K) in human; and leucine (L) at position 405 in rhesus versus phenylalanine (F) in human.

Example 9

Generation of Bispecific Antibodies Using GSH-Induced Fab-Arm Exchange Between Human IgG4 and Human IgG1 Containing Rhesus IgG4 CH3 Sequences It has been described for human antibodies that for allowing Fab-arm exchange to occur in IgG1 molecules, replacing the IgG1 core hinge sequence (CPPC) (SEQ ID NO: 4) with the human IgG4 sequence (CPSC) (SEQ ID NO: 5) by a P228S substitution had no effect, but that mutating CH3 to an IgG4-like sequence was required for Fab-arm exchange activity (Van der Neut Kolfschoten, 2007, Science).

Based on the Fab-arm exchange between human and rhesus IgG4 described in Example 7, it was analyzed whether the Chinese rhesus IgG4 CH3 sequence could engage human IgG1 for Fab-arm exchange. Therefore, the triple mutation T350I-K370T-F405L (referred to as ITL hereafter) was introduced in human IgG1-2F8 in addition to the P228S mutation that results in the hinge sequence CPSC (SEQ ID NO: 5). The human IgG1-2F8 mutants were combined with human IgG4-7D8 for in vitro GSH-induced Fab-arm exchange. The antibody mixtures, containing each antibody at a final concentration of 4 µg/mL in 0.5 mL PBS with 0.5 mM GSH, were incubated at 37° C. for 0-3-6-24h. To stop the reduction reaction, 0.5 mL PBS/0.05% Tween 20 (PBST) was added to the reaction mixture. Measurements of bispecific binding in an ELISA were performed as described in Example 7.

Figure 3:
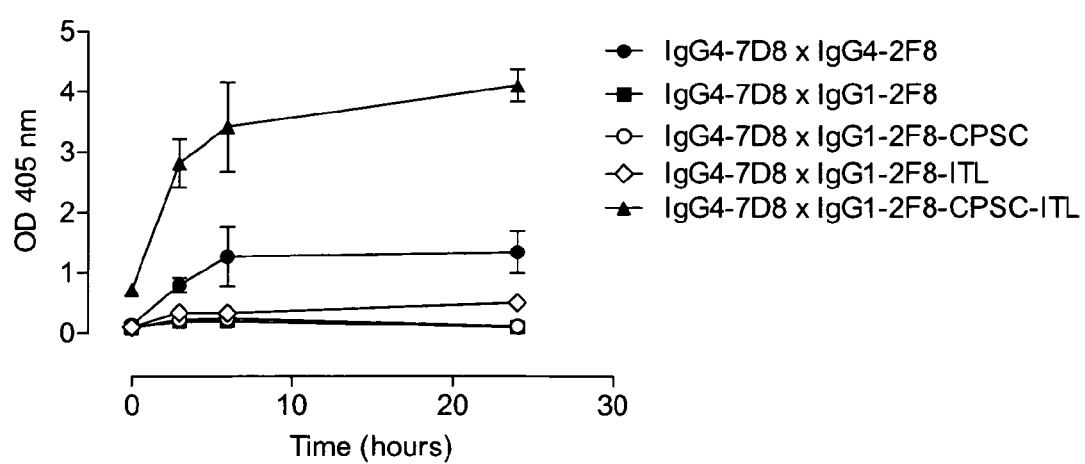
FIG. 3: Generation of bispecific antibodies using mutant human IgG1 engaged for Fab-arm exchange. The generation of bispecific antibodies after GSH-induced in vitro Fab-arm exchange between human CD20 (7D8) IgG4 antibody and the indicated human EGFR (2F8) IgG1 antibodies was determined by an ELISA. The presented graph shows average numbers of three independent Fab-arm exchange experiments, in which a total antibody concentration of 1 μg/mL was used for ELISA. Bispecific binding was higher after Fab-arm exchange between IgG1-2F8-CPSC-ITL and IgG4-7D8 than between two IgG4 antibodies. Combining IgG4-7D8 with either IgG1-2F8-CPSC or IgG1-2F8-ITL did not result in bispecific antibodies under the conditions used.

FIG. 3 confirms that introduction of a CPSC (SEQ ID NO: 5) hinge alone does not engage human IgG1-2F8 for GSH-induced Fab-arm exchange when combined with human IgG4-7D8. Also the introduction of the rhesus IgG4-specific CH3 interface amino acids (ITL) into human IgG1-2F8, while preserving the wild type IgG1 hinge, did not result in engagement for Fab-arm exchange when combined with human IgG4-7D8 under these conditions. In contrast, a variant human IgG1-2F8 backbone sequence that harbors both a CPSC (SEQ ID NO: 5) sequence in the hinge and the rhesus IgG4-specific CH3 interface amino acids (ITL) showed increased bispecific binding after GSH-induced Fab-arm exchange with human IgG4-7D8 compared to two human IgG4 antibodies. These data show that a CPSC (SEQ ID NO: 5)-containing hinge in combination with a CH3 domain containing I, T and L at positions 350, 370 and 405, respectively, is sufficient to engage human IgG1 for GSH-induced Fab-arm exchange and that the equilibrium of the exchange reaction is shifted towards the exchanged bispecific product when combined with human IgG4.

Example 10

Generation of Bispecific Antibodies by In Vivo Fab-Arm Exchange Between Human IgG4 and IgG1 or IgG4 Mutants To further identify the required characteristics for Fab-arm exchange engagement, human IgG4 and IgG1 variants were analyzed in vivo. Four female SCID mice (Charles River, Maastricht, The Netherlands) per group were i.v. injected with antibody mixtures, containing 600 g antibody (500 g 7D8+100 g 2F8) in a total volume of 300 μL. Blood samples were drawn from the saphenal vein at 3, 24, 48 and 72 hours after injection. Blood was collected in heparin-containing vials and centrifuged at 10,000 g for 5 min to separate plasma from cells. The generation of bispecific antibodies was followed by assessing CD20 and EGFR bispecific reactivity in an ELISA using serial diluted plasma samples in PBSTB as described in Example 7. Bispecific antibodies in plasma samples were quantified by non-linear regression curve-fitting (GraphPad Software, San Diego, Calif.) using an in vitro exchanged antibody mixture as reference.

Figure 4:
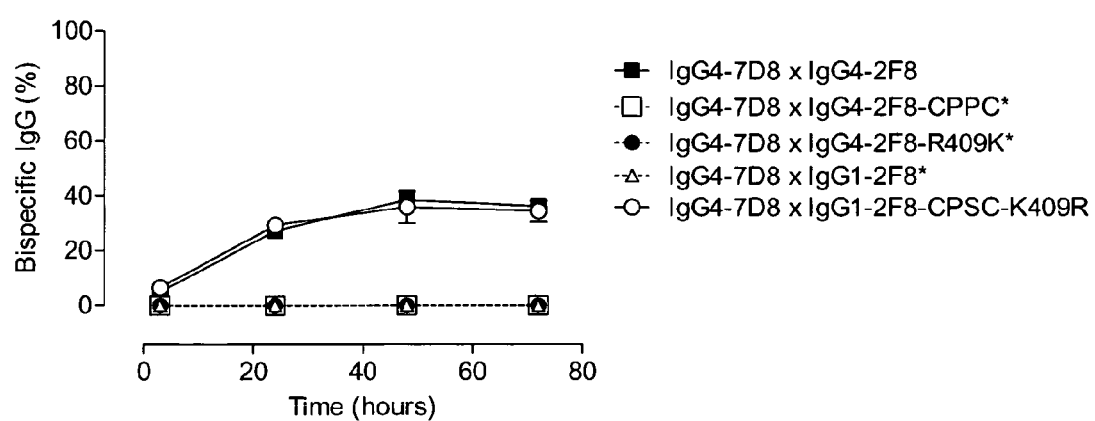
FIG. 4: Generation of bispecific antibodies by in vivo Fab-arm exchange of human IgG4 and mutant IgG1 antibodies. The generation of bispecific antibodies after in vivo Fab-arm exchange in immunodeficient mice between human CD20 (7D8) IgG4 and the indicated human EGFR (2F8) IgG1 and IgG4 mutant antibodies was determined by an ELISA. The presented graph shows average numbers (n=4). Bispecific reactivity is presented as the concentration bispecific antibodies relative to the total IgG concentration (percentage). Human IgG4 with a stabilized hinge (CPPC) or R409K mutation in the CH3 domain is not able to participate in Fab-arm exchange. IgG1 with both a CPSC sequence in the hinge and a K409R mutation in the CH3 domain is engaged for Fab-arm exchange. (*) Bispecific binding for the mixtures containing either IgG1-2F8, IgG4-2F8-CPPC or IgG4-2F8-R409K was below the detection limit and therefore arbitrarily set to zero.

FIG. 4 shows that human IgG4-2F8, in which either the hinge or the CH3 sequence is converted to the corresponding human IgG1 sequence (CPPC (SEQ ID NO: 4) or R409K, respectively), does not engage in Fab-arm exchange anymore in vivo. Vice versa, human IgG1, in which both the hinge region and the CH3 interface sequences are converted to the corresponding human IgG4 sequences (CPSC (SEQ ID NO: 5) and K409R), is able to participate in Fab-arm exchange in vivo. These data show that a CPSC (SEQ ID NO: 5)-containing hinge (S at position 228) in combination with a CH3 domain containing an arginine (R) at position 409 is enough to enable Fab-arm exchange by human IgG1 in vivo.

Example 11

Generation of Bispecific Antibodies by 2-MEA-Induced Fab-Arm Exchange: Bypass/Disruption of a Stabilized Hinge 2-Mercaptoethylamine.HCl (2-MEA) is a mild reducing agent that has been described to selectively cleave disulphide bonds in the hinge region of antibodies, while preserving the disulphide bonds between the heavy and light chains. Therefore, a concentration series of 2-MEA was tested for its ability to induce the generation of bispecific antibodies by Fab-arm exchange between two antibodies containing CPSC (SEQ ID NO: 5) or CPPC (SEQ ID NO: 4) hinge regions. The antibody mixtures, containing each antibody at a final concentration of 0.5 mg/mL, were incubated with a concentration series of 2-MEA (0, 0.5, 1.0, 2.0, 5.0, 7.0, 10.0, 15.0, 25.0 and 40.0 mM) in a total volume of 100 μL TE at 37° C. for 90 min. To stop the reduction reaction, the reducing agent 2-MEA was removed by desalting the samples using spin columns (Microcon centrifugal filters, 30k, Millipore) according to the manufacturer's recommendations. Bispecific binding was measured in an ELISA as described in Example 7.

Figure 5:
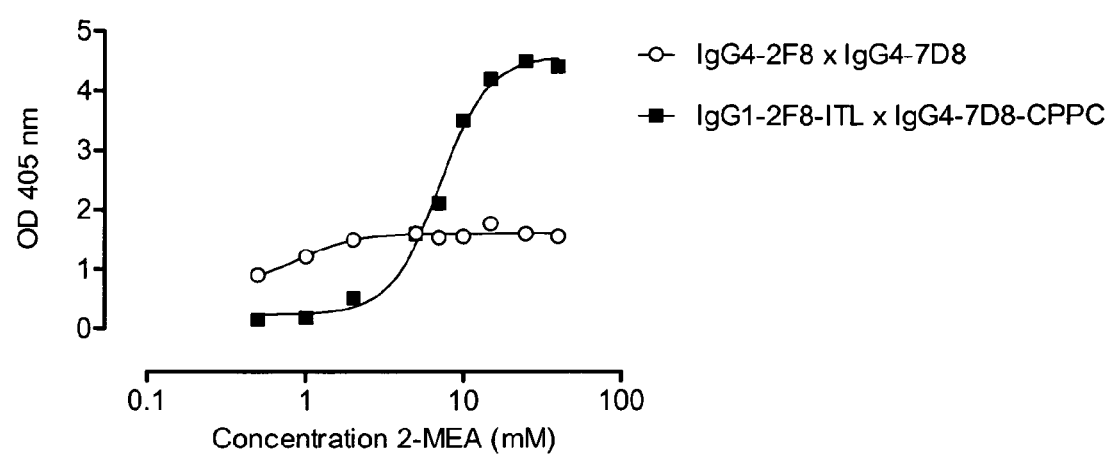
FIG. 5: Generation of bispecific antibodies using 2-mer-capto-ethylamine.HCl-(2-MEA-)induced Fab-arm exchange between human IgG1 and IgG4 antibodies. The generation of bispecific antibodies after 2-MEA-induced in vitro Fab-arm exchange between the indicated human EGFR (2F8) and CD20 (7D8) antibodies was determined by an ELISA. A concentration series of 0-40 mM 2-MEA was tested. The presented graph shows the result of the ELISA in which a total antibody concentration of 20 μg/mL was used. 2-MEA efficiently induced Fab-arm exchange, also between antibodies containing a stabilized hinge (CPPC). Concerning the CH3 domains, a combination of human IgG4×human IgG1 with the triple mutation T350I-K370T-F405L, resulted in higher levels of bispecific reactivity compared to two wild type IgG4 antibodies.

2-MEA-induced Fab-arm exchange was tested for the combination IgG4-2F8×IgG4-7D8, containing CPSC (SEQ ID NO: 5) hinge regions and known to participate in GSH-induced Fab-arm exchange, and for the combination IgG1-2F8-ITL×IgG4-7D8-CPPC (SEQ ID NO: 4), not participating in GSH-induced Fab-arm exchange due to the stabilized hinge regions (described in Example 9, FIG. 3). Surprisingly, 2-MEA was found to induce separation of light chains from heavy chains as determined by non-reducing SDS-PAGE (data not shown). Nonetheless, functional bispecific antibodies were generated as shown in FIG. 5. The maximal level of bispecific binding after Fab-arm exchange between wild type human IgG4-2F8 and IgG4-7D8 was reached at a concentration of 2.0 mM 2-MEA and was comparable to the level reached with 0.5 mM GSH as described in Example 9 (FIG. 3). However, 2-MEA was able to induce Fab-arm exchange between the human antibodies IgG1-2F8-ITL and IgG4-7D8-CPPC (SEQ ID NO: 4) (with stabilized hinge regions) in a dose-dependent manner. While little or no bispecific antibodies were formed at low 2-MEA concentrations, probably due to the presence of a CPPC (SEQ ID NO: 4) sequence in the hinge region of both antibodies, the generation of bispecific antibodies was very efficient at higher concentrations of 2-MEA. Maximal bispecific binding was reached at 25 mM 2-MEA and exceeded maximal binding after Fab-arm exchange between the two wild type IgG4 antibodies. These maximal binding levels were comparable to what is described in Example 9 (FIG. 3) for GSH treatment of the corresponding antibody with a CPSC (SEQ ID NO: 5) hinge (IgG1-2F8-CPSC-ITL) (SEQ ID NO: 5). As IgG1-2F8-ITL and IgG4-7D8-CPPC (SEQ ID NO: 4) both contain a CPPC (SEQ ID NO: 4) hinge, these data indicate that 2-MEA could bypass the requirement of a CPSC (SEQ ID NO: 5) hinge for in vitro Fab-arm exchange.

Example 12

Figure 6:
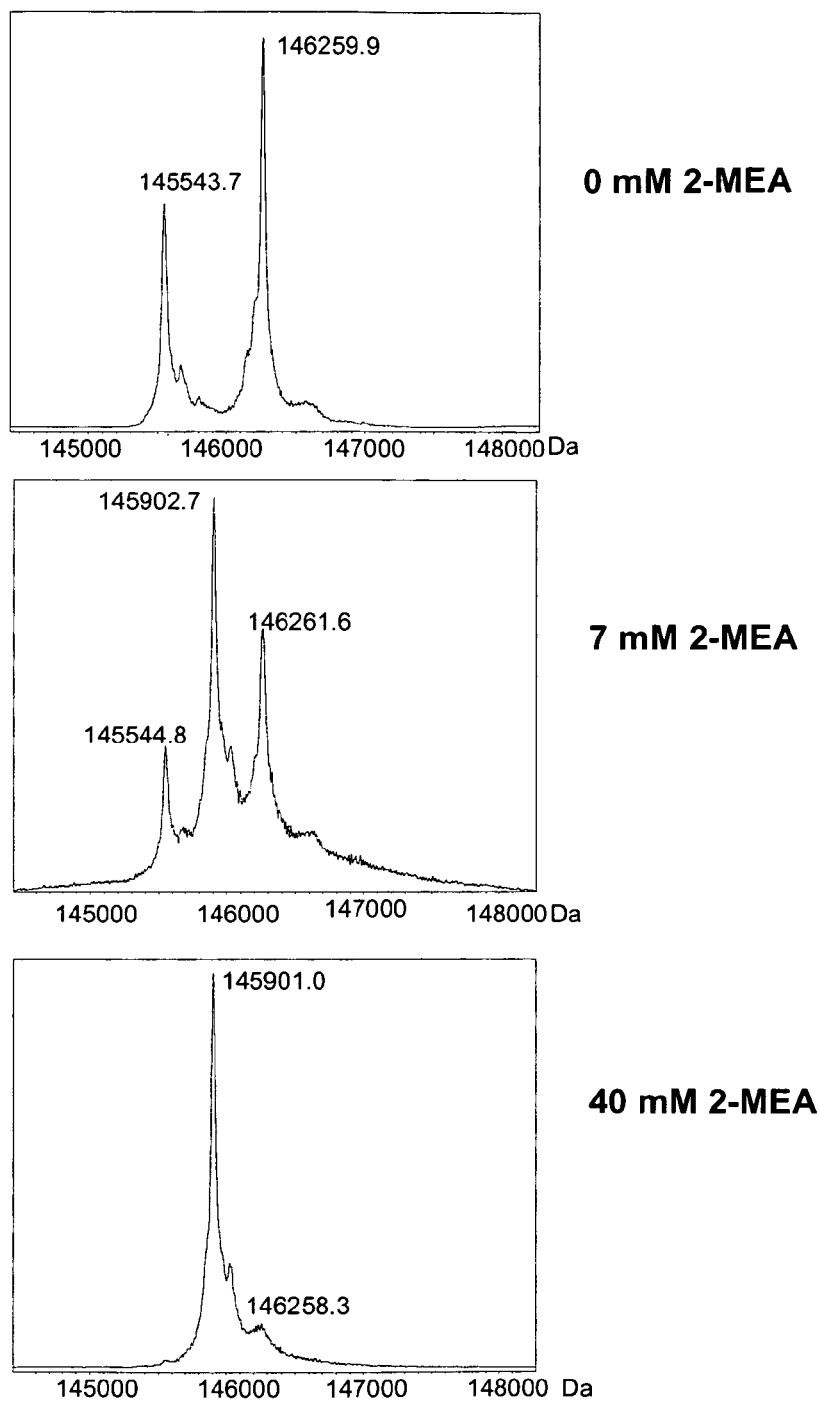
FIG. 6: Generation of bispecific antibodies using 2-MEA-induced Fab-arm exchange between human IgG1 and IgG4 antibodies.
The generation of bispecific antibodies after 2-MEA-induced in vitro Fab-arm exchange between the indicated human EGFR (2F8) and CD20 (7D8) antibodies was determined by mass spectrometry for all samples of the concentration series of 0-40 mM 2-MEA. (A) Representative examples of the mass spectrometry profiles for samples of Fab-arm exchange reactions between IgG1-2F8-ITL×IgG4-7D8-CPPC with 0 mM, 7 mM and 40 mM 2-MEA are shown. (B) After quantification of the mass spectrometry data, the percentage bispecific antibody was calculated and plotted against the concentration 2-MEA in the Fab-arm exchange reaction. IgG4-2F8×IgG4-7D8 resulted in ~50% bispecific antibody. IgG1-2F8-ITL×IgG4-7D8-CPPC resulted in ~95% bispecific antibody.
Figure 6:
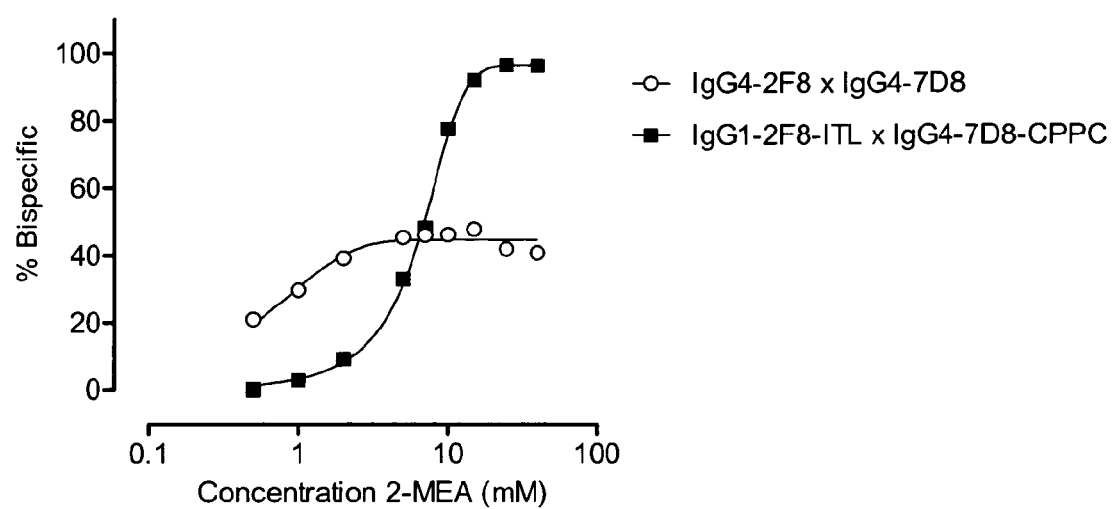

Mass Spectrometry to Follow the Generation of Bispecific Antibodies by 2-MEA-Induced Fab-Arm Exchange The generation of bispecific antibodies by 2-MEA-induced Fab-arm exchange is described in Example 11, where bispecific binding was shown by an ELISA (FIG. 5). To confirm that bispecific antibodies are formed, the samples were analyzed by electrospray ionization mass spectrometry (ESI-MS) to determine the molecular weights. First, samples were deglycosylated by incubating 200 g antibody overnight at 37° C. with 0.005 U N-Glycanase (cat. no. GKE-5006D; Prozyme) in 180 μL PBS. Samples were desalted on an Aquity UPLC™ (Waters, Milford, USA) with a BEH300 C18, 1.7 μm, 2.1×50 mm column at 60° C. and eluted with a gradient of a mixture of MQ water (Eluens A) and LC-MS grade acetonitrile (eluens B) (Biosolve, Valkenswaard, The Netherlands) containing 0.05% formic acid (Fluka Riedel-de Haen, Buchs, Germany). Time-of-flight electrospray ionization mass spectra were recorded on-line on a micrOTOF™ mass spectrometer (Bruker, Bremen, Germany) operating in the positive ion mode. Prior to analysis, a 500-4000 m/z scale was calibrated with ES tuning mix (Agilent Technologies, Santa Clara, USA). Mass spectra were deconvoluted by using Maximal Entropy that is provided with the DataAnalysis™ software v. 3.4 (Bruker, Bremen, Germany). Based on the molecular mass of the antibodies used for Fab-arm exchange in this experiment, the bispecific antibodies could be discriminated from the original antibodies (also described in Example 15, FIG. 9C for IgG1-2F8-ITL×IgG4-7D8-CPPC). For the peak of bispecific antibody, the area under the curve was determined and divided by the total area under the curves to calculate the percentage bispecific antibody in each sample. FIG. 6A shows three representative mass spectrometry profiles of the Fab-arm exchange reaction between IgG1-2F8-ITL and IgG4-7D8-CPPC with 0 mM 2-MEA (two peaks corresponding to the parental antibodies), 7 mM 2-MEA (three peaks corresponding to the parental and the bispecific antibodies), and 40 mM 2-MEA (one peak corresponding to the bispecific antibody). The homogenous peak of the bispecific product indicates that no light chain mispairing occurred, which would have resulted in subdivided peaks. The quantified data are presented in FIG. 6B and show that Fab-arm exchange between IgG1-2F8-ITL and IgG4-7D8-CPPC resulted in nearly 100% bispecific antibody. In contrast, Fab-arm exchange between wild type IgG4 antibodies resulted in less than 50% bispecific product. These data confirm the results from the bispecific binding ELISA described in Example 11 (FIG. 5).

Example 13

Stability of Bispecific Antibodies Generated by 2-MEA-Induced Fab-Arm Exchange

The stability of bispecific antibodies generated by 2-MEA-induced in vitro Fab-arm exchange was tested. Therefore, 2 µg of a bispecific sample generated from IgG1-2F8-ITL and IgG4-7D8-CPPC with 7.0 mM 2-MEA (as described in Example 11, FIG. 5) was used in a GSH-induced Fab-arm exchange reaction in the presence of a concentration series (0, 2, 20, 100 µg) irrelevant IgG4 (IgG4-MG against acetylcholine receptor), representing a 0, 1, 10, 50× excess of IgG4-MG compared to the 2 µg bispecific test sample. Fab-arm exchange in this reaction would result in loss of bispecific EGFR/CD20 binding. The conditions for the GSH reduction reaction were the same as described in Example 7 (24 h at 37° C. in 0.5 mL PBS/0.5 mM GSH). To stop the reduction reaction, 0.5 mL PBSTB was added to the reaction mixture. Bispecific binding was measured in an ELISA as described in Example 7. Bispecific binding after the GSH reduction reaction is presented relative to the bispecific binding measured in the starting material (control), which was set to 100%.

FIG. 7A shows that for the IgG1-2F8-ITL×IgG4-7D8-CPPC derived bispecific sample, EGFR/CD20 bispecific binding is not significantly changed after GSH-induced Fab-arm exchange in the presence of irrelevant IgG4. This indicates that the bispecific product is stable, i.e. does not participate in GSH-induced Fab-arm exchange. As a control, FIG. 7B shows that an IgG4-2F8×IgG4-7D8 derived sample shows diminished EGFR/CD20 bispecific binding after GSH-induced Fab-arm exchange in the presence of irrelevant IgG4, indicating that this product is not stable. These data show that the heterodimer consisting of a human IgG1 heavy chain containing the triple mutation T350I-K370T-F405L in the CH3 domain, and a human IgG4 heavy chain containing the S228P substitution resulting in a stabilized hinge (CPPC), is stable.

Example 14

In Vivo Analysis of the Pharmacokinetics and Stability of Bispecific Antibodies Generated by 2-MEA-Induced Fab-Arm Exchange The bispecific antibody generated by in vitro 2-MEA-induced Fab-arm exchange between IgG1-2F8-ITL×IgG4-7D8-CPPC was injected in SCID mice to analyze its stability (in vivo Fab-arm exchange) and pharmacokinetic properties (plasma clearance rate) in comparison to the parental antibodies IgG1-2F8-ITL and IgG4-7D8-CPPC. Three groups of mice (3 mice per group) were injected intravenously in the tail vein with 200 µL purified antibody: (1) 100 µg bispecific antibody; (2) 100 µg bispecific antibody+1,000 µg irrelevant IgG4 (natalizumab, anti-α4-integrin); (3) 50 µg IgG1-2F8-ITL+50 µg IgG4-7D8-CPPC. Blood samples (50-100 µL) were collected by cheek puncture at pre-determined time intervals after antibody administration (10 min, 3 h, 1, 2, 7, 14, 21 days). Blood was collected into heparin containing vials and centrifuged for 10 min at 14,000 g. Plasma was stored at −20° C. before further analysis.

Total IgG concentrations in the plasma samples were assayed by ELISA. The assay conditions of the succeeding steps were the same as for the ELISA described in Example 7. Specific compounds used for total IgG measurement were the following: coat with 2 µg/mL mouse anti-human IgG (clone MH16-1; CLB; cat. no. M1268); serum samples dilutions (1:500 and 1:2,500 for groups 1 and 3) and (1:2,500 and 1:10,000 for group 2); conjugate: HRP-conjugated goat anti-human IgG (clone 11H; Jackson; cat. no. 109-035-098; 1:10, 000). The presence of bispecific antibodies in the plasma samples was assayed and quantified by CD20 and EGFR bispecific reactivity in an ELISA as described in Example 10.

FIG. 8A shows total antibody plasma concentrations. The shape of the plasma clearance curves was identical in all groups, indicating that the plasma clearance of the bispecific antibody was the same as for the parental antibodies IgG1-2F8-ITL and IgG4-7D8-CPPC over the analyzed time interval. FIG. 8B shows the plasma concentrations of bispecific antibodies over time. The addition of a 10-fold excess irrelevant IgG4 to the bispecific antibody did not affect bispecific antibody concentrations, indicating that no Fab-arm exchange occurred in vivo. After injection of the parental antibodies (IgG1-2F8-ITL+IgG4-7D8-CPPC), no bispecific antibodies were detectable in the plasma, confirming that these antibodies do not participate in Fab-arm exchange in vivo. These data indicate that the bispecific antibody product, generated by in vitro 2-MEA-induced Fab-arm exchange between IgG1-2F8-ITL×IgG4-7D8-CPPC, was stable in vivo (no Fab-arm exchange) and showed comparable pharmacokinetic properties (plasma clearance rate) as the parental monovalent antibodies.

Example 15

Purity of the Bispecific Antibody Generated by 2-MEA-Induced Fab-Arm Exchange Between Two Antibodies A batch of bispecific antibody, generated by 2-MEA-induced Fab-arm exchange between human IgG1-2F8-ITL×IgG4-7D8-CPPC, was purified on a PD-10 desalting column (cat. no. 17-0851-01; GE Healthcare). Next, the purity of the bispecific product was analyzed by sodium dodecyl sulfate polyacrylamide gelelectrophoresis (SDS-PAGE), high performance size exclusion chromatography (HP-SEC) and mass spectrometry. The functionality of the generated bispecific antibody was confirmed by bispecific binding in an ELISA (data not shown).

Figure 9A:
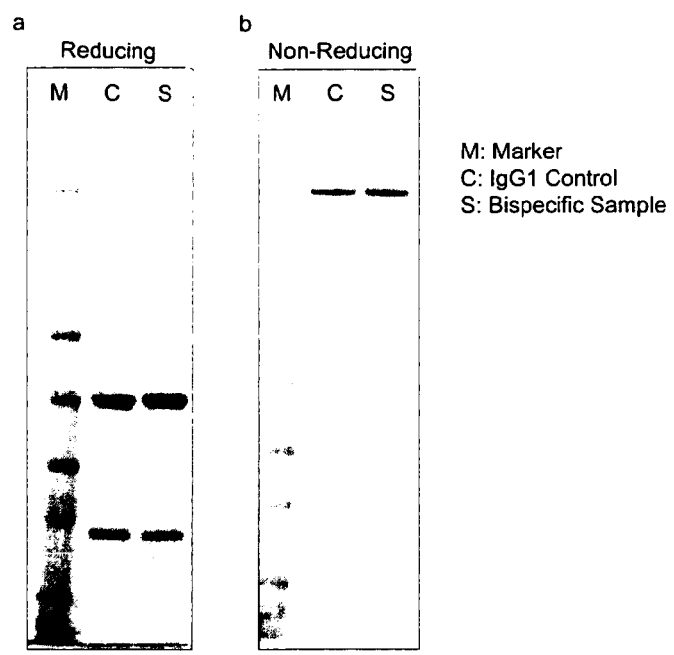
FIG. 9: Purity of bispecific antibody generated by Fab-arm exchange between human IgG1-2F8 and IgG4-7D8-CPPC. (A) Reducing SDS-PAGE (a) shows bands of the heavy and light chains for both the bispecific sample and the IgG1 control sample. Non-reducing SDS-PAGE (b). (B) The peak results from the HP-SEC analysis shows that >98% of the bispecific sample is homogenous, and practically no antibody aggregates were detectable. (C) Mass spectrometry shows that Fab-arm exchange resulted in approximately 100% bispecific product.
Figure 9B:
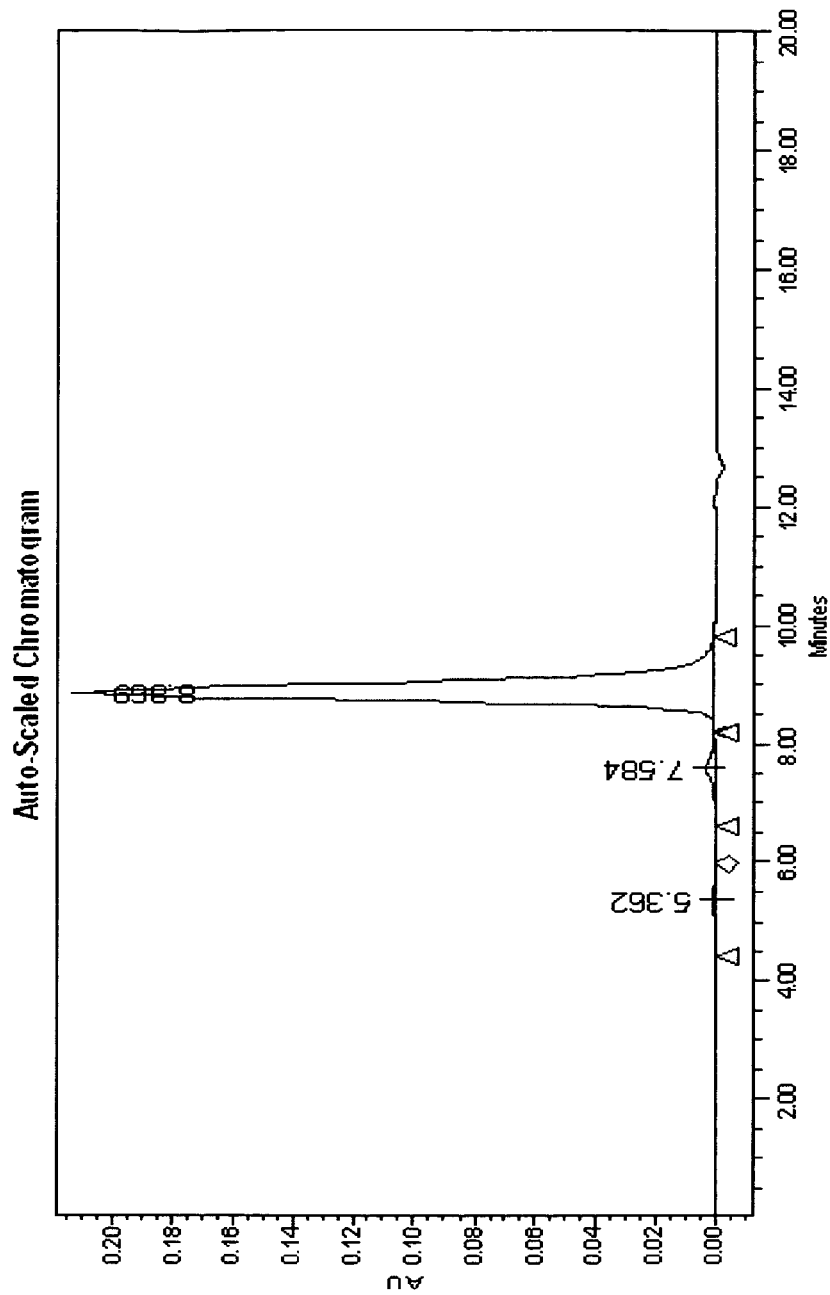

SDS-PAGE was performed under reducing and non-reducing conditions on 4-12% NuPAGE Bis-Tris gels (Invitrogen, Breda, The Netherlands) using a modified Laemli method (Laemli 1970 Nature 227(5259): 680-5), where the samples were run at neutral pH. The SDS-PAGE gels were stained with Coomassie and digitally imaged using the GeneGenius (Synoptics, Cambridge, UK). FIG. 9A shows that the antibody sample after Fab-arm exchange consists of intact IgG, with a trace of half molecules (H1L1) detectable on the non-reduced gel (FIG. 9A-b).

HP-SEC fractionation was performed using a Waters Alliance 2695 separation unit (Waters, Etten-Leur, The Netherlands) connected to a TSK HP-SEC column (G3000SW$_{xi}$; Toso Biosciences, via Omnilabo, Breda, The Netherlands) and a Waters 2487 dual λ absorbance detector (Waters). The samples were run at 1 mL/min. Results were processed using Empower software version 2002 and expressed per peak as percentage of total peak height. FIG. 9B shows that >98% of the sample consists of intact IgG, with practically no aggregates formed.

Figure 9C:
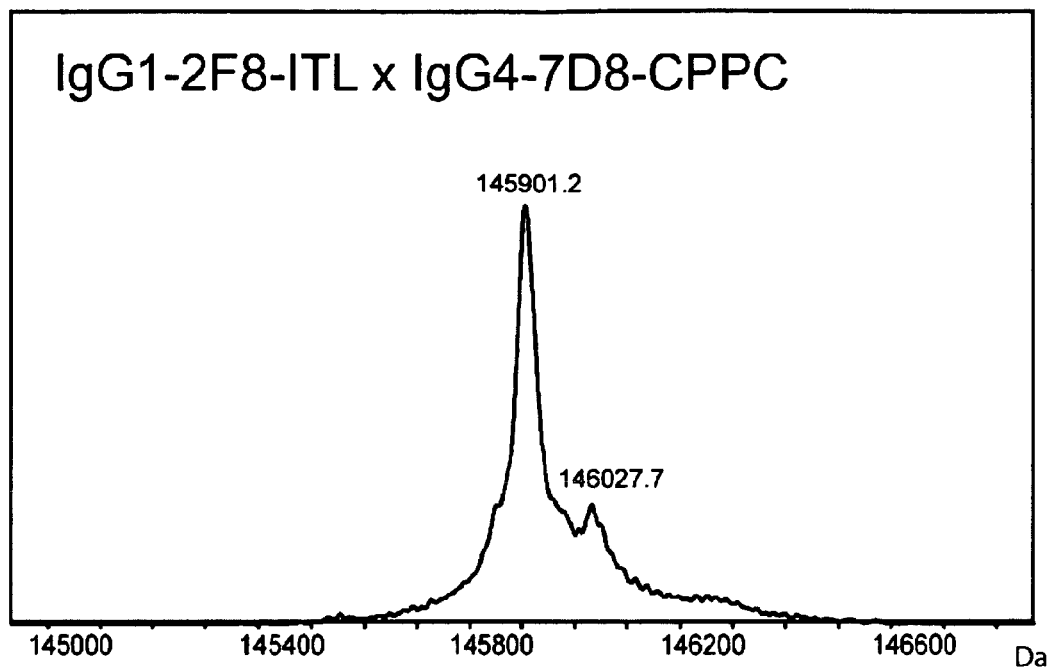

Mass spectrometry was performed as described in Example 12. FIG. 9C shows the mass spectrometry profiles of the starting materials IgG1-2F8-ITL and IgG4-7D8-CPPC and the bispecific product generated by Fab-arm exchange between IgG1-2F8-ITL×IgG4-7D8-CPPC. The product in the Fab-arm exchanged sample is 145,901 kDa, which perfectly matches with the bispecific product derived from IgG1-2F8-ITL (146,259.5/2=73,130)+IgG4-7D8-CPPC (145,542.0/2=72,771). Moreover, the bispecific antibody product showed a homogenous peak, indicating that no light chain mispairing occurred, which would have resulted in subdivided peaks. These data show that Fab-arm exchange resulted in 100% bispecific antibody. The small peaks detected in addition to the main peak (K0) of the IgG4-7D8-CPPC and bispecific sample can be attributed to the presence of one (K1) or two (K2) C-terminal lysines.

These data show that a ~100% functional bispecific antibody sample was generated by 2-MEA-induced Fab-arm exchange between IgG1-2F8-ITL×IgG4-7D8-CPPC.

Example 16

Unraveling the Requirement of the T350I, K370T and F405L Substitutions for Fab-Arm Exchange Engagement of Human IgG1

To further identify the determinants in the IgG1 CH3 domain that are required for IgG1 to be engaged in Fab-arm exchange, IgG1 containing the triple mutation T350I-K370T-F405L (ITL) was compared to the double mutants T350I-K370T (IT), T350I-F405L (IL) and K370T-F405L (TL). Also the single mutant F405L (L) was tested. 2-MEA was used as a reductant to induce in vitro Fab-arm exchange (50 µg of each antibody in 100 µL PBS/25 mM 2-MEA for 90 min at 37° C.). For the single mutant F405L antibody, unpurified antibody from supernatant of a transient transfection was used after buffer-exchange to PBS using Amicon Ultra centrifugal devices (30 k, Millipore, cat. no. UFC803096). To stop the reduction reaction, the reducing agent 2-MEA was removed by desalting the samples using spin columns as described in Example 11. The generation of bispecific antibodies was determined by bispecific binding measured in an ELISA as described in Example 7.

The triple (ITL), double mutations (IT, IL and TL) and single mutation (L) were introduced in IgG1-2F8. These mutants were combined with IgG4-7D8, containing a CPSC hinge (wild type) or a stabilized hinge (IgG4-7D8-CPPC), for Fab-arm exchange using 25 mM 2-MEA for 90 min at 37° C. FIG. 10A-B shows that the IgG1-2F8-IL and -TL mutants showed Fab-arm exchange to the same level as the triple mutant ITL, irrespective of the combined IgG4-7D8 (CPSC or CPPC hinge). In contrast, no bispecific binding was found for the combination with the IgG1-2F8-IT mutant. FIG. 10C shows that also the IgG1-2F8-F405L mutant showed Fab-arm exchange, irrespective of the combined IgG4-7D8 (CPSC or CPPC hinge). These data indicate that the F405L mutation is sufficient to engage human IgG1 for Fab-arm exchange under the conditions mentioned above.

Example 17

Generation of Bispecific Antibodies by 2-MEA-Induced Fab-Arm Exchange at Different Temperatures The ability of 2-MEA to induce the generation of bispecific antibodies by Fab-arm exchange between two different antibodies, was tested at different temperatures. The Fab-arm exchange reactions were started by incubating 160 g human IgG1-2F8-ITL with 160 µg IgG4-7D8-CPPC in 320 µl PBS/25 mM 2-MEA (final concentration of 0.5 mg/mL for each antibody) at either 0° C., 20° C. (RT) or 37° C. From these reactions, 20 L samples were taken at different time points (0, 2.5, 5, 10, 15, 30, 45, 60, 75, 90, 120, 150, 180 and 240 min). 20 L PBS was added to each sample before the reducing agent 2-MEA was removed by desalting the samples using a Zeba 96-well spin desalting plate (7 k, cat#89808 Thermo Fisher Scientific), according to the manufacturer's recommendations. The total antibody concentrations were determined by measuring absorbance at 280 nm wavelength using a Nanodrop ND-1000 spectrophotometer (Isogen Life Science, Maarssen, The Netherlands). Dilution series of the antibody samples (total antibody concentration 0-µg/mL in 25-fold dilutions) were used in an ELISA to measure bispecific binding as described in Example 7.

Figure 11:
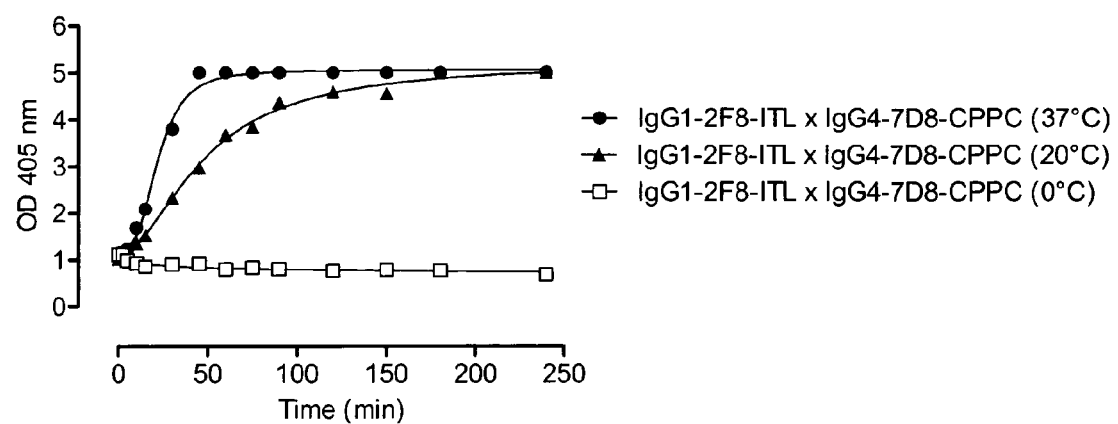
FIG. 11: Generation of bispecific antibodies using 2-MEA-induced Fab-arm exchange at different temperatures. The generation of bispecific antibodies by combining the indicated human EGFR (2F8) and CD20 (7D8) antibodies in 2-MEA-induced in vitro Fab-arm exchange reactions at 0° C., 20° C. and 37° C. was followed in time by an ELISA. Bispecific binding was most efficient at 37° C., and slower at 20° C. At 0° C., no generation of bispecific binding was measured.

FIG. 11 shows that the generation of bispecific antibodies by 2-MEA-induced Fab-arm exchange between human IgG1-2F8-ITL and IgG4-7D8-CPPC was found to be most efficient at 37° C., with maximal bispecific binding reached after 45 min. At room temperature, the generation of bispecific antibodies was slower, reaching maximal bispecific binding after 240 min. At 0° C., no generation of bispecific binding was observed during the analyzed time course.

Example 18

Analysis of Different Reducing Agents for their Ability to Induce the Generation of Bispecific Antibodies by In Vitro Fab-Arm Exchange It has been shown above that 0.5 mM GSH can induce in vitro Fab-arm exchange between human IgG4 and IgG1-CPSC-ITL, but not between human IgG4 and IgG1-ITL containing a stable hinge (FIG. 3). In addition, 2-MEA was found to be able to induce Fab-arm exchange between antibodies with stabilized hinge regions, such as IgG1-ITL×IgG4-CPPC (FIG. 5). To test whether other concentrations of GSH or 2-MEA or other reducing agents are capable of inducing in vitro Fab-arm exchange between two different antibodies, concentration series of 2-MEA, GSH and DTT (dithiothreitol) were tested. Therefore, combinations of 10 µg human IgG1-2F8-ITL and 10 µg IgG4-7D8-CPPC in 20 µl PBS (final concentration of 0.5 mg/mL for each antibody) were incubated at 37° C. with concentration series of the different reducing agents (0.0, 0.04, 0.1, 0.2, 0.5, 1.0, 2.5, 5.0, 12.5, 25.0 and 50.0 mM). After 90 min, 20 µL PBS was added to each sample and the reducing agent was removed by desalting the samples using spin desalting plate as described in Example 17. Total antibody concentrations were determined as described in Example 17. Dilution series of the antibody samples (total antibody concentration 0-μg/mL in 3-fold dilutions) were used in an ELISA to measure bispecific binding as described in Example 7.

Figure 12:
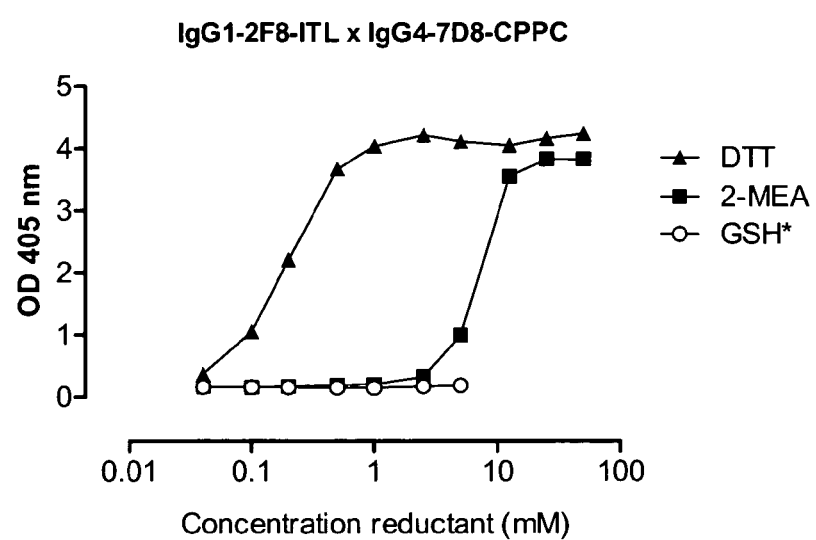
FIG. 12: Generation of bispecific antibodies by in vitro Fab-arm exchange induced by different reducing agents. An ELISA was used to measure the generation of bispecific antibodies by combining human IgG1-2F8-ITL and IgG4-7D8-CPPC in a reduction reaction with concentration series of the indicated reducing agents. Bispecific binding was measured after the reactions with DTT (maximum obtained at 2.5 mM DTT) and 2-MEA (maximum obtained at 25 mM 2-MEA), but not with GSH. (*) Data for GSH concentration >10 mM were excluded due to the formation of antibody aggregates.

FIG. 12 confirms that 2-MEA induces maximal bispecific binding at a concentration of 25 mM 2-MEA. DTT was found to be very effective in the generation of bispecific antibodies with maximal bispecific binding reached at 2.5 mM DTT. GSH concentrations in the range 0-5 mM were not able to induce the generation of bispecific antibodies by Fab-arm exchange between the IgG1-ITL and IgG4-CPPC antibodies, both containing stabilized hinge regions. Higher GSH concentrations (12.5-50 mM) resulted in the formation of antibody aggregates, as was determined by non-reducing SDS-PAGE (data not shown). Therefore, these samples were excluded from the analysis. These data show that the generation of bispecific antibodies by Fab-arm exchange between two different antibodies can be induced by different reducing agents.

Example 19

Determinants at the IgG1 409 Position for Engagement in 2-MEA-Induced Fab-Arm Exchange in Combination with IgG1-ITL 2-MEA can induce Fab-arm exchange between human IgG1-ITL and IgG4-CPPC, as described in Example 11 (FIG. 5). The CH3 interface residues of human IgG1 and IgG4 differ at position 409 only: lysine (K) in IgG1 and arginine (R) in IgG4 (described in Example 8, FIG. 2). Therefore, it was tested whether substitution of lysine at position 409 by arginine or any other amino acid (K409X) could enable IgG1 to engage in 2-MEA-induced Fab-arm exchange with IgG1-ITL. Combinations of 10 μg human IgG1-2F8-ITL and 10 μg IgG1-7D8-K409X in 20 μl PBS/25 mM 2-MEA (final concentration of 0.5 mg/mL for each antibody) were incubated for 90 min at 37° C. Unpurified antibodies from supernatants of transient transfections were used after buffer-exchange to PBS using Amicon Ultra centrifugal devices (30 k, Millipore, cat. no. UFC803096). After the Fab-arm exchange reaction, 20 μL PBS was added to each sample and the reducing agent was removed by desalting the samples using spin desalting plate as described in Example 17. Dilution series of the antibody samples (total antibody concentration 0-20 μg/mL in 3-fold dilutions) were used in an ELISA to measure bispecific binding as described in Example 7.

FIG. 13A shows the results of bispecific binding upon 2-MEA induced Fab-arm exchange between IgG1-2F8-ITL× IgG1-7D8-K409X. In FIG. 13B, the exchange is presented as bispecific binding relative to a purified batch of bispecific antibody derived from a 2-MEA-induced Fab-arm-exchange between IgG1-2F8-ITL and IgG4-7D8-CPPC, which was set to 100%. These data were also scored as (−) no Fab-arm exchange, (+/−) low, (+) intermediate or (++) high Fab-arm exchange, as presented in Table 1. No Fab-arm exchange (−) was found when the 409 position in IgG1-7D8 was K (=wild type IgG1), L or M. Fab-arm exchange was found to be intermediate (+) when the 409 position in IgG1-7D8 was F, I, N or Y and high (++) when the 409 position in IgG1-7D8 was A, D, E, G, H, Q, R, S, T, V or W.

TABLE 1

2-MEA-induced Fab-arm exchange between IgG1-2F8-ITL and IgG1-7D8-K409X mutants. The generation of bispecific antibodies after 2-MEA-induced in vitro Fab-arm exchange between IgG1-2F8-ITL and IgG1-7D8-K409X mutants was determined by a sandwich ELISA.

| IgG1-7D8-K409X | Fab-arm exchange x IgG1-2F8-ITL |
|---|---|
| A | ++ |
| D | ++ |
| E | ++ |
| F | + |
| G | ++ |
| H | ++ |
| I | + |
| K | − |
| L | − |
| M | − |
| N | + |
| Q | ++ |
| R | ++ |
| S | ++ |
| T | ++ |
| V | ++ |
| W | ++ |
| Y | + |

(−) no, (+/−) low, (+) intermediate, (++) high Fab-arm exchange.

Example 20

Antibody Deglycosylation does not Influence the Generation of Bispecific Antibodies by 2-MEA-Induced Fab-Arm Exchange IgG4-7D8 and IgG4-7D8-CPPC samples were deglycosylated by incubating 200 g antibody overnight at 37° C. with 0.005 U N-Glycanase (cat. no. GKE-5006D; Prozyme) in 180 L PBS. These samples were used directly in a Fab-arm exchange reaction. Fab-arm exchange was performed by incubating 50 μg of each antibody in 100 μl PBS/25 mM 2-MEA (final concentration of 0.5 mg/mL for each antibody) for 90 min at 37° C. The reducing agent 2-MEA was removed by desalting the samples using spin columns as described in Example 11. Dilution series of the antibody samples (total antibody concentration 0-20 μg/mL in 3-fold dilutions) were used in a sandwich ELISA to measure bispecific binding as described in Example 7.

Figure 14:
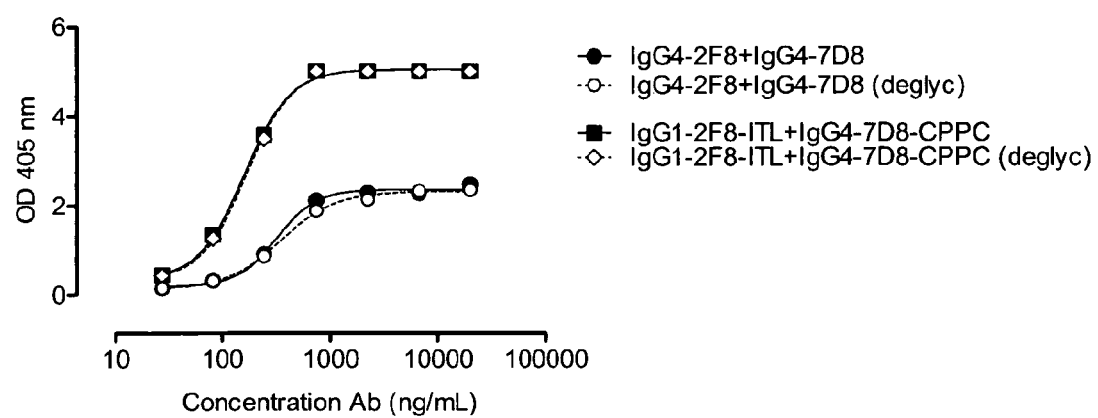
FIG. 14: Antibody deglycosylation does not affect the generation of bispecific antibodies by 2-MEA-induced Fab-arm exchange. The generation of bispecific antibodies after 2-MEA-induced in vitro Fab-arm exchange between the indicated EGFR (2F8) and CD20 (7D8) antibodies was determined by an ELISA. Exchange with the 7D8 antibodies was compared with their enzymatically deglycosylated variants. A concentration series (total antibody) of 0-20 μg/mL was analyzed in the ELISA. Fab-arm exchange reactions involving deglycosylated (deglyc) antibodies showed identical bispecific binding curves as the glycosylated variants from which they were derived.

Mass spectrometry analysis showed that the deglycosylation reaction resulted in 100% deglycosylated antibody product (data not shown). FIG. 14 shows that Fab-arm exchange involving deglycosylated antibodies did not differ from Fab-arm exchange with the corresponding glycosylated antibodies (IgG4-2F8×IgG4-7D8-deglycosylated versus IgG4-2F8× IgG4-7D8 and IgG1-2F8-ITL×IgG4-7D8-CPPC-deglycosylated versus IgG1-2F8-ITL×IgG4-7D8-CPPC). These data indicate that deglycosylation did not affect the generation of bispecific antibodies by 2-MEA-induced Fab-arm exchange.

Example 21

Quantification of the Non-Covalent CH3-CH3 Interaction

The strength of the interactions at the CH3 interface should be such that it is possible that both heavy chains in the parental antibodies dissociate in the Fab-arm exchange reaction and that they subsequently associate in the heterodimerization reaction. Therefore, the correlation between the ability to participate in Fab-arm exchange and the strength of the non-covalent CH3-CH3 interaction (dissociation constant, $K_D$) was analyzed. GSH-induced Fab-arm exchange was performed as described in Example 9 (0.5 mM GSH at 37° C.) for the following combinations of human antibodies:

IgG1-2F8×IgG1-7D8

IgG1-2F8-CPSC×IgG1-7D8-CPSC

IgG1-2F8-CPSC-T350I×IgG1-CPSC-7D8-T350I

IgG1-2F8-CPSC-K370T×IgG1-7D8-CPSC-K370T

IgG1-2F8-CPSC-ITL×IgG1-7D8-CPSC-ITL

IgG1-2F8-CPSC-K409R×IgG1-7D8-CPSC-K409R

IgG4-2F8×IgG4-7D8

IgG4-2F8-R409K×IgG4-7D8-R409K

IgG4-2F8-R409A×IgG4-7D8-R409A

IgG4-2F8-R409L×IgG4-7D8-R409L

IgG4-2F8-R409M×IgG4-7D8-R409M

IgG4-2F8-R409T×IgG4-7D8-R409T

IgG4-2F8-R409W×IgG4-7D8-R409W

IgG4-2F8-F405A×IgG4-7D8-F405A

IgG4-2F8-F405L×IgG4-7D8-F405L

IgG4-2F8-Y349D×IgG4-7D8-Y349D

IgG4-2F8-L351K×IgG4-7D8-L351K

IgG4-2F8-E357T×IgG4-7D8-E357T

IgG4-2F8-S364D×IgG4-7D8-S364D

IgG4-2F8-K370Q×IgG4-7D8-K370Q

IgG4-2F8-K370E×IgG4-7D8-K370E

The generation of bispecific antibodies was measured by determination of bispecific binding in a sandwich ELISA as described in Example 7. FIGS. 15A/B/C show the results of the bispecific binding after the Fab-arm exchange reaction.

To measure the effect of the above mentioned CH3 mutations on the strength of the CH3-CH3 interaction, fragments composed of only the CH2-CH3 domains were made. The lack of a hinge region in these fragments prevented covalent inter-heavy chain disulfide bonds. The fragments were analyzed by native mass spectrometry. Samples were buffer-exchanged to 100 mM ammonium acetate pH 7, using 10 kDa MWCO spin-filter columns. Aliquots (~1 µL) of serial diluted samples (20 µM-25 nM; monomer equivalent) were loaded into gold-plated borosilicate capillaries for analysis on a LCT mass spectrometer (Waters). The monomer signal, $M_s$, was defined as the area of the monomer peaks as a fraction of the area of all peaks in the spectrum ($M_s/(M_s+D_s)$ where $D_s$=the dimer signal). The concentration of monomer at equilibrium, $[M]_{eq}$, was defined as $M_s \cdot [M]_0$ where $[M]_0$ is the overall protein concentration in terms of monomer. The dimer concentration at equilibrium, $[D]_{eq}$, was defined as $([M]_0-[M]_{eq})/2$. The $K_D$, was then extracted from the gradient of a plot of $[D]_{eq}$ versus $[M]_{eq}^2$. The $K_D$ of the non-covalent CH3-CH3 interactions is presented in Table 2.

The correlation between the ability to engage in Fab-arm exchange and the strength of the non-covalent CH3-CH3 interactions was analyzed. FIGS. 15D/E show the percentage bispecific binding after Fab-arm exchange plotted against the measured $K_D$ of the corresponding CH2-CH3 fragment (FIG. 15D for IgG1; FIG. 15E for IgG4). These data suggest that under the tested conditions there is a specific range of apparent $K_D$ values of the CH3-CH3 interaction that allows efficient Fab-arm

TABLE 2

| The $K_D$ of the non-covalent CH3—CH3 interactions | | |
|---|---|---|
| CH2—CH3 construct | $K_D$ (M) | fold-difference* |
| G1 | $3.0 \times 10^{-9}$ | 1.0000 |
| G1-T350I | $7.0 \times 10^{-9}$ | 0.4000 |
| G1-K370T | $4.5 \times 10^{-8}$ | 0.0700 |
| G1-ITL | $1.0 \times 10^{-6}$ | 0.0030 |
| G1-K409R | $1.1 \times 10^{-7}$ | 0.0300 |
| G4 | $4.8 \times 10^{-8}$ | 1.0000 |
| G4-R409K | $8.0 \times 10^{-9}$ | 6.0000 |
| G4-R409A | $1.6 \times 10^{-7}$ | 0.3000 |
| G4-R409L | $1.5 \times 10^{-8}$ | 3.2000 |
| G4-R409M | $3.0 \times 10^{-9}$ | 16.0000 |
| G4-R409T | $7.2 \times 10^{-7}$ | 0.0700 |
| G4-R409W | $3.4 \times 10^{-5}$ | 0.0014 |
| G4-F405A | $1.9 \times 10^{-5}$ | 0.0025 |
| G4-F405L | $2.5 \times 10^{-5}$ | 0.0019 |
| G4-L351K | $7.4 \times 10^{-7}$ | 0.0600 |
| G4-E357T | $4.1 \times 10^{-5}$ | 0.0012 |
| G4-S364D | $4.7 \times 10^{-8}$ | 1.0200 |
| G4-K370Q | $1.1 \times 10^{-8}$ | 4.3000 |
| G4-K370E | $2.0 \times 10^{-9}$ | 24.0000 |

*Compared to the corresponding CH2—CH3 fragments of wild type IgG1 or IgG4

Example 22

Analysis of Different Reductantia for their Ability to Induce the Generation of Bispecific Antibodies by In Vitro Fab-Arm-Exchange Between IgG1-2F8-F405L and IgG1-7D8-K409R 2-MEA and DTT were found to induce in vitro Fab-arm-exchange between human IgG1-ITL and IgG4-CPPC (FIG. 12). It was tested whether these reductantia can also induce in vitro Fab-arm-exchange between human IgG1-2F8-F405L and IgG1-7D8-K409R. Concentration series of 2-MEA, DTT, GSH and TCEP (tris(2-carboxyethyl)phosphine) were tested. Fab-arm-exchange was performed as described in Example 18. The tested concentration series of the different reducing agents were as follows: 0.0, 0.04, 0.1, 0.2, 0.5, 1.0, 5.0, 25.0, 50.0 mM 2-MEA, GSH, DTT or TCEP.

Figure 17:
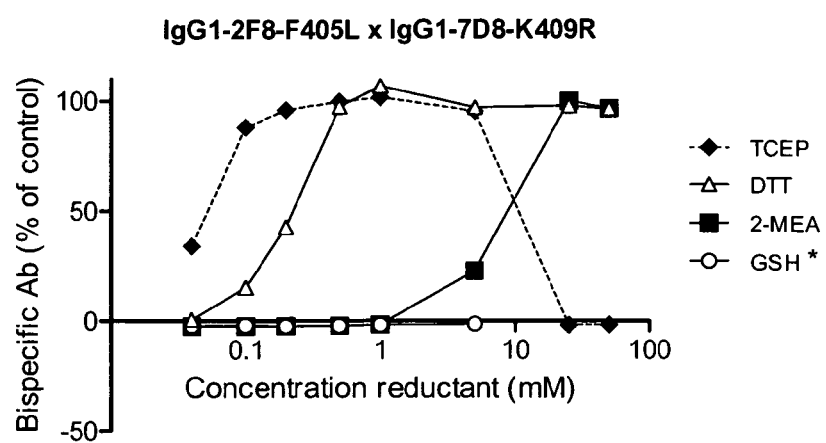
FIG. 17: Generation of bispecific antibodies by in vitro Fab-arm-exchange induced by different reducing agents. An ELISA was used to measure the generation of bispecific antibodies by combining human IgG1-2F8-F405L and IgG1-7D8-K409R in a reduction reaction with concentration series of the indicated reducing agents. Measured OD values were normalized to the signal of a bispecific control sample derived from 2-MEA-induced Fab-arm-exchange between IgG1-2F8-ITL×IgG4-7D8-CPPC, which was set to 100%. Maximal bispecific binding was measured after the reactions with DTT in the concentration range 0.5-50 mM, 2-MEA in the concentration range ≥25-50 mM and tris(2-carboxyethyl) phosphine (TCEP) in the concentration range 0.5-5.0 mM, but not with GSH. (*) Data for GSH concentration ≥25 mM were excluded due to the formation of antibody aggregates.

FIG. 17 confirms that 2-MEA induces maximal Fab-arm-exchange at a concentration of 25 mM 2-MEA, which persisted at the higher concentration of 50.0 mM 2-MEA. DTT was found to be very effective in the generation of bispecific antibodies with maximal Fab-arm-exchange reached at 0.5 mM DDT, which also persisted over higher concentrations of DTT (1.0-50.0 mM). Also TCEP was found to be very effective in the generation of bispecific antibodies with maximal Fab-arm-exchange reached at 0.5 mM. At a concentration ≥25.0 mM, Fab-arm-exchange by TCEP was disturbed. GSH concentrations in the range 0.0-5.0 mM were not able to induce the generation of bispecific antibodies by Fab-arm-exchange. Higher GSH concentrations (25.0-50.0 mM) resulted in the formation of antibody aggregates (data not shown). Therefore, these samples were excluded from the analysis. These data show that the generation of bispecific antibodies by Fab-arm-exchange between two different antibodies can be induced by different reducing agents.

Example 23

Generation of Bispecific Antibodies by 2-MEA-Induced Fab-Arm-Exchange Between IgG1-2F8-F405L and IgG1-7D8-K409R To confirm the formation of bispecific antibodies by 2-MEA-induced Fab-arm exchange between human IgG1-

2F8-F405L and IgG1-7D8-K409R, the molecular weights of samples from the Fab-arm-exchange reactions with a concentration series of 2-MEA were determined by ESI-MS. The tested concentration series was as follows: 0.0, 0.5, 1.0, 2.0, 5.0, 7.0, 10.0, 15.0, 25.0 and 40.0 mM 2-MEA. Fab-arm-exchange (in PBS) and sandwich ELISA were performed as described in Example 11. ESI-MS was performed as described in Example 12.

FIG. 18A shows that 2-MEA induced Fab-arm-exchange between IgG1-2F8-F405L and IgG1-7D8-K409R in a dose-dependent manner, efficiently leading to the generation of bispecific antibodies with a maximal level of bispecific binding at a concentration of 15.0 mM 2-MEA. The quantified ESI-MS data are presented in FIG. 18B and show that Fab-arm-exchange between IgG1-2F8-F405L and IgG1-7D8-K409R resulted in nearly 100% bispecific antibody, confirming the results from the bispecific-binding ELISA.

Example 24

Purity of the Bispecific Antibody Generated by 2-MEA-Induced Fab-Arm-Exchange Between Human IgG1-2F8-F405L×IgG1-7D8-K409R A batch of bispecific antibody, generated by 2-MEA-induced Fab-arm-exchange between human IgG1-2F8-F405L× IgG1-7D8-K409R, was purified using a PD-10 desalting column (cat. no. 17-0851-01; GE Healthcare). Next, the purity of the bispecific product was analyzed by mass spectrometry as described in Example 12.

Figure 19:
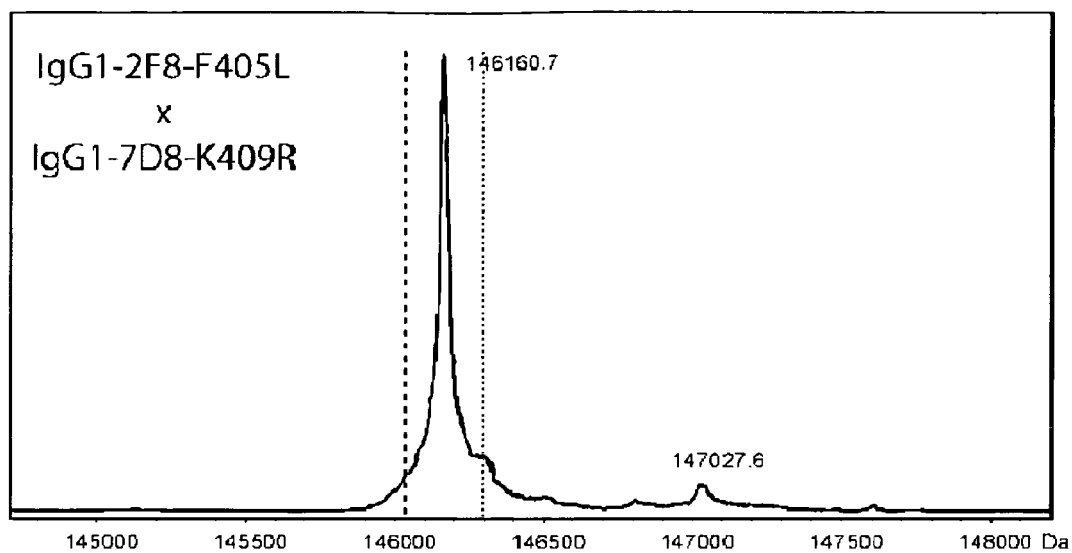
FIG. 19: Purity of bispecific antibody generated by Fab-arm-exchange between human IgG1-2F8-F405L×IgG1-7D8-K409R. Mass spectrometry shows that Fab-arm-exchange resulted in approximately 100% bispecific product.

FIG. 19 shows the mass spectrometry profiles of the starting materials IgG1-2F8-F405L and IgG1-7D8-K409R and the bispecific product generated by Fab-arm-exchange between IgG1-2F8-F405L×IgG1-7D8-K409R. The product in the Fab-arm-exchanged sample is 146,160.7 kDa, which matches with the bispecific product derived from IgG1-2F8-F405L (146,606.8/2=73,303.3)×IgG1-7D8-K409R (146,312.2/2=73,156.1)=146,459.4 kDa. Moreover, the bispecific antibody product showed a homogenous peak, indicating that no light chain mispairing occurred, which would have resulted in subdivided peaks. These data show that Fab-arm-exchange resulted in approximately 100% bispecific antibody.

Example 25

In Vivo Analysis of the Stability and Pharmacokinetics of Bispecific Antibodies Generated from IgG1-2F8-F405L×IgG1-7D8-K409R by 2-MEA-Induced Fab-Arm-Exchange The bispecific antibody generated by in vitro 2-MEA-induced Fab-arm-exchange between IgG1-2F8-F405L×IgG1-7D8-K409R was injected in SCID mice to analyze its stability (in vivo Fab-arm-exchange) and pharmacokinetic properties as described in Example 14. Two groups of mice (3 mice per group) were analyzed: (1) 100 μg bispecific antibody; (2) 100 μg bispecific antibody+1,000 μg irrelevant IgG4 (IgG4-637, described in WO2007068255). Total IgG concentrations in the plasma samples were assayed by ELISA as described in Example 14, with the exception that in this example, HRP-conjugated goat anti-human IgG (Jackson, cat. no. 109-035-098, 1/10,000) was used as a conjugate for detection. The presence of bispecific antibodies in the plasma samples was assayed and quantified by CD20 and EGFR bispecific reactivity in a sandwich ELISA as described in Example 14.

FIG. 20A shows total antibody plasma concentrations over time. The shape of the plasma clearance curves was identical in both groups. FIG. 20B shows the plasma concentrations of bispecific antibody over time. The addition of a 10-fold excess irrelevant IgG4 to the bispecific antibody did not affect bispecific antibody concentrations, indicating that no Fab-arm-exchange occurred in vivo. These data indicate that the bispecific antibody product, generated by in vitro 2-MEA-induced Fab-arm-exchange between IgG1-2F8-F405L× IgG1-7D8-K409R, was stable in vivo (no Fab-arm-exchange).

Example 26

CDC-Mediated Cell Kill by Bispecific Antibody Generated by 2-MEA-Induced Fab-Arm-Exchange Between Human IgG1-2F8-F405L×IgG1-7D8-K409R The CD20 antibody IgG1-7D8 can efficiently kill CD20-expressing cells by complement-dependent cytotoxicity (CDC). In contrast, the EGFR antibody IgG1-2F8 does not mediate CDC on target cells expressing EGFR. It was tested whether the mutant IgG1-7D8-K409R and the bispecific antibody generated by 2-MEA-induced Fab-arm-exchange between IgG1-2F8-F405L×IgG1-7D8-K409R were still able to induce CDC on CD20-expressing cells. $10^5$ Daudi or Raji cells were pre-incubated for min with a concentration series of antibody in 80 μL RPMI medium supplemented with 0.1% BSA in a shaker at room temperature. 20 μL normal human serum (NHS) was added as a source of complement (20% NHS final concentration) and incubated for 45 min at 37° C. 30 μL ice cold RPMI medium supplemented with 0.1% BSA was added to stop the CDC reaction. Dead and viable cells were discriminated by adding 10 μL 10 μg/mL propidium iodide (PI) (1 μg/mL final concentration) and FACS analysis.

FIG. 21 shows that CDC-mediated cell kill of CD20-expressing Daudi (FIG. 21A) and Raji (FIG. 21B) cells by IgG1-7D8 was not influenced by the introduction of the K409R mutation. Both Daudi and Raji cells do not express EGFR, resulting in monovalent binding of the bispecific antibody generated by 2-MEA-induced Fab-arm-exchange between IgG1-2F8-F405L×IgG1-7D8-K409R. Nonetheless, the bispecific antibody still induced CDC-mediated cell kill of the CD20-expressing cells. These data indicate that CDC capacity of a parental antibody was retained in the bispecific format.

Example 27

ADCC-Mediated Cell Kill by the Bispecific Antibody Generated by 2-MEA-Induced Fab-Arm-Exchange Between Human IgG1-2F8-F405L×IgG1-7D8-K409R The EGFR antibody IgG1-2F8 can kill EGFR-expressing cells, such as A431, by antibody-dependent cellular cytotoxicity (ADCC). A431 cells do not express CD20 and therefore the CD20 antibody IgG1-7D8 does not induce ADCC on these cells. It was tested whether the mutant IgG1-2F8-F405L and the bispecific antibody generated by 2-MEA-induced Fab-arm-exchange between IgG1-2F8-F405L×IgG1-7D8-K409R were still able to induce ADCC on A431 cells. For effector cell isolation, peripheral blood mononuclear cells (PBMCs) were isolated from whole blood of a healthy donor using Leucosep® tubes (Greiner Bio-one, cat.#227290) according to the manufacturer's recommendations. Target cells were labelled by adding 100 µCi $^{51}$Cr to 5×10$^6$ A431 cells in 1 mL RPMI medium supplemented with 0.1% BSA and incubating for 60 min in a 37° C. shaking water bath. Labelled cells were washed and resuspended in RPMI supplemented with 0.1% BSA. 5×10$^4$ labelled target cells in RPMI supplemented with 0.1% BSA were preincubated in 100 µL for 15 min with the antibody concentrations series (range 0-10 µg/mL final concentration in ADCC assay in 3-fold dilutions) at room temperature. The ADCC assay was started by adding 50 µL effector cells (5×10$^6$ cells) in an E:T ratio 100:1. After 4 hours at 37° C., $^{51}$Cr release from triplicate experiments was measured in a scintillation counter as counts per min (cpm). The percentage of cellular toxicity was calculated using the following formula: percentage of specific lysis=(experimental cpm−basal cpm)/(maximal cpm−basal cpm)×100. Maximal $^{51}$Cr release was determined by adding 50 µL 5% Triton X-100 to 50 µL target cells (5×10$^4$ cells), and basal release was measured in the absence of sensitizing antibody and effector cells.

Figure 22:
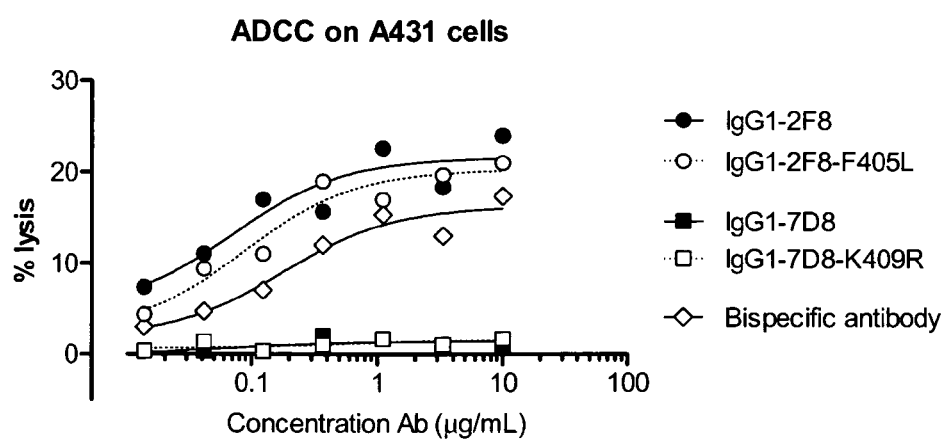
FIG. 22: ADCC-mediated cell kill of EGFR-expressing cells by a bispecific antibody generated by 2-MEA-induced Fab-arm-exchange between IgG1-2F8-F405L×IgG1-7D8-K409R. Concentration series of the indicated antibodies were used to test their capacity to mediate ADCC on A431 cells. IgG1-7D8 can not bind the CD20-negative A431 cells and consequently did not induce ADCC. ADCC was induced by the EGFR antibody IgG1-2F8, also after introduction of the F405L mutations in the CH3 domain. The ADCC effector function of IgG1-2F8-F405L was retained in the bispecific format obtained by Fab-arm-exchange between IgG1-2F8-F405L×IgG1-7D8-K409R.

FIG. 22 shows that the CD20-specific antibody IgG1-7D8 did not induce ADCC on the CD20-negative A431 cells. Both IgG1-2F8 and the mutant IgG1-2F8-F405L were able to induce ADCC on A431 cells, indicating that introduction of the F405L mutation in IgG1-2F8 did not affect its ADCC effector function. Also the bispecific antibody derived from IgG1-2F8-F405L×IgG1-7D8-K409R induced ADCC on A431 cells in a dose-dependent manner, indicating that the ADCC effector function was retained in the bispecific format.

Example 28

Determinants at the IgG1 405 Position for Engagement in 2-MEA-Induced Fab-Arm-Exchange in Combination with IgG1-K409R In Example 16 it is described that the F405L mutation is sufficient to enable human IgG1 to engage in Fab-arm-exchange when combined with IgG4-7D8. To further test the determinants at the IgG1 405 position for engagement in 2-MEA-induced Fab-arm-exchange in combination with human IgG1-K409R, all possible IgG1-2F8-F405X mutants (with the exception of C and P) were combined with IgG1-7D8-K409R. The procedure was performed with purified antibodies as described in Example 19.

FIG. 23 shows the results of bispecific binding upon 2-MEA-induced Fab-arm-exchange between IgG1-2F8-F405X×IgG1-7D8-K409R. These data were also scored as (−) no Fab-arm exchange, (+/−) low, (+) intermediate or (++) high Fab-arm exchange, as presented in Table 3. No Fab-arm exchange (−) was found when the 405 position in IgG1-2F8 was F (=wild type IgG1). Fab-arm exchange was found to be low (+/−) when the 405 position in IgG1-2F8 was G or R. Fab-arm exchange was found to be high (++) when the 405 position in IgG1-2F8 was A, D, E, H, I, K, L, M, N, Q, S, T, V, W or Y. These data indicate that particular mutations at the IgG1 405 position allow IgG1 to engage in 2-MEA-induced Fab-arm-exchange when combined with IgG1-K409R.

TABLE 3

2-MEA-induced Fab-arm-exchange between IgG1-2F8-F405X mutants and IgG1-7D8-K409R. The generation of bispecific antibodies after 2-MEA-induced in vitro Fab-arm-exchange between IgG1-2F8-F405X mutants and IgG1-7D8-K409R was determined by a sandwich ELISA.

| IgG1-2F8-F405X | Fab-arm-exchange x IgG1-7D8-K409R |
| --- | --- |
| A | ++ |
| D | ++ |
| E | ++ |
| F | − |
| G | +/− |
| H | ++ |
| I | ++ |
| K | ++ |
| L | ++ |
| M | ++ |
| N | ++ |
| Q | ++ |
| R | +/− |
| S | ++ |
| T | ++ |
| V | ++ |
| W | ++ |
| Y | ++ |

(−) no, (+/−) low, (+) intermediate, (++) high Fab-arm-exchange.

Example 29

Determinants at the IgG1 407 Position for Engagement in 2-MEA-Induced Fab-Arm-Exchange in Combination with IgG1-K409R In Example 28, it is described that certain single mutations at position F405 are sufficient to enable human IgG1 to engage in Fab-arm-exchange when combined with IgG1-K409R. To test whether other determinants implicated in the Fc:Fc interface positions in the CH3 domain could also mediate the Fab-arm-exchange mechanism, mutagenesis of the IgG1 407 position was performed and the mutants were tested for engagement in 2-MEA-induced Fab-arm-exchange in combination with human IgG1-K409R. All possible IgG1-2F8-Y407X mutants (with the exception of C and P) were combined with IgG1-7D8-K409R. The procedure was performed with purified antibodies as described in Example 19.

FIG. 24 shows the results of bispecific binding upon 2-MEA-induced Fab-arm-exchange between IgG1-2F8-Y407X×IgG1-7D8-K409R. These data were also scored as (−) no Fab-arm exchange, (+/−) low, (+) intermediate or (++) high Fab-arm exchange, as presented in Table 4. No Fab-arm exchange (−) was found when the 407 position in IgG1-2F8 was Y (=wild type IgG1), E, K, Q, or R. Fab-arm exchange was found to be low (+/−) when the 407 position in IgG1-2F8 was D, F, I, S or T and intermediate (+) when the 407 position in IgG1-2F8 was A, H, N or V, and high (++) when the 407 position in IgG1-2F8 was G, L, M or W. These data indicate that particular single mutations at the IgG1 407 position allow IgG1 to engage in 2-MEA-induced Fab-arm-exchange when combined with IgG1-K409R.

TABLE 4

2-MEA-induced Fab-arm-exchange between IgG1-2F8-Y407X mutants and IgG1-7D8-K409R
The generation of bispecific antibodies after 2-MEA-induced in vitro Fab-arm exchange between IgG1-2F8-Y407X mutants and IgG1-7D8-K409R was determined by a sandwich ELISA.

| IgG1-2F8-Y407X | Fab-arm-exchange x IgG1-7D8-K409R |
|---|---|
| A | + |
| D | +/− |
| E | − |
| F | +/− |
| G | ++ |
| H | + |
| I | +/− |
| K | − |
| L | ++ |
| M | ++ |
| N | + |
| Q | − |
| R | − |
| S | +/− |
| T | +/− |
| V | + |
| W | ++ |
| Y | − |

(−) no, (+/−) low, (+) intermediate, (++) high Fab-arm-exchange.

Example 30

Quantification of the Non-Covalent CH3-CH3 Interaction in IgG1 Heterodimers

It is described in Example 21 that there is a specific range in the strength of the interaction of the CH3-CH3 homodimers that allows efficient Fab-arm-exchange. The strength of the interactions at the CH3 interface should be such that it is possible that both heavy chains in the parental antibodies (homodimers) dissociate in the Fab-arm-exchange reaction and that they subsequently associate in the heterodimerization reaction. To generate a stable heterodimer, the strength of the heterodimer interaction should be greater than the strength of the homodimer interaction, such that it favors heterodimerization over homodimerization. To confirm this, the strength of the CH3-CH3 interaction in the heterodimers was measured and compared to the strength in the homodimers. The $K_D$ of the CH2-CH3 fragments derived from IgG1-K409R, IgG1-F405L and IgG1-ITL homodimers were measured as described in Example 21. For the determination of the $K_D$ in heterodimers, CH2-CH3 domain fragments (G1-F405L and G1-ITL) were mixed with the IgG1Δhinge fragment of IgG1-7D8-K409R, which contain all antibody domains except the hinge. The lack of hinge regions in both fragments prevented covalent inter-heavy chain disulfide bonds. The fragments were mixed and analyzed after 24 hours by native mass spectrometry as described in Example 21. The $K_D$ values of the non-covalent CH3-CH3 interactions in the indicated CH2-CH3 fragments or mixtures of CH2-CH3 fragments with IgG1Δhinge are presented in Table 5. These data suggest that under the tested conditions, the strength of the heterodimer interaction is greater (lower $K_D$) than the corresponding homodimer interactions.

TABLE 5

| CH2—CH3 construct/(IgG1Δhinge) | Interaction | $K_D$ (M) |
|---|---|---|
| G1-F405L/G1-K409R | Heterodimer | $1.2 \times 10^{-8}$ |
| G1-ITL/G1-K409R | Heterodimer | $1.7 \times 10^{-8}$ |
| G1-K409R | Homodimer | $1.1 \times 10^{-7}$ |
| G1-F405L | Homodimer | $8.5 \times 10^{-7}$ |
| G1-ITL | Homodimer | $1.2 \times 10^{-6}$ |

Example 31

Biochemical Analysis of a Bispecific Antibody Generated by 2-MEA-Induced Fab-Arm Exchange A batch of bispecific antibody, generated by 2-MEA-induced Fab-arm exchange between human IgG1-2F8-F405L×IgG1-7D8-K409R, was purified on a PD-10 desalting column (cat. no. 17-0851-01; GE Healthcare). Next, the purity of the bispecific product was analyzed by sodium dodecyl sulfate polyacrylamide gelelectrophoresis (SDS-PAGE), High Performance Size Exclusion Chromatography (HP-SEC), mass spectrometry, HPLC cation exchange chromatography (HPLC-CIEX), capillary isoelectrofocussing (cIEF).

Figure 25:
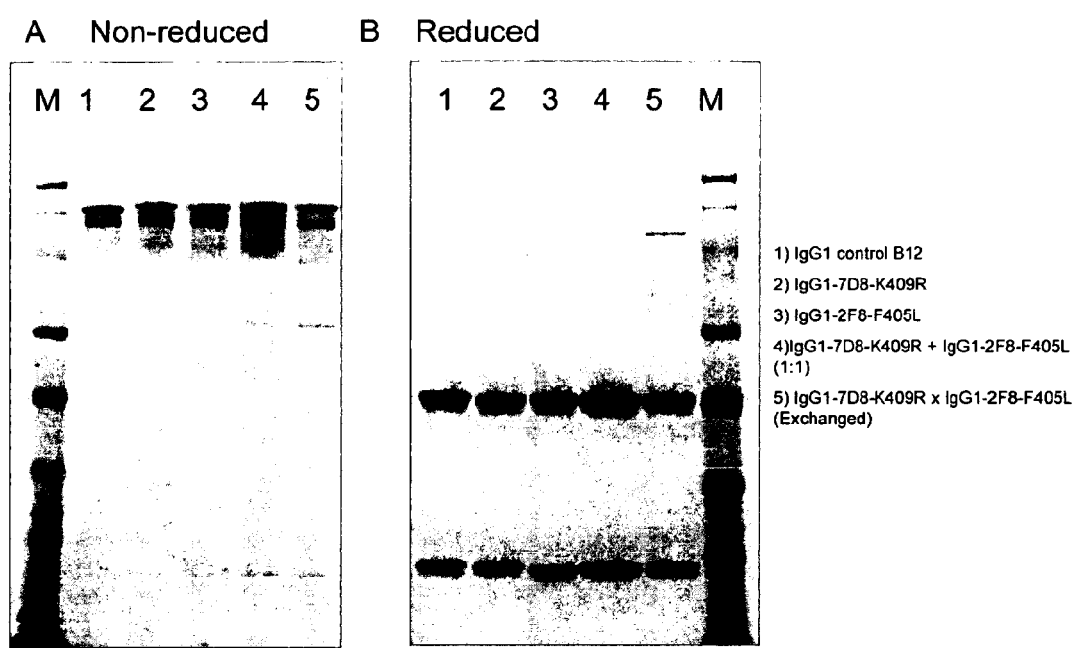
FIG. 25: Analysis of bispecific antibody generated by 2-MEA-induced Fab-arm exchange by SDS-PAGE under non-reducing (FIG. 25(A)) and reducing (FIG. 25(B)) conditions.

SDS-PAGE was performed under non-reducing (FIG. 25A) and reducing (FIG. 25B) conditions as described in Example 15. FIG. 25A show that the antibody sample after 2-MEA induced Fab-arm exchange consists of intact IgG, with a trace of half molecules (H1L1) detectable on the non-reduced gel.

Figure 26:
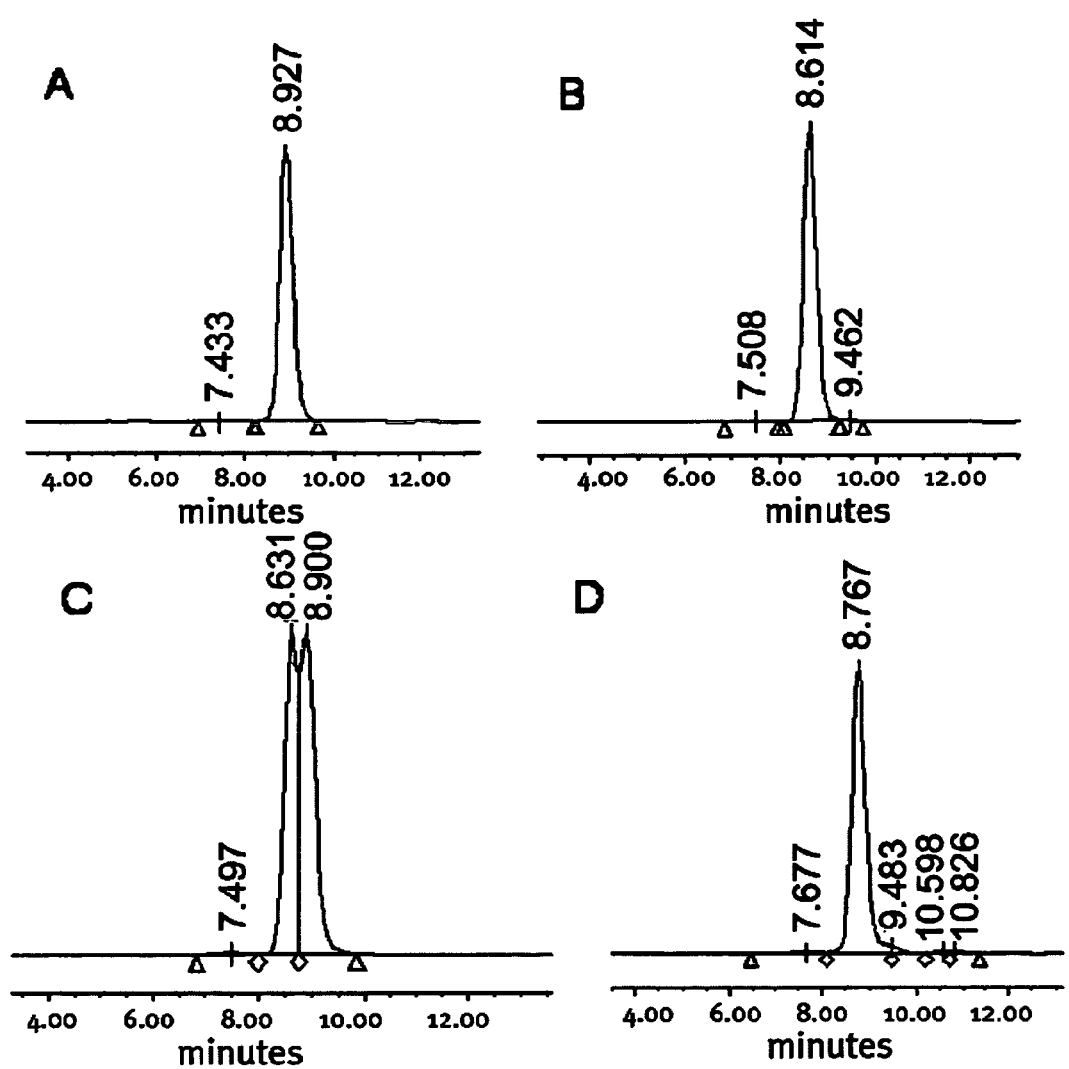
FIG. 26: HP-SEC profiles of the homodimer starting material IgG1-2F8-F405L (FIG. 26(B)), the homodimer starting material IgG1-7D8-K409R (FIG. 26(A)), the mixture (1:1) of both homodimers (FIG. 26(C)), and the bispecific product generated by 2-MEA-induced Fab-arm exchange between IgG1-2F8-F405L×IgG1-7D8-K409R (FIG. 26(D)).

HP-SEC was performed as described in Example 15. FIG. 26(B) and FIG. 26(A) show the HP-SEC profiles of the starting materials IgG1-2F8-F405L and IgG1-7D8-K409R, respectively. The mixture (1:1) of both antibodies and the bispecific product generated by 2-MEA induced Fab-arm exchange between IgG1-2F8-F405L×IgG1-7D8-K409R are shown in FIG. 26C and FIG. 26D, respectively. In addition, FIG. 26D shows that >99% of the sample consists of intact IgG with practically no aggregates formed.

Figure 27:
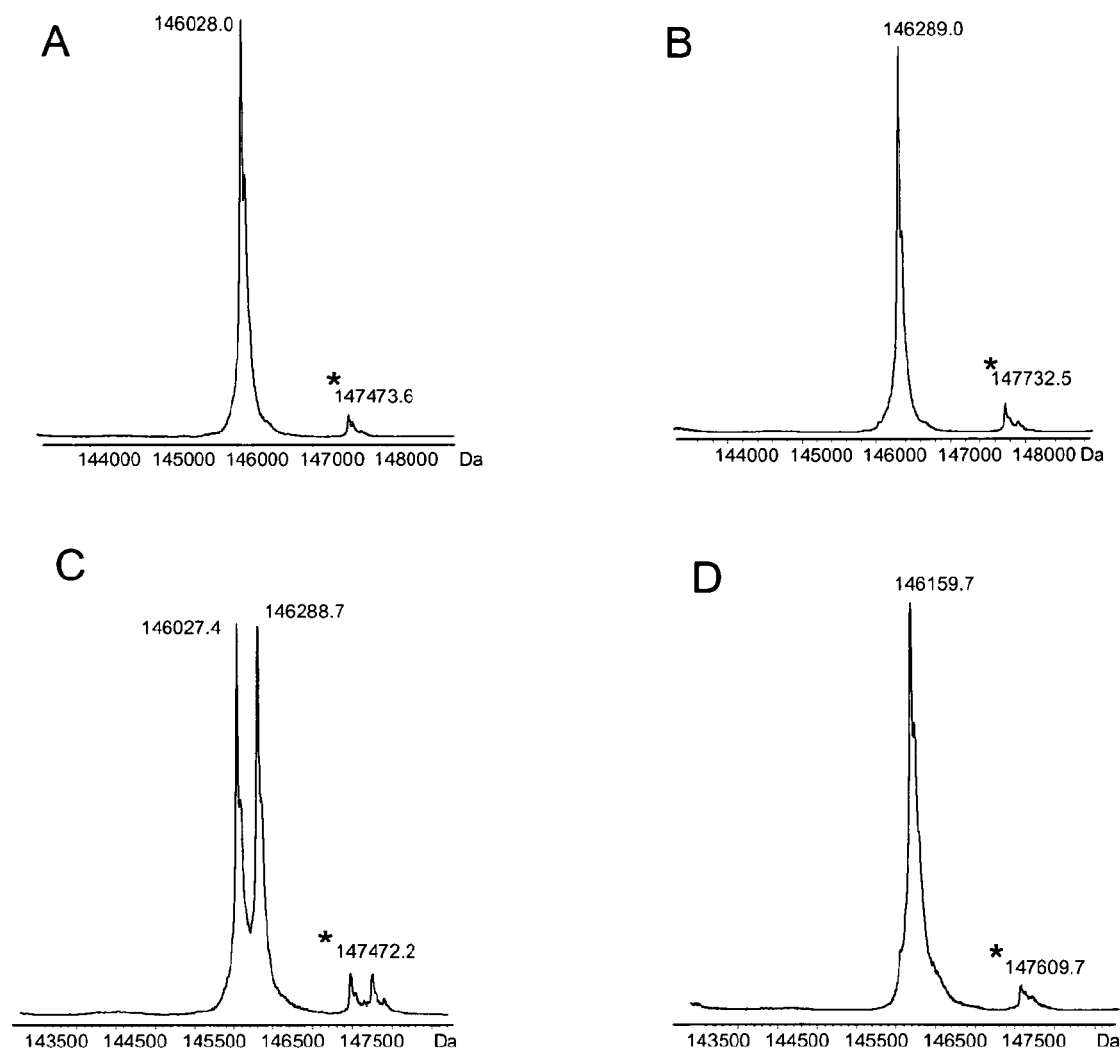
FIG. 27: Mass spectrometry (ESI-MS) of the homodimer starting material IgG1-2F8-F405L (FIG. 27(B)), the homodimer starting material IgG1-7D8-K409R (FIG. 27(A)), the mixture (1:1) of both homodimers (FIG. 27(C)), and the bispecific product generated by 2-MEA-induced Fab-arm exchange between IgG1-2F8-F405L×IgG1-7D8-K409R (FIG. 27(D)).

Mass spectrometry (ESI-MS) was performed as described in Example 12. FIG. 27(B) and FIG. 27(A) show the mass spectrometry profiles of the starting materials IgG1-2F8-F405L and IgG1-7D8-K409R, respectively. The mixture (1:1) of both antibodies and the bispecific product generated by 2-MEA induced Fab-arm exchange between IgG1-2F8-F405L×IgG1-7D8-K409R are shown in FIG. 27C and FIG. 27D, respectively. The product in the 2-MEA induced Fab-arm exchanged sample is 146,159.7 kDa, which perfectly matches with the bispecific product derived from IgG1-2F8-F405L (146,289.0/2=73,145)×IgG1-7D8-K409R (146,028.0/2=73,014). Moreover, the bispecific antibody product showed a homogenous peak, indicating that no light chain mispairing occurred, which would have resulted in subdivided peaks. These data show that 2-MEA induced Fab-arm exchange resulted in bispecific IgG. The small peaks indicated by (*) resulted from incomplete deglycosylation prior to analysis. These data show that a bispecific antibody sample was generated by 2-MEA-induced Fab-arm exchange between IgG1-2F8-F405L×IgG1-7D8-K409R.

Figure 28:
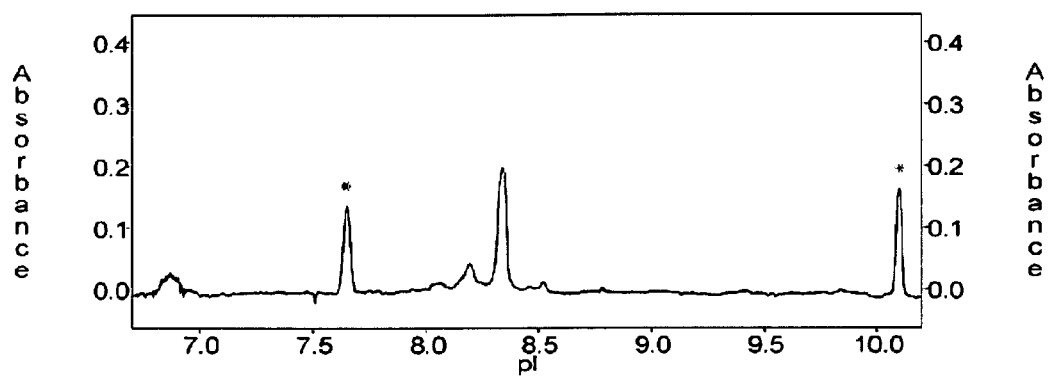
FIG. 28: Capillary isoelectrofocussing (cIEF) profiles of the homodimer starting material IgG1-2F8-F405L (FIG. 28(A)), the homodimer starting material IgG1-7D8-K409R (FIG. 28(B)), the mixture (1:1) of both homodimers (FIG. 28(C)), and the bispecific product generated by 2-MEA-induced Fab-arm exchange between IgG1-2F8-F405L×IgG1-7D8-K409R (FIG. 28(D)).

Capillary isoelectrofocussing (cIEF) was performed using an iCE280 Analyzer (Convergent Biosciences). FIG. 28A and FIG. 28B shows cIEF profiles of the starting materials IgG1-2F8-F405L and IgG1-7D8-K409R, respectively. The mixture (1:1) of both antibodies and the bispecific product generated by Fab-arm exchange between IgG1-2F8-F405L×IgG1-7D8-K409R are shown in FIG. 28C and FIG. 28D, respectively. All samples were desalted before use. Final concentrations in the assay mix were 0.3 mg/mL IgG (0.35% Methyl Cellulose; 2% Carrier Ampholytes 3-10; 6% Carrier Ampholytes 8-10.5;

0.5% pI marker 7.65 and 0.5% pI marker 10.10). Focusing was performed for 7 min at 3000 V and the whole-capillary absorption image was captured by a charge-coupled device camera. After calibration of the peak profiles, the data were analyzed by the EZChrom software. pI markers are indicated by (*). These data show that a bispecific antibody sample was generated by 2-MEA-induced Fab-arm exchange between IgG1-2F8-F405L×IgG1-7D8-K409R.

Figure 29:
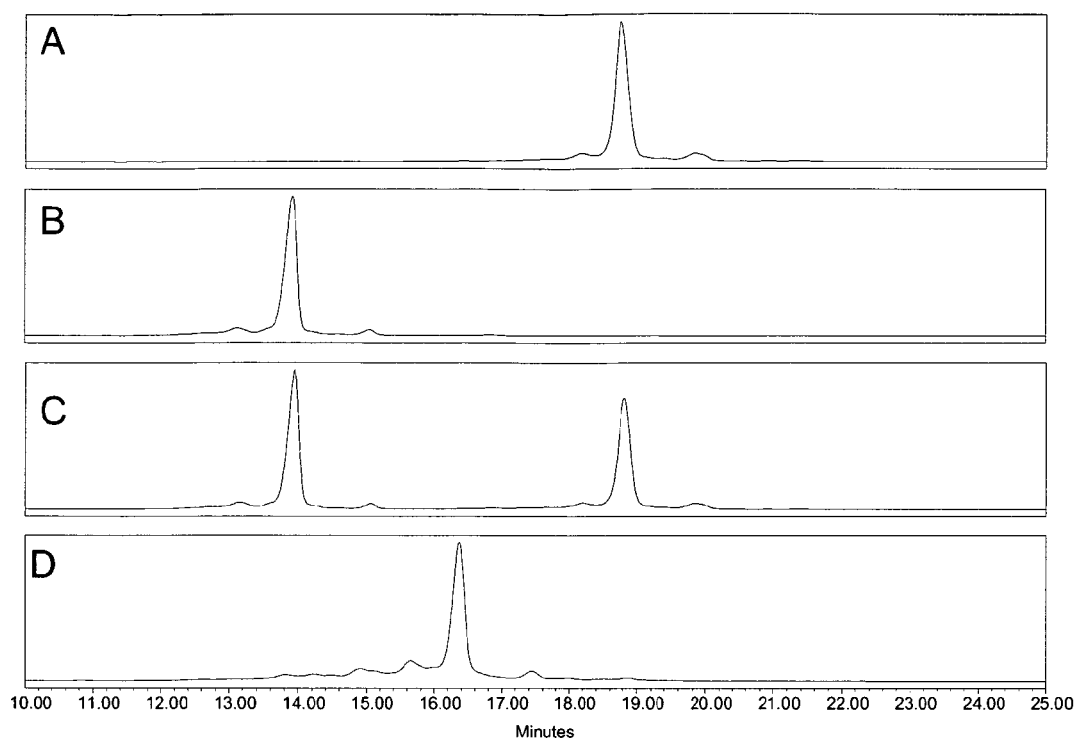
FIG. 29: HPLC-CIEX profiles of the homodimer starting material IgG1-2F8-F405L (FIG. 29(A)), the homodimer starting material IgG1-7D8-K409R (FIG. 29(B)), the mixture (1:1) of both homodimers (FIG. 29(C)), and the bispecific product generated by 2-MEA-induced Fab-arm exchange between IgG1-2F8-F405L×IgG1-7D8-K409R (FIG. 29(D)).

Another technique to study the charged isoforms of monoclonal antibodies is High Pressure Liquid Chromatography Cation Exchange (HPLC-CIEX). FIG. 29A and FIG. 29B show HPLC-CIEX profiles of the starting materials IgG1-2F8-F405L and IgG1-7D8-K409R, respectively. The mixture (1:1) of both antibodies and the bispecific product generated by 2-MEA induced Fab-arm exchange between IgG1-2F8-F405L×IgG1-7D8-K409R are shown in FIG. 29C and FIG. 29D, respectively. Samples were diluted to 1 mg/mL in mobile Phase A (10 mM NaPO4, pH 7.0) for injection onto the HPLC. The differently charged IgG molecules were separated by using a ProPac® WCX-10, 4 mm×250 mm, analytical column with a flow rate of 1 mL/min. Elution was performed with a gradient of Mobile Phase A to Mobile Phase B (10 mM NaPO$_4$, pH 7.0, 0.25 M NaCl) and detection occurred at 280 nm. These data show that a bispecific antibody sample was generated by 2-MEA-induced Fab-arm exchange between IgG1-2F8-F405L×IgG1-7D8-K409R. It also shows that cation exchange is a powerful tool to separate residual homodimers from the heterodimer. Another application of cation exchange chromatography is therefore the polishing of a bispecific heterodimer, i.e. to purify away any residual homodimers after exchange.

Example 32

Recombinant Expression of Heterodimers by Simultaneous Co-Expression of Both Homodimers To illustrate that heterodimer formation also occurs when the two homodimers are co-expressed recombinantly, HEK-293F cells were co-transfected with the four expression vectors (see Example 1) encoding the heavy and light chain of IgG1-7D8-K409R and IgG1-2F8-F405 in a 1:1:1:1 ratio. Antibodies were transiently produced under serum-free conditions as described in Example 4. Next, IgG was purified by Protein A chromatography as described in Example 5. Purified IgG was deglycosylated and subsequently analyzed by electrospray ionization mass spectrometry as described in Example 12.

The theoretic mass of heavy and light chain of IgG1-7D8-K409R and IgG1-2F8-F405 are shown in Table 6.

TABLE 6

Theoretical mass of the heavy and light chain of IgG1-7D8-K409R and IgG1-2F8-F405

| Homodimer | L-chain (Da) | H-Chain (Da) |
|---|---|---|
| IgG1-2F8-F405 | 23252.8 | 49894.6 |
| IgG1-7D8-K409R | 23438.1 | 49579.0 |

Figure 30:
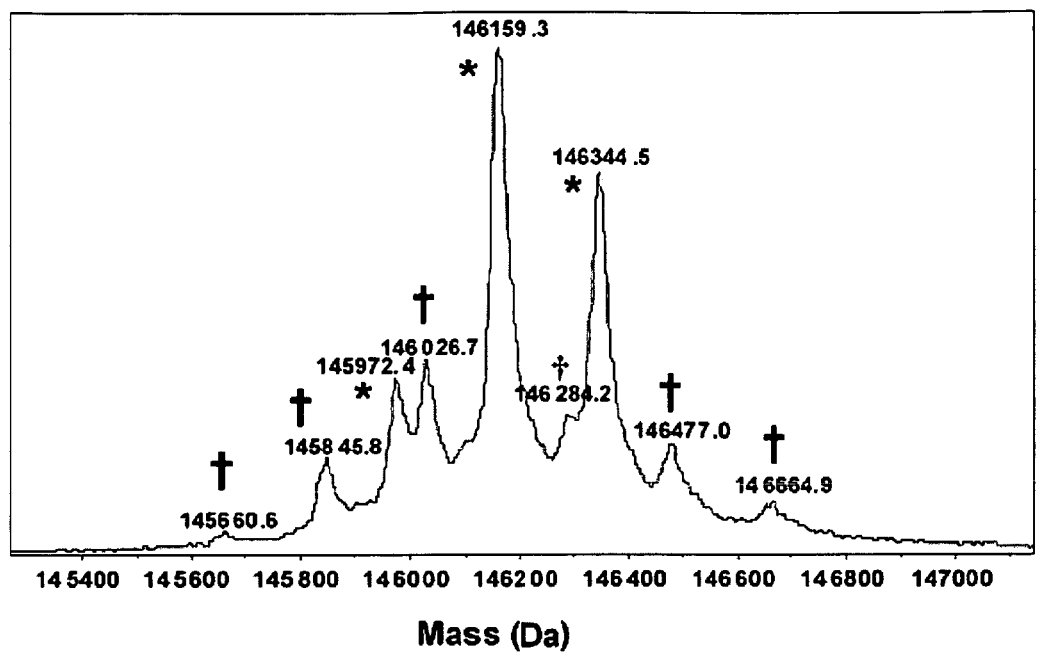
FIG. 30: Electrospray ionization mass spec analysis of IgG obtained by co-transfection of the expression vectors encoding the heavy and light chain of IgG1-7D8-K409R or IgG1-2F8-F405. Heterodimer peaks are indicated with an *. Homodimer peaks are indicated with an †.
Figure 31:
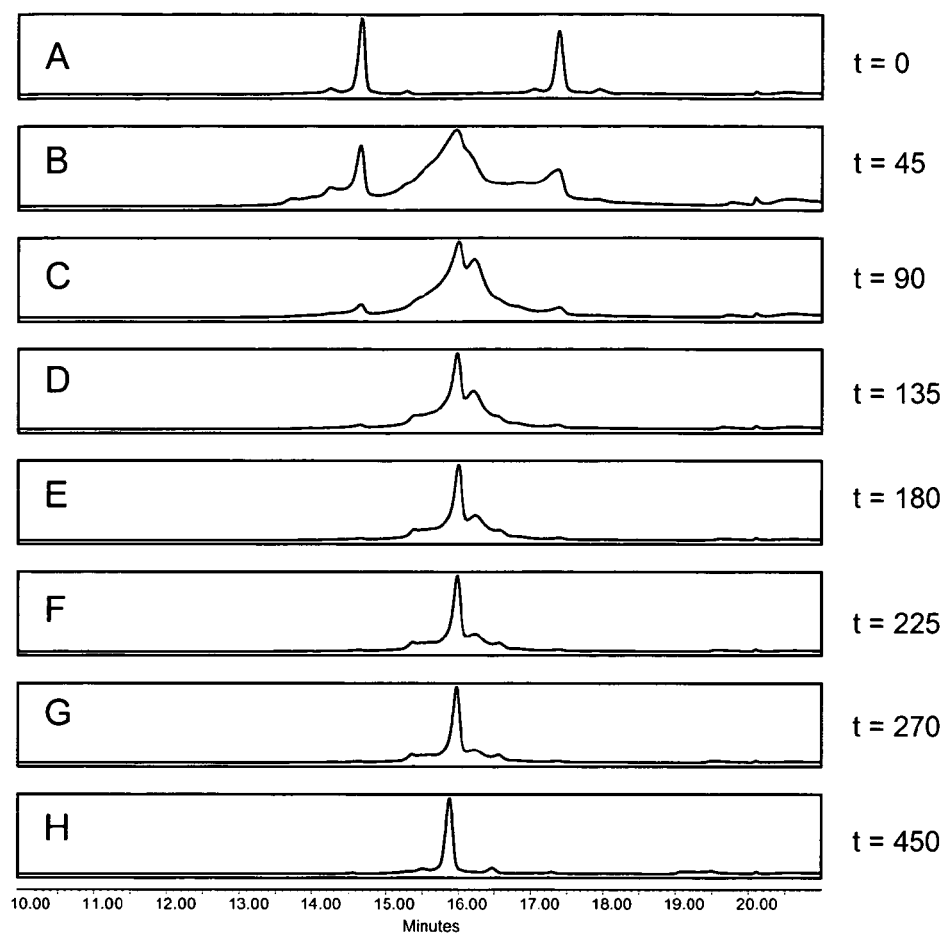
FIGS. 31A-31H: Exchange reaction of the homodimers IgG1-2F8-F405L and IgG1-7D8-K409R as monitored by High Pressure Liquid Chromatography Cation Exchange (HPLC-CIEX) after injection at different intervals (FIG. 31A, t=0.

On the basis of these masses, the following IgG molecules could theoretically be detected (Table 7). The measured masses (FIG. 30) are indicated in the final column.

TABLE 7

Theoretical detection of heavy and light chain of IgG1-7D8-K409R and IgG1-2F8-F40

| IgG1-2F8-F405 | | IgG1-7D8-K409R | | Theoretic mass (Da) | Mass measured (Da) |
|---|---|---|---|---|---|
| H-chain | L-chain | H-chain | L-chain | | |
| 2 | 2 | | | 146287 | 146284 |
| | | 2 | 2 | 146026 | 146026 |
| 2 | | | 2 | 146657 | 146664 |
| | 2 | 2 | | 145656 | 145660 |
| 2 | 1 | | 1 | 146472 | 146477 |
| | 1 | 2 | 1 | 145841 | 145846 |
| 1 | 1 | 1 | 1 | 146157 | 146159 |
| 1 | 2 | 1 | | 145971 | 145972 |
| 1 | | 1 | 2 | 146342 | 146345 |

The two most abundant peaks of 146345 and 146159 Da represented heterodimers with a single (from IgG1-7D8-K409R) or both light chains incorporated, respectively. Homodimers of both the heavy chain of IgG1-7D8-K409R or IgG1-2F8-F405 were detected, but only in minor amounts. These data show that hetero-dimerization also occurs when the two homodimers are co-expressed.

Example 33

Monitoring the Kinetics of 2-MEA-Induced Fab-Arm Exchange and Quantifying Residual Homodimers after Exchange by Using HPLC-CIEX The generation of bispecific antibodies by 2-MEA-induced Fab-arm exchange is described in Example 11. In this example the exchange reaction was monitored by conducting High Pressure Liquid Chromatography Cation Exchange (HPLC-CIEX; as described in Example 31) at various time points during the exchange reaction.

Figure 32:
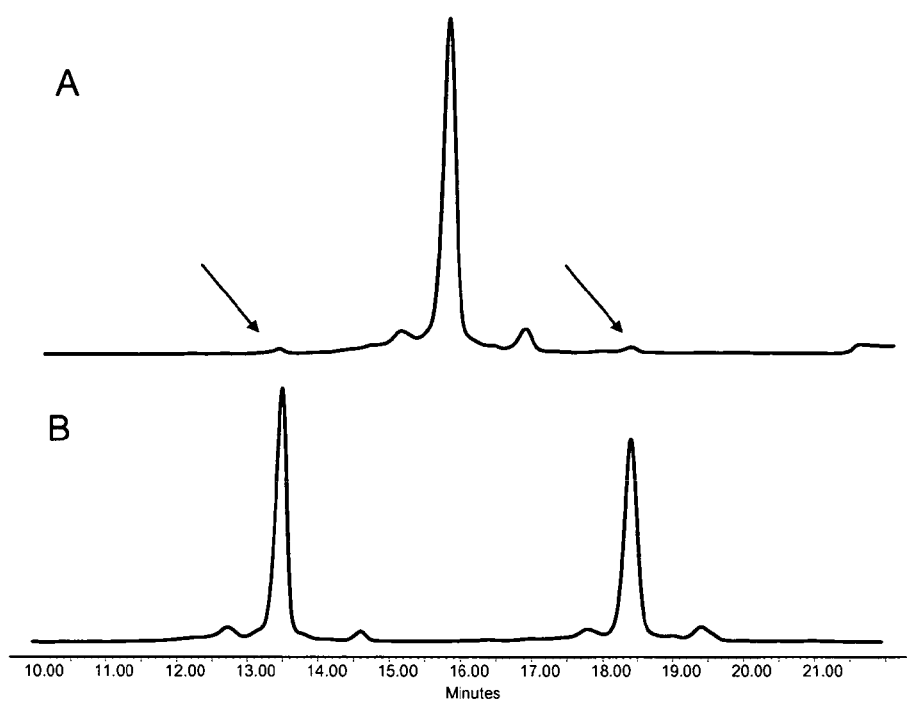
FIGS. 32A and 32B: Residual homodimers of the exchange reaction as shown in FIGS. 32A and 32B as detected with the CIEX method (indicated by arrows).
Figure 35:
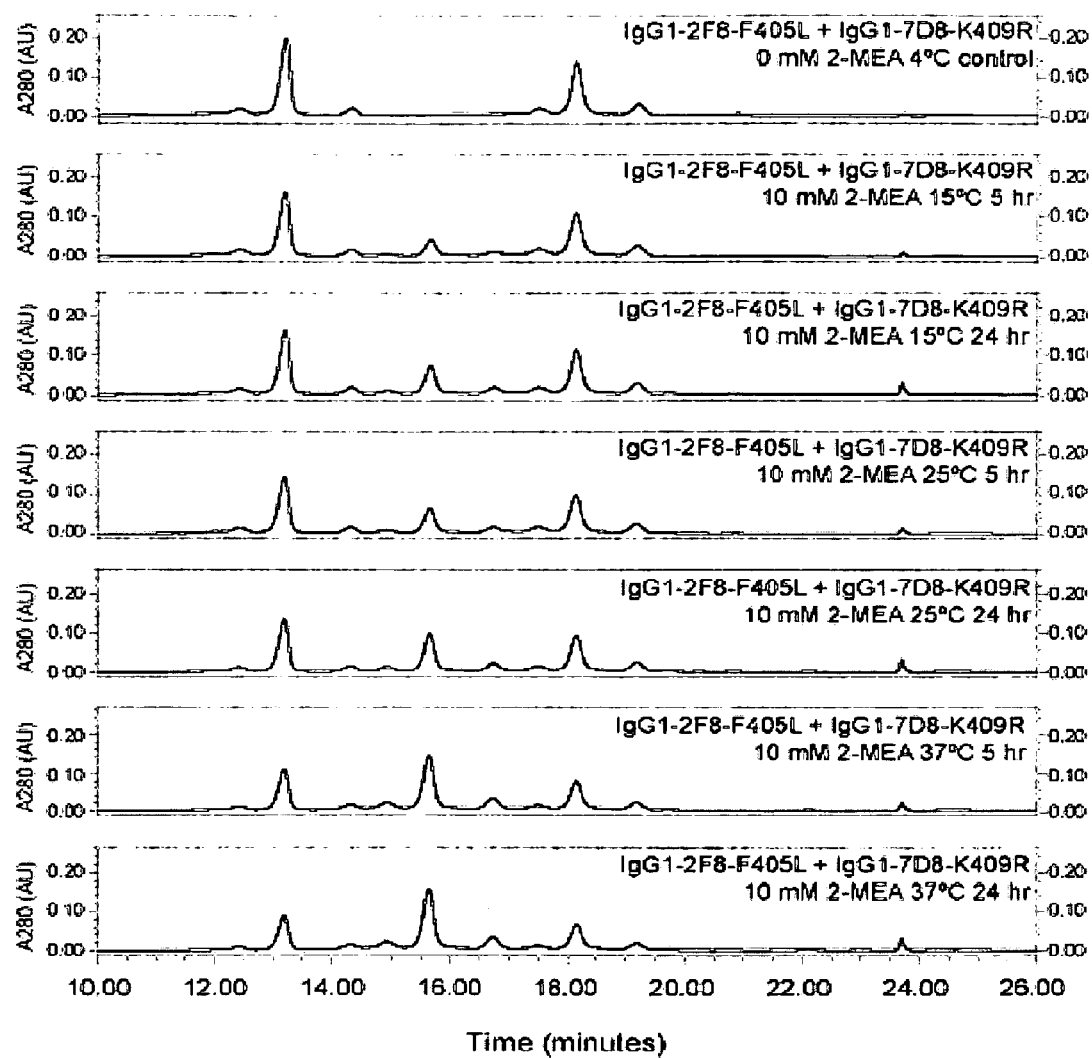
FIGS. 35A-35D show the generation of bispecific antibodies at various IgG concentrations, 2-MEA concentrations, incubation temperatures and times as analysed by HPLC-CIEX.
Figure 35:
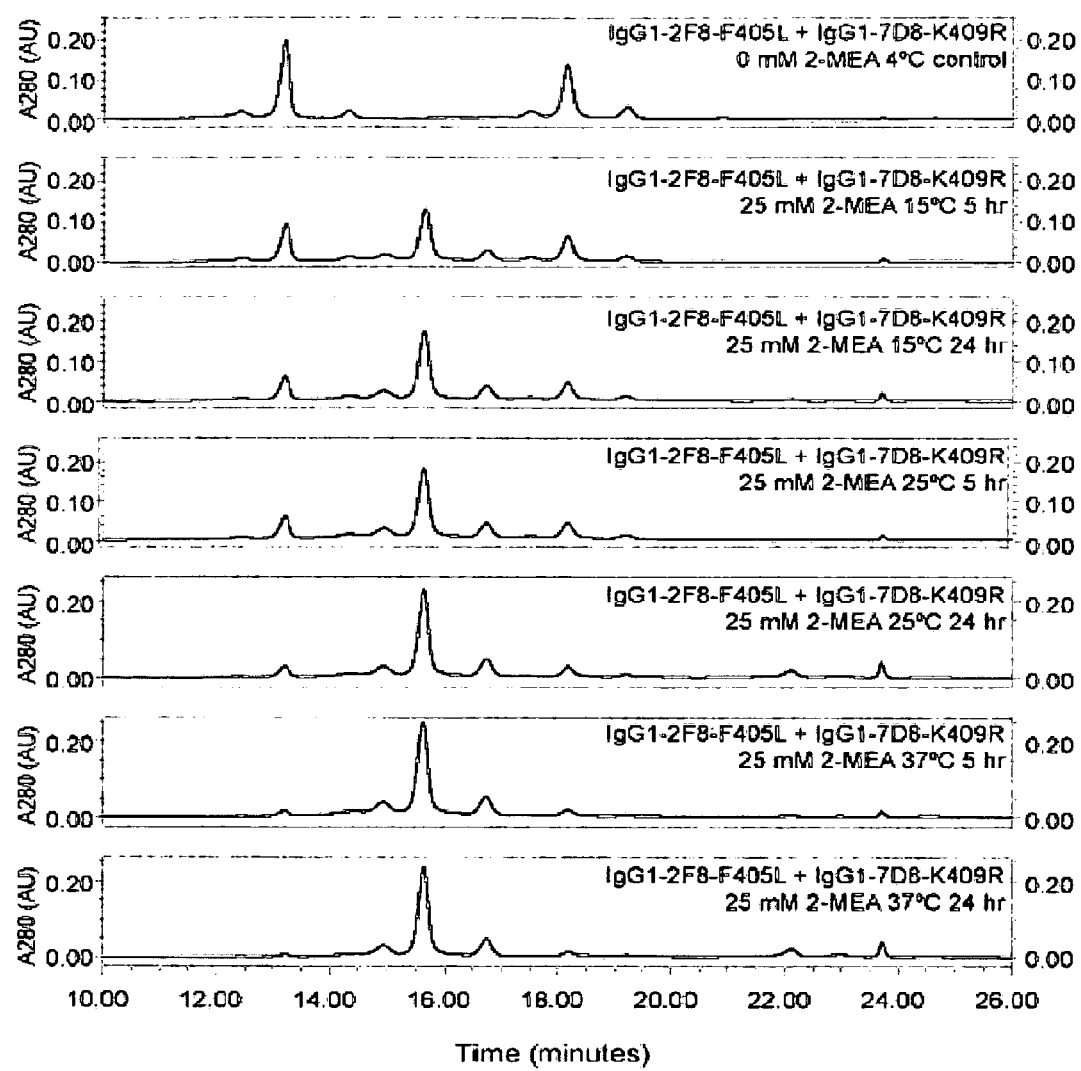
Figure 35:
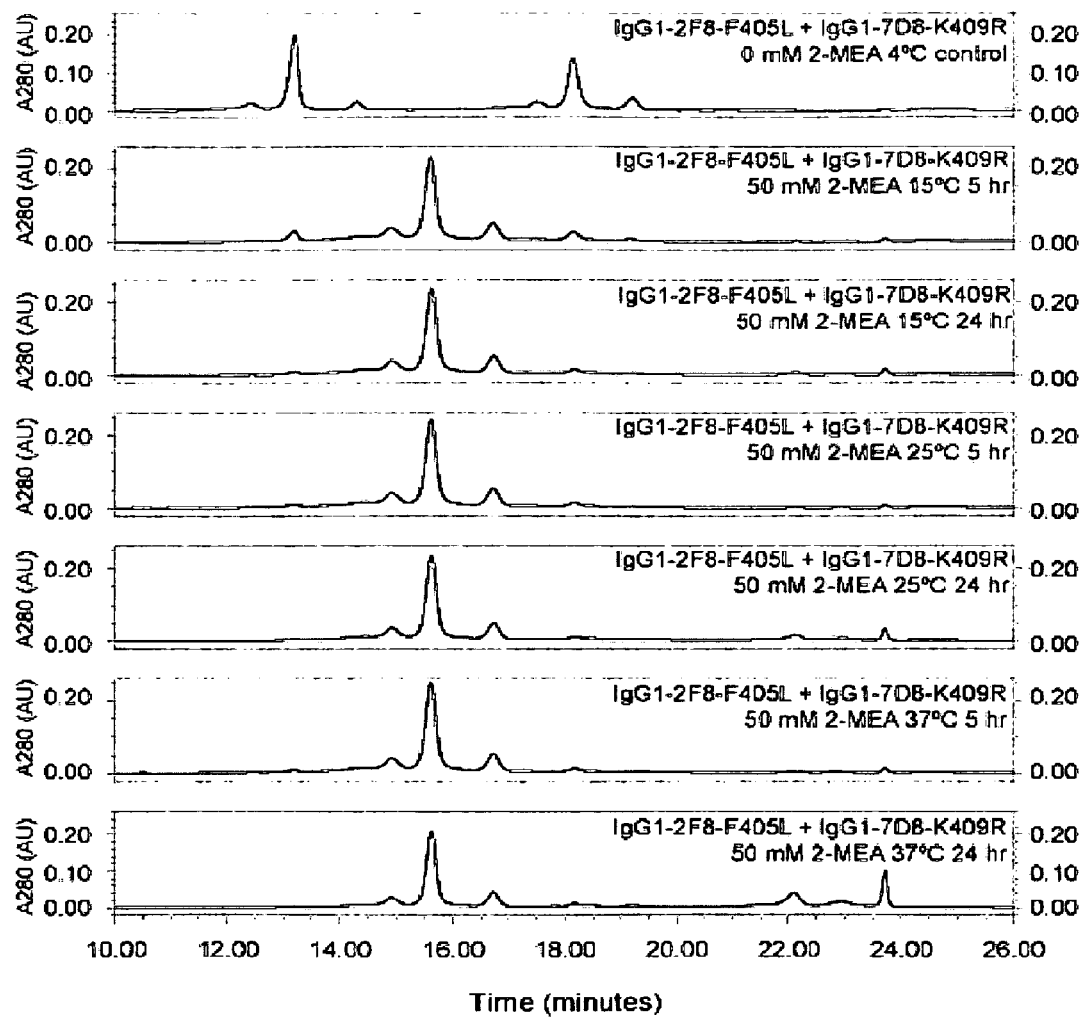
Figure 35:
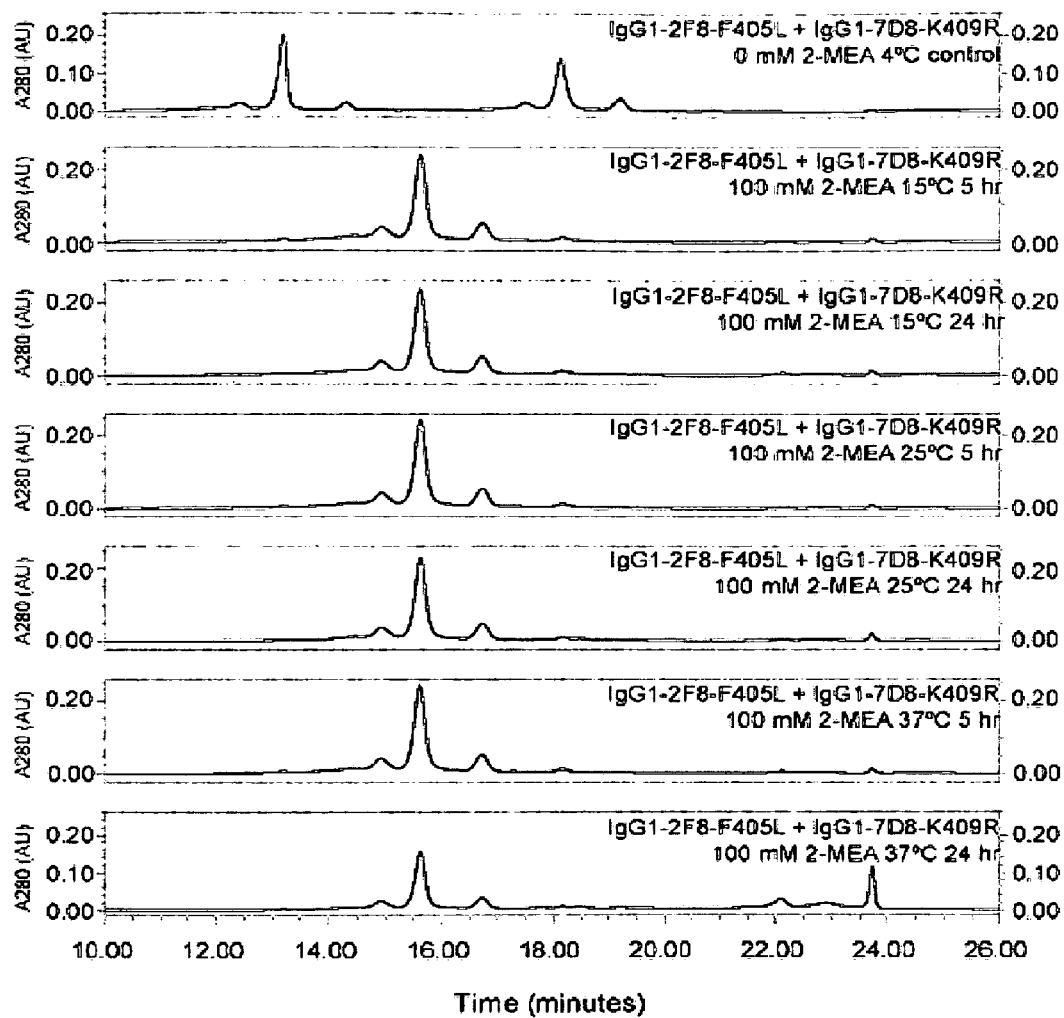

Homodimers IgG1-2F8-F405L and IgG1-7D8-K409R were mixed in the molar ratio 1:1 at a concentration of 1 mg/mL each. After the addition of 25 mM 2-MEA, the sample was placed in the autosampler of the HPLC, prewarmed at 25° C. FIG. 31A to 31H shows eight consecutive injections at different time intervals obtained by HPLC-CIEX ranging from t=0 min to t=450 min, respectively, after the addition of 2-MEA. The data show that bispecific IgG was formed rather quickly and most of the homodimer was exchanged after 135 min. The heterogeneous heterodimer peaks appearing after 45 min resolved into more homogeneous peaks after approximately 180 min, suggesting that exchange occurs in different phases. Furthermore, FIG. 32A shows that approximately 3% of residual homodimers was detected with the CIEX method (indicated by arrows). As shown this method is suitable for quantitating the remaining homodimer content (elution of the homodimers is shown in FIG. 32B) when exchange reaction was almost complete).

Example 34

Generation of Bispecific Antibodies by 2-MEA-Induced Fab-Arm Exchange at High Antibody Concentrations at Various 2-MEA Concentrations, Temperatures and Incubation Times 2-MEA induced Fab-arm exchange was performed at high IgG concentrations. The influence of 2-MEA concentration, incubation temperature and time on the amount of exchange was studied.

The exchange process was performed using the combination of IgG1-7D8-K409R×IgG1-2F8-F405L. Both materials were purified with affinity chromatography using protein A. After concentration of the material to >20 mg/mL, a successive anion exchange step was performed (in flow through mode) using HiPrep Q FF 16/10 (GE Health Care, #28-9365-43). The final purified material was buffer-exchanged to PBS.

The bispecific exchange was studied at final IgG concentrations of 20 mg/mL (each homodimer at a final concentration of 10 mg/mL) and 10 mg/mL (each homodimer at a final concentration of 5 mg/mL) in PBS. Separate mixtures were prepared for both IgG concentrations including 2-MEA at final concentrations of 10, 25, 50 and 100 mM. The mixtures were divided into 100 μL aliquots in eppendorf tubes and stored at 15, 25 and 37° C. Separate tubes were used for different incubation times of 90 min, 5 hours and 24 hours at each temperature.

The mixture was also prepared without 2-MEA for both IgG concentrations and stored at 4° C. as an untreated control. After the appropriate incubation times, the 90 min and 5 hours samples were collected for desalting to remove the 2-MEA (the 90 min samples were initially put on ice to stop the exchange reaction). The samples were desalted using a Zeba 96-well desalting plate (7 k, cat#89808, Thermo Fisher Scientific). The 24 hours samples were desalted separately after 24 hours incubation.

Serial dilutions of the antibody samples (total antibody concentration 10-0.123 μg/mL in 3-fold dilutions for the 90 min and 5 hours samples; 10-0.041 μg/mL in 3-fold dilutions for the 24 hours samples) were used in a sandwich ELISA to measure bispecific binding as described in Example 7. For each plate, a control was included of a purified batch of bispecific antibody derived from a 2-MEA-induced Fab-arm exchange between IgG1-2F8-ITL and IgG4-7D8-CPPC (as described in Example 15). FIG. 34(A)-(F) shows the results of the bispecific binding as measured in the individual ELISA plates. The top OD405 values (as determined for the 10 μg/mL concentrations in the ELISA) were used to calculate the bispecific binding in comparison to the control, which was arbitrarily set at 100%. This resulted in the percentage of controlled Fab-arm exchange (% cFAE) compared to the control as is shown in FIG. 34(A)-(D) for each 2-MEA concentration.

The data show that maximal level of bispecific binding (89-109% with respect to control) was reached at a concentration of 100 mM 2-MEA for both IgG concentrations at all temperature-time conditions. At 50 mM 2-MEA, maximal binding (88-10$^7$%) was achieved at 25° C. and 37° C. and also at 15° C. after 24 hours incubation. For the lower concentrations of 25 mM and 10 mM 2-MEA, the exchange was more efficient at higher temperatures and increased with prolonged incubation time, leading to maximal exchange at 37° C. upon 24 hours incubation at 25 mM 2-MEA. None of the conditions tested at 10 mM 2-MEA generated 100% bispecific product. The exchange process was slightly faster at IgG concentrations of 10 mg/mL compared to 20 mg/mL total IgG.

To confirm that bispecific antibodies were formed and to study the bispecific products in more detail, samples were analyzed with Cation Exchange (HPLC-CIEX) analysis. The HPLC-CIEX analysis was performed as described in Example 31 for the samples with IgG concentrations of 20 mg/mL after 5 hours and 24 hours incubation and all 2-MEA concentrations.

The CIEX chromatograms in FIG. 35(A)-(D) show that the highest yield of bispecific product was obtained at 50 and 100 mM 2-MEA confirming the results of the bispecific ELISA. However, minor amounts of residual homodimer were still detected at 50 and 100 mM 2-MEA (2-3.5% of each homodimer for samples incubated at 25° C. and 37° C.). Exchange at higher temperature, longer (24 hours) incubation time and increasing 2-MEA concentration result in the appearance of additional peaks at 22-24 min in the CIEX profile.

Minimal amounts of additional peaks were obtained when exchange was concluded within 5 hours. To identify the nature of these peaks, SDS-PAGE analysis and HP-SEC analysis was performed. HP-SEC showed that the amount of aggregates was below 1% for all conditions, suggesting that the additional peaks do not represent aggregates. However, non-reduced SDS-PAGE indicated that the extra peaks may represent heterodimer lacking one or two light chains. Minor amounts of half-molecules were detected as well.

The experiment shows that the exchange reaction takes place at high homodimer concentrations, which makes the process attractive for commercial scale, and that the yield of bispecific antibody depends on 2-MEA concentration, temperature and incubation time.

Example 35

Determinants at the IgG1 368 Position for Engagement in 2-MEA-Induced Fab-Arm Exchange in Combination with IgG1-K409R Example 28 and 29 show that certain single mutations at position F405 and Y407 are sufficient to enable human IgG1 to engage in Fab-arm exchange when combined with IgG1-K409R. As illustrated in this example further determinants implicated in the Fc:Fc interface positions in the CH3 domain may also mediate the Fab-arm exchange mechanism. To this effect mutagenesis of the IgG1 368 position was performed and the mutants were tested for engagement in 2-MEA-induced Fab-arm-exchange in combination with human IgG1-K409R. All possible IgG1-2F8-L368X mutants (with the exception of C and P) were combined with IgG1-7D8-K409R. The procedure was performed with purified antibodies as described in Example 19.

FIG. 36 shows the results of bispecific binding upon 2-MEA-induced Fab-arm exchange between IgG1-2F8-L368X×IgG1-7D8-K409R. These data were also scored as (−) no Fab-arm exchange, (+/−) low, (+) intermediate or (++) high Fab-arm exchange, as presented in Table 8. No Fab-arm exchange (−) was found when the 368 position in IgG1-2F8 was L (=wild type IgG1), F or M. Fab-arm exchange was found to be low (+/−) when the 368 position in IgG1-2F8 was Y. Fab-arm exchange was found to be intermediate (+) when the 368 position in IgG1-2F8 was K and high (++) when the 368 position in IgG1-2F8 was A, D, E, G, H, I, N, Q, R, S, T, V, or W. These data indicate that particular mutations at the IgG1 368 position allow IgG1 to engage in 2-MEA-induced Fab-arm exchange when combined with IgG1-K409R.

TABLE 8

2-MEA-induced Fab-arm exchange between IgG1-
2F8-L368X mutants and IgG1-7D8-K409R
The generation of bispecific antibodies after 2-MEA-induced
in vitro Fab-arm exchange between IgG1-2F8-L368X mutants
and IgG1-7D8-K409R was determined by a sandwich ELISA.

| IgG1-2F8-L368X | Fab-arm exchange x IgG1-7D8-K409R |
|---|---|
| A | ++ |
| D | ++ |
| E | ++ |
| F | − |
| G | ++ |
| H | ++ |
| I | ++ |
| K | + |
| L | − |
| M | − |
| N | ++ |
| Q | ++ |
| R | ++ |
| S | ++ |
| T | ++ |
| V | ++ |
| W | ++ |

(−) no, (+/−) low, (+) intermediate or (++) high Fab-arm exchange.

TABLE 9

2-MEA-induced Fab-arm exchange between IgG1-
2F8-K370X mutants and IgG1-7D8-K409R
The generation of bispecific antibodies after 2-MEA-induced
in vitro Fab-arm exchange between IgG1-2F8-K370X mutants
and IgG1-7D8-K409R was determined by a sandwich ELISA.

| IgG1-2F8-K370X | Fab-arm exchange x IgG1-7D8-K409R |
|---|---|
| A | − |
| D | − |
| E | − |
| F | − |
| G | − |
| H | − |
| I | − |
| K | − |
| L | − |
| M | − |
| N | − |
| Q | − |
| R | − |
| S | − |
| T | − |
| V | − |
| W | + |
| Y | − |

(−) no, (+/−) low, (+) intermediate or (++) high Fab-arm exchange.

Example 36

Determinants at the IgG1 370 Position for Engagement in 2-MEA-Induced Fab-Arm Exchange in Combination with IgG1-K409R Examples 28, 29 and 35 show that certain single mutations at positions F405, Y407 or L368 are sufficient to enable human IgG1 to engage in Fab-arm exchange when combined with IgG1-K409R. As illustrated in this example further determinants implicated in the Fc:Fc interface positions in the CH3 domain may also mediate the Fab-arm exchange mechanism. To this effect mutagenesis of the IgG1 370 position was performed and the mutants were tested for engagement in 2-MEA-induced Fab-arm-exchange in combination with human IgG1-K409R. All possible IgG1-2F8-K370X mutants (with the exception of C and P) were combined with IgG1-7D8-K409R. The procedure was performed with purified antibodies as described in Example 19.

FIG. 37 shows the results of bispecific binding upon 2-MEA-induced Fab-arm exchange between IgG1-2F8-K370X×IgG1-7D8-K409R. These data were also scored as (−) no Fab-arm exchange, (+/−) low, (+) intermediate or (++) high Fab-arm exchange, as presented in Table 9. No Fab-arm exchange (−) was found when the 370 position in IgG1-2F8 was K (=wild type IgG1), A, D, E, F, G, H, I, L, M, N, Q, R, S, T, V or Y. Only substitution of K370 with W resulted in intermediate Fab-arm exchange (+). These data indicate that only one mutation at the IgG1 370 position (K370W) allows IgG1 to engage in 2-MEA-induced Fab-arm exchange when combined with IgG1-K409R.

Example 37

Determinants at the IgG1 399 Position for Engagement in 2-MEA-Induced Fab-Arm Exchange in Combination with IgG1-K409R Examples 28, 29, 35 and 36 show that certain single mutations at positions F405, Y407, L368 or K370 are sufficient to enable human IgG1 to engage in Fab-arm exchange when combined with IgG1-K409R. As illustrated in this example further determinants implicated in the Fc:Fc interface positions in the CH3 domain may also mediate the Fab-arm exchange mechanism. To this effect mutagenesis of the IgG1 399 position was performed and the mutants were tested for engagement in 2-MEA-induced Fab-arm-exchange in combination with human IgG1-K409R. All possible IgG1-2F8-D399X mutants (with the exception of C and P) were combined with IgG1-7D8-K409R. The procedure was performed with purified antibodies as described in Example 19.

FIG. 38 shows the results of bispecific binding upon 2-MEA-induced Fab-arm exchange between IgG1-2F8-D399X×IgG1-7D8-K409R. These data were also scored as (−) no, (+/−) low, (+) intermediate or (++) high Fab-arm exchange, as presented in Table 10. No Fab-arm exchange (−) was found when the 399 position in IgG1-2F8 was D (=wild type IgG1), E and Q. Fab-arm exchange was found to be low (+/−) when the 399 position in IgG1-2F8 was V, intermediate (+) when the 399 position in IgG1-2F8 was G, I, L, M, N, S, T or W. Fab-arm exchange was found to be high (++) when the 399 position in IgG1-2F8 was A, F, H, K, R or Y. These data indicate that particular mutations at the IgG1 399 position allow IgG1 to engage in 2-MEA-induced Fab-arm exchange when combined with IgG1-K409R.

TABLE 10

2-MEA-induced Fab-arm exchange between IgG1-
2F8-D399X mutants and IgG1-7D8-K409R
The generation of bispecific antibodies after 2-MEA-induced
in vitro Fab-arm exchange between IgG1-2F8-D399X mutants
and IgG1-7D8-K409R was determined by a sandwich ELISA.

| IgG1-2F8-D399X | Fab-arm exchange x IgG1-7D8-K409R |
|---|---|
| A | ++ |
| D | − |
| E | − |
| F | ++ |
| G | + |
| H | ++ |
| I | + |
| K | ++ |
| L | + |
| M | + |
| N | + |
| Q | − |
| R | ++ |
| S | + |
| T | + |
| V | +/− |
| W | + |
| Y | ++ |

(−) no, (+/−) low, (+) intermediate or (++) high Fab-arm exchange.

Example 38

Determination of the Condition Range in which 2-MEA-Induced Fab-Arm Exchange Occurs Suboptimally to Discriminate Between Highly Efficient IgG1 Mutants The process of 2-MEA-induced Fab-arm exchange occurs efficiently at 37° C. when 25 mM 2-MEA is used. Under these conditions, the majority of permissive IgG1 mutants (IgG1 with certain single mutations at positions 368, 370, 399, 405 and 407 and/or 409 as described in Examples 19, 28, 29, and 35-37) show high levels of 2-MEA-induced Fab-arm exchange (80%-100%). To identify experimental conditions that would allow discrimination between the IgG1 mutants with the highest efficiency, 2-MEA-induced Fab-arm for four different mutant combinations (IgG1-2F8-F405S×IgG1-7D8-K409A, IgG1-2F8-D399R×IgG1-7D8-K409G, IgG1-2F8-L368R×IgG1-7D8-K409H and IgG1-2F8-F405L× IgG1-7D8-K409R) was studied over time at 15° C. and 20° C., respectively. Apart from changes in temperature, time period and antibody dilution (20, 2, 0.2 and 0.02 µg/mL) the procedure was performed as described in Example 19.

At 20° C. 2-MEA-induced Fab-arm exchange of the four mutant combinations occurred at different rates compared to the maximal exchange (positive control). After 105 min incubation IgG1-2F8-L368R×IgG1-7D8-K409H reached the maximal level of exchange, whereas IgG1-2F8-F405S× IgG1-7D8-K409A, IgG1-2F8-D399R×IgG1-7D8-K409G and IgG1-2F8-F405L×IgG1-7D8-K409R reached a maximum of 90%, 85% and 85%, respectively, after 200 min.

Figure 39:
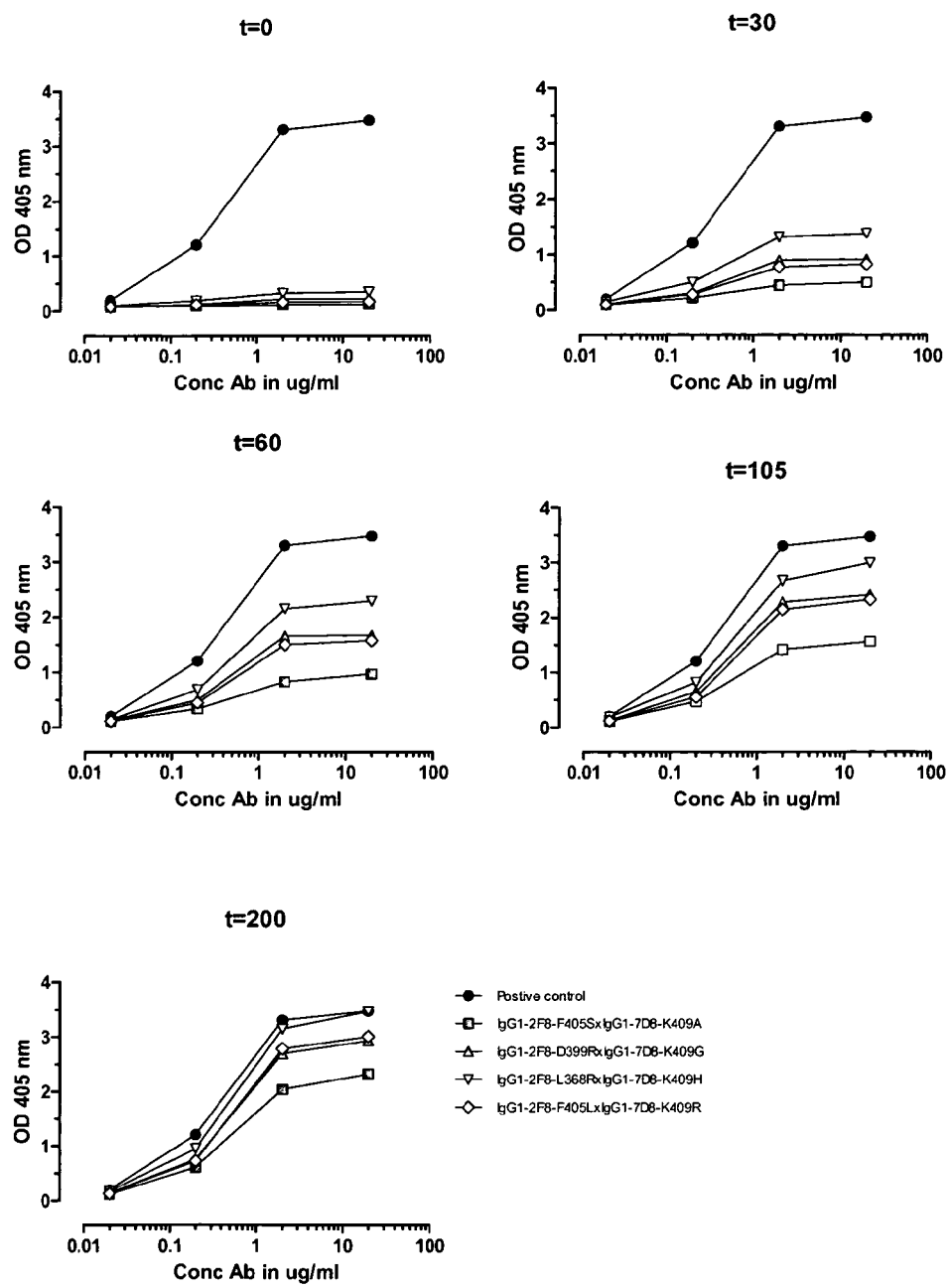
FIG. 39: 2-MEA-induced Fab-arm exchange between four different IgG1 mutant combinations at 15° C. after 0, 30, 60, 105 and 200 min incubations as determined by sandwich ELISA.

Incubation of the different IgG1 mutant combinations at 15° C. showed most prominent differences in exchange rates (shown in FIG. 39). After 60 and 105 min incubations, 2-MEA-induced Fab-arm exchange, the differences between the four mutant combinations were most extreme. Fab-arm exchange after 200 min incubation showed efficiencies of 100% (IgG1-2F8-L368R×IgG1-7D8-K409H), 85% (IgG1-2F8-F405L×IgG1-7D8-K409R and IgG1-2F8-D399R× IgG1-7D8-K409G) or 65% (IgG1-2F8-F405S×IgG1-7D8-K409A) compared to the positive control.

Example 39

Analyzing 2-MEA-Induced Fab-Arm Exchange Efficiencies of Mutants at Suboptimal Conditions The process of 2-MEA-induced Fab-arm exchange occurs efficiently at 37° C. when 25 mM 2-MEA is used. Under these conditions, the majority of permissive IgG1 mutants (IgG1 with certain single mutations at positions 368, 370, 399, 405 and 407 and/or 409 as described in Examples 19, 28, 29, and 35-37) show high levels of 2-MEA-induced Fab-arm exchange (80-100%). In Example 38 it is described that differences in 2-MEA-induced Fab-arm exchange efficiencies are most pronounced after incubation at socalled suboptimal conditions, namely at 15° C. for 60 to 105 min. In total 24 IgG1-2F8 mutants at the L368, D399, F405 and Y407 (see Table 11) that show >90% 2-MEA-induced Fab-arm exchange with IgG1-7D8-K409R (Example 28, 29, and 35-37) were selected and subjected to Fab-arm exchange analysis with IgG1-7D8-K409A, G, H or R (based on results reported in Example 19). To categorize these mutant combinations upon their efficiencies to generate bispecific antibodies, 2-MEA-induced Fab-arm exchange was performed at 15° C. for 90 min (suboptimal conditions). Two IgG1-2F8 mutants Y407Q and D399Q) that showed weak 2-MEA-induced Fab-arm exchange after incubation with IgG1-7D-K409R (Example 29 and 37) were taken along as additional negative controls and used to study whether incubation with another amino acid at the K409 position (G, H, or W) leads to a different result. Apart from a change in temperature and changes in antibody dilution (20, 2, 0.2 and 0.02 ug/mL), the procedure was performed as described in Example 19.

Incubation of all different IgG1 mutants combinations (as becomes clear from Table 11) at 15° C. for 90 min showed a range of different 2-MEA-induced Fab-arm exchange efficiencies. The result of bispecific binding at an antibody concentration of µg/mL, is shown in Table 11. Results were categorized in 4 classes; no (−), low (+/−) intermediate (+) and high (++) bispecific binding efficiency as is specified in the legend below for Table 11. From these results it becomes clear that under suboptimal conditions some combinations of amino acid mutations in IgG1 molecules will be favorable for 2-MEA-induced Fab-arm exchange.

TABLE 11

Bispecific binding (% relative to positive control) between permissive IgG1 mutants (20 µg/mL) at 15° C. for 90 min

| Fab-arm exchange | IgG1-7D8-K409A | IgG1-7D8-K409G | IgG1-7D8-K409R | IgG1-7D8-K409H |
|---|---|---|---|---|
| IgG1-2F8-L368A | 33 | 33 | 25 | 37 |
| IgG1-2F8-L368D | 49 | 50 | 41 | 54 |
| IgG1-2F8-L368E | 32 | 38 | 37 | 42 |
| IgG1-2F8-L368G | 46 | 53 | 44 | 53 |
| IgG1-2F8-L368H | 26 | 25 | 21 | 29 |
| IgG1-2F8-L368N | 47 | 52 | 43 | 54 |
| IgG1-2F8-L368R | 55 | 64 | 52 | 91 |
| IgG1-2F8-L368S | 39 | 45 | 37 | 53 |
| IgG1-2F8-L368T | 42 | 51 | 39 | 56 |
| IgG1-2F8-L368V | 42 | 49 | 33 | 51 |
| IgG1-2F8-L368W | 56 | 56 | 41 | 60 |
| IgG1-2F8-D399F | 13 | 15 | 14 | 15 |
| IgG1-2F8-D399H | 12 | 14 | 10 | 19 |
| IgG1-2F8-D399K | 40 | 43 | 34 | 46 |
| IgG1-2F8-D399R | 47 | 45 | 38 | 52 |
| IgG1-2F8-D399Q | 0 | 0 | 0 | 0 |
| IgG1-2F8-F405I | 32 | 49 | 39 | 60 |
| IgG1-2F8-F405K | 29 | 48 | 47 | 40 |
| IgG1-2F8-F405L | 31 | 44 | 39 | 46 |
| IgG1-2F8-F405S | 34 | 51 | 45 | 39 |
| IgG1-2F8-F405T | 35 | 47 | 42 | 46 |
| IgG1-2F8-F405V | 36 | 46 | 37 | 43 |
| IgG1-2F8-F405W | 17 | 20 | 16 | 18 |
| IgG1-2F8-Y407L | 44 | 41 | 49 | 49 |
| IgG1-2F8-Y407W | 48 | 53 | 47 | 62 |
| IgG1-2F8-Y407Q | 4 | 9 | 1 | 44 |

Legend for Table 11

| |
|---|
| No (0-3%) bispecific binding (-) |
| Low (4-39%) bispecific binding (+/-) |
| Intermediate (40-69%) bispecific binding (+) |
| High (70-100%) bispecific binding (++) |

Figure 40:
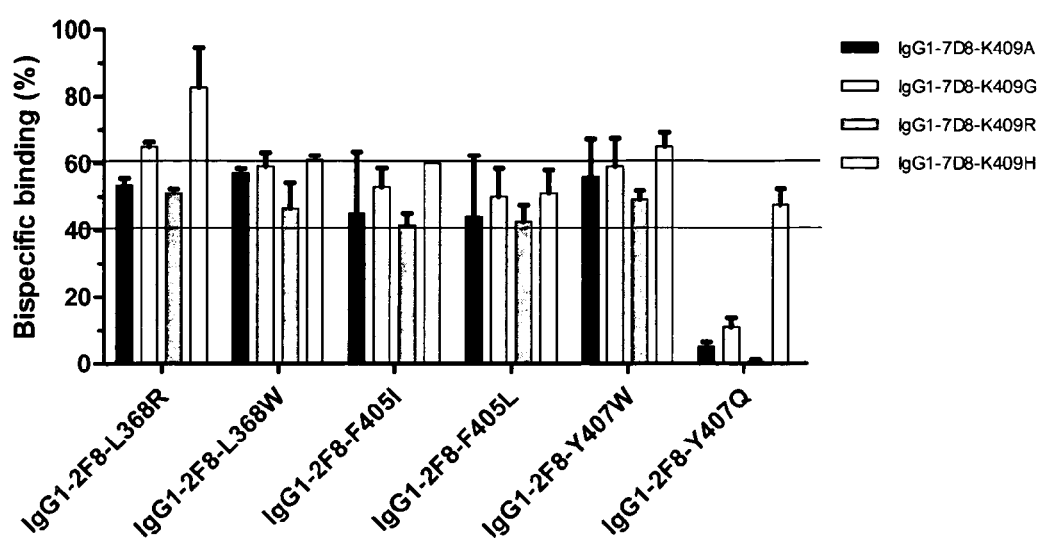
FIG. 40: 2-MEA-induced Fab-arm exchange between different IgG1 mutant combinations after antibody incubation at 15° C. for 90 min as determined by sandwich ELISA.

From the mutated IgG1-2F8 molecules tested (Table 11), six were selected for a second analysis to confirm the results obtained before (Table 11). Several mutants were selected for their high (IgG1-2F8-L368R) and intermediate (IgG1-2F8-L368W, IgG1-2F8-F405I, IgG1-2F8-F405L and IgG1-2F8-Y407W) 2-MEA-induced Fab-arm exchange efficiency. Also IgG1-2F8-Y407Q was analyzed for a second time since it showed an unexpected positive 2-MEA-induced Fab-arm exchange reaction with IgG1-7D8-K409H. In general, these results, presented in FIG. 40, confirmed the primary analysis (Table 11) and show that 2-MEA-induced Fab-arm exchange reactions of mutated IgG1-2F8 molecules with IgG1-7D8-K409H showed highest efficiency. Furthermore, 2-MEA-induced Fab-arm exchange reactions between mutated IgG1-2F8 molecules with IgG1-7D8-K409R that are reported in Examples 28, 29, and 35-37 as negative are still of interest as potentially promoting the IgG1 2-MEA-induced Fab-arm exchange.

Example 40

Using the Bispecific Format to Remove Undesired Agonistic Activity of Antagonistic C-Met Antibodies Converting them into a Monovalent, Bispecific Format Several bivalent antibodies developed for monoclonal antibody therapy show undesirable agonistic activity upon binding to their target. This is also the case for most IgG1 based antibodies targeting the receptor tyrosine kinase c-Met. These agonistic antibodies induce receptor dimerization followed by activation of several downstream signaling pathways. As a result growth and differentiation of (tumor) cells is induced. The use of monovalent antibody formats can prevent induction of receptor dimerization. Combination of an anti-c-Met antibody Fab-arm with a Fab-arm of an irrelevant antibody results in a bispecific antibody that is functionally monovalent and therefore completely antagonistic. Here we combined a partial-(IgG1-069) or a full (IgG1-058) agonistic antibody, with IgG1-b12 (first described in Burton D R, et al, "Efficient neutralization of primary isolates of HIV-1 by a recombinant human monoclonal antibody", Science. 1994 Nov. 11; 266(5187):1024-1027) in bispecific antibodies. IgG1-b12 was regarded as an irrelevant non-binding antibody since it is raised against a viral protein (HIV-gp120). The anti-c-Met antibodies used in this example are fully human monoclonal antibodies generated in transgenic mice. IgG1-058 and IgG1-069 bind to different epitopes on c-Met.

The two anti-c-Met antibodies used are IgG1,κ antibodies being modified in their Fc regions as further disclosed. They have the following heavy chain and light chain variable sequences.

058:

| SEQ ID NO | | |
|---|---|---|
| 12 | VH 058 | EVQLVESGGGLVKPGGSLKLSCAASGFTFSDYYMYW VRQTPEKRLEWVATISDDGSYTYYPDSVKGRFTISRD NAKNNLYLQMSSLKSEDTAMYYCAREGLYYYGSGSY YNQDYWGQGTLVTVSS |
| 13 | VL 058 | AIQLTQSPSSLSASVGDRVTITCRASQGLSSALAWYR QKPGKAPKLLIYDASSLESGVPSRFSGSGSGTDFTLTI SSLQPEDFATYYCQQFTSYPQITFGQGTRLEIK |

069:

| SEQ ID NO | | |
|---|---|---|
| 13 | VH 069 | QVQLVQSGAEVKKPGASVKVSCETSGYTFTSYGISW VRQAPGHGLEWMGWISAYNGYTNYAQKLQGRVTMT TDTSTSTAYMELRSLRSDDTAVYYCARDLRGTNYFDY WGQGTLVTVSS |
| 14 | VL 069 | DIQMTQSPSSVSASVGDRVTITCRASQGISNWLAWF QHKPGKAPKLLIYAASSLLSGVPSRFSGSGSGTDFTL TISSLQPEDFATYYCQQANSFPITFGQGTRLEIK |

Receptor Phosphorylation

Monovalent bispecific c-Met antibodies were generated by a Fab-arm exchange reaction with IgG1-058-F405L or IgG1-069-F405L and IgG1-b12-K409R as described in Example 23 using 25 mM 2-MEA. The effect of the bispecific antibody on c-Met phosphorylation was evaluated. Upon dimerization of two adjacent c-Met receptors by either the natural ligand HGF or by agonistic bivalent antibodies, three tyrosine residues (position 1230, 1234 and 1235) in the intracellular domain of c-Met are cross phosphorylated. This leads to phosphorylation of several other amino acids in the intracellular domain of c-Met and activation of a number of signaling cascades. The dimerization and activation of c-Met can be monitored by using antibodies specific for the phosphorylated receptor at these positions, which functions as a read out for the potential agonism of anti-c-Met antibodies.

Figure 41:
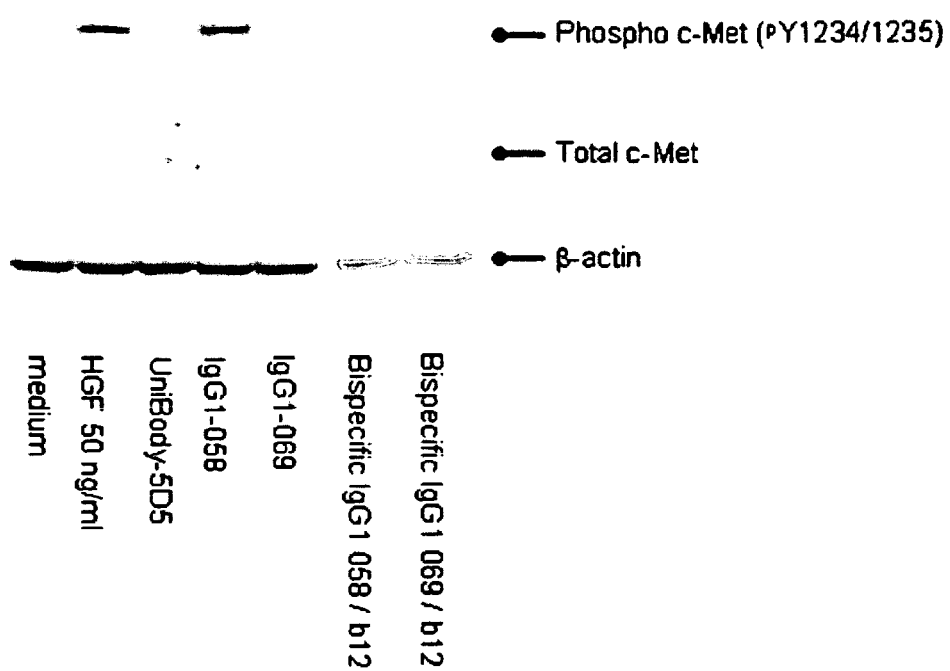
FIG. 41: Phosphorylation of c-Met by c-Met specific antibodies. A549 cells are incubated for 15 min with HGF or a panel of different antibodies. Proteins are separated by SDS-page gel electrophoresis and transferred to membranes by western blotting. Phosphorylated c-Met, total c-Met and β-actin are detected by antibodies against phosphorylated c-Met, total c-Met or β-actin.

A549 cells, CCL-185 obtained from ATCC, were grown in serum containing DMEM medium until 70% confluency was reached. Cells were trypsinized, washed and plated in a 6 well culture plate at 1*10e6 cells/well in serum containing culture medium. After overnight incubation the cells were treated with either HGF (R&D systems; cat. 294-HG) (50 ng/mL) or the panel of antibodies (30 µg/mL) and incubated for 15 minutes at 37° C. The cells were washed twice with ice cold PBS and lysed with lysis buffer (Cell Signaling; cat. 9803) supplemented with a protease inhibitor cocktail (Roche; cat. 11836170001). Cell lysate samples were stored at −80° C. Receptor activation was determined by detection of c-Met phosphorylation on Western blot using phospho c-Met specific antibodies. The proteins present in the cell lysate were separated on a 4-12% SDS-PAGE gel and transferred to nitrocellulose membrane that was subsequently stained with an antibody specific for phosphorylated c-Met (Y1234/1235) (Cell Signaling, cat: 3129). As a control for gel loading total β-actin and c-Met levels were determined using anti c-Met (Cell Signaling, Cat. No. 3127) and anti β-actin (Cell Signaling, Cat. No. 4967) antibodies. Results of the Western blots are shown in FIG. 41.

Tissue culture medium controls and cells treated with the monovalent format UniBody® (Genmab, WO2007059782 and WO2010063785) of antibody 5D5 (Genentech; WO 96/38557) did not show any c-Met receptor phosphorylation. The monovalent UniBody format as used herein is an IgG4, wherein the hinge region has been deleted and wherein the CH3 region has been mutated at positions 405 and 407. In contrast, Western blot analysis of cells treated with the positive control HGF or agonistic antibody IgG1-058 showed a clear band at the expected height of the phosphorylated c-Met. Partial agonistic antibody IgG1-069 showed less, but detectable receptor phosphorylation indicating that some cross linking of the receptor takes place. However, both bispecific IgG1 058/b12 and bispecific 069/b12 antibodies did not induce c-Met phosphorylation at all, showing that the agonistic activity associated with the parent antibodies was completely absent (FIG. 41).

Effect of C-Met Antibodies on NCI-H441 Proliferation In Vitro

The potential proliferative agonistic activity of c-Met antibodies was tested in vitro in the lung adenocarcinoma cell line NCI-H441 (ATCC, HTB-174™). This cell line expresses high levels of c-Met, but does not produce its ligand HGF. NCI-H441 cells were seeded in a 96-wells tissue culture plate (Greiner bio-one, Frickenhausen, Germany) (5,000 cells/well) in RPMI (Lonza) without serum. Anti c-Met antibody was diluted to 66.7 nM in RPMI medium without serum and added to the cells. After seven days incubation at 37° C./5% $CO_2$, the amount of viable cells was quantified with Alamarblue (BioSource International, San Francisco, US) according to the manufacturer's instruction. Fluorescence was monitored using the EnVision 2101 Multilabel reader (PerkinElmer, Turku, Finland) with standard Alamarblue settings.

Figure 42:
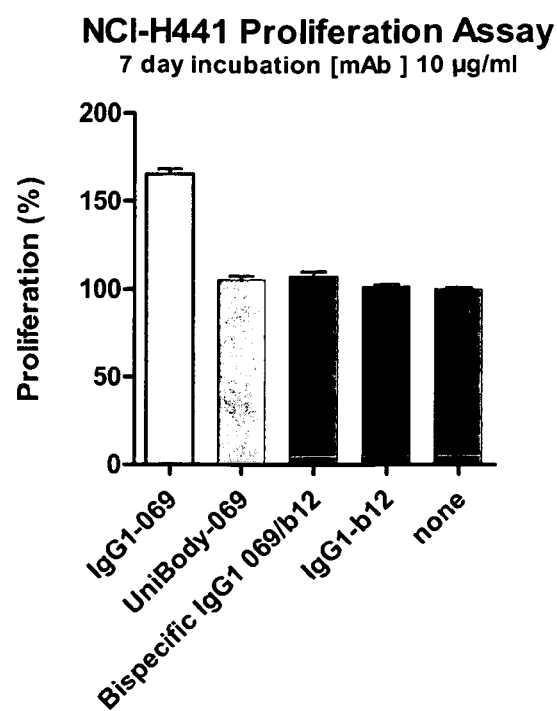
FIG. 42: Proliferation assay with NCI-H441 cells. NCI-H441 cells were incubated for seven days with monovalent bispecific IgG1 069/b12, control antibodies (IgG1-069, UniBody-069, IgG1-b12) left untreated. Cell mass was determined and plotted as percentage of non-treated samples (set as 100%)

In contradiction to IgG1-069, no proliferation was induced upon incubation of NCI-H441 cells with the bispecific IgG1-069/b12, as is shown in FIG. 42. Also the UniBody-069 control did not induce proliferation, which was comparable to the none- or IgG1-b12 treated.

Example 41

CDC-Mediated Cell Killing by Bispecific Antibodies Generated by 2-MEA-Induced Fab-Arm-Exchange Between Human IgG1-2F8-F405L or IgG1-7D8-F405L and IgG1-7D8-K409R The CD20 antibody IgG1-7D8 can efficiently kill CD20-expressing cells by complement-dependent cytotoxicity (CDC). In contrast, the EGFR antibody IgG1-2F8 does not mediate CDC on target cells expressing EGFR. Both IgG1-7D8-K409R and the bispecific antibody generated by 2-MEA-induced Fab-arm-exchange between IgG1-2F8-F405LxIgG1-7D8-K409R are able to induce CDC on CD20-expressing cells (as is described in Example 26). It was tested whether the bispecific antibody generated by 2-MEA-induced Fab-arm-exchange between IgG1-7D8-F405L and IgG1-7D8-K409R could also induce CDC on CD20 expressing cells. $10^5$ Daudi or Raji cells were pre-incubated for 15 min with a concentration series of antibody in 100 μL RPMI medium supplemented with 0.1% BSA in a shaker at room temperature. 25 μL normal human serum (NHS) was added as a source of complement (20% NHS final concentration) and incubated for 45 min at 37° C. After incubation, plate was placed on ice to stop the CDC reaction. Dead and viable cells were discriminated by adding μL 10 μg/mL propidium iodide (PI) (0.6 μg/mL final concentration) and FACS analysis.

FIG. 43 shows that IgG1-7D8 and the bispecific product generated by 2-MEA-induced Fab-arm-exchange between IgG1-7D8-F405L and IgG1-7D8-K409R have the same potency to induce CDC-mediated cell kill of CD20-expressing Daudi (FIG. 43A) and Raji (FIG. 43B). Both Daudi and Raji cells do not express EGFR, resulting in monovalent binding of the bispecific antibody generated by 2-MEA-induced Fab-arm-exchange between IgG2-2F8-F405LxIgG1-7D8-K409R This bispecific product also induced CDC mediated cell kill, albeit slightly less efficient. These data indicate that CDC capacity of a parental antibody was retained in the bispecific format. Induction of CDC mediated cell killing by the bivalent bispecific product (IgG1-7D8-F405LxIgG1-7D8-K409R) was slightly more efficient compared to the monovalent bispecific product (IgG2-2F8-F405LxIgG1-7D8-K409R). The CD20 targeting 11B8 antibody is not able to induce CDC mediated cell kill and functions as a negative control.

Example 42

HER2xHER2 Bispecific Antibodies Tested in an In Vitro Kappa-Directed ETA' Killing Assay The example shows that HER2xHER2 bispecific antibodies can deliver a cytotoxic agent into tumor cells after internalization in a generic in vitro cell-based killing assay using kappa-directed pseudomonas-exotoxin A (anti-kappa-ETA'). This assay makes use of a high affinity anti-kappa domain antibody conjugated to a truncated form of the pseudomonas-exotoxin A. Similar fusion proteins of antibody binding proteins (IgG-binding motif from Streptococcal protein A or protein G) and diphtheria toxin or *Pseudomonas* exotoxin A have previously been (Mazor Y. et al., *J. Immunol. Methods* 2007; 321:41-59); Kuo S R. et al., 2009 *Bioconjugate Chem.* 2009; 20:1975-1982). These molecules in contrast to anti-kappa-ETA' bound the Fc part of complete antibodies. Upon internalization and endocytic sorting the anti-kappa-ETA' domain antibody undergoes proteolysis and disulfide-bond reduction, separating the catalytic from the binding domain. The catalytic domain is then transported from the Golgi to the endoplasmic reticulum via a KDEL retention motif, and subsequently translocated to the cytosol where it inhibits protein synthesis and induces apoptosis (Kreitman R J. et. al., *BioDrugs* 2009; 23:1-13).

The anti-HER2 antibodies used in this example and the following Examples 43-45 are fully human monoclonal antibodies generated in transgenic mice. They bind to different epitopes on HER2.

They are all IgG1,κ antibodies being modified in their Fc regions as further disclosed. They have the following heavy chain and light chain variable sequences.
005:

| SEQ ID NO | | |
|---|---|---|
| 16 | VH 005 | EVQLVQSGAEVKKPGESLKISCKASGYSFHFYWIGWVRQMPGK GLEWMGSIYPGDSDTRYRPSFQGQVTISADKSISTAYLQWTSL KASDTAIYYCARQRGDYYYFYGMDVWGQGTTVTVSS |
| 17 | VL 005 | EIVLTQSPGTLSLSPGERATLSCRASQSVSSSYLAWYQQKPGQ VPRLLIYGASSRATGIPDRFSGSGSGTDFTLTISRLEPEDFAV YYCQQYGSS-LTFGGGTKVEIK |

025:

| SEQ ID NO | | |
|---|---|---|
| 18 | VH 025 | QVQLQQWGAGLLKPSETLSLTCAVYGGSFSDYYWNW IRQPPGKGLEWIGEIHHSGSTNYNPSLKSRVTISVD TSKNQFSLKLSSVTAADTAVYYCARGYYDSGVYYFD YWAQGTLVTVSS |
| 19 | VL 025 | DIQMTQSPSSLSASVGDRVTITCRASQGISRWLAWY QQKPEKAPKSLIYAASSLRSGVPSRFSGSGSGTDFT LTISSLQPEDFATYYCQQYNSYPITFGQGTRLEIK |

153:

| SEQ ID NO | | |
|---|---|---|
| 20 | VH 153 | QVQLVESGGGVVQPGRSLRLSCAASGFTFSDYVIHWV RQAPGKGLEWVTVISYDGSNKYYADSVKGRFTISRDN SKNTLYLQMNSLSAEDTAMYYCARGGITGTTGVFDYW GQGTLVTVSS |

```
         21    VL 153    DIQMTQSPSSLSASVGDRVTITCRASQGISSWLAWYQ
                        QKPEKAPKSLIYDASSLQSGVPSRFSGSGYGTDFSLT
                        ISSLQPEDFAIYYCQQYKSYPITFGQGTRLEIK
```

169:

```
SEQ ID NO

22    VH 169    QVQLVQSGAEVKKPGASVKVSCKASGYTFTNYGISWV
                        RQAPGQGLEWMGWLSAYSGNTIYAQKLQGRVTMTTDT
                        STTTAYMELRSLRSDDTAVYYCARDRIVVRPDYFDYW
                        GQGTLVTVSS

23    VL 169    EIVLTQSPATLSLSPGERATLSCRASQSVSSYLAWYQ
                        QKPGQAPRLLIYDASNRATGIPARFSGSGSGTDFTLT
                        ISSLEPEDFAVYYCQQRSNWPRTFGQGTKVEIK
```

HER2×HER2 bispecific antibodies were pre-incubated with the anti-kappa-ETA' before incubation with A431 cells. A431 cells express ~15,000 HER2 antibodies per cell (determined via Qifi analysis) and are not sensitive to treatment with 'naked' HER2-antibodies.

First, the optimal concentration of anti-kappa-ETA' was determined for each cell line, i.e. the maximally tolerated dose that does not lead to induction of non-specific cell death. A431 cells (2500 cells/well) were seeded in normal cell culture medium in a 96-wells tissue culture plate (Greiner bio-one) and allowed to adhere for at least 4 hours. These cells were incubated with an anti-kappa-ETA' dilution series, 100, 10, 1, 0.1, 0.01, 0.001 and 0 µg/mL in normal cell culture medium. After 3 days, the amount of viable cells was quantified with Alamarblue (BioSource International, San Francisco, US) according to the manufacturer's instruction. Fluorescence was monitored using the EnVision 2101 Multilabel reader (PerkinElmer, Turku, Finland) with standard Alamarblue settings. The highest concentration anti-kappa-ETA' that did not kill the cells by itself (1 µg/mL for A431 cells) was used for following experiments.

Next, the effect of HER2×HER2 bispecific antibodies and HER2 monospecific antibodies pre-incubated with anti-kappa-ETA' was tested for their ability to induce cell kill. A431 cells were seeded as described above. A dilution series of the HER2 specific antibodies (monospecific and bispecific antibodies) was made and pre-incubated for 30 min with the predetermined concentration of anti-kappa-ETA' before adding them to the cells. After 3 days incubation at 37° C., the amount of viable cells was quantified as described above. The Alamarblue signal of cells treated with anti-kappa-ETA' pre-incubated with the antibodies was plotted compared to cells treated without antibody treatment. $EC_{50}$ values and maximal cell death were calculated using GraphPad Prism 5 software. Staurosporin (23.4 µg/mL) was used as positive control for cell killing. An isotype control antibody (IgG1/kappa; IgG1-3G8-QITL) was used as negative control.

Figure 44:
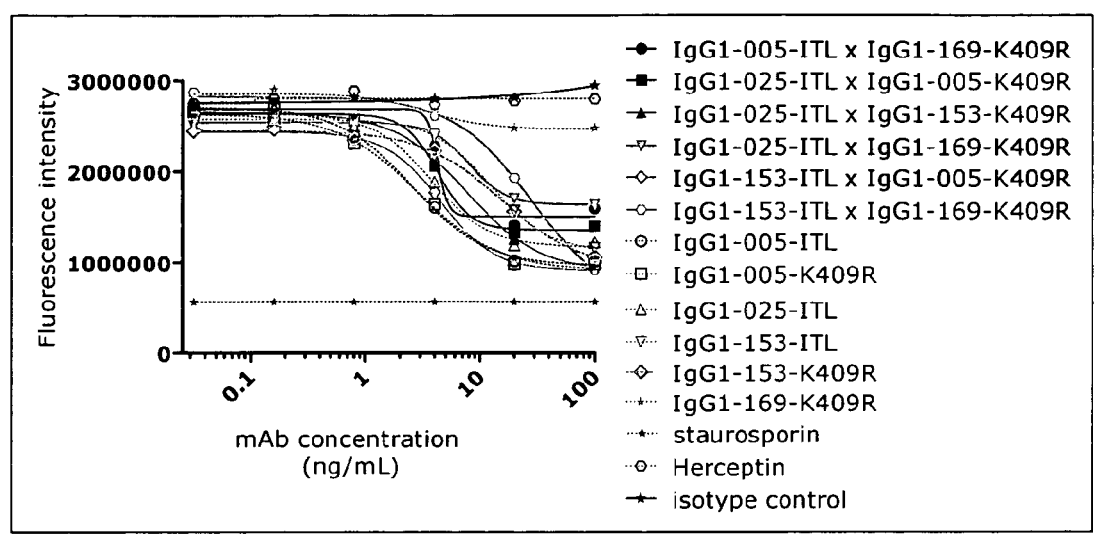
FIG. 44: Killing of A431 cells induced by anti-kappa-ETA' pre-incubated HER2×HER2 bispecific antibodies. The viability of A431 cells after 3 days incubation with HER2 antibodies, pre-incubated with anti-kappa-ETA'. Cell viability was quantified using Alamarblue. Data shown are fluorescence intensities (FI) of one experiment with A431 cells treated with anti-kappa-ETA'-conjugated HER2 antibodies and HER2×HER2 bispecific antibodies. Staurosporin was used as positive control, whereas an isotype control antibody was used as negative control.

FIG. 44 shows that all anti-kappa-ETA' pre-incubated HER2 bispecific antibodies were able to kill A431 cells in a dose-dependent manner. These results demonstrate that most HER2 bispecific antibodies tested were more effective than the monospecific antibody present in the combination in this anti-kappa-ETA' assay. In addition, the efficacy of bispecific antibody 005×169, 025×169 and 153×169 showed that the efficacy of a monospecific antibody which lacks activity in this in vitro kappa-directed ETA' killing, HER2 specific antibody 169, can be increased through bispecific combination with another HER2 specific antibody.

Example 43

HER2 Receptor Downmodulation by Incubation with Bispecific Antibodies Targeting Different HER2 Epitopes HER2×HER2 bispecific antibodies may bind two different epitopes on two spatially different HER2 receptors. This may allow other HER2×HER2 bispecific antibodies to bind to the remaining epitopes on these receptors. This could result in multivalent receptor cross-linking (compared to dimerization induced by monovalent antibodies) and consequently enhance receptor downmodulation. To investigate whether HER2×HER2 bispecific antibodies induce enhanced downmodulation of HER2, AU565 cells were incubated with antibodies and bispecific antibodies for three days. Total levels of HER2 and levels of antibody bound HER2 were determined.

AU565 cells were seeded in a 24-well tissue culture plate (100.000 cells/well) in normal cell culture medium and cultured for three days at 37° C. in the presence of 10 µg/mL HER2 antibody or HER2×HER2 bispecific antibodies. After washing with PBS, cells were lysed by incubating them for 30 min at room temperature with 25 µL Surefire Lysis buffer (Perkin Elmer, Turku, Finland). Total protein levels were quantified using bicinchoninic acid (BCA) protein assay reagent (Pierce) following manufacturer's protocol. HER2 protein levels in the lysates were analyzed using a HER2-specific sandwich ELISA. Rabbit-anti-human HER2 intracellular domain antibody (Cell Signaling) was used to capture HER2 and biotinylated goat-anti-human HER2 polyclonal antibody R&D systems, Minneapolis, USA), followed by streptavidin-poly-HRP, were used to detect bound HER2. The reaction was visualized using 2,2'-azino-bis 3-ethylbenzothiazoline-6-sulfonic acid (one ABTS tablet diluted in 50 mL ABTS buffer [Roche Diagnostics, Almere, The Netherlands]) and stopped with oxalic acid (Sigma-Aldrich, Zwijndrecht, The Netherlands). Fluorescence at 405 nm was measured on a microtiter plate reader (Biotek Instruments, Winooski, USA) and the amount of HER2 was expressed as a percentage relative to untreated cells.

Figure 45:
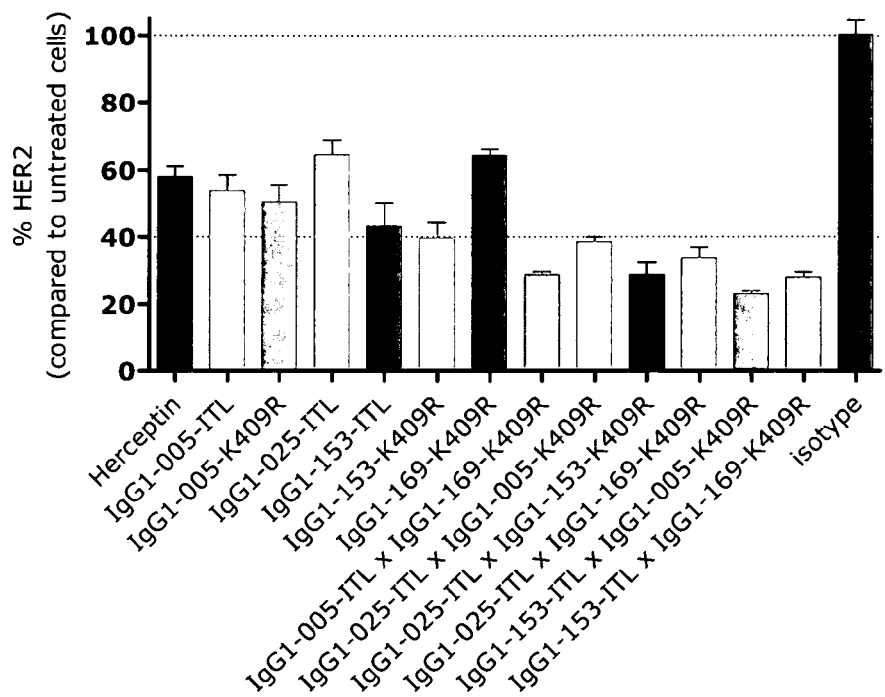
FIG. 45: HER2×HER2 bispecific molecules induced downmodulation of HER2 receptor. Relative percentage of HER2 expression levels in AU565 cell lysates after 3 days incubation with 10 μg/mL mAb. The amount of HER2 was quantified using a HER2-specific capture ELISA and depicted as percentage inhibition compared to untreated cells. Data shown is the mean of two experiments plus standard deviation.

The results are shown in FIG. 45 which demonstrates that all the tested HER2×HER2 bispecific antibodies induced ≥40% HER2 downmodulation. Interestingly, all HER2× HER2 bispecific antibodies demonstrated increased HER2 downmodulation compared to both of their monospecific counterparts.

Example 44

Colocalization of HER2×HER2 Bispecific Antibodies with Lysosomal Marker LAMP1 Analyzed by Confocal Microscopy The HER2 downmodulation assay as described in Example 43 indicated that HER2×HER2 bispecific antibodies were able to increase lysosomal degradation of HER2. To confirm these findings, confocal microscopy technology was applied. AU565 cells were grown glass coverslips (thickness 1.5 micron, Thermo Fisher Scientific, Braunschweig, Germany) in standard tissue culture medium for 3 days at 37° C. Cells were pre-incubated for 1 hour with leupeptin (Sigma) to block lysosomal activity after which 10 ug/mL HER2 monospecific antibodies or HER2×HER2 bispecific antibodies were added. The cells were incubated for an additional 3 or 18 hours at 37° C. Hereafter they were washed with PBS and incubated for 30 min. at room temperature with 4% formaldehyde (Klinipath). Slides were washed with blocking buffer (PBS supplemented with 0.1% saponin [Roche] and 2% BSA [Roche]) and incubated for 20 min with blocking buffer containing 20 mM $NH_4Cl$ to quench formaldehyde. Slides were washed again with blocking buffer and incubated for 45 min at room temperature with mouse-anti-human CD107a (LAMP1) (BD Pharmingen) to stain lysosomes. Following washing with blocking buffer the slides were incubated min at room temperature with a cocktail of secondary antibodies; goat-anti-mouse IgG-Cy5 (Jackson) and goat-anti-human IgG-FITC (Jackson). Slides were washed again with blocking buffer and mounted overnight on microscope slides using µL mounting medium (6 gram Glycerol [Sigma] and 2.4 gram Mowiol 4-88 [Omnilabo] was dissolved in 6 mL distilled water to which 12 mL 0.2M Tris [Sigma] pH8.5 was added followed by incubation for 10 min at 50-60° C. Mounting medium was aliquoted and stored at −20° C.). Slides were imaged with a Leica SPE-II confocal microscope (Leica Microsystems) equipped with a 63×1.32-0.6 oil immersion objective lens and LAS-AF software. To allow for quantification of overlapping pixel intensities, saturation of pixels should be avoided. Therefore the FITC laser intensity was decreased to 10%, smart gain was set at 830 V and smart offset was set at −9.48%. By using these settings, the bispecific antibodies were clearly visualized without pixel saturation, but the monospecific antibodies were sometimes difficult to detect. To compare lysosomal colocalization between monospecific and bispecific antibodies, these settings were kept the same for all analyzed confocal slides.

12-bit images were analyzed for colocalisation using MetaMorph® software (version Meta Series 6.1, Molecular Devices Inc, Sunnyvale Calif., USA). FITC and Cy5 images were imported as stacks and background was subtracted. Identical thresholds settings were used (manually set) for all FITC images and all Cy5 images. Colocalisation was depicted as the pixel intensity of FITC in the region of overlap (ROI), were the ROI is composed of all Cy5 positive regions. To compare different slides stained with several HER2 antibodies or HER2×HER2 bispecific antibodies, the images were normalized using the pixel intensity of Cy5. Goat-anti-mouse IgG-Cy5 was used to stain the lysosomal marker LAMP1 (CD107a). The pixel intensity of LAMP1 should not differ between various HER2 antibodies or the HER2×HER2 bispecific antibodies tested (one cell had a pixel intensity of Cy5 of roughly 200.000).

Normalized values for colocalization of FITC and Cy5=[(TPI-FITC×percentage FITC-Cy5 colocalization)/100]×[200.000/TPI-Cy5]

In this formula, TPI stands for Total Pixel Intensity.

presents percentage of viable cells, as measured by the FITC pixel intensity overlapping with Cy5 for various monospecific HER2 antibodies and HER2×HER2 bispecific antibodies. For each antibody or bispecific molecule depicted, three different images were analyzed from one slide containing ~1, 3 or >5 cells. Significant variation was observed between the different images within each slide. However, it was evident that all HER2×HER2 bispecific antibodies demonstrate increased colocalisation with the lysosomal marker LAMP1, when compared with their monospecific counterparts. These results indicate that once internalized, HER2×HER2 bispecific antibodies are efficiently sorted towards lysosomal compartments, making them suitable for a bispecific antibody drug conjugate approach.

Example 45

Inhibition of Proliferation of AU565 Cells Upon Incubation with HER2 Monospecific or HER2×HER2 Bispecific Antibodies HER2 bispecific antibodies were tested for their ability to inhibit proliferation of AU565 cells in vitro. Due to the high HER2 expression levels on AU565 cells (~1.000.000 copies per cell as determined with Qifi-kit), HER2 is constitutively active in these cells and thus not dependent on ligand-induced heterodimerization. In a 96-wells tissue culture plate (Greiner bio-one, Frickenhausen, Germany), 9.000 AU565 cells were seeded per well in the presence of 10 µg/mL HER2 antibody or HER2×HER2 bispecific antibodies in serum-free cell culture medium. As a control, cells were seeded in serum-free medium without antibody or bispecific antibodies. After three days, the amount of viable cells was quantified with Alamarblue (BioSource International, San Francisco, US) according to the manufacturer's instructions. Fluorescence was monitored using the EnVision 2101 Multilabel reader (PerkinElmer, Turku, Finland) with standard Alamarblue settings. The Alamarblue signal of antibody-treated cells was plotted as a percentage relative to untreated cells.

Figure 47:
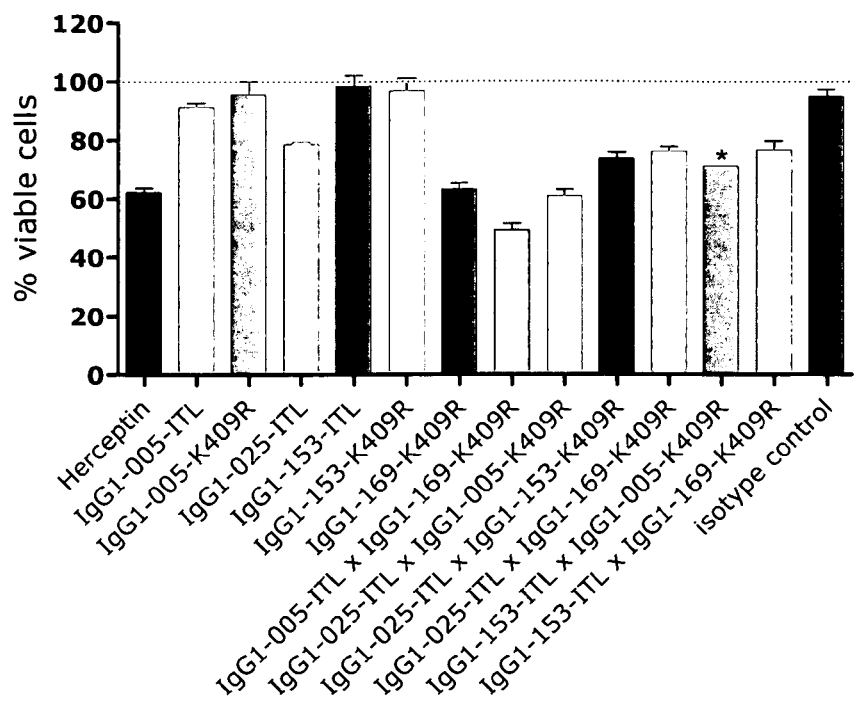
FIG. 47: Inhibition of proliferation by HER-2 mono and bispecific antibodies. AU565 cells were seeded in the presence of 10 μg/mL HER2 antibody or HER2×HER2 bispecific antibody in serum-free cell culture medium. After three days, the amount of viable cells was quantified with Alamarblue and cell viability was presented as a percentage relative to untreated cells. An isotype control antibody was used as negative control. Data shown are percentage viable AU565 cells compared to untreated cells measured in five-fold±the standard deviation. * indicates only one data point was depicted.

FIG. 47 depicts the fluorescent intensity of Alamarblue of AU565 cells after incubation with HER2 antibodies and HER2×HER2 bispecific antibodies. Herceptin® (trastuzumab) was included as positive control and demonstrated inhibition of proliferation as described by Juntilla T T. et al., Cancer Cell 2009; 15: 429-440. All HER2×HER2 bispecific antibodies were able to inhibit proliferation of AU565 cells. Bispecific antibodies: IgG1-005-ITL×IgG1-169-K409R and IgG1-025-ITL×IgG1-005-K409R were more effective compared to their monospecific antibody counterparts in this assay.

Example 46

In Vitro and In Vivo Analysis of FcRn Binding by Bispecific IgG1 Antibodies and Hinge-Deleted IgG1 Bispecific Antibodies Containing One or Two FcRn Binding Sites in the Fc Region The present example illustrates the generation of asymmetrical bispecific molecules, i.e. molecules with different characteristics in each Fab-arm according to the invention.

The neonatal Fc receptor (FcRn) is responsible for the long plasma half-life of IgG by protecting IgG from degradation. After internalization of the antibody, FcRn binds to antibody Fc regions in endosomes, where the interaction is stable in the mildly acidic environment (pH 6.0). Upon recycling to the plasma membrane, where the environment is neutral (pH 7.4), the interaction is lost and the antibody is released back into the circulation. The Fc region of an antibody contains 2 FcRn binding sites, one in each heavy chain at the CH2-CH3 interfaces. An H435A mutation in the Fc region of the antibody abrogates binding to FcRn (Shields, R. L., et al, J Biol Chem, 2001, Firan, M., et al, Int Immunol, 2001) and also the hinge region is thought to influence FcRn binding (Kim, J. K., et al., Mol. Immunol., 1995). Furthermore, a role for bivalent over monovalent antibody binding to FcRn has been suggested in efficient recycling (Kim, J. K., et al., Scand J. Immunol., 1994).

In this example the influence of FcRn binding valency is evaluated by asymmetric bispecific IgG1 molecules, containing a single FcRn binding site. The additional contribution of the hinge region is evaluated by asymmetric bispecific hinge-deleted IgG1 (Uni-G1) molecules.

FcRn binding of bispecific IgG1 or hinge-deleted IgG1 (Uni-G1) molecules containing no, 1 or 2 FcRn binding sites was measured by human and mouse FcRn ELISA. Antibodies IgG1-2F8-ITL, IgG1-7D8-K409R and IgG1-7D8-K409R-H435A monospecific molecules were produced as described in example 2, 3, 4 and 5. Hinge-deleted IgG1 molecules Uni-G1-2F8-ITL, Uni-G1-7D8-K409R and Uni-G1-7D8-K409R-H435A monospecific molecules were produced as described in example 11. Bispecific IgG1 molecules were generated by 2-MEA induced Fab-arm exchange between IgG1-2F8-ITL and IgG1-7D8-K409R or IgG1-7D8-K409R-H435A molecules. Bispecific hinge-deleted IgG1 molecules were produced by incubation of Uni-G1-2F8-ITL with Uni-G1-7D8-K409R or Uni-G1-7D8-K409R-H435A. A 3-fold dilution series of monospecific and bispecific IgG1 molecules and hinge-deleted IgG1 molecules were added to biotinylated human- or mouse-FcRn captured on a streptavidin-coated elisa plate followed by incubation at pH 6.0 and 7.4 for 1 hour. Bound antibody and hinge-deleted IgG1 molecules were visualized using horseradishperoxidase-labeled goat-anti-human (Fab')₂ as conjugate and ABTS as substrate. Results were measured as optical density at a wavelength of 405 nm using the EL808-Elisa-reader.

Figure 48:
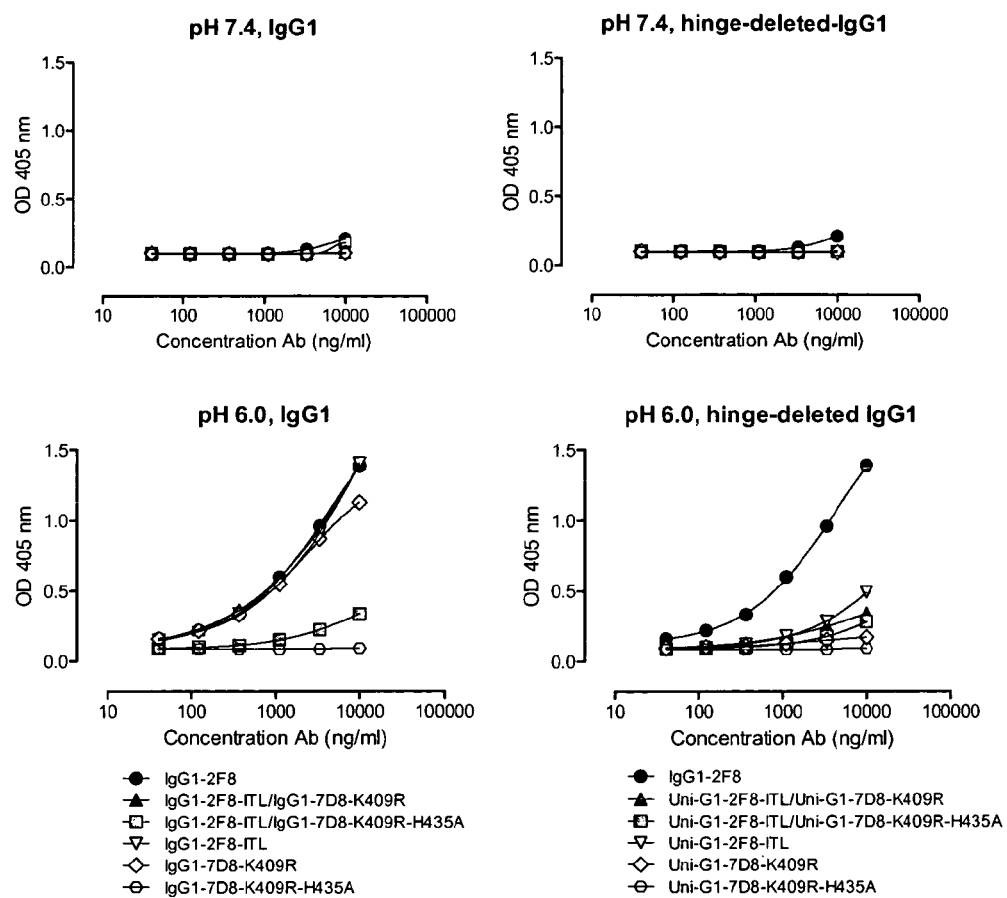
FIG. 48: Binding of mono and bispecific IgG1 and hinge-deleted IgG1 antibodies to human and mouse FcRn at different pH. Plates with human and mouse FcRn were incubated with different mono- and bispecific IgG1 antibodies or hinge-deleted IgG1 molecules. Binding to FcRn was analyzed by ELISA at 405 nm. (A) Binding of mono and bispecific IgG1 antibodies and hinge-deleted IgG1 (Uni-G1) molecules to human FcRn at pH 7.4 and 6.0. Binding to human FcRn is very low at neutral pH. At pH 6.0 (bispecific) antibodies bind efficiently to human FcRn, unless they contain the H435A mutation. Hinge-deleted IgG1 (Uni-G1) molecules bind human FcRn with low efficiency. (B) Binding of mono and bispecific IgG1 antibodies and hinge-deleted IgG1 (Uni-G1) molecules to mouse FcRn at pH 7.4 and 6.0. Binding to mouse FcRn is very low at neutral pH. At pH 6.0 (bispecific) antibodies bind very efficiently to mouse FcRn, unless they contain the H435A mutation in both Fab-arms. The bispecific molecule harboring the H435A mutation in only one Fab-arm is still able to bind mouse FcRn. Hinge-deleted IgG1 (Uni-G1) molecules bind mouse FcRn with intermediate efficiency and the hinge-deleted IgG1 (Uni-G1) bispecific molecule harboring the H435A mutation in only one Fab-arm is slightly less efficient.
Figure 48:
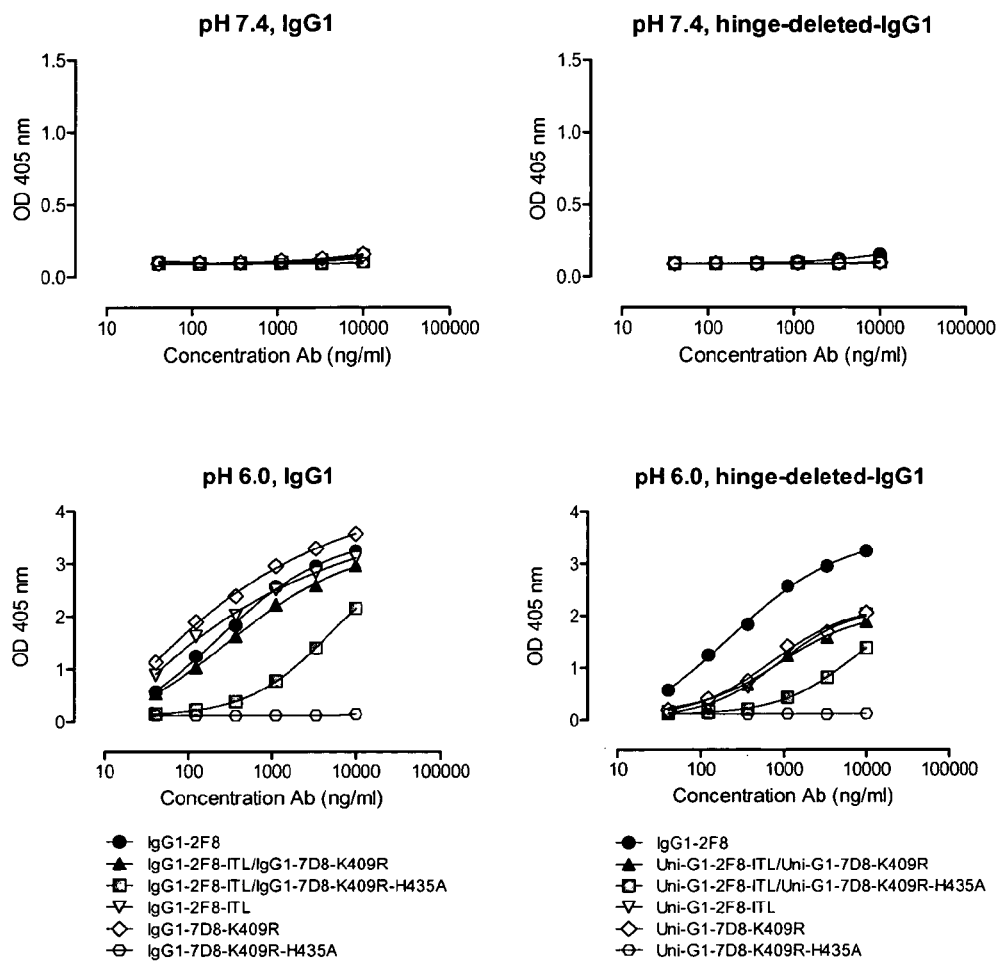

FIG. 48 shows the binding results of monovalent or bivalent IgG1 antibodies and hinge-deleted IgG1 molecules to human FcRn (A) and mouse FcRn (B) at pH 6.0 and pH 7.4. As expected, all antibodies tested, both (bispecific) IgG1 and hinge-deleted IgG1 molecules, do not bind efficiently to FcRn (both human and mouse) at pH 7.4. At slightly acidic condition (pH 6.0) monospecific IgG1-2F8-ITL and bispecific IgG1 generated from IgG1-2F8-ITL and IgG1-7D8-K409R show bivalent binding efficiencies to FcRn, albeit for mouse FcRn 3 fold higher compared to human, which mimics the positive control (IgG1-2F8) for FcRn binding. This indicates that the ITL mutation and the K409R do not disturb binding to FcRn.

A clear effect of 2 vs 1 vs 0 FcRn interaction sites can be seen when the binding of the IgG1 molecules to human and mouse FcRn is compared at pH 6.0 (Figure XXA and B, pH6, left panel). IgG1-2F8-ITL, IgG1-7D8-K409R and IgG1-2F8-ITL/IgG1-7D8-K409R (2 FcRn binding sites) bind comparable to the control (IgG1-2F8). The molecules with 0 FcRn binding sites, IgG1-7D8-K409R-H435A show no binding at all. The molecules with 1 FcRn binding site, IgG1-2F8-ITL/IgG1-7D8-K409R-H435A, show intermediate binding when compared to the molecules with 2 FcRn binding sites.

FIG. 48(A), pH 6.0, right panel shows the binding to human FcRn of hinge-deleted IgG1 molecules (Uni-G1). All hinge-deleted molecules are impaired in their interaction to human FcRn when compared to the control IgG1 molecules (IgG1-2F8) indicating that the hinge is indeed of influence in the interaction with FcRn when evaluated in an FcRn binding ELISA. No clear effect of 2 vs 1 vs 0 FcRn interaction sites can be seen when the binding to human FcRn at pH6.0 is compared of these hinge-deleted molecules.

However, since the binding of human IgG to mouse FcRn is stronger, a clear effect of 2 vs 1 vs 0 FcRn interaction sites can be seen when the binding of these hinge-deleted IgG molecules to mouse FcRn at pH 6.0 is compared (FIG. 48(B), pH 6.0, right panel). The binding of Uni-G1-7D8-K409R-H435A/Uni-G1-2F8-ITL (1 FcRn binding site) is intermediate when compared to the binding of Uni-G1-2F8-ITL, Uni-G1-7D8-409R and Uni-G1-2F8-ITL/Uni-G1-7D8-K409R (2 FcRn binding sites) and Uni-G1-2F8-ITL-H435A (0 FcRn binding sites, no binding).

Example 47

Her2×CD3 Bispecific Antibodies Tested in an In Vitro Cytotoxicity Assay

CD3 is a co-receptor in the T cell receptor complex expressed on mature T cells. Combination of a CD3 specific antibody Fab-arm with a tumor antigen specific antibody Fab-arm in a bispecific antibody would result in the specific targeting of T cells to tumor cells, leading to T cell mediated tumor cell lysis. Likewise, CD3 positive T cells could be targeted to other derailed cells in the body, to infected cells or directly to pathogens.

Her2×CD3 bispecific antibodies were generated. Heavy and light chain variable region sequences for the Her2 specific Fab-arm were as indicated for antibody 153 and 169 in Example 42. The following heavy and light chain variable region sequences for the CD3 specific Fab-arm were used: YTH12.5 (Sequence as described by Routledge et al., Eur J Immunol. 1991, 21(11):2717-25.)

| SEQ ID NO | | |
|---|---|---|
| 24 | VH YTH12.5 | EVQLLESGGGLVQPGGSLRLSCAASGFTFSSFPMAWVRQAPG KGLEWVSTISTSGGRTYYRDSVKGRFTISRDNSKNTLYL QMNSLRAEDTAVYYCAKFRQYSGGFDYWGQGTLVTVSS |
| 25 | VL YTH12.5 | DIQLTQPNSVSTSLGSTVKLSCTLSSGNIENNYVHWYQLYEG RSPTTMIYDDDKRPDGVPDRFSGSIDRSSNSAFLTIHNV AIEDEAIYFCHSYVSSFNVFGGGTKLTVL | huCLB-T3/4 (Sequence as described by Parren et al., Res Immunol. 1991, 142(9):749-63. Minor amino acid substitutions were introduced to make the sequence resemble the closest human germline.)

| SEQ ID NO | | |
|---|---|---|
| 26 | VH huCLB-T3/4 | EVQLVESGGGLVKPGGSLRLSCAASGFTFSSYGMFWVRQAPG KGLEWVATISRYSRYIYYPDSVKGRFTISRDNAKNSLYL QMNSLRAEDTAVYYCARRPLYGSSPDYWGQGTLVTVSS |
| 27 | VL huCLB-T3/4 | EIVLTQSPATLSLSPGERATLSCSASSSVTYVHWYQQKPGQA PRLLIYDTSKLASGIPARFSGSGSGTDFTLTISSLEPED FAVYYCFQGSGYPLTFGSGTKLEMR |

All antibodies were expressed as IgG1,κ being modified in their Fc regions as described as follows: IgG1-Her2-153-K409R and IgG1-Her2-153-N297Q-K409R, IgG1-Her2-169-K409R, IgG1-hu-CLB-T3/4-F405L and IgG1-hu-CLB-T3/4-N297Q-F405L, IgG1-YTH12.5-F405L and IgG1-YTH12.5-N297Q-F405L.

Bispecific antibodies from these Her2 and CD3 specific antibodies were generated as described in Example 11 and tested in an in vitro cytotoxicity assay using AU565 cells.

AU565 cells were cultured to near confluency. Cells were washed twice with PBS, and trypsinized for 5 minutes at 37° C. 12 mL culture medium was added to inactivate trypsin and cells were spun down for 5 min, 800 rpm. Cells were resuspended in 10 mL culture medium and a single cell suspension was made by passing the cells through a cellstrainer. 100 μL of a $5 \times 10^5$ cells/mL suspension was added to each well of a 96-well culture plate, and cells were incubated at least 3 hrs at 37° C., 5% CO2 to allow adherence to the plate.

Peripheral blood mononuclear cells (PBMC) were isolated from blood from healthy volunteers using Leucosep 30 mL tubes, according to the manufacturer's protocol (Greiner Bio-one). T cells were isolated from PBMC preparations by negative selection using the Untouched Human T-cells Dynabead kit (Dynal). Isolated cells were resuspended in culture medium to a final concentration op $7 \times 10^6$ cells/mL.

Culture medium was removed from the adhered AU565 cells, and replaced with 50 μl/well 2× concentrated antibody-dilution and 50 μl/well $7 \times 10^6$ T cells/mL (ratio effector:target=7:1). Plates were incubated for 3 days at 37° C., 5% CO$_2$. Supernatants were removed and plates were washed twice with PBS. To each well 150 μL culture medium and 15 μL Alamar blue was added. Plates were incubated for 4 hours at 37° C., 5% CO$_2$, and absorbance was measured (Envision, Perkin Elmer).

Figure 49:
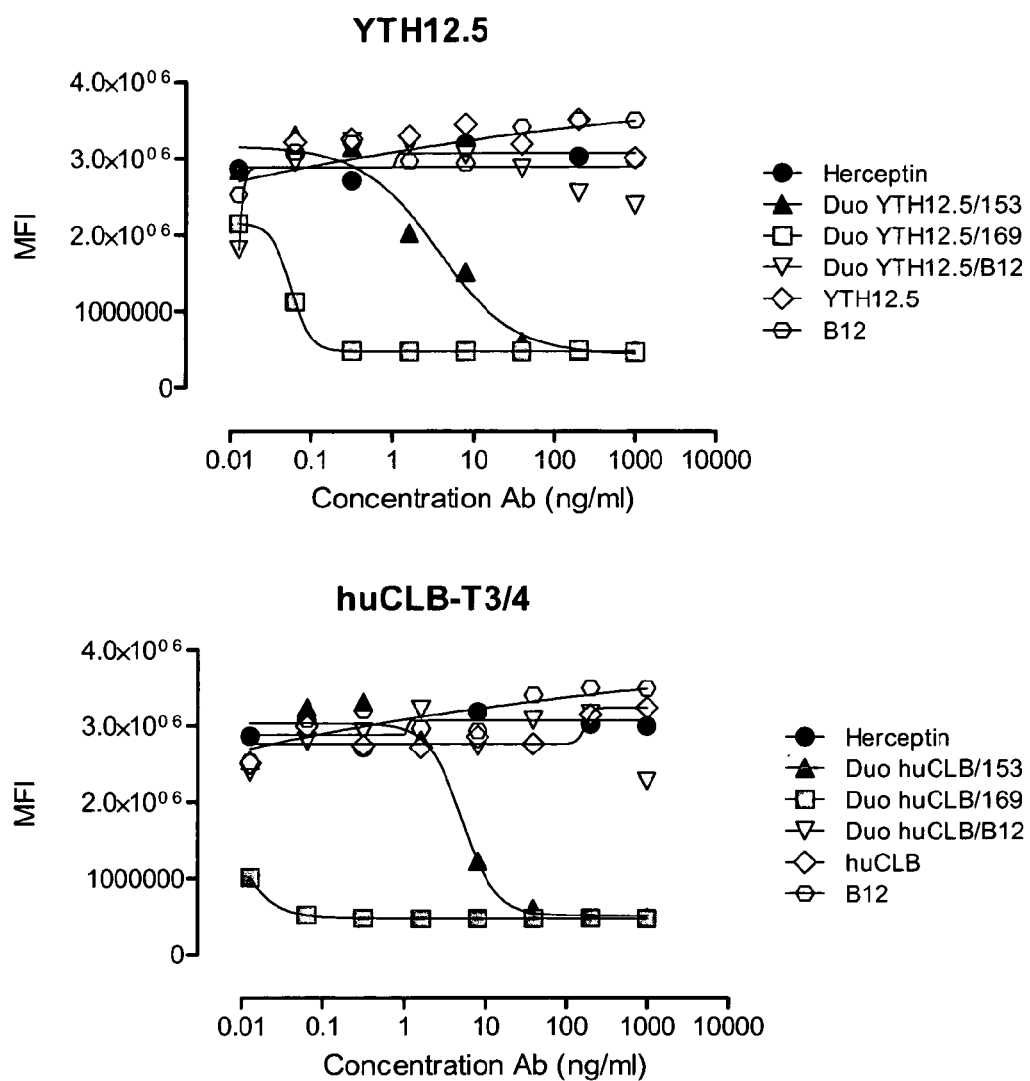
FIG. 49: T cell mediated cytotoxicity of AU565 cells by Her2×CD3 bispecific antibodies as well as by N297Q mutants of Her2×CD3 bispecific antibodies.
Figure 49:
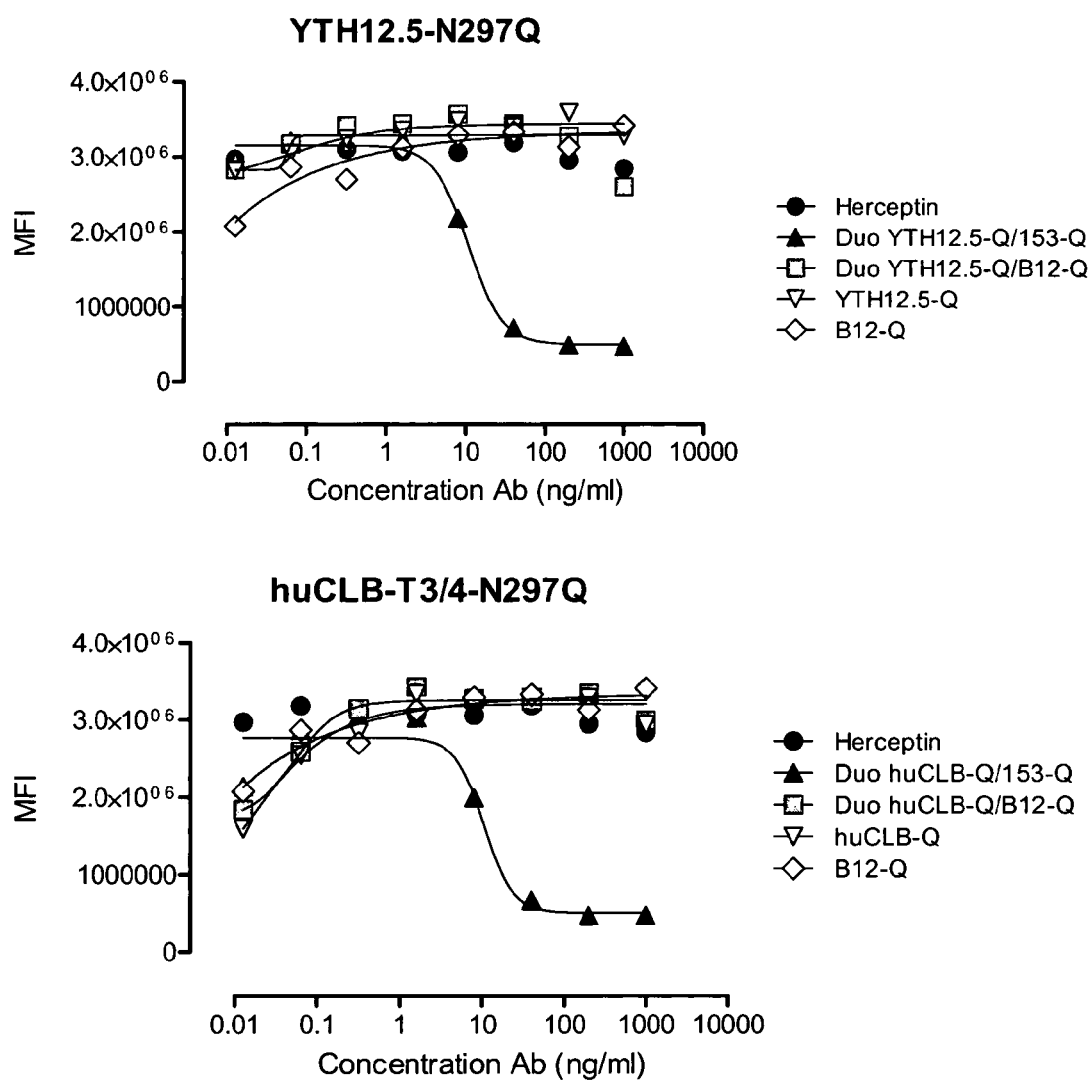

FIG. 49 shows that whereas control antibodies (Her2 monospecific IgG1-Herceptin, CD3 monospecific IgG1-YTH12.5 and monospecific IgG1-huCLB-T3/4, irrelevant antigen monospecific IgG1-b12, and CD3×b12 bispecific antibodies) did not induce T cell mediated cytotoxicity, bispecific (Duo) Her2×CD3 antibodies huCLB/Her2-153, huCLB/Her2-169, YTH12.5/Her2-153 and YTH12.5/Her2-169 induced dose dependent T cell mediated cytotoxicity of AU565 cells. Bispecific antibodies containing Her2-169 were more potent than those containing Her2-153.

Mutants of IgG1-hu-CLB-T3/4, IgG1-YTH12.5 and Her2-153 were made containing a N297Q mutation to remove a glycosylation site; glycosylation at this site is critical for IgG-Fcgamma receptor interactions (Bolt S et al., Eur J Immunol 1993, 23:403-411). FIG. 49 shows that N297Q mutation and therefore absence of Fc glycosylation of Her2× CD3 bispecific antibodies YTH12.5/Her2-153 and huCLB/Her2-153 did not impact the potential to induce dose dependent T cell mediated cytotoxicity of AU565 cells.

The invention claimed is:

1. An in vitro method for generating a heterodimeric antibody, said method comprising the following steps:
   a) providing a first chimeric, humanized, or human homodimeric antibody comprising an Fc region, said Fc region comprising the CH3 region of SEQ ID NO: 1, but with an amino acid substitution at a position selected from the group consisting of: 366, 368, 370, 399, 405, 407, and 409 (numbering according to the EU Index);
   b) providing a second chimeric, humanized, or human homodimeric antibody comprising an Fc region, said Fc region comprising the CH3 region of SEQ ID NO: 1, but with an amino acid substitution at a position selected from the group consisting of: 366, 368, 370, 399, 405, 407, and 409 (numbering according to the EU Index), wherein the sequences of said first and second antibody CH3 regions are different,
   c) incubating said first antibody together with said second antibody under reducing conditions sufficient to allow the cysteines in the hinge region to undergo disulfide-bond isomerization, wherein the heterodimeric interaction between said first and second antibodies in the resulting heterodimeric antibody is such that no Fab-arm exchange occurs at 0.5 mM GSH after 24 hours at 37° C., and
   d) obtaining said heterodimeric antibody.

2. The in vitro method according to claim 1, wherein said first and second homodimeric antibodies bind different epitopes.

3. The in vitro method according to claim 1, wherein the Fc regions of both said first and said second homodimeric antibodies are of the IgG1 isotype, except for the specified substitutions.

4. The in vitro method according to claim 1, wherein the heterodimeric interaction between said first and second antibodies in the resulting heterodimeric antibody is such that no Fab-arm exchange occurs in vivo in mice under the conditions described in Example 14.

5. The in vitro method according to claim 1, wherein the heterodimeric interaction between said first and second antibodies in the resulting heterodimeric antibody is more than two times stronger than the corresponding homodimeric interactions, when determined as described in Example 30.

6. The in vitro method according to claim 1, wherein the sequences of said first and second CH3 regions are such that the dissociation constants of the heterodimeric interaction between said first and second antibodies in the resulting heterodimeric antibody is below 0.05 micromolar when assayed as described in Example 30.

7. The in vitro method according to claim 1, wherein the sequences of said first and second CH3 regions are such that the dissociation constants of both homodimeric interactions are above 0.01 micromolar when assayed as described in Example 21.

8. The in vitro method according to claim 1, wherein said first homodimeric antibody has an amino acid other than Lys, Leu or Met at position 409 and said second homodimeric antibody has an amino acid substitution at a position selected from the group consisting of: 366, 368, 370, 399, 405 and 407.

9. The in vitro method according to claim 1, wherein said first homodimeric antibody has an amino acid other than Lys, Leu or Met at position 409 and said second homodimeric antibody has an amino acid other than Phe at position 405.

10. The in vitro method according to claim 1, wherein said first homodimeric antibody has an amino acid other than Lys, Leu or Met at position 409 and said second homodimeric antibody has an amino acid other than Phe, Arg or Gly at position 405.

11. The in vitro method according to claim 1, wherein said first homodimeric antibody comprises an amino acid other than Lys, Leu or Met at position 409 and said second homodimeric antibody comprises an amino acid other than Phe at position 405.

12. The in vitro method according to claim 1, wherein said first homodimeric antibody comprises an amino acid other than Lys, Leu or Met at position 409 and said second homodimeric antibody comprises an amino acid other than Phe, Arg or Gly at position 405.

13. The in vitro method according to claim 1, wherein said first homodimeric antibody comprises an amino acid other than Lys, Leu or Met at position 409 and said second homodimeric antibody comprises a Leu at position 405.

14. The in vitro method according to claim 1, wherein said first homodimeric antibody comprises an Arg at position 409 and said second homodimeric antibody comprises an amino acid other than Phe, Arg or Gly at position 405.

15. The in vitro method according to claim 1, wherein said first homodimeric antibody comprises an Arg at position 409 and said second homodimeric antibody comprises a Leu at position 405.

16. The in vitro method according to claim 1, wherein neither said first nor said second homodimeric antibody comprises a Cys-Pro-Ser-Cys (SEQ ID NO: 5) sequence in the hinge region.

17. The in vitro method according to claim 1, wherein both said first and said second homodimeric antibodies comprise a Cys-Pro-Pro-Cys (SEQ ID NO: 4) sequence in the hinge region.

18. The in vitro method according to claim 1, wherein said first and/or said second homodimeric antibody comprises a mutation removing the acceptor site for Asn-linked glycosylation.

19. The in vitro method according to claim 1, wherein said first and second homodimeric antibodies provided in steps a) and b) are purified.

20. The in vitro method according to claim 1, wherein said first and/or second homodimeric antibody is conjugated to a drug, a prodrug or a toxin or contains an acceptor group for the same.

21. The in vitro method according to claim 2, wherein said epitopes are located on a tumor cell.

22. The in vitro method according to claim 2, wherein one epitope is located on a tumor cell and the other epitope is located on an effector cell.

23. The in vitro method according to claim 22, wherein the effector cell is a T cell.

24. The in vitro method according to claim 2, wherein one epitope is located on a tumor cell and the other epitope is located on a radioisotope, a toxin, a drug or a prodrug.

25. The in vitro method according to claim 2, wherein one epitope is located on a tumor cell and the other epitope is located on an electron dense vesicle or minicell.

26. The in vitro method according to claim 2, wherein the first antibody and the second antibody bind to different epitopes on the same tumor cell.

27. The in vitro method according to claim 1, wherein the first antibody binds to an epitope on a tumor cell, and the other antibody is an irrelevant or inactive antibody without any relevant in vivo binding activity for the application intended.

28. The in vitro method according to claim 1, wherein the reducing conditions in step c) comprise the addition of a reducing agent.

29. The in vitro method according to claim 1, wherein step c) is performed under reducing conditions with a redox potential between −150 and −600 mV.

30. The in vitro method according to claim 1, wherein step c) comprises incubation for at least 90 min at a temperature of at least 20° C. in the presence of at least 25 mM 2-mercaptoethylamine or in the presence of at least 0.5 mM dithiothreitol.

31. The in vitro method according to claim 1, wherein step d) comprises removal of a reducing agent.

32. A method for producing a heterodimeric protein, said method comprising the following steps:
    a) providing a first nucleic-acid construct encoding a first polypeptide comprising a first Fc region of an immunoglobulin, said first Fc region comprising the CH3 region of SEQ ID NO: 1, but with Arg at position 409 (numbering according to the EU Index),
    b) providing a second nucleic-acid construct encoding a second polypeptide comprising a second Fc region of an immunoglobulin, said second Fc region comprising the CH3 region of SEQ ID NO: 1, but with an amino acid substitution at a position selected from the group consisting of: 366, 368, 370, 399, 405 and 407 (numbering according to the EU Index),
    c) co-expressing said first and second nucleic-acid constructs in a host cell, and
    d) obtaining said heterodimeric protein from the cell culture.

33. The method according to claim 32, wherein said first and second polypeptides are full-length heavy chains of two antibodies that bind different epitopes.

34. The method according to claim 32, wherein step c) further comprises co-expressing one or more nucleic-acid constructs encoding a light-chain in said host cell.

35. The method according to claim 32 wherein said first Fc region comprises an Arg at position 409 and said second Fc region comprises a Leu at position 405.

36. An in vitro method for generating a heterodimeric antibody, said method comprising the following steps:
    a) providing a first chimeric, humanized, or human homodimeric antibody comprising an Fc region, said Fc region comprising the CH3 region of SEQ ID NO: 1, but with an amino acid substitution at position 409 (numbering according to the EU Index);
    b) providing a second chimeric, humanized, or human homodimeric antibody comprising an Fc region, said Fc region comprising the CH3 region of SEQ ID NO: 1, but with an amino acid substitution at position 405 (numbering according to the EU Index), c) incubating said first antibody together with said second antibody under reducing conditions sufficient to allow the cysteines in the hinge region to undergo disulfide-bond isomerization, wherein the heterodimeric interaction between said first and second antibodies in the resulting heterodimeric antibody is such that no Fab-arm exchange occurs at 0.5 mM GSH after 24 hours at 37° C., and d) obtaining said heterodimeric antibody.

37. The heterodimeric antibody of claim 36, wherein the Lys at position 409 of the CH3 region of the first antibody is substituted with Ala, Asp, Glu, Phe, Gly, His, Ile, Asn, Gln, Arg, Ser, Thr, Val, Trp, or Tyr, and wherein the Phe at position 405 of the CH3 region of the second antibody is substituted with Ala, Asp, Glu, His, Ile, Lys, Leu, Met, Asn, Gln, Ser, Thr, Val, Trp, or Tyr.

* * * * *

SEQUENCE LISTING

```
<160> NUMBER OF SEQ ID NOS: 33

<210> SEQ ID NO 1
<211> LENGTH: 107
<212> TYPE: PRT
<213> ORGANISM: homo sapiens

<400> SEQUENCE: 1

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95
```

-continued

Thr Gln Lys Ser Leu Ser Leu Ser Pro Gly Lys
            100                 105

<210> SEQ ID NO 2
<211> LENGTH: 107
<212> TYPE: PRT
<213> ORGANISM: homo sapiens

<400> SEQUENCE: 2

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 3
<211> LENGTH: 107
<212> TYPE: PRT
<213> ORGANISM: homo sapiens

<400> SEQUENCE: 3

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Gly Leu His Asn His Tyr
                85                  90                  95

Thr Gln Lys Ser Leu Ser Leu Ser Pro Gly Lys
            100                 105

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide

<400> SEQUENCE: 4

Cys Pro Pro Cys
1

<210> SEQ ID NO 5
<211> LENGTH: 4
<212> TYPE: PRT

```
<213> ORGANISM: Artificial Sequence
<220> FEATURE:
<223> OTHER INFORMATION: Synthetic peptide

<400> SEQUENCE: 5

Cys Pro Ser Cys
1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide

<400> SEQUENCE: 6

Gly Ser Ser Gly
1

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide

<400> SEQUENCE: 7

Lys Leu Ala Lys Lys Leu Ala Lys
1               5

<210> SEQ ID NO 8
<211> LENGTH: 440
<212> TYPE: PRT
<213> ORGANISM: Artificial Sequence
<220> FEATURE:
<223> OTHER INFORMATION: Synthetic peptide

<400> SEQUENCE: 8

Gln Val Gln Leu Val Glu Ser Gly Gly Gly Val Val Gln Pro Gly Arg
1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
```

Val Val Thr Val Pro Ser Ser Leu Gly Thr Gln Thr Tyr Ile Cys
            180                 185                 190

Asn Val Asn His Lys Pro Ser Asn Thr Lys Val Asp Lys Arg Val Ala
            195                 200                 205

Pro Glu Leu Leu Gly Gly Pro Ser Val Phe Leu Phe Pro Pro Lys Pro
210                 215                 220

225                 230                 235                 240

Lys Asp Thr Leu Met Ile Ser Arg Thr Pro Glu Val Thr Cys Val Val
            245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
            275                 280                 285

Tyr Asn Ser Thr Tyr Arg Val Val Ser Val Leu Thr Val Leu His Gln
            290                 295                 300

Asp Trp Leu Asn Gly Lys Glu Tyr Lys Cys Lys Val Ser Asn Lys Ala
305                 310                 315                 320

Leu Pro Ala Pro Ile Glu Lys Thr Ile Ser Lys Ala Lys Gly Gln Pro
            325                 330                 335

Arg Glu Pro Gln Val Tyr Thr Leu Pro Pro Ser Arg Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
            370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
            405                 410                 415

Ser Cys Ser Val Met His Glu Ala Leu His Asn His Tyr Thr Gln Lys
            420                 425                 430

Ser Leu Ser Leu Ser Pro Gly Lys
            435                 440

<210> SEQ ID NO 9
<211> LENGTH: 327
<212> TYPE: PRT
<213> ORGANISM: Homo sapiens

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

```
Glu Phe Leu Gly Gly Pro Ser Val Phe Leu Phe Pro Lys Pro Lys
            115                 120                 125

Asp Thr Leu Met Ile Ser Arg Thr Pro Glu Val Thr Cys Val Val
130                 135                 140

Asp Val Ser Gln Glu Asp Pro Glu Val Gln Phe Asn Trp Tyr Val
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 10
<211> LENGTH: 324
<212> TYPE: PRT
<213> ORGANISM: Rhesus sp.

<400> SEQUENCE: 10

Ser Thr Lys Gly Pro Ser Val Phe Pro Leu Ala Ser Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Val Cys Asn Val Val His Glu Pro Ser Asn Thr Lys Val Asp Lys Arg
                85                  90                  95

Val Glu Phe Thr Pro Pro Cys Pro Ala Cys Pro Ala Pro Glu Leu Leu
            100                 105                 110

Gly Gly Pro Ser Val Phe Leu Phe Pro Pro Lys Pro Lys Asp Thr Leu
        115                 120                 125

Met Ile Ser Arg Thr Pro Glu Val Thr Cys Val Val Val Asp Val Ser
    130                 135                 140

Gln Glu Asp Pro Glu Val Gln Phe Asn Trp Tyr Val Asp Gly Ala Glu
145                 150                 155                 160
```

```
Val His His Ala Gln Thr Lys Pro Arg Glu Arg Gln Phe Asn Ser Thr
                165                 170                 175

Tyr Arg Val Val Ser Val Leu Thr Val Thr His Gln Asp Trp Leu Asn
        180                 185                 190

Gly Lys Glu Tyr Thr Cys Lys Val Ser Asn Lys Gly Leu Pro Ala Pro
    195                 200                 205

Ile Glu Lys Thr Ile Ser Lys Ala Lys Gly Gln Pro Arg Glu Pro Gln
210                 215                 220

Val Tyr Ile Leu Pro Pro Gln Glu Glu Leu Thr Lys Asn Gln Val
225                 230                 235                 240

Ser Leu Thr Cys Leu Val Thr Gly Phe Tyr Pro Ser Asp Ile Ala Val
                245                 250                 255

Glu Trp Glu Ser Asn Gly Gln Pro Glu Asn Thr Tyr Lys Thr Thr Pro
            260                 265                 270

Pro Val Leu Asp Ser Asp Gly Ser Tyr Leu Leu Tyr Ser Lys Leu Thr
            275                 280                 285

Val Asn Lys Ser Arg Trp Gln Pro Gly Asn Ile Phe Thr Cys Ser Val
290                 295                 300

Met His Glu Ala Leu His Asn His Tyr Thr Gln Lys Ser Leu Ser Val
305                 310                 315                 320

Ser Pro Gly Lys

<210> SEQ ID NO 11
<211> LENGTH: 106
<212> TYPE: PRT
<213> ORGANISM: Rhesus sp.

<400> SEQUENCE: 11

Ala Val Ala Ala Pro Ser Val Phe Ile Phe Pro Pro Ser Glu Asp Gln
1               5                   10                  15

Val Lys Ser Gly Thr Val Ser Val Val Cys Leu Leu Asn Asn Phe Tyr
            20                  25                  30

Pro Arg Glu Ala Ser Val Lys Trp Lys Val Asp Gly Val Leu Lys Thr
        35                  40                  45

Gly Asn Ser Gln Glu Ser Val Thr Glu Gln Asp Ser Lys Asp Asn Thr
    50                  55                  60

Tyr Ser Leu Ser Ser Thr Leu Thr Leu Ser Ser Thr Asp Tyr Gln Ser
65                  70                  75                  80

His Asn Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 12
<211> LENGTH: 125
<212> TYPE: PRT
<213> ORGANISM: Artificial Sequence
<220> FEATURE:
<223> OTHER INFORMATION: Synthetic peptide

<400> SEQUENCE: 12

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
```

```
                35                  40                  45
Ala Thr Ile Ser Asp Asp Gly Ser Tyr Thr Tyr Tyr Pro Asp Ser Val
            50                  55                  60
Lys Gly Arg Phe Thr Ile Ser Arg Asp Asn Ala Lys Asn Asn Leu Tyr
 65                 70                  75                  80
Leu Gln Met Ser Ser Leu Lys Ser Glu Asp Thr Ala Met Tyr Tyr Cys
                85                  90                  95
Ala Arg Glu Gly Leu Tyr Tyr Tyr Gly Ser Gly Ser Tyr Tyr Asn Gln
            100                 105                 110
Asp Tyr Trp Gly Gln Gly Thr Leu Val Thr Val Ser Ser
            115                 120                 125

<210> SEQ ID NO 13
<211> LENGTH: 108
<212> TYPE: PRT
<213> ORGANISM: Artificial Sequence
<220> FEATURE:
<223> OTHER INFORMATION: Synthetic peptide

<400> SEQUENCE: 13

Ala Ile Gln Leu Thr Gln Ser Pro Ser Ser Leu Ser Ala Ser Val Gly
 1               5                  10                  15
Asp Arg Val Thr Ile Thr Cys Arg Ala Ser Gln Gly Leu Ser Ser Ala
            20                  25                  30
Leu Ala Trp Tyr Arg Gln Lys Pro Gly Lys Ala Pro Lys Leu Leu Ile
            35                  40                  45
Tyr Asp Ala Ser Ser Leu Glu Ser Gly Val Pro Ser Arg Phe Ser Gly
            50                  55                  60
Ser Gly Ser Gly Thr Asp Phe Thr Leu Thr Ile Ser Ser Leu Gln Pro
 65                 70                  75                  80
Glu Asp Phe Ala Thr Tyr Tyr Cys Gln Gln Phe Thr Ser Tyr Pro Gln
                85                  90                  95
Ile Thr Phe Gly Gln Gly Thr Arg Leu Glu Ile Lys
            100                 105

<210> SEQ ID NO 14
<211> LENGTH: 119
<212> TYPE: PRT
<213> ORGANISM: Artificial Sequence
<220> FEATURE:
<223> OTHER INFORMATION: Synthetic peptide

<400> SEQUENCE: 14

Gln Val Gln Leu Val Gln Ser Gly Ala Glu Val Lys Lys Pro Gly Ala
 1               5                  10                  15
Ser Val Lys Val Ser Cys Glu Thr Ser Gly Tyr Thr Phe Thr Ser Tyr
            20                  25                  30
Gly Ile Ser Trp Val Arg Gln Ala Pro Gly His Gly Leu Glu Trp Met
            35                  40                  45
Gly Trp Ile Ser Ala Tyr Asn Gly Tyr Thr Asn Tyr Ala Gln Lys Leu
            50                  55                  60
Gln Gly Arg Val Thr Met Thr Thr Asp Thr Ser Thr Ser Thr Ala Tyr
 65                 70                  75                  80
Met Glu Leu Arg Ser Leu Arg Ser Asp Thr Ala Val Tyr Tyr Cys
                85                  90                  95
Ala Arg Asp Leu Arg Gly Thr Asn Tyr Phe Asp Tyr Trp Gly Gln Gly
            100                 105                 110
```

Thr Leu Val Thr Val Ser Ser
            115

<210> SEQ ID NO 15
<211> LENGTH: 107
<212> TYPE: PRT
<213> ORGANISM: Artificial Sequence
<220> FEATURE:
<223> OTHER INFORMATION: Synthetic peptide

<400> SEQUENCE: 15

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Phe Gln His Lys Pro Gly Lys Ala Pro Lys Leu Leu Ile
        35                  40                  45

Tyr Ala Ala Ser Ser Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 16
<211> LENGTH: 122
<212> TYPE: PRT
<213> ORGANISM: Artificial Sequence
<220> FEATURE:
<223> OTHER INFORMATION: Synthetic peptide

<400> SEQUENCE: 16

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Ser Phe His Phe Tyr
            20                  25                  30

Trp Ile Gly Trp Val Arg Gln Met Pro Gly Lys Gly Leu Glu Trp Met
        35                  40                  45

Gly Ser Ile Tyr Pro Gly Asp Ser Asp Thr Arg Tyr Arg Pro Ser Phe
    50                  55                  60

Gln Gly Gln Val Thr Ile Ser Ala Asp Lys Ser Ile Ser Thr Ala Tyr
65                  70                  75                  80

Leu Gln Trp Thr Ser Leu Lys Ala Ser Asp Thr Ala Ile Tyr Tyr Cys
                85                  90                  95

Ala Arg Gln Arg Gly Asp Tyr Tyr Tyr Phe Tyr Gly Met Asp Val Trp
            100                 105                 110

Gly Gln Gly Thr Thr Val Thr Val Ser Ser
        115                 120

<210> SEQ ID NO 17
<211> LENGTH: 107
<212> TYPE: PRT
<213> ORGANISM: Artificial Sequence
<220> FEATURE:
<223> OTHER INFORMATION: Synthetic peptide

<400> SEQUENCE: 17

Glu Ile Val Leu Thr Gln Ser Pro Gly Thr Leu Ser Leu Ser Pro Gly

```
            1               5                  10                 15
         Glu Arg Ala Thr Leu Ser Cys Arg Ala Ser Gln Ser Val Ser Ser
                         20                  25                 30

Tyr Leu Ala Trp Tyr Gln Gln Lys Pro Gly Gln Val Pro Arg Leu Leu
                         35                  40                  45

Ile Tyr Gly Ala Ser Ser Arg Ala Thr Gly Ile Pro Asp Arg Phe Ser
                         50                  55                  60

Gly Ser Gly Ser Gly Thr Asp Phe Thr Leu Thr Ile Ser Arg Leu Glu
         65                  70                  75                  80

Pro Glu Asp Phe Ala Val Tyr Tyr Cys Gln Gln Tyr Gly Ser Ser Leu
                              85                  90                  95

Thr Phe Gly Gly Gly Thr Lys Val Glu Ile Lys
                         100                 105
```

<210> SEQ ID NO 18
<211> LENGTH: 120
<212> TYPE: PRT
<213> ORGANISM: Artificial Sequence
<220> FEATURE:
<223> OTHER INFORMATION: Synthetic peptide

<400> SEQUENCE: 18

```
         Gln Val Gln Leu Gln Gln Trp Gly Ala Gly Leu Leu Lys Pro Ser Glu
         1               5                  10                  15

Thr Leu Ser Leu Thr Cys Ala Val Tyr Gly Gly Ser Phe Ser Asp Tyr
                         20                  25                  30

Tyr Trp Asn Trp Ile Arg Gln Pro Pro Gly Lys Gly Leu Glu Trp Ile
                         35                  40                  45

Gly Glu Ile His His Ser Gly Ser Thr Asn Tyr Asn Pro Ser Leu Lys
                 50                  55                  60

Ser Arg Val Thr Ile Ser Val Asp Thr Ser Lys Asn Gln Phe Ser Leu
         65                  70                  75                  80

Lys Leu Ser Ser Val Thr Ala Ala Asp Thr Ala Val Tyr Tyr Cys Ala
                         85                  90                  95

Arg Gly Tyr Tyr Asp Ser Gly Val Tyr Tyr Phe Asp Tyr Trp Ala Gln
                         100                 105                 110

Gly Thr Leu Val Thr Val Ser Ser
                         115                 120
```

<210> SEQ ID NO 19
<211> LENGTH: 107
<212> TYPE: PRT
<213> ORGANISM: Artificial Sequence
<220> FEATURE:
<223> OTHER INFORMATION: Synthetic peptide

<400> SEQUENCE: 19

```
         Asp Ile Gln Met Thr Gln Ser Pro Ser Ser Leu Ser Ala Ser Val Gly
         1               5                  10                  15

Asp Arg Val Thr Ile Thr Cys Arg Ala Ser Gln Gly Ile Ser Arg Trp
                         20                  25                  30

Leu Ala Trp Tyr Gln Gln Lys Pro Glu Lys Ala Pro Lys Ser Leu Ile
                         35                  40                  45

Tyr Ala Ala Ser Ser Leu Arg Ser Gly Val Pro Ser Arg Phe Ser Gly
                 50                  55                  60

Ser Gly Ser Gly Thr Asp Phe Thr Leu Thr Ile Ser Ser Leu Gln Pro
         65                  70                  75                  80
```

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 20
<211> LENGTH: 121
<212> TYPE: PRT
<213> ORGANISM: Artificial Sequence
<220> FEATURE:
<223> OTHER INFORMATION: Synthetic peptide

<400> SEQUENCE: 20

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
                20                  25                  30

Val Ile His Trp Val Arg Gln Ala Pro Gly Lys Gly Leu Glu Trp Val
            35                  40                  45

Thr Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Met Tyr Tyr Cys
                85                  90                  95

Ala Arg Gly Gly Ile Thr Gly Thr Thr Gly Val Phe Asp Tyr Trp Gly
            100                 105                 110

Gln Gly Thr Leu Val Thr Val Ser Ser
        115                 120

<210> SEQ ID NO 21
<211> LENGTH: 107
<212> TYPE: PRT
<213> ORGANISM: Artificial Sequence
<220> FEATURE:
<223> OTHER INFORMATION: Synthetic peptide

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Asp Ala Ser Ser Leu Gln Ser Gly Val Pro Ser Arg Phe Ser Gly
        50                  55                  60

Ser Gly Tyr Gly Thr Asp Phe Ser Leu Thr Ile Ser Ser Leu Gln Pro
65                  70                  75                  80

Glu Asp Phe Ala Ile Tyr Tyr Cys Gln Gln Tyr Lys Ser Tyr Pro Ile
                85                  90                  95

Thr Phe Gly Gln Gly Thr Arg Leu Glu Ile Lys
            100                 105

<210> SEQ ID NO 22
<211> LENGTH: 121
<212> TYPE: PRT
<213> ORGANISM: Artificial Sequence
<220> FEATURE:
<223> OTHER INFORMATION: Synthetic peptide

```
<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Leu Ser Ala Tyr Ser Gly Asn Thr Ile Tyr Ala Gln Lys Leu
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Ile Val Val Arg Pro Asp Tyr Phe Asp Tyr Trp Gly
            100                 105                 110

Gln Gly Thr Leu Val Thr Val Ser Ser
        115                 120

<210> SEQ ID NO 23
<211> LENGTH: 107
<212> TYPE: PRT
<213> ORGANISM: Artificial Sequence
<220> FEATURE:
<223> OTHER INFORMATION: Synthetic peptide

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105

<210> SEQ ID NO 24
<211> LENGTH: 119
<212> TYPE: PRT
<213> ORGANISM: Artificial Sequence
<220> FEATURE:
<223> OTHER INFORMATION: Synthetic peptide

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Pro Met Ala Trp Val Arg Gln Ala Pro Gly Lys Gly Leu Glu Trp Val
        35                  40                  45

Ser Thr Ile Ser Thr Ser Gly Gly Arg Thr Tyr Tyr Arg Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Arg Gln Tyr Ser Gly Gly Phe Asp Tyr Trp Gly Gln Gly
            100                 105                 110

Thr Leu Val Thr Val Ser Ser
            115
```

<210> SEQ ID NO 25
<211> LENGTH: 110
<212> TYPE: PRT
<213> ORGANISM: Artificial Sequence
<220> FEATURE:
<223> OTHER INFORMATION: Synthetic peptide

<400> SEQUENCE: 25

```
Asp Ile Gln Leu Thr Gln Pro Asn Ser Val Ser Thr Ser Leu Gly Ser
 1               5                  10                  15

Thr Val Lys Leu Ser Cys Thr Leu Ser Ser Gly Asn Ile Glu Asn Asn
                 20                  25                  30

Tyr Val His Trp Tyr Gln Leu Tyr Glu Gly Arg Ser Pro Thr Thr Met
             35                  40                  45

Ile Tyr Asp Asp Asp Lys Arg Pro Asp Gly Val Pro Asp Arg Phe Ser
 50                  55                  60

Gly Ser Ile Asp Arg Ser Ser Asn Ser Ala Phe Leu Thr Ile His Asn
 65                  70                  75                  80

Val Ala Ile Glu Asp Glu Ala Ile Tyr Phe Cys His Ser Tyr Val Ser
                 85                  90                  95

Ser Phe Asn Val Phe Gly Gly Gly Thr Lys Leu Thr Val Leu
            100                 105                 110
```

<210> SEQ ID NO 26
<211> LENGTH: 119
<212> TYPE: PRT
<213> ORGANISM: Artificial Sequence
<220> FEATURE:
<223> OTHER INFORMATION: Synthetic peptide

<400> SEQUENCE: 26

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                 20                  25                  30

Gly Met Phe Trp Val Arg Gln Ala Pro Gly Lys Gly Leu Glu Trp Val
             35                  40                  45

Ala Thr Ile Ser Arg Tyr Ser Arg Tyr Ile Tyr Tyr Pro Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Pro Leu Tyr Gly Ser Pro Asp Tyr Trp Gly Gln Gly
            100                 105                 110

Thr Leu Val Thr Val Ser Ser
            115
```

<210> SEQ ID NO 27

<211> LENGTH: 106
<212> TYPE: PRT
<213> ORGANISM: Artificial Sequence
<220> FEATURE:
<223> OTHER INFORMATION: Synthetic peptide

<400> SEQUENCE: 27

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Thr Tyr Val
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Gly Tyr Pro Leu Thr
                85                  90                  95

Phe Gly Ser Gly Thr Lys Leu Glu Met Arg
            100                 105
```

<210> SEQ ID NO 28
<211> LENGTH: 5
<212> TYPE: PRT
<213> ORGANISM: Homo sapiens

<400> SEQUENCE: 28

```
Cys Pro Pro Cys Pro
1               5
```

<210> SEQ ID NO 29
<211> LENGTH: 16
<212> TYPE: PRT
<213> ORGANISM: Homo sapiens

<400> SEQUENCE: 29

```
Gln Tyr Thr Leu Thr Leu Lys Lys Thr Pro Val Leu Asp Phe Tyr Lys
1               5                   10                  15
```

<210> SEQ ID NO 30
<211> LENGTH: 455
<212> TYPE: PRT
<213> ORGANISM: Artificial Sequence
<220> FEATURE:
<223> OTHER INFORMATION: Synthetic peptide

<400> SEQUENCE: 30

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Asp Gly Ile Thr Met Val Arg Gly Val Met Lys Asp Tyr Phe
            100                 105                 110
Asp Tyr Trp Gly Gln Gly Thr Leu Val Thr Val Ser Ser Ala Ser Thr
        115                 120                 125
Lys Gly Pro Ser Val Phe Pro Leu Ala Pro Ser Ser Lys Ser Thr Ser
    130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Gln Thr Tyr Ile Cys
        195                 200                 205
Asn Val Asn His Lys Pro Ser Asn Thr Lys Val Asp Lys Arg Val Glu
    210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys
    450                 455

<210> SEQ ID NO 31
<211> LENGTH: 452
<212> TYPE: PRT
<213> ORGANISM: Artificial Sequence
<220> FEATURE:
<223> OTHER INFORMATION: Synthetic peptide

<400> SEQUENCE: 31
```

```
Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Thr Tyr
             20                  25                  30

Gly Met His Trp Val Arg Gln Ala Pro Gly Lys Gly Leu Glu Trp Val
         35                  40                  45

Ala Val Ile Trp Asp Asp Gly Ser Tyr Lys Tyr Tyr Gly Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ile Thr Met Val Arg Gly Val Met Lys Asp Tyr Phe
             100                 105                 110

Asp Tyr Trp Gly Gln Gly Thr Leu Val Thr Val Ser Ser Ala Ser Thr
         115                 120                 125

Lys Gly Pro Ser Val Phe Pro Leu Ala Pro Cys Ser Arg Ser Thr Ser
 130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
             165                 170                 175

Thr Phe Pro Ala Val Leu Gln Ser Ser Gly Leu Tyr Ser Leu Ser Ser
         180                 185                 190

Val Val Thr Val Pro Ser Ser Ser Leu Gly Thr Lys Thr Tyr Thr Cys
     195                 200                 205

Asn Val Asp His Lys Pro Ser Asn Thr Lys Val Asp Lys Arg Val Glu
 210                 215                 220

Ser Lys Tyr Gly Pro Pro Cys Pro Ser Cys Pro Ala Pro Glu Phe Leu
225                 230                 235                 240

Gly Gly Pro Ser Val Phe Leu Phe Pro Pro Lys Pro Lys Asp Thr Leu
             245                 250                 255

Met Ile Ser Arg Thr Pro Glu Val Thr Cys Val Val Val Asp Val Ser
         260                 265                 270

Gln Glu Asp Pro Glu Val Gln Phe Asn Trp Tyr Val Asp Gly Val Glu
     275                 280                 285

Val His Asn Ala Lys Thr Lys Pro Arg Glu Glu Gln Phe Asn Ser Thr
 290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
             325                 330                 335

Ile Glu Lys Thr Ile Ser Lys Ala Lys Gly Gln Pro Arg Glu Pro Gln
         340                 345                 350

Val Tyr Thr Leu Pro Pro Ser Gln Glu Glu Met Thr Lys Asn Gln Val
     355                 360                 365

Ser Leu Thr Cys Leu Val Lys Gly Phe Tyr Pro Ser Asp Ile Ala Val
 370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
             405                 410                 415

Val Asp Lys Ser Arg Trp Gln Glu Gly Asn Val Phe Ser Cys Ser Val
```

```
                    420                 425                 430
Met His Glu Ala Leu His Asn His Tyr Thr Gln Lys Ser Leu Ser Leu
                435                 440                 445

Ser Leu Gly Lys
    450

<210> SEQ ID NO 32
<211> LENGTH: 97
<212> TYPE: PRT
<213> ORGANISM: Artificial Sequence
<220> FEATURE:
<223> OTHER INFORMATION: Synthetic peptide

<400> SEQUENCE: 32

Asn Val Asn His Lys Pro Ser Asn Thr Lys Val Asp Lys Arg Val Glu
1               5                   10                  15

Leu Lys Thr Pro Leu Gly Asp Thr Thr His Thr Cys Pro Arg Cys Pro
                20                  25                  30

Glu Pro Lys Ser Cys Asp Thr Pro Pro Cys Pro Arg Cys Pro Glu
            35                  40                  45

Pro Lys Ser Cys Asp Thr Pro Pro Pro Cys Pro Arg Cys Pro Glu Pro
        50                  55                  60

Lys Ser Cys Asp Thr Pro Pro Pro Cys Pro Arg Cys Pro Ala Pro Glu
65                  70                  75                  80

Leu Leu Gly Gly Pro Ser Val Phe Leu Phe Pro Pro Lys Pro Lys Asp
                85                  90                  95

Thr

<210> SEQ ID NO 33
<211> LENGTH: 4
<212> TYPE: PRT
<213> ORGANISM: Artificial Sequence
<220> FEATURE:
<223> OTHER INFORMATION: Synthetic peptide

<400> SEQUENCE: 33

Cys Pro Ala Cys
1
```